US008217027B2

(12) United States Patent
Wallace et al.

(10) Patent No.: US 8,217,027 B2
(45) Date of Patent: Jul. 10, 2012

(54) SPHINGOSINE-1-PHOSPHATE RECEPTOR AGONIST AND ANTAGONIST COMPOUNDS

(75) Inventors: Grier A. Wallace, Sterling, MA (US); Eric C. Breinlinger, Charlton, MA (US); Kevin P. Cusack, Holden, MA (US); Shannon R. Fix-Stenzel, Chicago, IL (US); Thomas D. Gordon, Medway, MA (US); Adrian D. Hobson, Shrewsbury, MA (US); Martin E. Hayes, Lowell, MA (US); Graham K. Ansell, Millbury, MA (US); Pintipa Grongsaard, Shrewsbury, MA (US)

(73) Assignee: Abbott Laboratories, Abbott Park, IL (US)

( * ) Notice: Subject to any disclaimer, the term of this patent is extended or adjusted under 35 U.S.C. 154(b) by 953 days.

(21) Appl. No.: 12/075,378

(22) Filed: Mar. 11, 2008

(65) Prior Publication Data

US 2009/0029947 A1 Jan. 29, 2009

Related U.S. Application Data

(63) Continuation-in-part of application No. 12/004,583, filed on Dec. 21, 2007, now abandoned.

(60) Provisional application No. 60/876,288, filed on Dec. 21, 2006, provisional application No. 60/876,318, filed on Dec. 21, 2006.

(51) Int. Cl.
C07D 205/02 (2006.01)
A61K 31/397 (2006.01)

(52) U.S. Cl. .................. 514/210.17; 514/567; 514/646; 540/1; 560/19; 562/11; 562/452; 562/469; 564/443

(58) Field of Classification Search .................. None
See application file for complete search history.

(56) References Cited

U.S. PATENT DOCUMENTS

| 2,967,125 | A | * | 1/1961 | Carlson | 514/646 |
| 3,345,405 | A | * | 10/1967 | Burger | 562/452 |
| 4,841,079 | A | | 6/1989 | Urban | |
| 6,069,176 | A | * | 5/2000 | Tsuchiya et al. | 514/646 |
| 6,828,460 | B2 | * | 12/2004 | Browning et al. | 564/256 |
| 2002/0161041 | A1 | * | 10/2002 | Browning et al. | 514/489 |
| 2005/0197334 | A1 | | 9/2005 | Wang et al. | |
| 2005/0250798 | A1 | | 11/2005 | Dollings et al. | |
| 2006/0051846 | A1 | | 3/2006 | Ohishi et al. | |
| 2006/0246553 | A1 | | 11/2006 | Suzuki et al. | |
| 2006/0264457 | A1 | | 11/2006 | Devasthale et al. | |

FOREIGN PATENT DOCUMENTS

| EP | 0306764 A2 * | 3/1989 |
| WO | 93/07111 A1 | 4/1993 |
| WO | WO 93/10092 | 5/1993 |
| WO | WO 9517393 A1 * | 6/1995 |
| WO | WO 2006/088944 | 8/2006 |
| WO | WO 2007/098474 | 8/2007 |

OTHER PUBLICATIONS

Fourneau et al, Bulletin de la Societe Chimique de France (1931), 49, pp. 1161-1172.*
Wu et al., Toxicology, 236, pp. 1-6, 2007.*
West, Anthony R., Solid State Chemistry and its Applications, Wiley, New York, 1988, pp. 358 & 365.*
Cieplak, et al, Journal of the American Chemical Society (1989), 111(22), pp. 8447-8462.*
Translation of Fourneau et al, Bulletin de la Societe Chimique de France, (1931) 49, pp. 1161-1172.*
Wolf, Burger's Medicinal Chemistry and Drug Discovery, Fifth Edition, vol. 1, 1995, pp. 975-977.*
Mandala et al., "Alteration of Lymphocyte Trafficking by Sphingosine—1-Phosphate Receptor Agonists", Science, (2002); 296: 346-349.
Jo et al., "S1P1-Selective In Vivo-Active Agonists from High-Throughput Screening: Off-the-Shelf Chemical Probes of Receptor Interactions, Signaling, and Fate". Chemistry & Biology, (2005); 12: 703-715.
Hale et al., "A Rational Utilization of High-Throughput Screening Affords Selective, Orally Bioavailable 1-Benzyl-3-carboxyazetidine Sphingosine-1-phosphate-1 Receptor Agonists". J. Med. Chem. (2004); 47: 6662-6665.
Clemens et al., "Synthesis of benzimidazole based analogues of sphingosine—1-phosphate: discovery of potent, subtype-selective S1P4 receptor agonists". Bioorganic & Medicinal Chemistry Letters, (2004); 14: 4903-4906.
Clemens et al., "Synthesis of *Para*-Alkyl Aryl Amide Analogues of Sphingosine-1-phosphate: Discovery of Potent S1P Receptor Agonists". Bioorganic & Medicinal Chemistry Letters, (2003); 13: 3401-3404.
Clemens et al., "Synthesis of 4(5)-phenylimidazole-based analogues of sphingosine-1-phosphate and FTY720: Discovery of potent S1P1 receptor agonists". Bioorganic & Medicinal Chemistry Letters (2005); 1-5.
Aspinall et al., "BINAP: An industrial approach to manufacture". Speciality Chemicals Magazine, Jan./Feb. 2005, p. 34-35.
Froestl et al., "Phosphinic Acid Analogues of GABA. 2. Selective, Orally Active GABAb Antagonists". J. Med. Chem. (1995); 38: 3313-3331.
B. W. Gung, et al., "Total synthesis of two novel brominated acetylenic diols (+)-diplyne C and E: stereoselective construction of the (*E*)-1-bromo-1-alkene". Tetrahedron: Asymmetry (2005); 16: 3107-3114.
Grison, et al., "Synthesis of P-chiral enephosphonic acid derivatives". J. Organomet. Chem. (2002); 662: 83-97.
Prashad, "Phosphonate vs. Phosphinate Elimination During Olefination of Aldehydes". Tetrahedron Letters (1993); 34: 1585-1588.
Li, Zhen, Discovery of Potent 3, 5-Diphenyl-1, 2, 4-oxadiazole Sphingosine-1-phosphate-1 (S1P1), Journal of Medicinal Chemistry, (2005) pp. 6169-6173, vol. 48(20).
Otomaru et al., Journal of Organic Chemistry (2005) 70; pp. 2503-2508.

* cited by examiner

*Primary Examiner* — Zinna Northington Davis
(74) *Attorney, Agent, or Firm* — Gayle B. O'Brien

(57) ABSTRACT

The present invention is directed to novel, potent, and selective agents, which are agonists or antagonists of the one or more of the individual receptors of the S1P receptor family. The compounds of the invention are useful as therapeutics for treating medical conditions associated with agonism or antagonism of the individual receptors of the S1P receptor family.

18 Claims, No Drawings

SPHINGOSINE-1-PHOSPHATE RECEPTOR AGONIST AND ANTAGONIST COMPOUNDS

CROSS REFERENCE TO RELATED APPLICATION

This application is a continuation-in-part of U.S. Ser. No. 12/004,583 filed Dec. 21, 2007, and claims priority to U.S. Provisional Application Ser. No. 60/876,288 filed on Dec. 21, 2006 and U.S. Provisional Application Ser. No. 60/876,318 filed Dec. 21, 2006.

BACKGROUND OF THE INVENTION

Sphingosine-1-phosphate (S1P) is part of the sphingomyelin biosynthetic pathway and is known to affect multiple biological processes. S1P is formed through phosphorylation of sphingosine by sphingosine kinases (SK1 and SK2) and it is degraded through cleavage by sphingosine lyase to form palmitaldehyde and phosphoethanolamine or through dephosphorylation by phospholipid phosphatases. It is present at high levels (~500 nM) in serum, and it is found in most tissues. It can be synthesized in a wide variety of cells in response to several stimuli, which include cytokines, growth factors and G protein-coupled receptor (GPCR) ligands. The GPCRs that bind S1P (currently known as the S1P receptors $S1P_{1-5}$), couple through pertusis toxin sensitive (Gi) pathways as well as pertusis toxin insensitive pathways to stimulate a variety of processes. The individual receptors of the S1P family are both tissue and response specific and therefore are attractive as therapeutic targets.

S1P evokes many responses from cells and tissues. In particular, S1P has been shown to be an agonist at all five GPCRs, $S1P_1$ (Edg-1), $S1P_2$ (Edg-5), $S1P_3$ (Edg-3), $S1P_4$ (Edg-6) and $S1P_5$ (Edg-8). The action of S1P at the S1P receptors has been linked to resistance to apoptosis, changes in cellular morphology, cell migration, growth, differentiation, cell division, angiogenesis and modulation of the immune system via alterations of lymphocyte trafficking. Therefore, S1P receptors are targets for therapy of, for example, neoplastic diseases, autoimmune disorders and tissue rejection in transplantation. These receptors also share 50-55% amino acid identity with three other lysophospholipid receptors, LPA1, LPA2, and LPA3 of the structurally related lysophosphatidic acid (LPA).

GPCRs are excellent drug targets with numerous examples of marketed drugs across multiple disease areas. GPCRs are cell surface receptors that bind hormones on the extracellular surface of the cell and transduce a signal across the cellular membrane to the inside of the cell. The internal signal is amplified through interaction with G proteins which in turn interact with various second messenger pathways. This transduction pathway is manifested in downstream cellular responses that include cytoskeletal changes, cell motility, proliferation, apoptosis, secretion and regulation of protein expression, to name a few. S1P receptors make good drug targets because individual receptors are expressed in different tissues and signal through different pathways, making the individual receptors both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

The physiologic implications of stimulating individual S1P receptors are largely unknown due in part to a lack of receptor type selective ligands. Isolation and characterization of S1P analogs that have potent agonist or antagonist activity for S1P receptors have been limited.

$S1P_1$ for example is widely expressed, and the knockout causes embryonic lethality due to large vessel rupture. Adoptive cell transfer experiments using lymphocytes from $S1P_1$ knockout mice have shown that $S1P_1$ deficient lymphocytes sequester to secondary lymph organs. Conversely, T cells overexpressing $S1P_1$ partition preferentially into the blood compartment rather than secondary lymph organs. These experiments provide evidence that $S1P_1$ is the main sphingosine receptor involved in lymphocyte homing and trafficking to secondary lymphoid compartments Currently, there is a need for novel, potent, and selective agents, which are agonists or antagonists of the individual receptors of the S1P receptor family in order to address unmet medical needs associated with agonism or antagonism of the individual receptors of the S1P receptor family.

SUMMARY OF THE INVENTION

The present invention provides compounds of Formula I

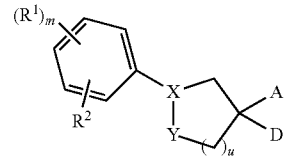

Formula I pharmaceutically acceptable salts, prodrugs, metabolites and isomers thereof wherein D is H, $N(R^5)_2$ or $OR^6$;

X is CH, $C(CH_3)$ or N;

Y is $CH_2$, O, S or $NR^3$; wherein $R^3$ is hydrogen, or straight or branched ($C_1$-$C_{10}$) alkyl;

A is H, hydroxy, —$CH_2OH$, —$CH(OH)CH_3$, —C(O)—$OCH_3$, —C(OH)($CH_3$)$_2$, —O($CH_2$)$_t$—COOH—, —C(O)—$NR^6$, optionally substituted —($CH_2$)$_n$—P(=O)($OR^7$)($OR^7$), optionally substituted —($CH_2$)$_n$—O—P(=O)($OR^7$)($OR^7$), optionally substituted —($CH_2$)$_n$—P(=O)($OR^7$)($R^7$), —CH=CH—P(=O)($OR^7$)($OR^7$), C(O)—$NHCH_3$, CN, $COOR^6$ or —$R^4$—COOH, wherein $R^4$ is straight or branched ($C_1$-$C_{20}$) alkylene, straight or branched ($C_1$-$C_{20}$) alkenylene, straight or branched ($C_1$-$C_{20}$) alkynylene, ($C_3$-$C_{20}$)cycloalkyl, or optionally substituted azetidinyl;

$R^1$ and $R^2$ are independently selected from the group consisting of hydrogen, $CF_3$, halo, ($C_1$-$C_{20}$) alkyl, ($C_1$-$C_{20}$) alkoxy, ($C_3$-$C_{20}$) cycloalkyl substituted alkyl, ($C_3$-$C_{20}$) cycloalkyl substituted alkoxy, ($C_2$-$C_{20}$) alkenyl, aryl substituted ($C_2$-$C_{20}$) alkenyl, ($C_2$-$C_{20}$) alkynyl, aryl substituted ($C_2$-$C_{20}$) alkynyl, aryl, aryl substituted ($C_1$-$C_{20}$)alkyl, heteroaryl substituted ($C_2$-$C_{20}$)alkyl, aryl substituted alkoxy, heteroaryl substituted alkoxy, alkyl substituted aryl, arylalkyl, aryl substituted arylalkyl, arylalkyl substituted arylalkyl, CN and —O-indolizinyl;

wherein such $R^1$ and $R^2$ groups may be optionally substituted with one or more substitutents independently selected from ($C_1$-$C_{20}$) alkyl, $CF_3$, halo, hydroxy, ($C_1$-$C_{20}$) alkoxy, $OCF_3$, and CN;

wherein one or more of the carbon atoms in the $R^1$ or $R^2$ groups can be independently replaced with non-peroxide oxygen, sulfur or $NR^8$;

wherein $R^8$ is hydrogen or $(C_1-C_{20})$ alkyl group;

wherein one of $R^1$ and $R^2$ is other than hydrogen; and wherein the alkyl, alkenyl, and alkynyl groups in $R^1$ and $R^2$ are optionally substituted with oxo or halo;

each $R^5$ is independently H, optionally substituted $(C_1-C_3)$ alkyl, or —C(O)—O—$(C_1-C_3)$alkyl-optionally substituted phenyl;

each $R^6$ is independently H or optionally substituted $(C_1-C_2)$alkyl;

each $R^7$ is independently H, optionally substituted $(C_1-C_2)$ alkyl or optionally substituted phenyl;

m is 1 or 2;

n is 1, 2 or 3;

t is 1, 2 or 3; and u is 0, 1 or 2;

provided that A and D are not both H at the same time; and provided the compound is not

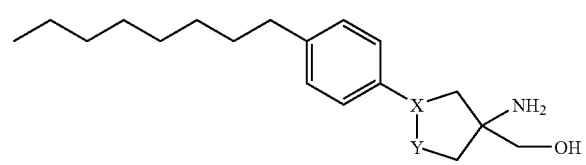

wherein X is CH or N;

Y is $CH_2$, NH, $N(CH_3)$, S or O.

In a second embodiment the invention provides compounds of the foregoing embodiment wherein A is H, —C(O)—$OCH_3$, —C(O)—$NR^6$, CN, C(O)—$NHCH_3$, $COOR^6$, —$R^4$—COOH, or optionally substituted azetidinyl, wherein $R^4$ is straight or branched $(C_1-C_{20})$ alkylene, straight or branched $(C_1-C_{20})$ alkenylene, straight or branched $(C_1-C_{20})$ alkynylene;

$R^1$ and $R^2$ are independently selected from the group consisting of hydrogen, halo, $(C_1-C_{10})$ alkyl, $(C_1-C_{10})$ alkoxy, $(C_3-C_{20})$ cycloalkyl substituted alkyl, $(C_3-C_{10})$ cycloalkyl substituted alkoxy, $(C_2-C_{10})$ alkenyl, aryl substituted $(C_2-C_{10})$ alkenyl, $(C_2-C_{10})$ alkynyl, aryl substituted $(C_2-C_{10})$ alkynyl, aryl, aryl substituted $(C_1-C_{10})$ alkyl, heteroaryl substituted $(C_1-C_{10})$ alkyl, aryl substituted $(C_1-C_{10})$ alkoxy, heteroaryl substituted $(C_1-C_{10})$ alkoxy, $(C_1-C_{10})$ alkyl substituted aryl, arylalkyl and aryl substituted arylalkyl;

wherein such $R^1$ and $R^2$ groups may be optionally substituted with $(C_1-C_{10})$ alkyl, halo, hydroxy, $(C_1-C_{10})$ alkoxy, or CN;

wherein one or more of the carbon atoms in the $R^1$ or $R^2$ groups can be independently replaced with non-peroxide oxygen, sulfur or $NR^8$;

wherein $R^8$ is hydrogen or $(C_1-C_{10})$ alkyl group;

wherein one of $R^1$ and $R^2$ is other than hydrogen; and wherein the alkyl, alkenyl, and alkynyl groups in $R^1$ and $R^2$ are optionally substituted with oxo or halo;

In a third embodiment the invention provides compounds according to any of the foregoing embodiments wherein the compound is a formula of Formula Ia:

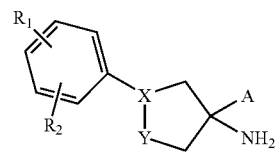

Formula Ia and isomers, stereoisomers, esters, prodrugs, and pharmaceutically-acceptable salts thereof, wherein;

X is CH; Y is $CH_2$ or O;

A is —C(O)—$OCH_3$, —COOH, —$R^4$—COOH, —C(O)—$NHCH_3$, or optionally substituted azetidinyl;

wherein $R^4$ is straight or branched $(C_1-C_{10})$ alkylene, straight or branched $(C_1-C_{10})$ alkenylene, or straight or branched $(C_1-C_{10})$ alkynylene;

$R^1$ and $R^2$ are independently selected from the group consisting of hydrogen, halo, $(C_1-C_{10})$ alkyl, $(C_1-C_{10})$ alkoxy, $(C_3-C_{10})$ cycloalkyl substituted alkyl, $(C_3-C_{10})$ cycloalkyl substituted alkoxy, $(C_2-C_{10})$ alkenyl, aryl substituted $(C_2-C_{10})$ alkenyl, $(C_2-C_{10})$ alkynyl, aryl substituted $(C_2-C_{10})$ alkynyl, aryl, aryl substituted $(C_1-C_{10})$alkyl, heteroaryl substituted $(C_1-C_{10})$alkyl, aryl substituted $(C_1-C_{10})$alkoxy, heteroaryl substituted $(C_1-C_{10})$alkoxy, $(C_1-C_{10})$alkyl substituted aryl, arylalkyl and aryl substituted arylalkyl;

wherein such $R^1$ and $R^2$ groups may be optionally substituted with $(C_1-C_{10})$ alkyl, $CF_3$, halo, hydroxy, $(C_1-C_{10})$ alkoxy, or CN;

wherein one or more of the carbon atoms in the $R^1$ or $R^2$ groups can be independently replaced with non-peroxide oxygen, sulfur or $NR^8$;

wherein $R^8$ is hydrogen or $(C_1-C_{10})$ alkyl group;

wherein one of $R^1$ and $R^2$ is other than hydrogen;

wherein the alkyl, alkenyl, and alkynyl groups in $R^2$ are optionally substituted with oxo or halo; and n is 1 or 2.

In a fourth embodiment the invention provides compounds according to any of the foregoing embodiments wherein Y is $CH_2$;

A is —$CH_2$—COOH, COOH or

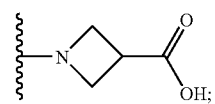

$R^1$ and $R^2$ are independently selected from the group consisting of hydrogen, $(C_1-C_{10})$ alkyl, $(C_2-C_{10})$ alkenyl, $(C_2-C_{10})$ alkynyl and aryl substituted $(C_1-C_{10})$ alkyl;

wherein such $R^1$ and $R^2$ groups may be optionally substituted with $(C_1-C_{10})$ alkyl, halo, hydroxy, $(C_1-C_{10})$ alkoxy, or cyano;

wherein one or more of the carbon atoms in the $R^1$ or $R^2$ groups can be independently replaced with non-peroxide oxygen; wherein one of $R^1$ and $R^2$ is other than hydrogen.

In a fifth embodiment the invention provides compounds according to any of the foregoing embodiments wherein
X is CH; Y is $CH_2$; A is COOH;

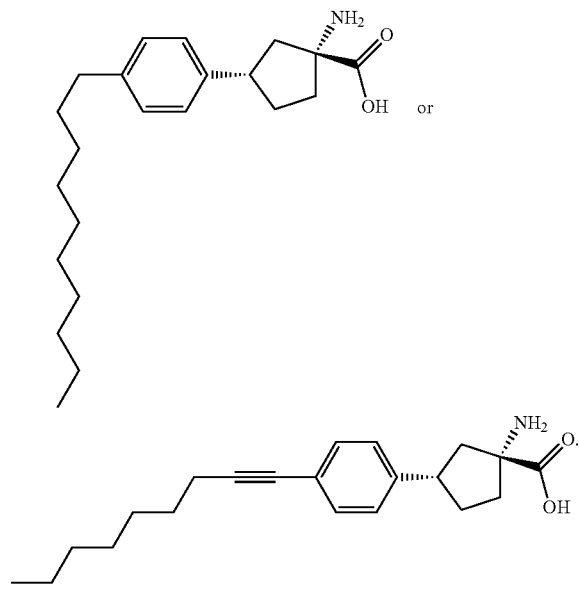

$R^1$ is $(C_1-C_{10})$alkyl, $(C_2-C_{10})$alkenyl or $(C_2-C_{10})$alkynyl; $R^2$ is H; and m is 1.

In a sixth embodiment the invention provides compounds according to any of the foregoing embodiments wherein the compound is In a seventh embodiment the invention provides compounds according to the first embodiment wherein Y is $CH_2$, O, S or $NR^3$; wherein $R^3$ is hydrogen, or $(C_1-C_{10})$ alkyl;

A is H, —$CH_2OH$, —$CH_2OH$, —C(O)—$OCH_3$, -optionally substituted —$(CH_2)_n$—P(=O)($OR^7$)($OR^7$), optionally substituted —$(CH_2)_n$—O—P(=O)($OR^7$)($OR^7$), —CH=CH—O—P(=O)($OR^7$)($OR^7$ or CN;

$R^1$ and $R^2$ are independently selected from the group consisting of hydrogen, halo, straight or branched $(C_1-C_{10})$ alkyl, $(C_1-C_{10})$ alkoxy, $(C_3-C_{10})$ cycloalkyl substituted alkyl, $(C_3-C_{10})$ cycloalkyl substituted alkoxy, $(C_2-C_{10})$ alkenyl, aryl substituted $(C_2-C_{10})$ alkenyl, $(C_2-C_{10})$ alkynyl, aryl substituted $(C_2-C_{10})$ alkynyl, aryl, aryl substituted alkyl, heteroaryl substituted $(C_1-C_{10})$alkyl, aryl substituted alkoxy, heteroaryl substituted alkoxy, $(C_1-C_{10})$alkyl substituted aryl, arylalkyl, aryl substituted arylalkyl, arylalkyl substituted arylalkyl, cyano and —O-indolizinyl;

wherein such $R^1$ and $R^2$ groups may be optionally substituted with one or more substitutents independently selected from straight or branched $(C_1-C_{10})$ alkyl, halo, hydroxy, $(C_1-C_{20})$ alkoxy, $OCF_3$, and CN;

wherein one or more of the carbon atoms in the $R^1$ or $R^2$ groups can be independently replaced with non-peroxide oxygen, sulfur or $NR^8$;

wherein $R^8$ is hydrogen or $(C_1-C_{10})$ alkyl group; wherein one of $R^1$ and $R^2$ is other than hydrogen; and wherein the alkyl, alkenyl, and alkynyl groups in $R^2$ are optionally substituted with oxo or halo;

$R^6$ is independently selected from H or optionally substituted $(C_1-C_2)$alkyl;

$R^7$ is independently selected from H or optionally substituted $(C_1-C_2)$alkyl; and
u is 1 or 2.

In an eighth embodiment the invention provides compounds according to embodiments one and seven wherein the compound is a compound of Formula Ib:

Formula Ib

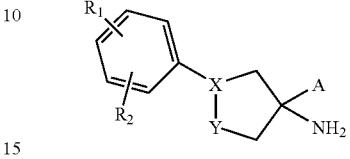

wherein;
X is CH or N;
Y is $CH_2$, O, S or $NR^3$;
wherein $R^3$ is hydrogen, or $(C_1-C_{20})$ alkyl;
A is —$CH_2$—OH, optionally substituted —$CH_2$—P(=O)($OR^7$)($OR^7$) or optionally substituted —$CH_2$—O—P(=O)($OR^7$)($OR^7$);

$R^1$ and $R^2$ are independently selected from the group consisting of hydrogen, halo, $(C_1-C_{20})$ alkyl, $(C_1-C_{20})$ alkoxy, $(C_3-C_{20})$ cycloalkyl substituted alkyl, $(C_3-C_{20})$ cycloalkyl substituted alkoxy, $(C_2-C_{20})$ alkenyl, aryl substituted $(C_2-C_{20})$ alkenyl, $(C_2-C_{20})$ alkynyl, aryl substituted $(C_2-C_{20})$ alkynyl, aryl, aryl substituted alkyl, heteroaryl substituted alkyl, aryl substituted alkoxy, heteroaryl substituted alkoxy, alkyl substituted aryl, arylalkyl and aryl substituted arylalkyl;

wherein such $R^2$ groups may be optionally substituted with $(C_1-C_{20})$ alkyl, halo, hydroxy, $(C_1-C_{20})$ alkoxy, or cyano;

wherein one or more of the carbon atoms in the $R^1$ or $R^2$ groups can be independently replaced with non-peroxide oxygen, sulfur or $NR^8$; wherein $R^8$ is hydrogen or $(C_1-C_{20})$ alkyl group; and wherein the alkyl, alkenyl, and alkynyl groups in $R^2$ are optionally substituted with oxo or halo.

In a ninth embodiment the invention provides compounds of any of the embodiments one, seven and eight wherein
X is CH;
Y is $CH_2$;
A is —$CH_2OH$, optionally substituted —$(CH_2)_n$—O—P(=O)($OR^7$)($OR^7$) or optionally substituted —$(CH_2)_n$—P(=O)($OR^7$)($OR^7$);

$R^1$ and $R^2$ are independently selected from the group consisting of hydrogen, halo, straight or branched $(C_1-C_{10})$ alkyl, aryl substituted $(C_1-C_{10})$ alkyl, heteroaryl substituted alkyl, aryl substituted alkoxy, heteroaryl substituted alkoxy, $(C_1-C_{10})$alkyl substituted aryl, arylalkyl, aryl substituted arylalkyl, arylalkyl substituted arylalkyl, CN and —O-indolizinyl;

wherein such $R^1$ and $R^2$ groups may be optionally substituted with one or more substitutents independently selected from $(C_1-C_{10})$ alkyl, halo and $(C_1-C_{10})$ alkoxy;

wherein one or more of the carbon atoms in the $R^1$ or $R^2$ groups can be independently replaced with non-peroxide oxygen; wherein one of $R^1$ and $R^2$ is other than hydrogen; and wherein the alkyl, alkenyl, and alkynyl groups in $R^2$ are optionally substituted with oxo or halo;

each $R^6$ is independently selected from H or optionally substituted $(C_1-C_2)$alkyl; and
u is 1 or 2.

In a tenth embodiment, the invention provides compounds of embodiments one, seven, eight and nine wherein
A is —$CH_2OH$ or optionally substituted —$(CH_2)_n$—O—P(=O)($OR^7$)($OR^7$);

D is NH$_2$;
R$^1$ and R$^2$ are independently selected from the group consisting of hydrogen, optionally substituted (C$_1$-C$_{10}$) alkyl;
wherein one or more of the carbon atoms in the R$^1$ or R$^2$ groups can be independently replaced with non-peroxide oxygen;
wherein one of R$^1$ and R$^2$ is other than hydrogen;
m is 1; and
u is 1.

In an eleventh embodiment the invention provides compounds of embodiments one, seven, eight, nine and ten wherein the compound is

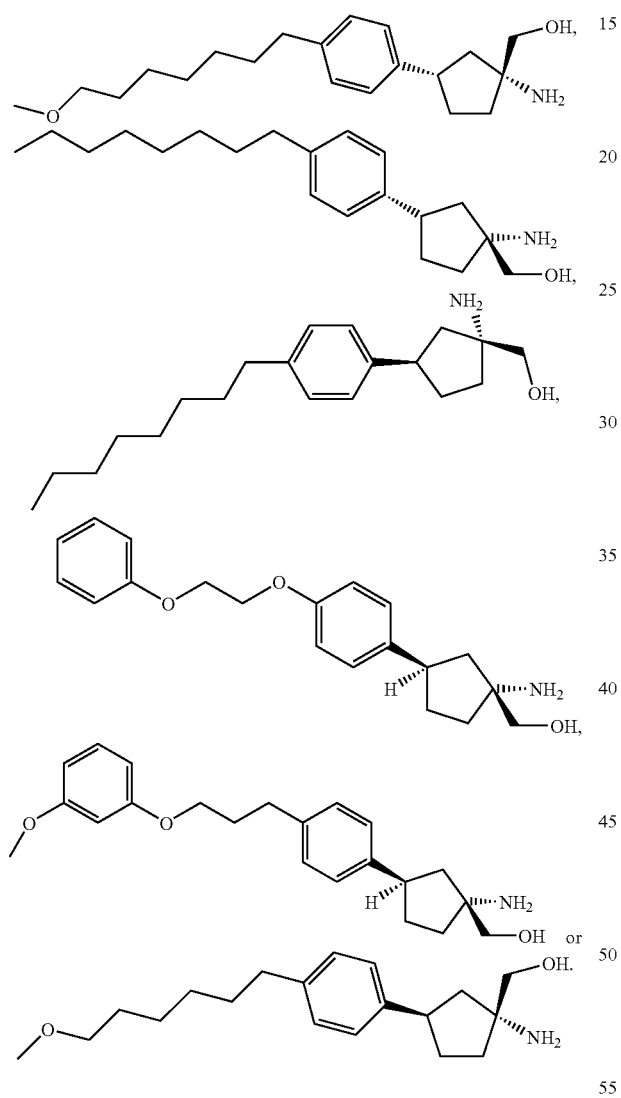

In a twelfth embodiment the invention provides compounds of the formula

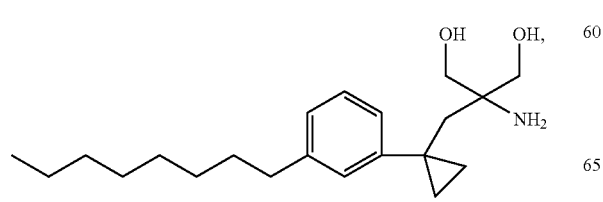

-continued

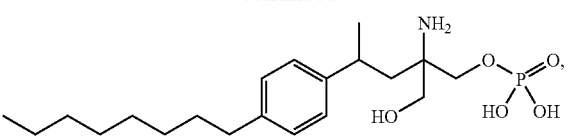

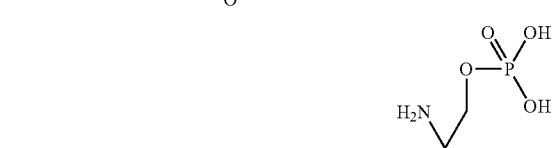

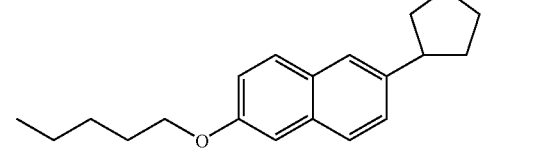

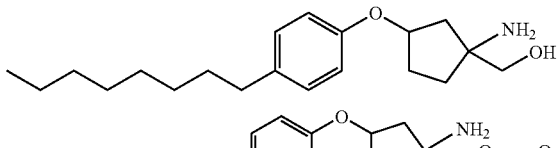

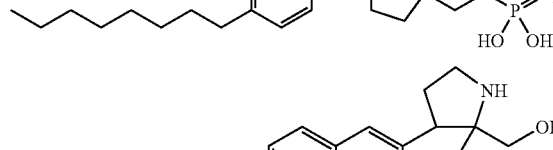

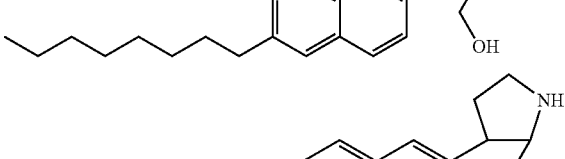

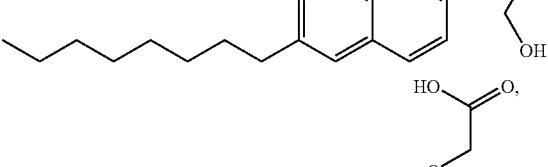

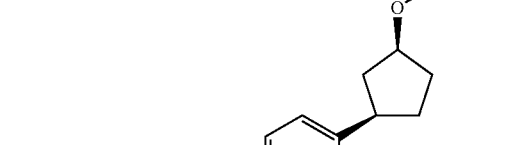

-continued

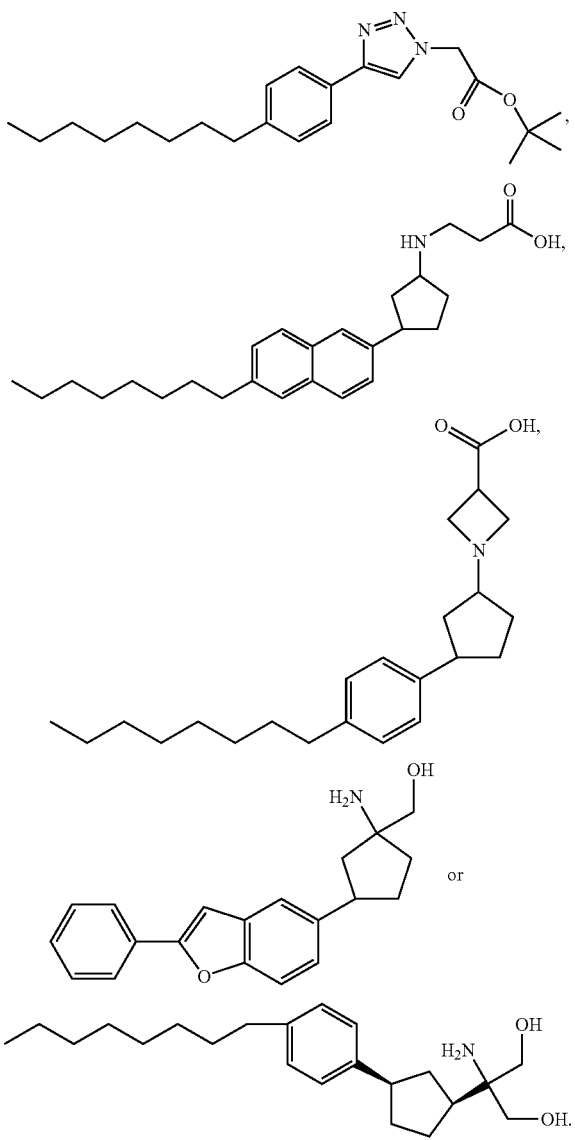

In a thirteenth embodiment the invention provides a pharmaceutical composition comprising a compound of Formula I

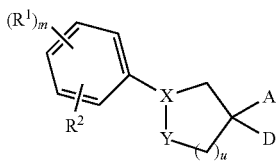

Formula I pharmaceutically acceptable salts, prodrugs, metabolites and isomers thereof wherein D is H, N(R$^5$)$_2$, or OR$^6$;

X is CH, C(CH$_3$) or N;

Y is CH$_2$, O, S or NR$^3$; wherein R$^3$ is hydrogen, or straight or branched (C$_1$-C$_{10}$) alkyl;

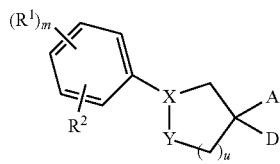

Formula I

A is H, hydroxy, —CH$_2$OH, —CH(OH)CH$_3$, —C(O)—OCH$_3$, —C(OH)(CH$_3$)$_2$, —O(CH$_2$)$_t$—COOH—, —C(O)—NR$^6$, optionally substituted —(CH$_2$)$_n$—P(═O)(OR$^7$)(OR$^7$), optionally substituted —(CH$_2$)$_n$—O—P(═O)(OR$^7$)(OR$^7$), optionally substituted —(CH$_2$)$_n$—P(═O)(OR$^7$)(R$^7$), —CH═CH—P(═O)(OR$^7$)(OR$^7$), C(O)—NHCH$_3$, CN, COOR$^6$ or —R$^4$—COOH, wherein R$^4$ is straight or branched (C$_1$-C$_{20}$) alkylene, straight or branched (C$_1$-C$_{20}$) alkenylene, straight or branched (C$_1$-C$_{20}$) alkynylene, (C$_3$-C$_{20}$)cycloalkyl, or optionally substituted azetidinyl;

R$^1$ and R$^2$ are independently selected from the group consisting of hydrogen, CF$_3$, halo, (C$_1$-C$_{20}$) alkyl, (C$_1$-C$_{20}$) alkoxy, (C$_3$-C$_{20}$) cycloalkyl substituted alkyl, (C$_3$-C$_{20}$) cycloalkyl substituted alkoxy, (C$_2$-C$_{20}$) alkenyl, aryl substituted (C$_2$-C$_{20}$) alkenyl, (C$_2$-C$_{20}$) alkynyl, aryl substituted (C$_2$-C$_{20}$) alkynyl, aryl, aryl substituted alkyl, heteroaryl substituted alkyl, aryl substituted alkoxy, heteroaryl substituted alkoxy, alkyl substituted aryl, arylalkyl, aryl substituted arylalkyl, arylalkyl substituted arylalkyl, CN and —O-indolizinyl; wherein such R$^1$ and R$^2$ groups may be optionally substituted with one or more substitutents independently selected from (C$_1$-C$_{20}$) alkyl, CF$_3$, halo, hydroxy, (C$_1$-C$_{20}$) alkoxy, OCF$_3$, and CN;

wherein one or more of the carbon atoms in the R$^1$ or R$^2$ groups can be independently replaced with non-peroxide oxygen, sulfur or NR$^8$;

wherein R$^8$ is hydrogen or (C$_1$-C$_{20}$) alkyl group;

wherein one of R$^1$ and R$^2$ is other than hydrogen; and wherein the alkyl, alkenyl, and alkynyl groups in R$^2$ are optionally substituted with oxo or halo;

each R$^5$ is independently H, optionally substituted (C$_1$-C$_3$) alkyl, or —C(O)—O—(C$_1$-C$_3$)alkyl-optionally substituted phenyl;

each R$^6$ is independently H or optionally substituted (C$_1$-C$_2$)alkyl;

each R$^7$ is independently H, optionally substituted (C$_1$-C$_2$) alkyl or optionally substituted phenyl;

m is 1 or 2;

n is 1, 2 or 3;

t is 1, 2 or 3; and u is 0, 1 or 2; or a pharmaceutically acceptable salt, solvate, hydrate, metabolite, prodrug, enantiomer or stereoisomer thereof and a pharmaceutically acceptable diluent or carrier.

In a fourteenth embodiment the invention provides a method of treating a disorder comprising administering to a subject in need thereof a therapeutically effective amount of one or more compounds of Formula I wherein D is H, N(R$^5$)$_2$, or OR$^6$;

X is CH, C(CH$_3$) or N;

Y is CH$_2$, O, S or NR$^3$; wherein R$^3$ is hydrogen, or straight or branched (C$_1$-C$_{10}$) alkyl;

A is H, hydroxy, —CH$_2$OH, —CH(OH)CH$_3$, —C(O)—OCH$_3$, —C(OH)(CH$_3$)$_2$, —O(CH$_2$)$_t$—COOH—, —C(O)—NR$^6$, optionally substituted —(CH$_2$)$_n$—P(═O)(OR$^7$)(OR$^7$), optionally substituted —(CH$_2$)$_n$—O—P(═O)(OR$^7$)(OR$^7$), optionally substituted —(CH$_2$)$_n$—P(=O)(OR$^7$)(R$^7$), —CH=CH—P(=O)(OR$^7$)(OR$^7$), C(O)—NHCH$_3$, CN, COOR$^6$ or —R$^4$—COOH, wherein R$^4$ is straight or branched (C$_1$-C$_{20}$) alkylene, straight or branched (C$_1$-C$_{20}$) alkenylene, straight or branched (C$_1$-C$_{20}$) alkynylene, (C$_3$-C$_{20}$)cycloalkyl, or optionally substituted azetidinyl;

R$^1$ and R$^2$ are independently selected from the group consisting of hydrogen, CF$_3$, halo, (C$_1$-C$_{20}$) alkyl, (C$_1$-C$_{20}$) alkoxy, (C$_3$-C$_{20}$) cycloalkyl substituted alkyl, (C$_3$-C$_{20}$) cycloalkyl substituted alkoxy, (C$_2$-C$_{20}$) alkenyl, aryl substituted (C$_2$-C$_{20}$) alkenyl, (C$_2$-C$_{20}$) alkynyl, aryl substituted (C$_2$-C$_{20}$) alkynyl, aryl, aryl substituted alkyl, heteroaryl substituted alkyl, aryl substituted alkoxy, heteroaryl substituted alkoxy, alkyl substituted aryl, arylalkyl, aryl substituted arylalkyl, arylalkyl substituted arylalkyl, CN and —O-indolizinyl; wherein such R$^1$ and R$^2$ groups may be optionally substituted with one or more substitutents independently selected from (C$_1$-C$_{20}$) alkyl, CF$_3$, halo, hydroxy, (C$_1$-C$_{20}$) alkoxy, OCF$_3$, and CN;

wherein one or more of the carbon atoms in the R$^1$ or R$^2$ groups can be independently replaced with non-peroxide oxygen, sulfur or NR$^8$;

wherein R$^8$ is hydrogen or (C$_1$-C$_{20}$) alkyl group;

wherein one of R$^1$ and R$^2$ is other than hydrogen; and wherein the alkyl, alkenyl, and alkynyl groups in R$^2$ are optionally substituted with oxo or halo;

each R$^5$ is independently H, optionally substituted (C$_1$-C$_3$) alkyl, or —C(O)—O—(C$_1$-C$_3$)alkyl-optionally substituted phenyl;

each R$^6$ is independently H or optionally substituted (C$_1$-C$_2$)alkyl;

each R$^7$ is independently H, optionally substituted (C$_1$-C$_2$) alkyl or optionally substituted phenyl;

m is 1 or 2;
n is 1, 2 or 3;
t is 1, 2 or 3; and
u is 0, 1 or 2;

or a pharmaceutically acceptable salt, solvate, hydrate, metabolite, prodrug, enantiomer or stereoisomer thereof.

In a fifteenth embodiment the invention provides a method of claim 14 wherein the disorder is rheumatoid arthritis, lupus, Crohn's disease, asthma, diabetes, pain or psoriasis.

In a sixteenth embodiment the invention provides a method of treating a central nervous system disorder comprising administering to a subject in need thereof a therapeutically effective amount of one or more compounds of Formula I, wherein D is H, N(R$^5$)$_2$, or OR$^6$;
X is CH, C(CH$_3$) or N;
Y is CH$_2$, O, S or NR$^3$; wherein R$^3$ is hydrogen, or straight or branched (C$_1$-C$_{10}$) alkyl;
A is H, hydroxy, —CH$_2$OH, —CH(OH)CH$_3$, —C(O)—OCH$_3$, —C(OH)(CH$_3$)$_2$, —O(CH$_2$)$_t$—COOH—, —C(O)—NR$^6$, optionally substituted —(CH$_2$)$_n$—P(=O)(OR$^7$)(OR$^7$), optionally substituted —(CH$_2$)$_n$—O—P(=O)(OR$^7$)(OR$^7$), optionally substituted —(CH$_2$)$_n$—P(=O)(OR$^7$)(R$^7$), —CH=CH—P(=O)(OR$^7$)(OR$^7$), C(O)—NHCH$_3$, CN, COOR$^6$ or —R$^4$—COOH, wherein R$^4$ is straight or branched (C$_1$-C$_{20}$) alkylene, straight or branched (C$_1$-C$_{20}$) alkenylene, straight or branched (C$_1$-C$_{20}$) alkynylene, (C$_3$-C$_{20}$)cycloalkyl, or optionally substituted azetidinyl;

R$^1$ and R$^2$ are independently selected from the group consisting of hydrogen, CF$_3$, halo, (C$_1$-C$_{20}$) alkyl, (C$_1$-C$_{20}$) alkoxy, (C$_3$-C$_{20}$) cycloalkyl substituted alkyl, (C$_3$-C$_{20}$) cycloalkyl substituted alkoxy, (C$_2$-C$_{20}$) alkenyl, aryl substituted (C$_2$-C$_{20}$) alkenyl, (C$_2$-C$_{20}$) alkynyl, aryl substituted (C$_2$-C$_{20}$) alkynyl, aryl, aryl substituted alkyl, heteroaryl substituted alkyl, aryl substituted alkoxy, heteroaryl substituted alkoxy, alkyl substituted aryl, arylalkyl, aryl substituted arylalkyl, arylalkyl substituted arylalkyl, CN and —O-indolizinyl; wherein such R$^1$ and R$^2$ groups may be optionally substituted with one or more substitutents independently selected from (C$_1$-C$_{20}$) alkyl, CF$_3$, halo, hydroxy, (C$_1$-C$_{20}$) alkoxy, OCF$_3$, and CN;

wherein one or more of the carbon atoms in the R$^1$ or R$^2$ groups can be independently replaced with non-peroxide oxygen, sulfur or NR$^8$;

wherein R$^8$ is hydrogen or (C$_1$-C$_{20}$) alkyl group;

wherein one of R$^1$ and R$^2$ is other than hydrogen; and wherein the alkyl, alkenyl, and alkynyl groups in R$^2$ are optionally substituted with oxo or halo;

each R$^5$ is independently H, optionally substituted (C$_1$-C$_3$) alkyl, or —(O)—O—(C$_1$-C$_3$)alkyl-optionally substituted phenyl;

each R$^6$ is independently H or optionally substituted (C$_1$-C$_2$)alkyl;

each R$^7$ is independently H, optionally substituted (C$_1$-C$_2$) alkyl or optionally substituted phenyl;

m is 1 or 2;
n is 1, 2 or 3;
t is 1, 2 or 3; and
u is 0, 1 or 2;

or a pharmaceutically acceptable salt, solvate, hydrate, metabolite, prodrug, enantiomer or stereoisomer thereof.

In a seventeenth embodiment the invention provides a method of treating multiple sclerosis comprising administering to a subject in need thereof a therapeutically effective amount of one or more compounds of any of the foregoing embodiments or a pharmaceutically acceptable salt, solvate, hydrate, metabolite, prodrug, enantiomer or stereoisomer thereof.

In an eighteenth embodiment the invention provides a packaged pharmaceutical comprising one or more compounds according to Formula I

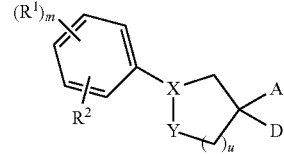

Formula I wherein

D is H, N(R$^5$)$_2$, or OR$^6$;
X is CH, C(CH$_3$) or N;
Y is CH$_2$, O, S or NR$^3$; wherein R$^3$ is hydrogen, or straight or branched (C$_1$-C$_{10}$) alkyl;
A is H, hydroxy, —CH$_2$OH, —CH(OH)CH$_3$, —C(O)—OCH$_3$, —C(OH)(CH$_3$)$_2$, —O(CH$_2$)$_t$—COOH—, —C(O)—NR$^6$, optionally substituted —(CH$_2$)$_n$—P(=O)(OR$^7$)(OR$^7$), optionally substituted —(CH$_2$)$_n$—O—P(=O)(OR$^7$)(OR$^7$), optionally substituted —(CH$_2$)$_n$—P(=O)(OR$^7$)(R$^7$), —CH=CH—P(=O)(OR$^7$)(OR$^7$), C(O)—NHCH$_3$, CN, COOR$^6$ or —R$^4$—COOH, wherein R$^4$ is straight or branched (C$_1$-C$_{20}$) alkylene, straight or branched (C$_1$-C$_{20}$) alkenylene, straight or branched (C$_1$-C$_{20}$) alkynylene, (C$_3$-C$_{20}$)cycloalkyl, or optionally substituted azetidinyl;

R$^1$ and R$^2$ are independently selected from the group consisting of hydrogen, CF$_3$, halo, (C$_1$-C$_{20}$) alkyl, (C$_1$-C$_{20}$) alkoxy, (C$_3$-C$_{20}$) cycloalkyl substituted alkyl, (C$_3$-C$_{20}$) cycloalkyl substituted alkoxy, (C$_2$-C$_{20}$) alkenyl, aryl substituted ($C_2$-$C_{20}$) alkenyl, ($C_2$-$C_{20}$) alkynyl, aryl substituted ($C_2$-$C_{20}$) alkynyl, aryl, aryl substituted alkyl, heteroaryl substituted alkyl, aryl substituted alkoxy, heteroaryl substituted alkoxy, alkyl substituted aryl, arylalkyl, aryl substituted arylalkyl, arylalkyl substituted arylalkyl, CN and —O-indolizinyl; wherein such $R^1$ and $R^2$ groups may be optionally substituted with one or more substitutents independently selected from ($C_1$-$C_{20}$) alkyl, $CF_3$, halo, hydroxy, ($C_1$-$C_{20}$) alkoxy, $OCF_3$, and CN;

wherein one or more of the carbon atoms in the $R^1$ or $R^2$ groups can be independently replaced with non-peroxide oxygen, sulfur or $NR^8$;

wherein $R^8$ is hydrogen or ($C_1$-$C_{20}$) alkyl group;

wherein one of $R^1$ and $R^2$ is other than hydrogen; and wherein the alkyl, alkenyl, and alkynyl groups in $R^2$ are optionally substituted with oxo or halo;

each $R^5$ is independently H, optionally substituted ($C_1$-$C_3$) alkyl, or —C(O)—O—($C_1$-$C_3$)alkyl-optionally substituted phenyl;

each $R^6$ is independently H or optionally substituted ($C_1$-$C_2$)alkyl;

each $R^7$ is independently H, optionally substituted ($C_1$-$C_2$) alkyl or optionally substituted phenyl;

m is 1 or 2;

n is 1, 2 or 3;

t is 1, 2 or 3; and u is 0, 1 or 2;

or a pharmaceutically acceptable salt, solvate, hydrate, metabolite, prodrug, enantiomer or stereoisomer thereof and instructions for use.

In a nineteenth embodiment the invention provides the packaged pharmaceutical according to embodiment eighteen wherein the compound or compounds are present in a therapeutically effective amount.

In a twentieth embodiment, the invention provides a compound of Formula 2, Formula 3 or Formula 4

In a twenty-first embodiment, the invention provides a compound of Formula 5, Formula 6, Formula 7, Formula 8, Formula 9 or Formula 10

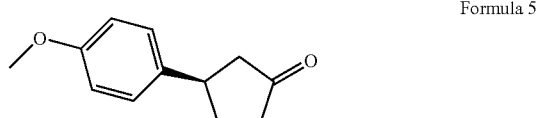

Formula 5

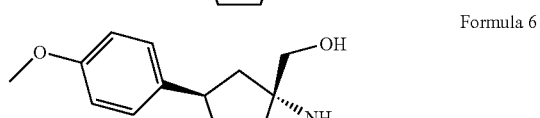

Formula 6

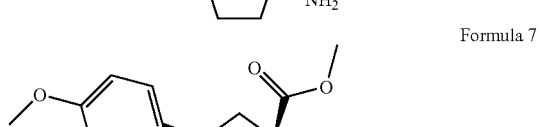

Formula 7

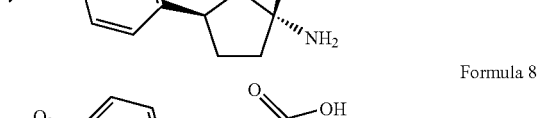

Formula 8

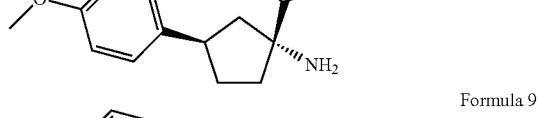

Formula 9

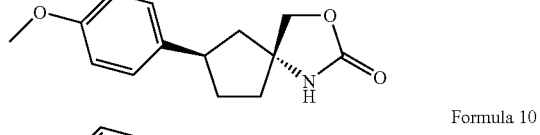

Formula 10

In a twenty-second embodiment the invention provides a compound of Formula 11 or Formula 12

Formula 2

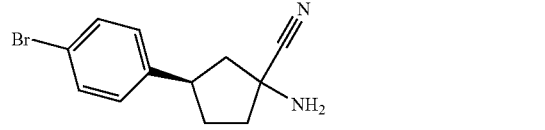

Formula 11

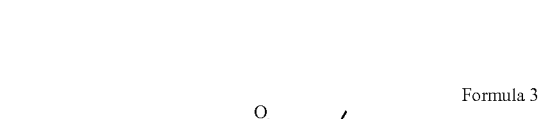

Formula 3

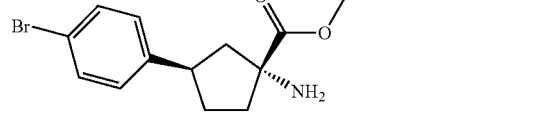

Formula 12

In a twenty-third embodiment, the invention provides a method of making a compound of Formula (Id)

Formula 4

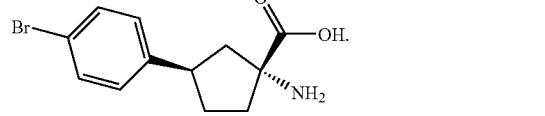

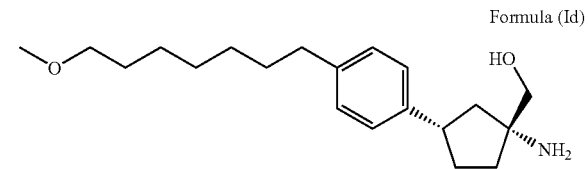

Formula (Id)

comprising the step of reacting a compound of Formula (Ic)

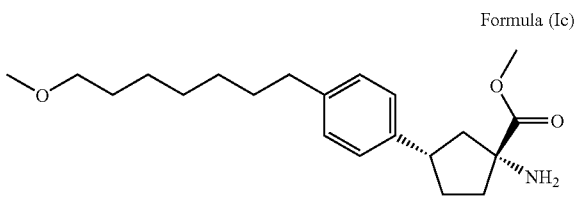

Formula (Ic)

with a reducing reagent until the reaction is substantially complete to form a compound of Formula (Id)

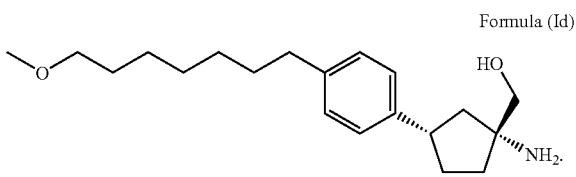

Formula (Id)

In a twenty-fourth embodiment, the invention provides a method of making a compound of Formula (Id) wherein the reducing agent is LAH, NaBH$_4$, LiBH$_4$, DIBAL-H, diisopropyl aluminum hydride, lithium triethylborohydride, borane, triethoxy silane, sodium in ethanol or another suitable hydride source.

In a twenty-fifth embodiment, the invention provides a method of making a compound of Formula (Id) according to the twenty-fourth embodiment wherein a solvent is used.

In a twenty-sixth embodiment, the invention provides a method of making a compound of Formula (Id) according to the twenty-fifth embodiment wherein the solvent is THF or ethanol.

In a twenty-seventh embodiment, the invention provides a method of making a compound of Formula (Id) according to any one of the twenty-fourth through twenty-sixth embodiments wherein the reducing agent is LAH or NaBH$_4$.

In a twenty-eighth embodiment, the invention provides a method of making a compound of Formula (Id) according to any one of the twenty-fourth through twenty-seventh embodiments wherein the reducing agent is LAH.

In a twenty-ninth embodiment, the invention provides a method of making a compound of Formula (Id) according to the twenty-eighth embodiment wherein the solvent is THF.

In a thirtieth embodiment, the invention provides a method of making a compound of Formula (Id) according to any one of the twenty-fourth to twenty-ninth embodiments wherein the reaction is performed at a temperature less than the boiling point of the solvent used.

In a thirty-first embodiment, the invention provides a method of making a compound of Formula (Id) according to thirtieth embodiment wherein the reaction is performed at a temperature between about −10° C. and the boiling point of the solvent used.

In a thirty-second embodiment, the invention provides a method of making a compound of Formula (Id) according to the thirty-first embodiment wherein the reaction is performed at a temperature between about 0° C. and room temperature.

In a thirty-third embodiment, the invention provides a method of making a compound of Formula (Id) according to the thirty-second embodiment wherein the reaction is performed at room temperature.

In another embodiment, R$^1$ or R$^2$ are independently fluorine or chlorine or fluoro- or chloro-substituted alkyl.

In another embodiment, Z is hydroxy or —OPO$_3$H$_2$.

In another embodiment, the α-substituted phosphonate is —CHFPO$_3$H$_2$, —CF$_2$PO$_3$H$_2$, —CHOHPO$_3$H$_2$, —C=OPO$_3$H$_2$ or —PO$_2$SH$_2$.

In a further embodiment, the α-substituted phosphonate is CHFPO$_3$H$_2$, —CF$_2$PO$_3$H$_2$, —CHOHPO$_3$H$_2$, or —C=OPO$_3$H$_2$.

In another embodiment, R$^1$ is hydrogen and R$^2$ is alkyl, alkenyl, or alkynyl having 5, 6, 7, 8, or 9 carbon atoms.

In another embodiment, R$^1$ is hydrogen and R$^2$ is heptyl, octyl, nonyl, —O-heptyl, —O-octyl, or —O-nonyl.

In another embodiment, R$^1$ is hydrogen and R$^2$ is —(CH$_2$)$_n$—OCH$_3$, —(CH$_2$)$_n$—OCF$_3$, —O—(CH$_2$)$_n$—OCH$_3$, or —O—(CH$_2$)$_n$—OCF$_3$, where n is an integer from 1-20, preferably 5, 6, 7, 8, or 9.

In compounds of Formula I, the R$^2$ group may be an ortho, meta or para substituent on the phenyl ring, preferably para. The R$^1$ group may be an ortho, meta or para substituent on the phenyl ring, preferably meta.

Preferred embodiments of compounds according to Formula I exhibit greater specificity for particular S1P receptors or greater potency than S1P receptor agonist compounds reported previously.

In another aspect, the invention provides a pharmaceutical composition comprising one or more compounds according to Formula I, or pharmaceutically acceptable salts, solvates, hydrates, metabolites, prodrugs or stereoisomers thereof, and a pharmaceutically acceptable diluent or carrier. In a preferred aspect, the invention provides a pharmaceutical composition wherein the compound or compounds are present in a therapeutically effective amount. In a related aspect, the invention provides a pharmaceutical composition wherein the compound or compounds are present in a prophylactically effective amount.

In still another aspect, the invention provides a packaged pharmaceutical comprising one or more compounds according to Formula I or pharmaceutically acceptable salts, solvates, hydrates, metabolites, prodrugs or stereoisomers thereof and instructions for use. In one embodiment, the invention provides a packaged pharmaceutical wherein the compound or compounds are present in a therapeutically effective amount. In another embodiment, the invention provides a packaged pharmaceutical wherein the compound or compounds are present in a prophylactically effective amount.

DETAILED DESCRIPTION OF THE INVENTION

The present invention provides novel compounds of Formula I:

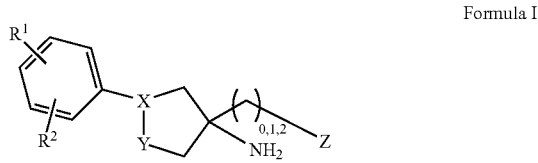

Formula I and isomers, stereoisomers, esters, prodrugs, and pharmaceutically-acceptable salts thereof, wherein;

X is CH or N,

Y is CH$_2$, O, S or NR$^3$; wherein R$^3$ is hydrogen, or (C$_1$-C$_{10}$) alkyl;

Z is hydroxy, phosphate, phosphonate, or α-substituted phosphonate;

$R^1$ is selected from the group consisting of hydrogen, halo, $(C_1-C_{20})$ alkyl, $(C_1-C_{20})$ alkyl substituted with halo, hydroxy, $(C_1-C_{20})$ alkoxy, or cyano; and $R^2$ is selected from the group consisting of hydrogen, halo, $(C_1-C_{20})$ alkyl, $(C_1-C_{20})$ alkoxy, $(C_3-C_{20})$ cycloalkyl substituted alkyl, $(C_3-C_{20})$ cycloalkyl substituted alkoxy, $(C_2-C_{20})$ alkenyl, aryl substituted $(C_2-C_{20})$ alkenyl, $(C_2-C_{20})$ alkynyl, aryl substituted $(C_2-C_{20})$ alkynyl, aryl, aryl substituted alkyl, heteroaryl substituted alkyl, aryl substituted alkoxy, heteroaryl substituted alkoxy, alkyl substituted aryl, arylalkyl and aryl substituted arylalkyl; wherein such $R^2$ groups may be optionally substituted with $(C_1-C_{20})$ alkyl, halo, hydroxy, $(C_1-C_{20})$ alkoxy, or cyano;

wherein one or more of the carbon atoms in the $R^1$ or $R^2$ groups can be independently replaced with non-peroxide oxygen, sulfur or $NR^4$; wherein $R^4$ is hydrogen or $(C_1-C_{20})$ alkyl; and wherein the alkyl, alkenyl, and alkynyl groups in $R^2$ are optionally substituted with oxo or halo.

Exemplary compounds according to the invention include, e.g.,

[(1R,3S)-1-Amino-3-(4-oct-1-ynyl-phenyl)-cyclopentyl]-methanol;
[(1R,3S)-1-Amino-3-(4-octyl-phenyl)-cyclopentyl]-methanol;
{(1R,3S)-1-Amino-3-[4-(3-phenoxy-propyl)-phenyl]-cyclopentyl}-methanol;
[(1R,3R)-1-Amino-3-(4-oct-1-ynyl-phenyl)-cyclopentyl]-methanol;
{(1R,3R)-1-Amino-3-[4-(4-phenyl-but-1-ynyl)-phenyl]-cyclopentyl}-methanol;
[(1R,3R)-1-Amino-3-(4-hex-1-ynyl-phenyl)-cyclopentyl]-methanol;
[(1R,3R)-1-Amino-3-(4-hept-1-ynyl-phenyl)-cyclopentyl]-methanol;
{(1R,3R)-1-Amino-3-[4-(6-methoxy-hex-1-ynyl)-phenyl]-cyclopentyl}-methanol;
{(1R,3R)-1-Amino-3-[4-(3-phenyl-prop-1-ynyl)-phenyl]-cyclopentyl}-methanol;
{(1R,3R)-1-Amino-3-[4-(5-phenyl-pent-1-ynyl)-phenyl]-cyclopentyl}-methanol;
[(1R,3R)-1-Amino-3-(4-octyl-phenyl)-cyclopentyl]-methanol;
{(1R,3R)-1-Amino-3-[4-(4-phenyl-butyl)-phenyl]-cyclopentyl}-methanol;
{(1R,3R)-1-Amino-3-[4-(3-phenoxy-propyl)-phenyl]-cyclopentyl}-methanol;
{(1R,3R)-1-Amino-3-[4-(6-methoxy-hexyl)-phenyl]-cyclopentyl}-methanol;
{(1R,3R)-1-Amino-3-[4-(3-phenyl-propyl)-phenyl]-cyclopentyl}-methanol;
{(1R,3R)-1-Amino-3-[4-(5-phenyl-pentyl)-phenyl]-cyclopentyl}-methanol;
{(1R,3R)-1-Amino-3-[4-(4-propoxy-butyl)-phenyl]-cyclopentyl}-methanol;
[(1R,3R)-1-Amino-3-(4-octyloxy-phenyl)-cyclopentyl]-methanol;
{(1R,3R)-1-Amino-3-[4-(2-m-tolyloxy-ethoxy)-phenyl]-cyclopentyl}-methanol;
((1R,3R)-1-Amino-3-{4-[2-(4-methoxy-phenyl)-ethoxy]-phenyl}-cyclopentyl)-methanol;
{(1R,3R)-1-Amino-3-[4-(2-p-tolyloxy-ethoxy)-phenyl]-cyclopentyl}-methanol;
[(1R,3R)-1-Amino-3-(4-heptyloxy-phenyl)-cyclopentyl]-methanol;
[(1R,3R)-1-Amino-3-(4-nonyloxy-phenyl)-cyclopentyl]-methanol;
{(1R,3R)-1-Amino-3-[4-(2-pentyloxy-ethoxy)-phenyl]-cyclopentyl}-methanol;
{(1R,3R)-1-Amino-3-[4-(2-p-tolyl-ethoxy)-phenyl]-cyclopentyl}-methanol;
((1R,3R)-1-Amino-3-{4-[3-(4-methoxy-phenyl)-propoxy]-phenyl}-cyclopentyl)-methanol;
((1R,3R)-1-Amino-3-{4-[2-(2-methoxy-ethoxy)-ethoxy]-phenyl}-cyclopentyl)-methanol;
((1R,3R)-1-Amino-3-{4-[2-(4-ethoxy-phenyl)-ethoxy]-phenyl}-cyclopentyl)-methanol;
{(1R,3R)-1-Amino-3-[4-(4-methanesulfonyl-butoxy)-phenyl]-cyclopentyl}-methanol;
{(1R,3R)-1-Amino-3-[4-(5-methoxy-pentyloxy)-phenyl]-cyclopentyl}-methanol;
{(1R,3R)-1-Amino-3-[4-(2-phenoxy-ethoxy)-phenyl]-cyclopentyl}-methanol;
((1R,3R)-1-Amino-3-{4-[2-(3-methoxy-phenyl)-ethoxy]-phenyl}-cyclopentyl)-methanol;
((1R,3R)-1-Amino-3-{4-[3-(3-methoxy-phenyl)-propoxy]-phenyl}-cyclopentyl)-methanol;
((1R,3R)-1-Amino-3-{4-[3-(3,5-dimethoxy-phenyl)-propoxy]-phenyl}-cyclopentyl)-methanol;
((1R,3R)-1-Amino-3-{4-[2-(4-methoxy-3,5-dimethyl-phenyl)-ethoxy]-phenyl}-cyclopentyl)-methanol;
((1R,3R)-1-Amino-3-{4-[2-(4-benzyloxy-phenyl)-ethoxy]-phenyl}-cyclopentyl)-methanol;
{(1R,3R)-1-Amino-3-[4-(3-phenyl-propoxy)-phenyl]-cyclopentyl}-methanol;
Phosphoric acid mono-{(1R,3R)-1-amino-3-[4-(4-phenyl-butyl)-phenyl]-cyclopentylmethyl} ester;
Phosphoric acid mono-{(1R,3R)-1-amino-3-[4-(3-phenoxy-propyl)-phenyl]-cyclopentylmethyl} ester;
Phosphoric acid mono-[(1R,3S)-1-amino-3-(4-octyl-phenyl)-cyclopentylmethyl] ester;
Phosphoric acid mono-[(1R,3R)— 1-amino-3-(4-octyl-phenyl)-cyclopentylmethyl] ester;
Phosphoric acid mono-[(1R,3S)-1-amino-3-(3-decyl-phenyl)-cyclopentylmethyl] ester;
Phosphoric acid mono-[(1R,3R)-1-amino-3-(4-nonyloxy-phenyl)-cyclopentylmethyl] ester;
Phosphoric acid mono-{(1R,3R)-1-amino-3-[4-(2-p-tolyloxy-ethoxy)-phenyl]-cyclopentylmethyl} ester;
Phosphoric acid mono-((1R,3R)-1-amino-3-{4-[2-(4-methoxy-phenyl)-ethoxy]-phenyl}-cyclopentylmethyl) ester;
Phosphoric acid mono-{(1R,3R)-1-amino-3-[4-(3-phenyl-propyl)-phenyl]-cyclopentylmethyl} ester;
Phosphoric acid mono-[(1R,3R)-1-amino-3-(4-octyloxy-phenyl)-cyclopentylmethyl] ester;
Phosphoric acid mono-{(1R,3R)-1-amino-3-[4-(6-methoxy-hexyl)-phenyl]-cyclopentylmethyl} ester;
Phosphoric acid mono-[(1R,3S)-1-amino-3-(4-octyl-phenyl)-cyclopentylmethyl] ester;
Phosphoric acid mono-[(1R,3S)-1-amino-3-(4-heptyl-phenyl)-cyclopentylmethyl] ester;
Phosphoric acid mono-{(1R,3R)-1-amino-3-[4-(2-pentyloxy-ethoxy)-phenyl]-cyclopentylmethyl} ester;
Phosphoric acid mono-{(1R,3R)-1-amino-3-[4-(2-m-tolyloxy-ethoxy)-phenyl]-cyclopentylmethyl} ester;
Phosphoric acid mono-{(1R,3R)-1-amino-3-[4-(2-p-tolyl-ethoxy)-phenyl]-cyclopentylmethyl} ester;
Phosphoric acid mono-[(1R,3R)-1-amino-3-(4-heptyloxy-phenyl)-cyclopentylmethyl] ester;
Phosphoric acid mono-((1R,3R)-1-amino-3-{4-[3-(4-methoxy-phenyl)-propoxy]-phenyl}-cyclopentylmethyl) ester;

Phosphoric acid mono-((1R,3R)-1-amino-3-{4-[2-(2-methoxy-ethoxy)-ethoxy]-phenyl}-cyclopentylmethyl) ester;
Phosphoric acid mono-((1R,3R)-1-amino-3-{4-[2-(4-ethoxy-phenyl)-ethoxy]-phenyl}-cyclopentylmethyl) ester;
Phosphoric acid mono-{(1R,3R)-1-amino-3-[4-(2-phenoxy-ethoxy)-phenyl]-cyclopentylmethyl} ester;
Phosphoric acid mono-((1R,3R)-1-amino-3-{4-[2-(3-methoxy-phenyl)-ethoxy]-phenyl}-cyclopentylmethyl) ester;
Phosphoric acid mono-((1R,3R)-1-amino-3-{4-[3-(3-methoxy-phenyl)-propoxy]-phenyl}-cyclopentylmethyl) ester;
Phosphoric acid mono-((1R,3R)-1-amino-3-{4-[3-(3,5-dimethoxy-phenyl)-propoxy]-phenyl}-cyclopentylmethyl) ester;
Phosphoric acid mono-((1R,3R)-1-amino-3-{4-[2-(4-hydroxy-phenyl)-ethoxy]-phenyl}-cyclopentylmethyl) ester;
Phosphoric acid mono-{(1R,3R)-1-amino-3-[4-(3-phenyl-propoxy)-phenyl]-cyclopentylmethyl} ester;
Phosphoric acid mono-{(1R,3S)-1-amino-3-[4-(3-phenoxy-propyl)-phenyl]-cyclopentylmethyl} ester.

Exemplary compounds of Formula I include:
(1R,3R)-1-Amino-3-(4-oct-1-ynyl-phenyl)-cyclopentanecarboxylic acid;
(1R,3S)-1-Amino-3-(4-non-1-ynyl-phenyl)-cyclopentanecarboxylic acid
(1R,3S)-1-Amino-3-(4-nonyl-phenyl)-cyclopentanecarboxylic acid;
(1R,3S)-1-Amino-3-(4-dec-1-ynyl-phenyl)-cyclopentanecarboxylic acid;
(1R,3S)-1-Amino-3-(4-decyl-phenyl)-cyclopentanecarboxylic acid
(1R,3S)-1-Amino-3-[4-(7-methoxy-hept-1-ynyl)-phenyl]-cyclopentanecarboxylic acid;
(1R,3R)-1-Amino-3-[4-(3-phenoxy-propyl)-phenyl]-cyclopentanecarboxylic acid;
(1R,3S)-1-Amino-3-(4-oct-1-ynyl-phenyl)-cyclopentanecarboxylic acid
(1R,3S)-1-Amino-3-(4-hept-1-ynyl-phenyl)-cyclopentanecarboxylic acid
(1R,3S)-1-Amino-3-(4-heptyl-phenyl)-cyclopentanecarboxylic acid.

Definitions

In this invention, the following definitions are applicable:

A "therapeutically effective amount" is an amount of a compound of Formula I or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Physiologically acceptable salts" or "pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, L-aspartic acid, L-mandelic, L-succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula I which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula I and their salts may exist in more than one crystal form and the present invention includes each crystal form and mixtures thereof.

Certain compounds of Formula I and their salts may also exist in the form of solvates, for example hydrates, and the present invention includes each solvate and mixtures thereof.

Certain compounds of Formula I may contain one or more chiral centers, and exist in different optically active forms. When compounds of Formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula I contains more than one chiral center, it may exist in diastereoisomeric forms. The diastereoisomeric compounds may be separated by methods known to those skilled in the art, for example chromatography or crystallization and the individual stereoisomers may be separated as described above. The present invention includes each diastereoisomer of compounds of Formula I and mixtures thereof.

Certain compounds of Formula I may exist in different tautomeric forms or as different geometric isomers, and the present invention includes each tautomer and/or geometric isomer of compounds of Formula I and mixtures thereof.

Certain compounds of Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula I and mixtures thereof.

Certain compounds of Formula I may exist in zwitterionic form and the present invention includes each zwitterionic form of compounds of Formula I and mixtures thereof.

As used herein the term "pro-drug" or "prodrug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the active metabolite. They may, for instance, be bioavailable by oral administration whereas the parent drug is not. The pro-drug may also have improved solubility in pharmacological compositions over the active metabolite. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial Pro-drugs have many useful properties. For example, a pro-drug may be more water soluble than the ultimate drug, thereby facilitating oral administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —(CH$_2$)C(O)OH or a moiety that contains a carboxylic acid) wherein the free hydrogen is replaced by (C$_1$-C$_4$) alkyl, (C$_2$-C$_{12}$) alkanoyloxymethyl, (C$_4$-C$_9$) 1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C$_1$-C$_2$)alkylamino(C$_2$-C$_3$)alkyl (such as β-dimethylaminoethyl), carbamoyl-(C$_1$-C$_2$)alkyl, N,N-di(C$_1$-C$_2$)-alkylcarbamoyl-(C$_1$-C$_2$)alkyl and piperidino-, pyrrolidino- or morpholino(C$_2$-C$_3$)alkyl.

Other exemplary pro-drugs release an alcohol of Formula I wherein the free hydrogen of the hydroxy substituent (e.g., Z contains hydroxy) is replaced by phosphate (PO$_4$), (C$_1$-C$_6$)alkanoyloxymethyl, 1-((C$_1$-C$_6$)alkanoyloxy)ethyl, 1-methyl-1-((C$_1$-C$_6$)alkanoyloxy)ethyl, (C$_1$-C$_6$)alkoxycarbonyloxymethyl, N—(C$_1$-C$_6$)alkoxycarbonylamino-methyl, succinoyl, (C$_1$-C$_6$)alkanoyl, α-amino(C$_1$-C$_4$)alkanoyl, arylacyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O(C$_1$-C$_6$)alkyl)$_2$ or glycosyl (the radical resulting from detachment of the hydroxy of the hemiacetal of a carbohydrate).

The terms "heterocyclic" or "heterocyclyl", as used herein, include non-aromatic ring systems, including, but not limited to, monocyclic, bicyclic and tricyclic rings, which can be completely saturated or which can contain one or more units of unsaturation (for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indolinyl, indazolyl, isoindolinyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl or tropanyl.

When the term "substituted heterocyclic" (or heterocyclyl) or "substituted heteroaryl" is used, what is meant is that the heterocyclic group is substituted with one or more substituents that can be made by one of ordinary skill in the art and results in a molecule that is an agonist or antagonist of the sphingosine receptor family. For purposes of exemplification, which should not be construed as limiting the scope of this invention, preferred substituents for the heterocycle of this invention are each independently selected from the optionally substituted group consisting of alkenyl, alkoxy, alkoxyalkoxy, alkoxyalkyl, alkoxycarbonyl, alkoxycarbonylheterocycloalkoxy, alkyl, alkylcarbonyl, alkylester, alkyl-O—C(O)—, alkyl-heterocyclyl, alkyl-cycloalkyl, alkyl-nitrile, alkynyl, amido groups, amino, aminoalkyl, aminocarbonyl, carbonitrile, carbonylalkoxy, carboxamido, —CF$_3$, —CN, —C(O)OH, —C(O)H, —C(O)—C(CH$_3$)$_3$, —OH, —C(O)O-alkyl, —C(O)O-cycloalkyl, —C(O)O-heterocyclyl, —C(O)-alkyl, —C(O)-cycloalkyl, —C(O)-heterocyclyl, cycloalkyl, dialkylaminoalkoxy, dialkylaminocarbonylalkoxy, dialkylaminocarbonyl, halogen, heterocyclyl, a heterocycloalkyl group, heterocyclyloxy, hydroxy, hydroxyalkyl, nitro, —OCF$_3$, oxo, phenyl, —SO$_2$CH$_3$, —SO$_2$CR$_3$, tetrazolyl, thienylalkoxy, trifluoromethylcarbonylamino, trifluoromethylsulfonamido, heterocyclylalkoxy, heterocyclyl-S(O)$_p$, cycloalkyl-S(O)$_p$, alkyl-S—, heterocyclyl-S, heterocloalkyl, cycloalkylalkyl, heterocyclolthio, cycloalkylthio, —Z$^{105}$-C(O)N(R)$_2$, —Z$^{105}$-N(R)—C(O)—Z$^{200}$, —Z$^{105}$-N(R)—S(O)$_2$—Z$^{200}$, —Z$^{105}$-N(R)—C(O)—N(R)—Z$^{200}$, —N(R)—C(O)R, —N(R)—C(O)OR, OR—C(O)-heterocyclyl-OR, R$_c$ and —CH$_2$OR;

wherein R is C$_1$-C$_4$ alkyl, C$_3$-C$_6$ cycloalkyl or phenyl;

wherein p is 0, 1 or 2;

where R$_c$ for each occurrence is independently hydrogen, optionally substituted alkyl, optionally substituted aryl, —(C$_1$-C$_6$)—NR$_d$R$_e$, -E-(CH$_2$)$_t$—NR$_d$R$_e$, -E-(CH$_2$)$_t$—O-alkyl, -E-(CH$_2$)$_t$—S-alkyl, or -E-(CH$_2$)$_t$—OH;

wherein t is an integer from 1 to 6;

Z$^{105}$ for each occurrence is independently a covalent bond, alkyl, alkenyl or alkynyl; and Z$^{200}$ for each occurrence is independently selected from an optionally substituted group selected from the group consisting of alkyl, alkenyl, alkynyl, phenyl, alkyl-phenyl, alkenyl-phenyl or alkynyl-phenyl;

E is a direct bond, O, S, S(O), S(O)$_2$, or NR$_f$, wherein R$_f$ is H or alkyl and R$_d$ and R$_e$ are independently H, alkyl, alkanoyl or SO$_2$-alkyl; or R$_d$, R$_e$ and the nitrogen atom to which they are attached together to form a five- or six-membered heterocyclic ring.

An "heterocycloalkyl" group, as used herein, is a heterocyclic group that is linked to a compound by an aliphatic group having from one to eight carbon atoms. For example, a preferred heterocycloalkyl group is a morpholinomethyl group.

As used herein, "aliphatic" or "an aliphatic group" or notations such as "(C$_1$-C$_{20}$)" include straight chained or branched hydrocarbons which are completely saturated or which contain one or more units of unsaturation, and, thus, includes alkyl, alkenyl, alkynyl and hydrocarbons comprising a mixture of single, double and triple bonds. When the group is a $C_0$ it means that the moiety is not present or in other words, it is a bond. As used herein, "alkyl" means $C_1$-$C_{20}$ and includes straight chained or branched hydrocarbons, which are completely saturated. Preferred alkyls are methyl, ethyl, propyl, butyl, pentyl, hexyl, heptyl, octyl, nonyl, decyl, etc. up to twenty carbon atoms, and isomers thereof. As used herein, "alkenyl" and "alkynyl" means $C_2$-$C_{20}$ and includes straight chained or branched hydrocarbons which contain one or more units of unsaturation, one or more double bonds for alkenyl and one or more triple bonds for alkynyl.

As used herein, aromatic groups (or aryl groups) include aromatic carbocyclic ring systems (e.g., phenyl and cyclopentyldienyl) and fused polycyclic aromatic ring systems (e.g., naphthyl, biphenylenyl and 1,2,3,4-tetrahydronaphthyl).

As used herein, "cycloalkyl" means $C_3$-$C_{20}$ monocyclic or multicyclic (e.g., bicyclic, tricyclic, etc.) hydrocarbons that is completely saturated or has one or more unsaturated bonds but does not amount to an aromatic group. Preferred examples of a cycloalkyl group are cyclopropyl, cyclobutyl, cyclopentyl, cyclopentenyl, cyclohexyl and cyclohexenyl.

As used herein, the term "phosphate" means —R—O—P(=O)(OH)(OH), the term "phosphonate" means —R—P(=O)(OH)(OH) wherein R is not O or S.

As used herein, the term "aryl substituted alkyl" or "aryl substituted alkenyl" means moieties such as methylphenyl, ethylphenyl, methylnaphthyl, ethylnapthyl, ethylenylphenyl ethylenylnaphthyl and so on wherein the alkyl portion of the moiety ranges from 1 to 20 carbons and the alkenyl portion of the moiety ranges from 2 to 20 carbons.

As used herein, the term "heteroaryl substituted alkyl" means moieties such as methylpyridinyl, ethylpyridinyl and so on wherein the alkyl portion of the moiety ranges from 1 to 20 carbons and the heteroaryl can be any heteroaryl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: alkenyl groups, alkoxy group (which itself can be substituted, such as —O—($C_1$-$C_6$)alkyl-OR, —O—($C_1$-$C_6$)alkyl-N(R)$_2$, and —OCF$_3$), alkoxyalkoxy, alkoxycarbonyl, alkoxycarbonylpiperidinylalkoxy, alkyl groups (which itself can also be substituted, such as —$C_1$-$C_6$-alkyl-OR, —$C_1$-$C_6$-alkyl-N(R)$_2$, and —CF$_3$), alkylamino, alkylcarbonyl, alkylester, alkylnitrile, alkylsulfonyl, amino, aminoalkoxy, —CF$_3$, —COH, —COOH, —CN, cycloalkyl, dialkylamino, dialkylaminoalkoxy, dialkylaminocarbonyl, dialkylaminocarbonylalkoxy, dialkylaminosulfonyl, esters (—C(O)—OR, where R is groups such as alkyl, heterocycloalkyl (which can be substituted), heterocyclyl, etc., which can be substituted), halogen or halo group (F, Cl, Br, I), hydroxy, morpholinoalkoxy, morpholinoalkyl, nitro, oxo, —OCF$_3$, optionally substituted phenyl, —S(O)$_2$CH$_3$, —S(O)$_2$CF$_3$, and sulfonyl, N-alkylamino or N,N-dialkylamino (in which the alkyl groups can also be substituted).

The compounds according to the invention may be prepared following synthesis schemes set forth in detail in the Examples below.

Methods of Use

The present invention provides compounds described by general Formula I which are effective as antagonists or agonists of the G protein-coupled S1P receptor family. These compounds reduce the number of circulating and infiltrating T- and B-lymphocytes, affording a beneficial immunosuppressive effect.

The present invention also provides compounds that exhibit activity within the S1P receptor family.

In a related aspect the invention provides a method for modulating receptors of the S1P family in a human subject suffering from a disorder in which modulation of S1P activity is beneficial, comprising administering to the human subject a compound of Formula I such that modulation of S1P activity in the human subject is triggered and treatment is achieved.

In another related aspect the invention provides a method of modulating sphingosine-1-phosphate receptor 1 (S1P$_1$) activity comprising contacting a cell with one or more compounds of Formula I.

A compound of Formula I or a salt thereof or pharmaceutical compositions containing a therapeutically effective amount thereof is useful in the treatment of a disorder selected from the group comprising CNS system disorders, arthritis, rheumatoid arthritis, osteoarthritis, juvenile chronic arthritis, Lyme arthritis, psoriatic arthritis, reactive arthritis, and septic arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection (including but not limited to bone marrow and solid organ rejection), acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, *chlamydia, yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, α-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphederma, malaria, malignamt Lymphoma, malignant histiocytosis, malignant melanoma, meningitis, meningococcemia, metabolic/idiopathic, migraine headache, mitochondrial multisystem disorder, mixed connective tissue disease, monoclonal gammopathy, multiple myeloma, multiple systems degenerations (Mencel Dejerine-Thomas Shi-Drager and Machado-Joseph), myasthenia gravis, *mycobacterium avium* intracellulare, *mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-hodgkins lymphoma, occlusion of the abdominal aorta and its branches, occulsive arterial disorders, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as, edema, ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as glomerulonephritis, diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, Crow-Fukase syndrome (POEMS), preeclampsia, menometrorrhagia, cat scratch fever, rubeosis, neovascular glaucoma and retinopathies such as those associated with diabetic retinopathy, retinopathy of prematurity, age-related macular degeneration or a central nervous system disorder. In addition, these compounds can be used as active agents against solid tumors, malignant ascites, von Hippel Lindau disease, hematopoietic cancers and hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Combination Therapy

Compounds of Formula I of the invention can be used alone or in combination with another therapeutic agent to treat such diseases. It should be understood that the compounds of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the S1P receptor agonists or antagonists of this invention. Non-limiting examples of therapeutic agents for rheumatoid arthritis with which a compound of Formula I of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. S/T kinase inhibitors of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, HUMIRA™, (U.S. Pat. No. 6,090,382), CA2 (REMICADE™), CDP 571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula I of the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula I of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g., IRAK, NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g., soluble p55 or p75 TNF receptors, sIL-1RI, sIL-1RII, sIL-6R) and antiinflammatory cytokines (e.g., IL-4, IL-10, IL-11, IL-13 and TGFβ). Preferred examples of therapeutic agents for Crohn's disease with which a compound of Formula I can be combined include the following: TNF antagonists, for example, anti-TNF antibodies, HUMIRA™, U.S. Pat. No. 6,090,382, CA2 (REMICADE™), CDP 571, TNFR-Ig constructs, (p75TNFRIgG (ENBREL™) and p55TNFRIgG (Lenercept™)) inhibitors and PDE4 inhibitors. A compound of Formula I can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors 6-mercaptopurines; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula I can be combined include the following: corticosteroids; prednisolone; methylprednisolone; azathioprine; cyclophosphamide; cyclosporine; methotrexate; 4-aminopyridine; tizanidine; interferon-β1a (Avonex®; Biogen); interferon-β1b (Betaseron®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; Copaxone®; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula I can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula I may also be combined with agents such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R) and anti-inflammatory cytokines (e.g. IL-4, IL-10, IL-13 and TGFβ).

Preferred examples of therapeutic agents for multiple sclerosis in which a compound of Formula I can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula I may also be combined with agents, such as alemtuzumab, dronabinol, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for angina with which a compound of Formula I of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil HCl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril and bisoprolol fumarate.

Non-limiting examples of therapeutic agents for ankylosing spondylitis with which a compound of Formula I can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, etanercept, and infliximab.

Non-limiting examples of therapeutic agents for asthma with which a compound of Formula I can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone and metaproterenol sulfate.

Non-limiting examples of therapeutic agents for COPD with which a compound of Formula I can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for HCV with which a compound of Formula I can be combined include the following: Interferon-α-2a, Interferon-α-2b, Interferon-α con1, Interferon-α-n1, pegylated interferon-α-2a, pegylated interferon-α-2b, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of Formula I can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-α, methotrexate, mycophenolate mofetil and interferon-gamma-1β.

Non-limiting examples of therapeutic agents for myocardial infarction with which a compound of Formula I can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril HCl/mag carb, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of Formula I can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, and sulfasalazine.

Non-limiting examples of therapeutic agents for psoriatic arthritis with which a compound of Formula I can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept and efalizumab.

Non-limiting examples of therapeutic agents for restenosis with which a compound of Formula I can be combined include the following: sirolimus, paclitaxel, everolimus, tacrolimus, ABT-578, and acetaminophen.

Non-limiting examples of therapeutic agents for sciatica with which a compound of Formula I can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene napsylate/apap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of Formula I can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula I may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula I may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula I can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula I may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, HUMIRA™ (U.S. Pat. No. 6,090,382), CA2 (REMICADE™), CDP 571, TNFR-Ig constructs, (p75TNFRIgG (ENBREL™) and p55TNFRIgG (LENERCEPT™)).

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

One or more compounds of the invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Pharmaceutical Compositions and Modes of Administration

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 400, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

Dosage

For any compound used in a method of the present invention, the therapeutically effective dose can be estimated initially from cellular assays. For example, a dose can be formulated in cellular and animal models to achieve a circulating concentration range that includes the $EC_{50}$ as determined in cellular assays (i.e., the concentration of the test compound which achieves a half-maximal inhibition of a given receptor activity). In some cases it is appropriate to determine the $EC_{50}$ in the presence of 3 to 5% serum albumin since such a determination approximates the binding effects of plasma protein on the compound. Such information can be used to more accurately determine useful doses in humans. Further, advantageous compounds for systemic administration effectively modulate receptors of the S1P family in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1, p. 1). In the treatment of crises, the administration of an acute bolus or an infusion approaching the MTD may be advantageous to obtain a rapid response.

Dosage amount and interval may be adjusted individually to provide plasma levels of the active moiety which are sufficient to modulate receptors of the S1P family, or minimal effective concentration (MEC). The MEC will vary for each compound but can be estimated from in vitro data; e.g. the concentration necessary to achieve 50-90% inhibition of binding of the natural ligand using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and more preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

Exemplary Formulations

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients:

|  | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

The present invention also comprises the use of a compound of Formula I as a medicament.

A further aspect of the present invention provides the use of a compound of Formula I or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of Formula I to a mammal, particularly a human being, in need thereof.

The teachings of all references, including journal articles, patents and published patent applications, are incorporated herein by reference in their entirety.

EXAMPLES

Compounds of the present invention were synthesized and their activity assayed as described below.

S1P Receptor GTPγS Assays

The [$^{35}$S]GTPγS binding assay was performed using both scintillation proximity assay (SPA) and filtration methods. Both formats are advantageously run in 96 well plates and utilize membranes from stable or transient CHO human cell lines overexpressing $S1P_1$, $S1P_2$, $S1P_3$, $S1P_4$ or $S1P_5$. Compound stocks were made up to 10 mM using DMSO and serial dilutions were carried out using 100% DMSO. Compounds were transferred to 96 well plates to yield a final DMSO concentration of 1% for all assays (1 ul for a 100 ul assay volume). Frozen membranes were thawed and diluted in assay buffer containing of 20 mM HEPES pH 7.4, 0.1% fatty acid-free BSA, 100 mM NaCl, 5 mM $MgCl_2$ and 10 µM GDP. For the SPA assay membranes are premixed with WGA-SPA beads to yield a final concentration per well of 5 ug membrane and 500 ug of bead. For the filtration assay, membranes are added directly to the incubation plate at 5 ug per well. The assay begins with the addition of 50 ul of the membrane or membrane/bead mixture to each well of the assay plate. Next, 50 ul of 0.4 nM [$^{35}$S]GTPγS is added to each well and incubated for 30 minutes. Nonspecific binding is measured using 10 uM unlabeled GTPγS. For the SPA assay the plates are spun and then read on the Topcount. For the filtration assay the plate is harvested onto GF-C filtration plates using a Packard 96 well harvester.

Inhibition of [$^{33}$P]S1P Binding to S1P Receptors

Radio ligand binding was carried out using membranes from transiently transfected HEK cells overexpressing $S1P_1$, $S1P_2$, $S1P_3$, $S1P_4$ or $S1P_5$. All compounds are dissolved in DMSO and serial dilutions were carried out in DMSO prior to addition to assay buffer. Final assay DMSO concentrations are 1% (v/v). [$^{33}$P]S1P is purchased from Perkin Elmer and used at 50 µM in all assays. Frozen membranes are thawed and resuspended in assay buffer containing 50 mM HEPES pH7.4, 100 mM NaCl, 10 mM $MgCl_2$ and 0.1% fatty acid free BSA. Membrane is added to give 5-10 ug of membrane per well. Non-specific binding is determined in the presence of cold 1 uM S1P. Incubations are carried out at room temperature for 45-60 minutes before filtering onto GF/C filtration plates using a Packard 96 well harvester. Plates are dried before adding Microscint to each well, sealed and counted on a Topcount.

ABBREVIATIONS acac Acetylacetonate
ACN Acetonitrile
9-BBN 9-Borabicyclononane
$BBr_3$ Borane tribromide
BINAP 2,2'-Bis(diphenylphosphino)-1,1'-binaphthalene
$C_2H_4$ Ethylene
CuI Copper(I) iodide
DBAD Di-tert-butyl azodicarboxylate
DCC Dicyclohexyl carbodiimide
DCM Dichloromethane
DIEA N,N-Diisopropylethylamine
DMA N,N-Dimethylacetamide
DME Dimethoxyethane
DMF N,N-Dimethylformamide
DMSO Dimethyl sulfoxide
DMSO-$d_6$ Deuterated DMSO
Dppf 1,1'-Bis(diphenylphosphino)ferrocene
EDC (3-Dimethylamino-propyl)-ethyl-carbodiimide
$Et_3N$ Triethylamine
$Et_2O$ Diethyl ether
EtOAc Ethyl acetate
$H_2$ Hydrogen gas
HCl Hydrochloric acid
HOAc Acetic acid
HOBt 1-hydroxy-1H-benzotriazole
HPLC High Performance Liquid Chromatography
$K_2CO_3$ Potassium carbonate
LAH Lithium tetrahydroaluminate
LCMS Liquid chromatography mass spectrometry
LDA Lithium diisopropylamide
LiHMDS Lithium hexamethyldisilazide
$MgSO_4$ Magnesium sulfate
MeOH-$d_4$ Deuterated methanol
MeOH Methanol
$NaHCO_3$ Sodium bicarbonate
NaOH Sodium hydroxide
NMO N-methylmorpholine-N-oxide
$Pd(PPh_3)_2Cl_2$ Bis(triphenylphosphine)palladium(II) chloride
$PPh_3$ Triphenylphosphine
PS-$PPh_3$ Polymer-supported triphenylphosphine
Rh Rhodium
RP Reverse Phase
$R_t$ Retention time
(S)-BINAP (S)-(−)-2,2'-Bis(diphenylphosphino)-1,1'-binaphthalene
TBAF Tetrabutylammoniumfluoride
TFA Trifluoroacetic acid
THF Tetrahydrofuran
TLC Thin layer chromatography
Analytical Methods Analytical data is defined either within the general procedures or in the tables of examples. Unless otherwise stated, all $^1$H or $^{13}$C NMR data were collected on a Varian Mercury Plus 400 MHz or a Bruker DRX 400 MHz instrument; chemical shifts are quoted in parts per million (ppm). High-pressure liquid chromatography (HPLC) analytical data are either detailed within the experimental or referenced to the table of HPLC conditions, using the lower case method letter, in Table 1.

TABLE 1

List of HPLC methods

| Method | HPLC Conditions<br>Unless indicated otherwise mobile phase A was 10 mM ammonium acetate, mobile phase B was HPLC grade acetonitrile. |
|---|---|
| a | 5-95% B over 3.7 min with a hold at 95% B for 1 min (1.3 mL/min flow rate). 4.6 × 50 mm Waters Zorbaz XDB C18 column (5 μm particles). Detection methods are diode array (DAD) and evaporative light scattering (ELSD) detection as well as pos/neg electrospray ionization. |
| b | 30% to 95% B over 2.0 min; 95% B for 3.5 min at 1.0 mL/min; UV λ = 190-400 nm; 4.6 × 30 mm Vydac Genesis C8 column (4 μm particles); Detection methods are diode array (DAD) and evaporative light scattering (ELSD) detection as well as pos/neg electrospray ionization. |
| c | 5-95% B in 2.7 min with a hold at 95% B for 1.0 min (1.3 mL/min flow rate on a 4.6 × 30 mm Vydac Genesis C8 column (4 μm particles). Detection methods are diode array (DAD) recording 250 nm (8 nm BW) and pos/neg atmospheric pressure chemical ionization (APCI). |
| d | 5-95% B over 3.7 min with a hold at 95% B for 1 min (1.3 mL/min flow rate). 4.6 × 50 mm Waters Zorbaz XDB C18 column (5 μm particles). Detection methods are diode array (DAD) and evaporative light scattering (ELSD) detection as well as pos/neg atmospheric pressure chemical ionization (APCI). |
| e | 5-60% B over 1.5 min then 60-95% B to 2.5 min with a hold at 95% B for 1.2 min (1.3 mL/min flow rate). 4.6 × 30 mm Vydac Genesis C8 column (4 μm particles). Detection methods are diode array (DAD) and evaporative light scattering (ELSD) detection as well as pos/neg electrospray ionization. |
| f | 30-95% B in 2 min. then hold at 95% B to 5.7 min (1 mL/min flow rate). Mobile phase A was 10 mM ammonium acetate, mobile phase B was HPLC grade acetonitrile. The column used for the chromatography was a 4.6 × 30 mm Vydac Genesis C8 column (4 μm particles). Detection methods are diode array (DAD) and evaporative light scattering (ELSD) detection as well as pos/neg electrospray ionization. |

General Synthetic Schemes

The general synthetic schemes that were utilized to construct the majority of compounds disclosed in this application are described below in (Schemes 1-5).

Scheme 1. General synthetic route to ((1R,3S)-1-amino-3-substitutedphenyl-cyclopentyl)methanol
(general procedures A, B, C, D, E, F, G, H)
(General procedures are noted in parentheses).

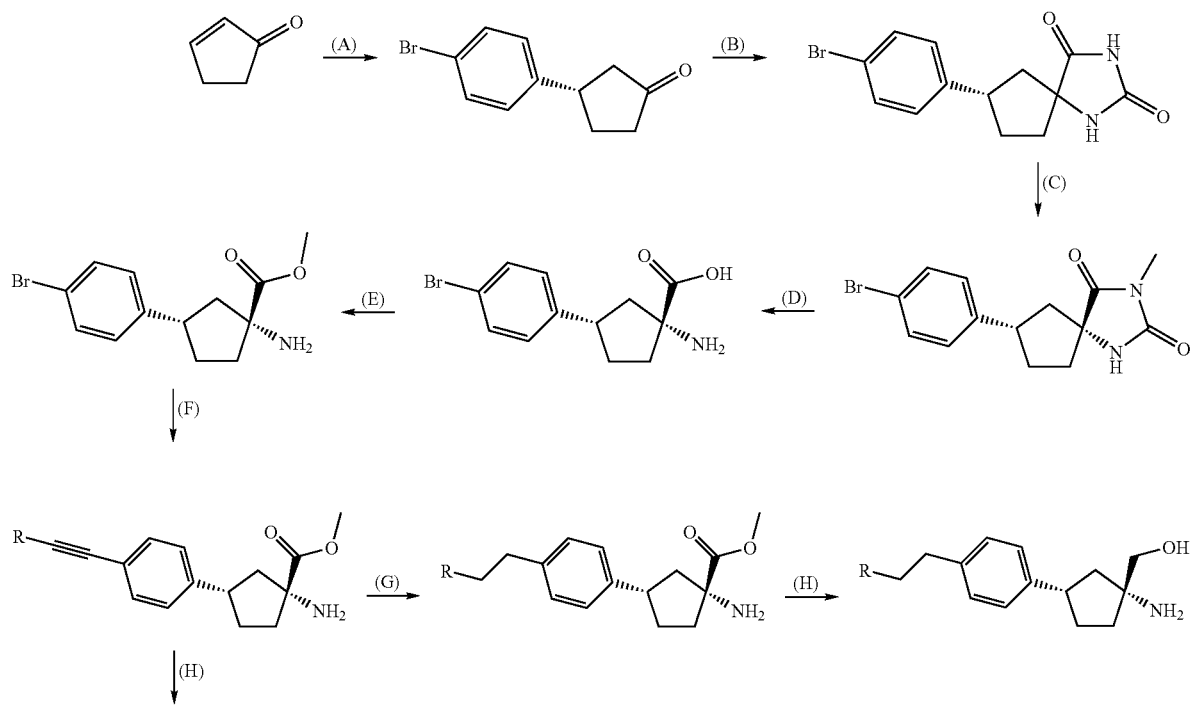

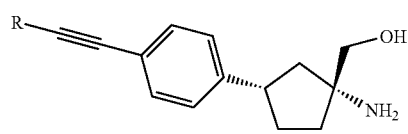
-continued
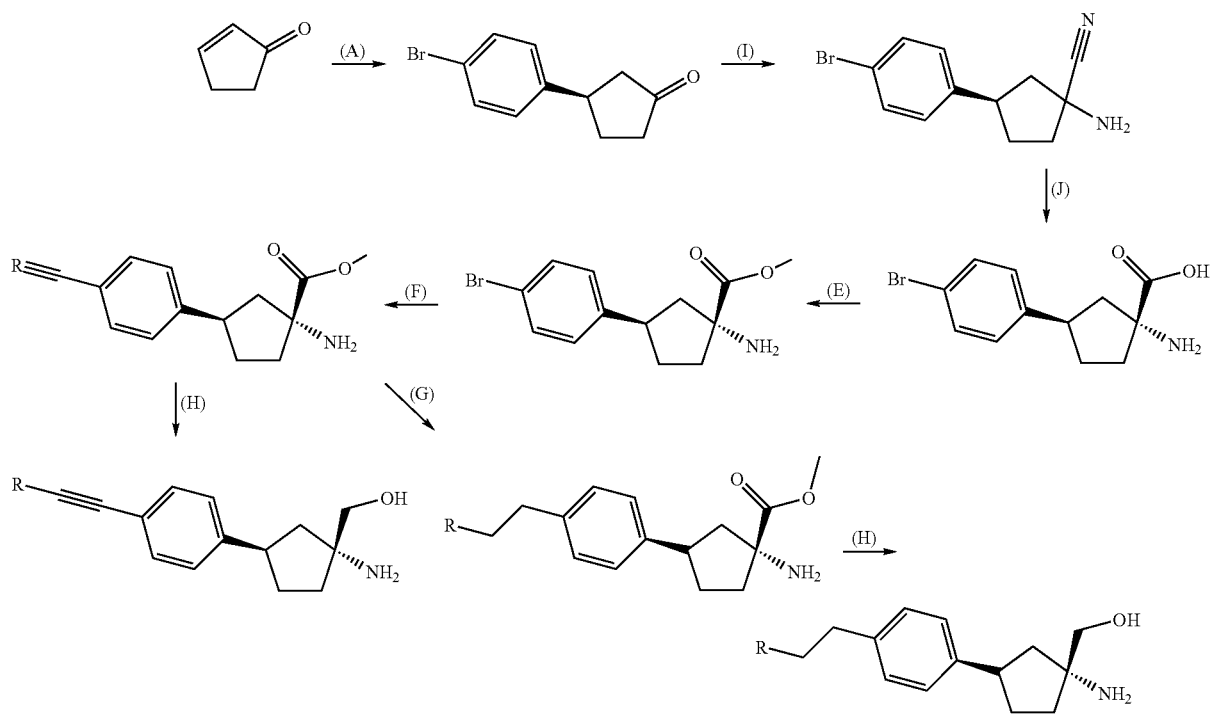
Scheme 2. General synthetic route to ((1R,3R)-1-amino-3-substitutedphenyl-cyclopentyl)methanol (general procedures A, I, J, E, F, G, H)
(General procedures are noted in parentheses).
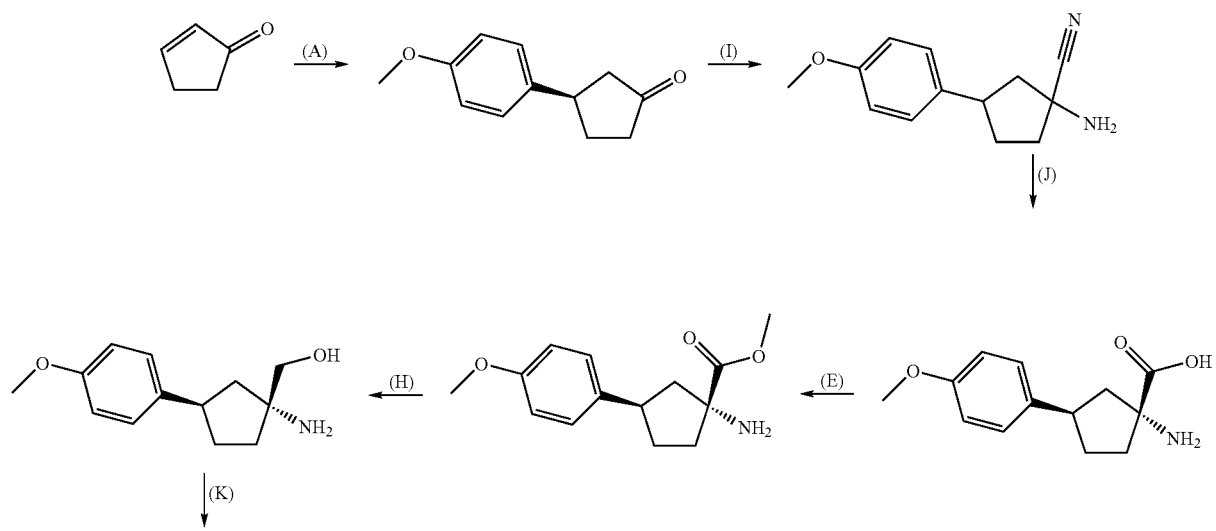
Scheme 3. General synthetic route to ((1R,3R)-1-amino-3-(4-substituted-oxyphenyl)cyclopentyl)methanol (general procedures A, I, J, E, H, K, L, M, N)
(General procedures are noted in parentheses).

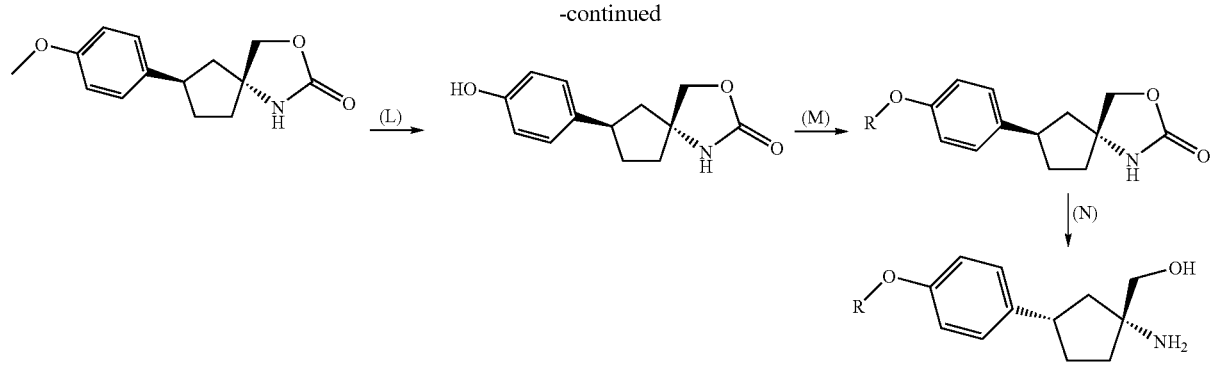

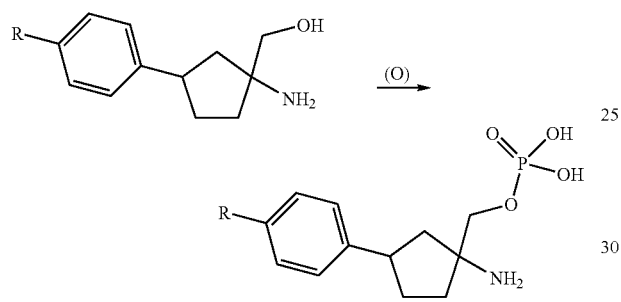

Scheme 4. General synthetic route to (1-amino-3-substituted phenyl-cyclopentyl)methyl dihydrogen phosphate (general procedure O)
(General procedures are noted in parentheses).

Scheme 5. General synthetic route to 1-amino-3-substituted phenyl-cyclopentanecarboxylic acid
(general procedure P)
(General procedures are noted in parentheses).

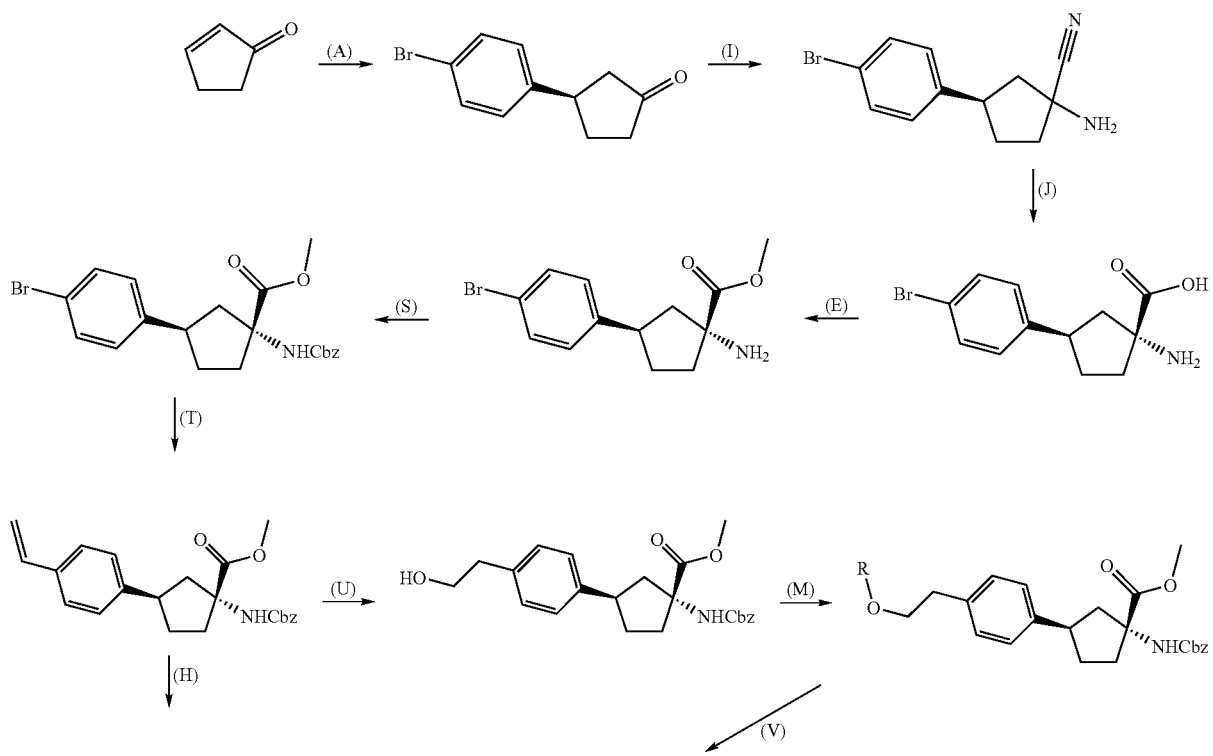

Scheme 6. General synthetic route to ((1R,3R)-1-amino-3-substitutedphenyl-cyclopentyl)methanol (general procdures A, I, J, E, S, T, U, M, V, H)
(General procedures are noted in parentheses).

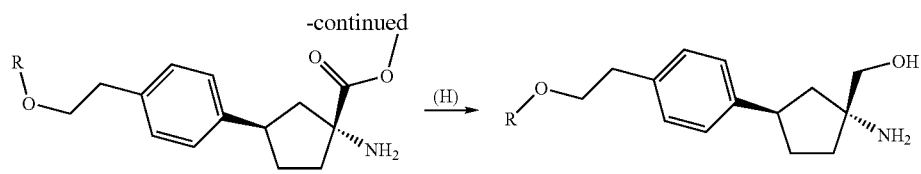

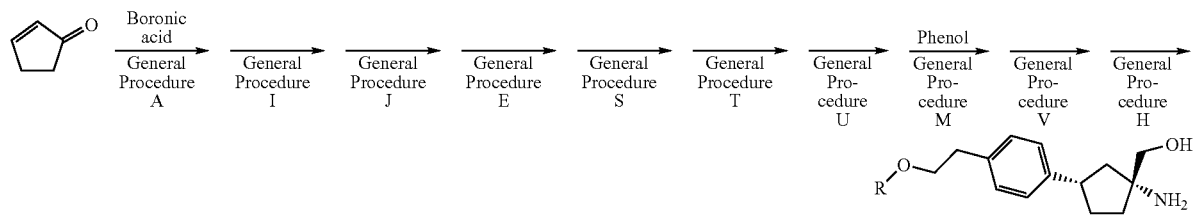

Scheme 7. General synthetic route to ((1R,3R)-1-amino-3-substitutedphenyl-cyclopentyl)methanol (general procedures A, I, J, E, S, T, U, M, V, H)

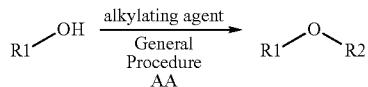

Scheme 8. General synthetic route for preparation of ethers

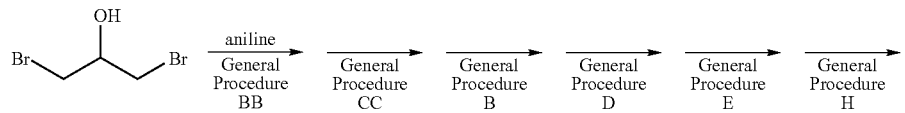

Scheme 9. General synthetic route to (3-Amino-1-substitutedphenyl-pyrrolidin-3-yl)-methanol (general procedures BB, CC, B, D, E, H)

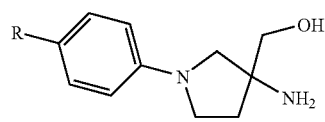

50

Scheme 10. General synthetic route to ((1R,3R)-1-amino-3-substitutedphenyl-cyclopentyl) methanol (general procedures A, I, J, E, H, K, F, M, N)

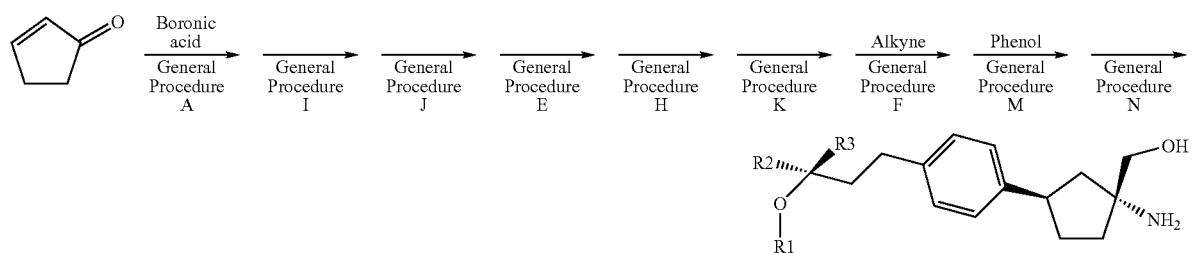

Scheme 11. General synthetic route to ((1R,3R)-1-amino-3-substitutedphenyl-cyclopentyl)methanol (general procedures A, I, J, E, H, K, F, G, L, M, N)

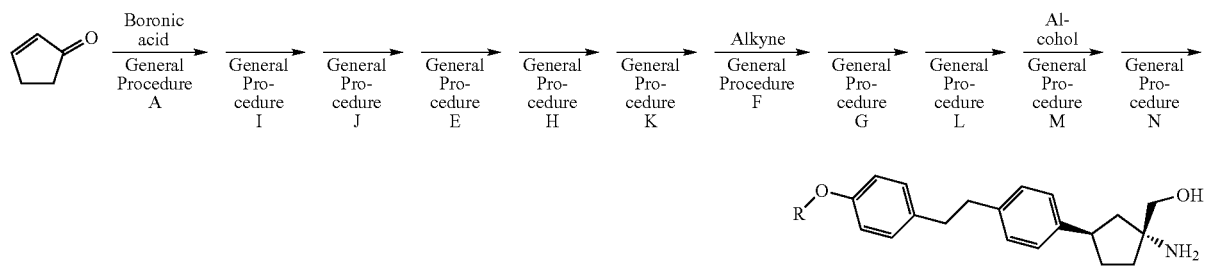

Scheme 12. General synthetic route to 3-Amino-5-substitutedphenyl-tetrahydro-furan-3-carboxylic acid (general procedure D)

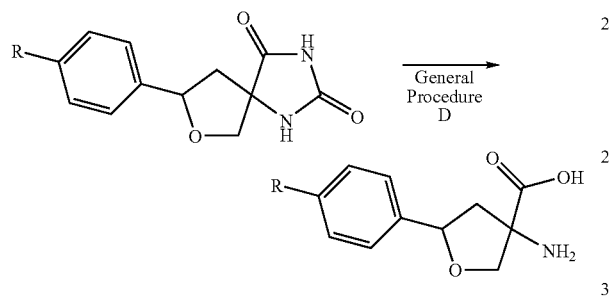

Scheme 13. General synthetic route to 3-substitutedphenyl-cyclopentylsubstitutedamine (general procedures A, F, G, DD)

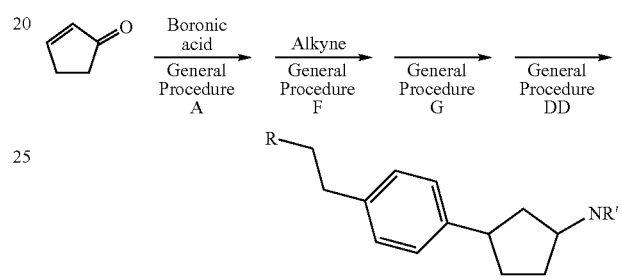

Scheme 14. General synthetic route to (1R,3S)-1-Amino-3-(4-substituted-phenyl)-cyclopentanecarboxylic acid methyl ester (general procedures A, I, J, E, F)

Scheme 15. General synthetic route to (1R,3S)-1-Amino-3-subtitutedphenyl-cyclopentanecarboxylic acid methyl ester (general procedures A, I, J, E, F, G)

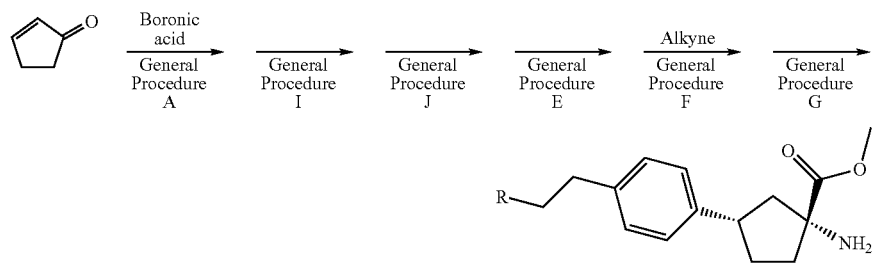

Alternative Synthetic Strategies

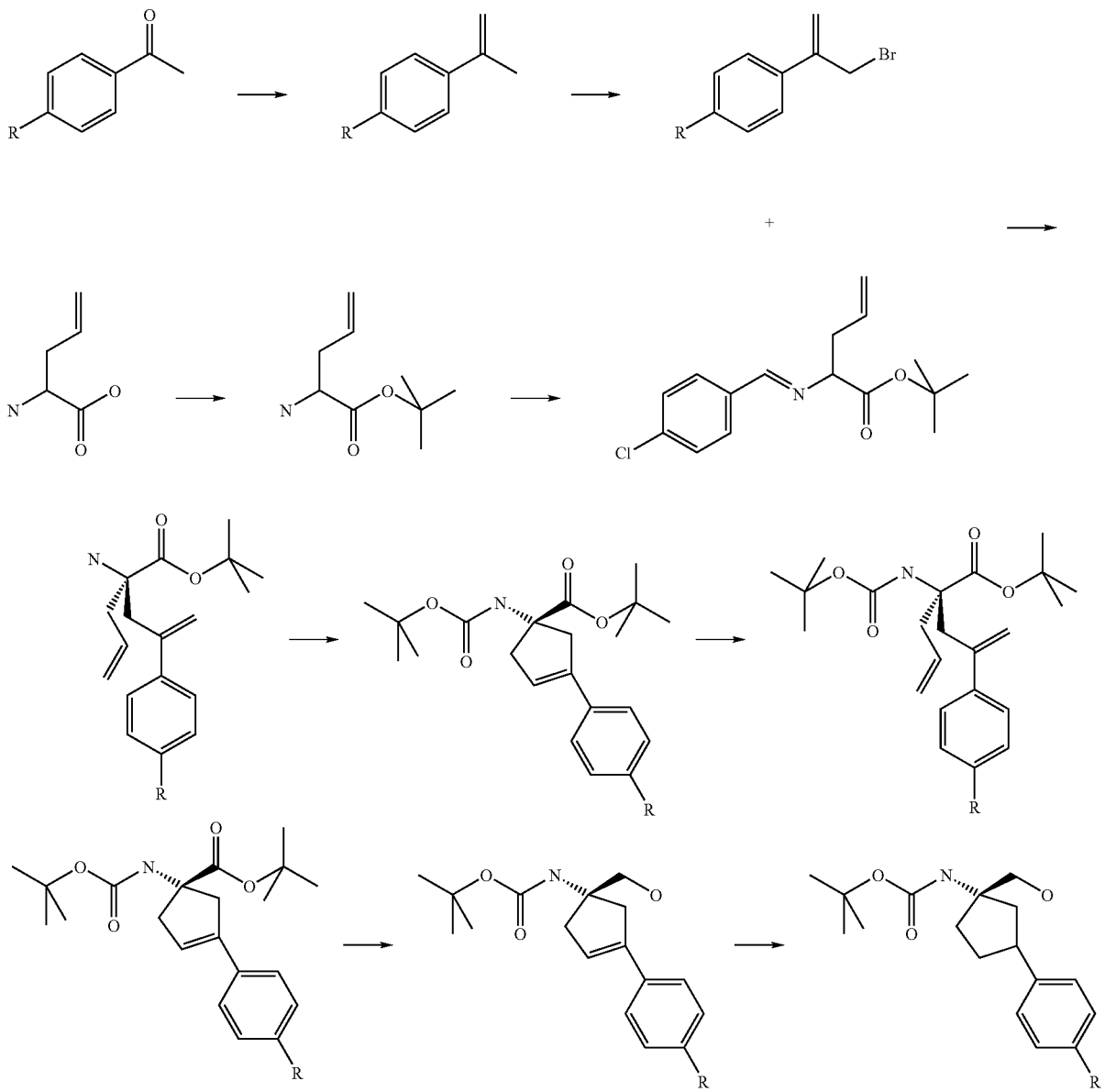

Homologation of a phenyl-substituted acetophenone such as p-bromoacetophenone with for example methyl triphenylphosphonium bromide and a base such as butyl lithium in an organic solvent such as THF followed by allylic halogenation with for example N-bromosuccinimide can produce the corresponding allyl halide. Esterification of a suitable α-substituted amino acid such as allyl glycine with an alkene such as isobutylene under acidic conditions such as sulfuric acid followed by reaction with an appropriate benzaldehyde such as p-chlorobenzaldehyde under dehydrating conditions such as the use of molecular sieves can produce the corresponding protected allyl amino ester. Reaction of the protected allyl amino ester with a base such as cesium hydroxide followed by alkylation under the influence of a chiral catalyst such as (R,R)-3,4,5-trifluorophenyl-NAS bromide (J. Am. Chem. Soc, 2000, Vol. 122, 5228-5229) and an allyl halide can produce the α,α-di-substituted chiral amino ester in high enantiomeric excess. The imine can be hydrolyzed with mild acid such as citric acid and the nitrogen liberated in this process can be re-protected with a suitable protecting group such as a BOC group. Ring formation can be completed under the influence of a suitable catalyst such as (1,3-Bis-(2,4,6-trimethylphenyl)-2-imidazolidinylidene)dichloro(o-isopropoxyphenylmethylene) ruthenium to generate the corresponding cyclopentenone. In the case of R=halogen, a suitably substituted alkyl chain such as that coming from n-octylboronic acid can be introduced under the influence of palladium catalyst such as tetrakis(triphenylphosphine) palladium(0) under basic conditions such as cesium carbonate in an organic solvent such as dioxane. Reduction of the ester group can be carried out with a suitable hydride reagent such as lithium borohydride and the cyclopentene can be stereoselectively reduced with for example palladium/barium sulfate or non-selectively with for example hydrogen gas over palladium on carbon.

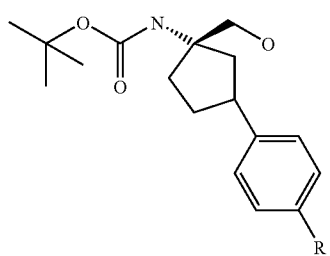

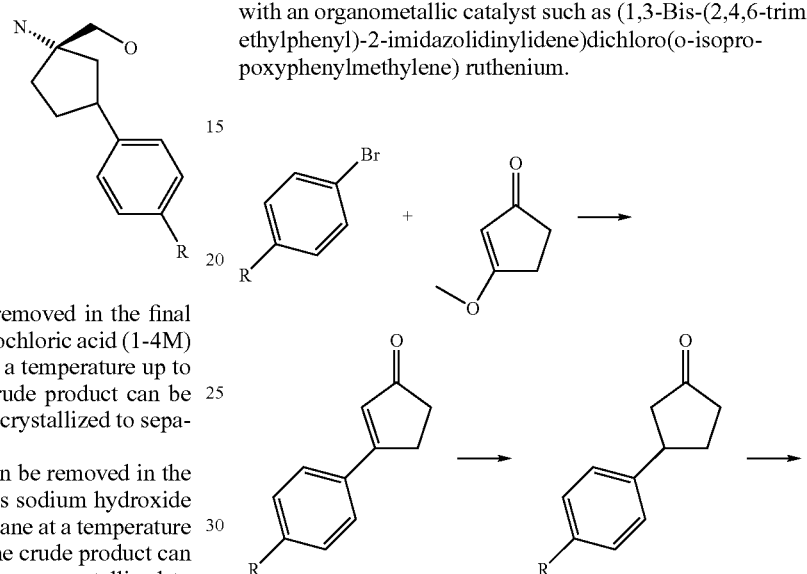

Alternatively, the corresponding intermediate suitably protected cyclopentene can be prepared as follows:

An imidazolidine such as (R)-2-tert-butyl-3-methyl-4-oxo-imidazolidine-1-carboxylic acid tert-butyl ester can be reacted with an allyl halide under basic conditions such as lithium-bistrimethylsilylamide then reacted with a second equivalent of base and an allyl halide to produce the corresponding chiral α,α-di-substituted imidazolidine. Cyclization to the corresponding cyclopentene can be accomplished with an organometallic catalyst such as (1,3-Bis-(2,4,6-trimethylphenyl)-2-imidazolidinylidene)dichloro(o-isopropoxyphenylmethylene) ruthenium.

The amine protecting group can be removed in the final step with a suitable reagent such as hydrochloric acid (1-4M) in an organic solvent such as dioxane at a temperature up to the boiling point of the solvent. The crude product can be further purified using chiral HPLC or cocrystallized to separate the stereoisomers.

Alternatively, the protecting group can be removed in the final step with a suitable reagent such as sodium hydroxide (1-7M) in a suitable solvent such as dioxane at a temperature up to the boiling point of the solvent. The crude product can be further purified using chiral HPLC or cocrystallized to separate the stereoisomers.

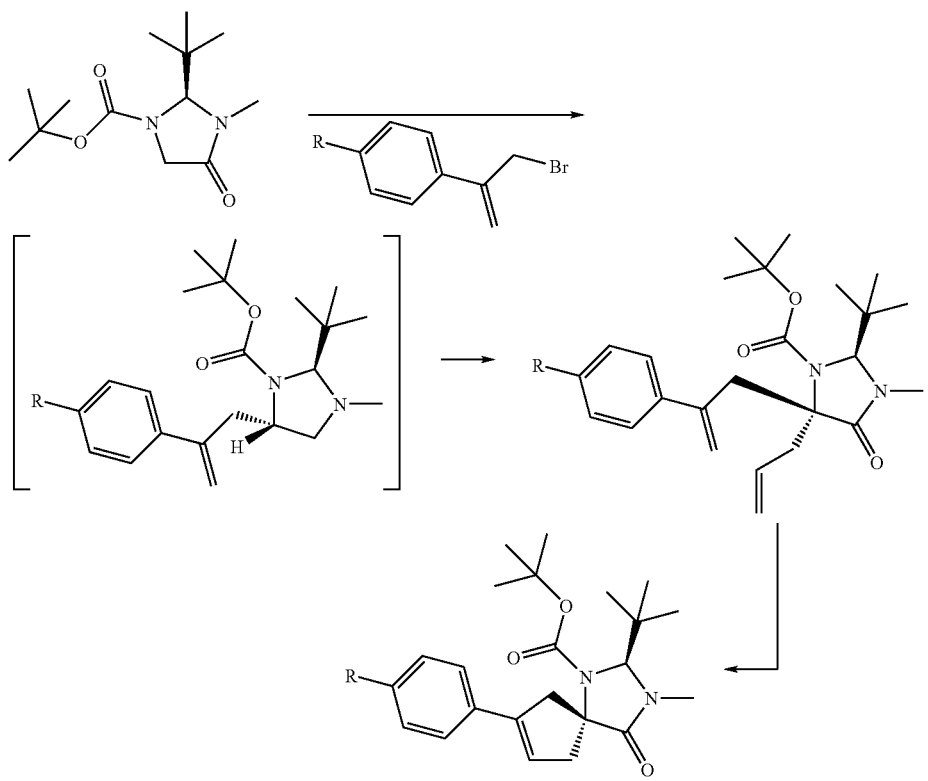

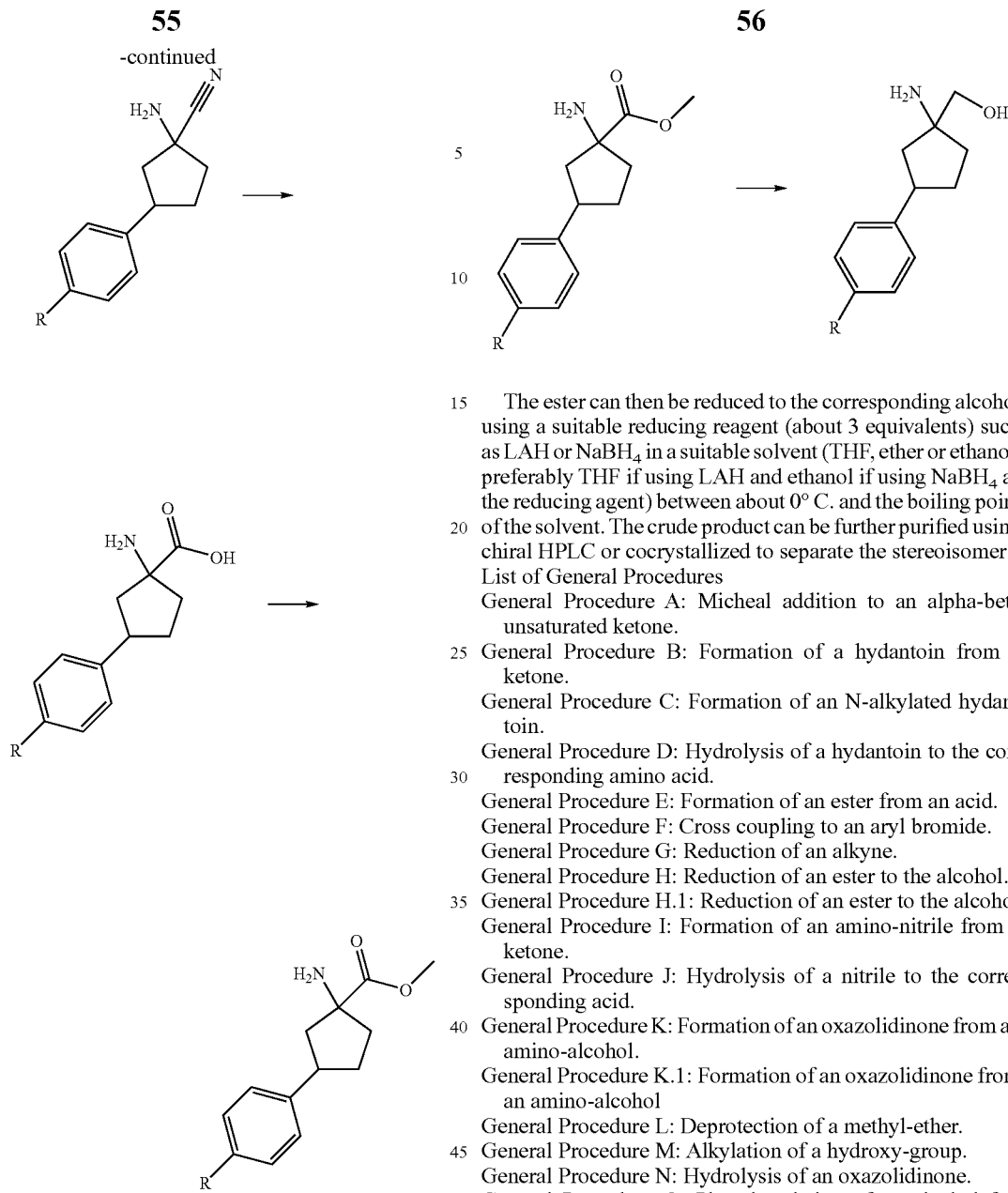

Alternatively, the product can be synthesized in a racemic fashion. A suitably substituted aryl halide such as 1-bromo-4-octyl-benzene can be converted to the corresponding Grignard reagent with magnesium metal then reacted with an electrophilic species such as 3-methoxy-cyclopent-2-enone to generate the corresponding aryl-substituted cyclopentenone. Reduction of the α,β unsaturated system to the corresponding racemic saturated ketone can be accomplished with hydrogen gas over palladium metal or copper hydride for example. The ketone can then be converted to the racemic aminonitrile using ammonia and sodium cyanide for example; or alternatively the ketone isomers can be separated by chiral HPLC and then converted to a chiral amino nitrile using chiral auxiliaries such as a α-substituted chiral benzylic amine or through chiral induction via chiral catalysis. Hydrolysis of the nitrile can be accomplished with strong acid such as concentrated hydrochloric acid. The corresponding acid can be converted to the ester by conversion to the acid chloride using sulfuryl chloride for example followed by reaction with an alcohol such as methanol for example.

The ester can then be reduced to the corresponding alcohol using a suitable reducing reagent (about 3 equivalents) such as LAH or NaBH$_4$ in a suitable solvent (THF, ether or ethanol, preferably THF if using LAH and ethanol if using NaBH$_4$ as the reducing agent) between about 0° C. and the boiling point of the solvent. The crude product can be further purified using chiral HPLC or cocrystallized to separate the stereoisomers.

List of General Procedures

General Procedure A: Micheal addition to an alpha-beta unsaturated ketone.
General Procedure B: Formation of a hydantoin from a ketone.
General Procedure C: Formation of an N-alkylated hydantoin.
General Procedure D: Hydrolysis of a hydantoin to the corresponding amino acid.
General Procedure E: Formation of an ester from an acid.
General Procedure F: Cross coupling to an aryl bromide.
General Procedure G: Reduction of an alkyne.
General Procedure H: Reduction of an ester to the alcohol.
General Procedure H.1: Reduction of an ester to the alcohol
General Procedure I: Formation of an amino-nitrile from a ketone.
General Procedure J: Hydrolysis of a nitrile to the corresponding acid.
General Procedure K: Formation of an oxazolidinone from an amino-alcohol.
General Procedure K.1: Formation of an oxazolidinone from an amino-alcohol
General Procedure L: Deprotection of a methyl-ether.
General Procedure M: Alkylation of a hydroxy-group.
General Procedure N: Hydrolysis of an oxazolidinone.
General Procedure O: Phosphorylation of an alcohol followed by deprotection.
General Procedure P: Hydrolysis of an ester to the acid.
General Procedure Q: Alkylation of phenol
General Procedure R: Reduction of carboxylic acid
General Procedure S: Cbz protection of an amine.
General Procedure T: Cross coupling of an aryl bromide to a boronic acid.
General Procedure U: Hydroboration reaction of an alkene.
General Procedure V: Deprotection of a Cbz group from an amine.
General Procedure W: Synthesis of an alpha-beta unsaturated ketone
General Procedure X: Addition of an organometallic reagent to an ester.
General Procedure Y: Conversion of a tertiary alcohol to an alkane
General Procedure Z: Hydration of an alkyne
General Procedure AA: Synthesis of an alkylether
General Procedure BB: Synthesis of an N-aryl prolinol
General Procedure CC: Oxidation of an alcohol to the ketone General Procedure DD: Reductive Amination on a Ketone
Example of Use of General Procedures The general procedure letter codes constitute a synthetic route to the final product. A worked example of how the route is determined is given below using Example D.2 as a non-limiting illustration. The synthesis of Example D.2 was completed using general procedure H as detailed in Table D, i.e.,

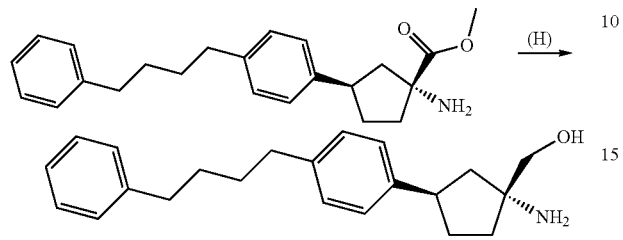

The starting material was prepared using the route (A, B, I, J, E, F, G) (as detailed in Table C). This translates into the following sequence, where the ester starting material used in general procedure H is the product of following the procedures A, I, J, E, F and G, in the given order.

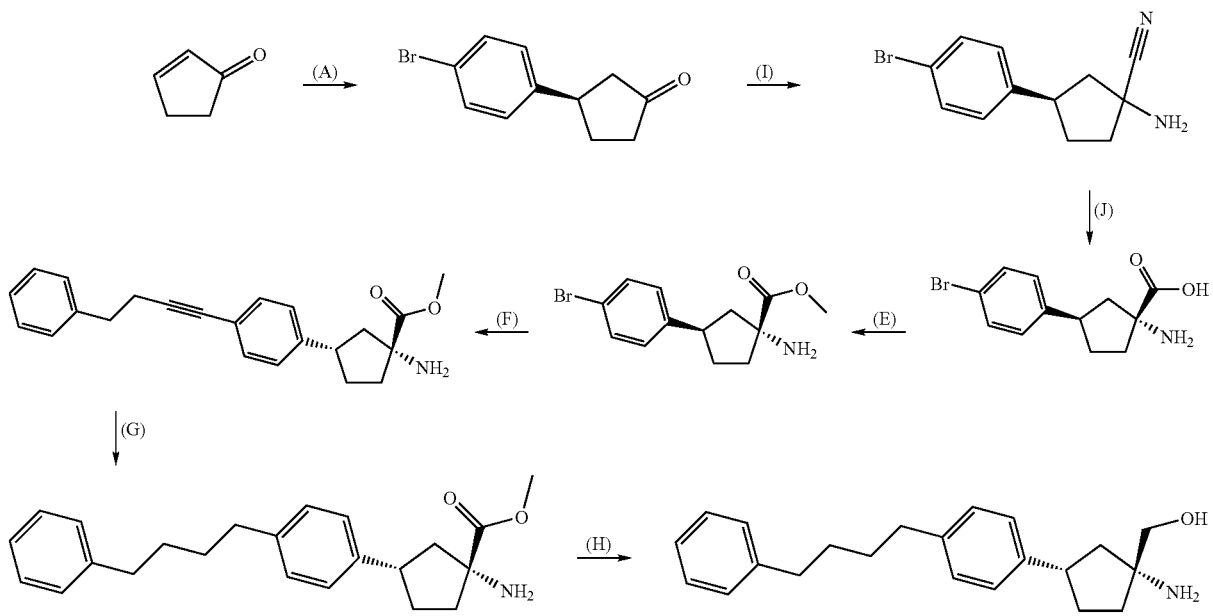

General Procedures

The following describe the synthetic methods illustrated by the foregoing General Procedures schemes and are followed by an example of a compound that was synthesized by the General Procedure. None of the specific conditions and reagents noted in the following are to be construed as limiting the scope of the instant invention and are provided for illustrative purposes only.

General Procedure A: Micheal Addition to an Alpha-Beta Unsaturated Ketone

A solution of substituted phenylboronic acid (1-3 equivalents, preferably 1.5 equivalents) and a rhodium catalyst such as hydroxyl[(S)-BINAP]rodium(I) dimmer, or Rh(acac)(C$_2$H$_4$)$_2$/(R)-BINAP (preferably hydroxyl[(S)-BINAP]rodium(I) dimmer for (S)-product, Rh(acac)(C$_2$H$_4$)$_2$/(R)-BINAP for (R)-product) (1-5 mol %, preferably 1.25 mol %) in an organic solvent (such as tetrahydrofuran, or dioxane) (preferably dioxane) and water is degassed with nitrogen. 2-cyclopenten-1-one is added to the mixture. The reaction is stirred at about 20-100° C. (preferably about 35° C.) for a period of 1-24 hours (preferably about 16 hours) under inert atmosphere. The reaction mixture is concentrated under reduced pressure and the crude product is purified via flash chromatography.

Exemplification of General Procedure A:

Preparation of
(S)-3-(4-bromo-phenyl)-cyclopentanone

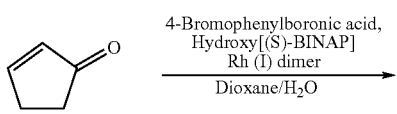

A 3 L three-necked round-bottomed flask equipped with temperature probe and nitrogen bubbler was charged with 4-bromophenylboronic acid (100 g, 498 mmol) and hydroxy[(S)-BINAP]rhodium(I) dimer (6.20 g, 4.17 mmol) in dioxane (1667 µL) and water (167 mL) at room temperature. The resulting suspension was degassed with nitrogen and 2-cyclopenten-1-one (27.8 mL, 332 mmol) was added in one portion. The mixture was further degassed for 5 minutes and heated at 35° C. for about 16 hours. The reaction mixture was cooled to room temperature and concentrated. The brown residue was treated with EtOAc (500 mL) and filtered. The filtrate was washed with a saturated solution of NaHCO$_3$ (500 mL) and brine (500 mL), dried over MgSO$_4$, filtered, and concentrated to afford a dark brown solid. The crude reaction product was purified by silica gel chromatography (1:9 EtOAc:heptane as eluant). Fractions containing product were combined and concentrated to afford (S)-3-(4-bromo-phenyl)-cyclopentanone (70.4 g, 89%, 95% ee as determined by chiral HPLC) as an ivory solid.

LCMS (Table 1, Method a) R$_f$=3.54 min; m/z: poor ionization; $^1$H NMR (400 MHz, DMSO-d$_6$) δ. 7.47 (d, 2H), 7.27 (d, 2H), 3.35 (m, 1H), 2.55 (m, 1H), 2.25 (m, 4H), 1.85 (m, 1H)

General Procedure B: Formation of a Hydantoin from a Ketone

To a mixture of ammonium carbonate (1-10 equivalents, preferably 4.5 equivalents) and a cyanide salt (such as potassium cyanide, or sodium cyanide) (1-3 equivalents, preferably 1.1 equivalents) in water is added a ketone (1 equivalent). The reaction mixture is heated to reflux for a period of 2-40 hours (preferably 16 hours). The reaction mixture is cooled to room temperature and the solid is collected by filtration, washed with water to give the crude product which can be purified by trituration with a suitable solvent.

Exemplification of General Procedure B:

Preparation of (S)-7-(4-bromo-phenyl)-1,3-diaza-spiro[4.4]nonane-2,4-dione

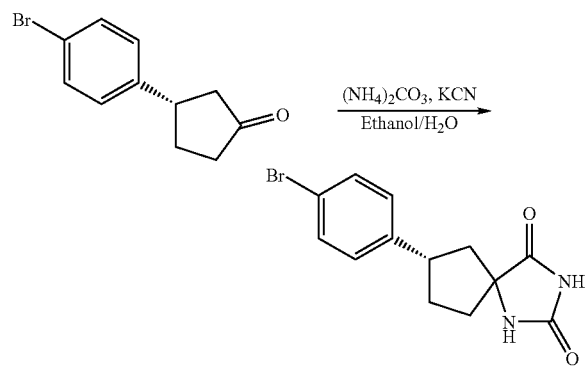

To a round bottom flask charged with ammonium carbonate (268 g, 2.79 mol) and potassium cyanide (44.4 g, 0.681 mol) was added water (1500 mL, 82 mol). The mixture was heated at 80° C. and a solution of (S)-3-(4-bromo-phenyl)-cyclopentanone (148.09 g, 0.62 mol) in ethanol (1500 mL, 25 mol) was added. The reaction mixture was heated to reflux overnight. The reaction mixture was cooled to room temperature. The crude reaction mixture was filtered and washed with water. The solid was triturated with ether (1.5 L), filtered, washed with ether and dried under vacuum to yield (S)-7-(4-bromo-phenyl)-1,3-diaza-spiro[4.4]nonane-2,4-dione (181.29 g, 95%) as a 1:1 mixture of diastereomers.

LCMS (Table 1, Method a) R$_f$=2.24 min; m/z: 307 (M–H)$^-$; $^1$H NMR (400 MHz, DMSO-d$_6$) δ 10.61 (s, 1H), 8.29 (s, 1H), 8.24 (s, 1H), 7.49 (d, 2H), 7.27 (d, 1H), 7.24 (d, 1H), 3.14-3.35 (m, 1H), 2.45 (dd, 0.5H), 1.68-2.27 (m, 5.5H)

General Procedure C: Formation of an N-Alkylated Hydantoin

To s flask containing the hydantoin (1 equivalent) is added a base (such as potassium carbonate, or sodium carbonate) (1-3 equivalents, preferably 1.5 equivalents) and an organic solvent (such as DMF, or DMA) (preferably DMF). The mixture is stirred at room temperature for a period of 10-30 minutes (preferably about 15 minutes), then methyl iodide (1-2 equivalents, preferably 1.1 equivalents) is added. The reaction is stirred at room temperature for a period of 24-72 hours (preferably about 48 hours). The reaction mixture is concentrated, cooled down with ice-water bath and water is added. The precipitate is collected by filtration to give the crude product. The two stereoisomers can be separated by crystallization.

Exemplification of General Procedure C:

Preparation of (5R,7S)-7-(4-bromo-phenyl)-3-methyl-1,3-diaza-spiro[4.4]nonane-2,4-dione

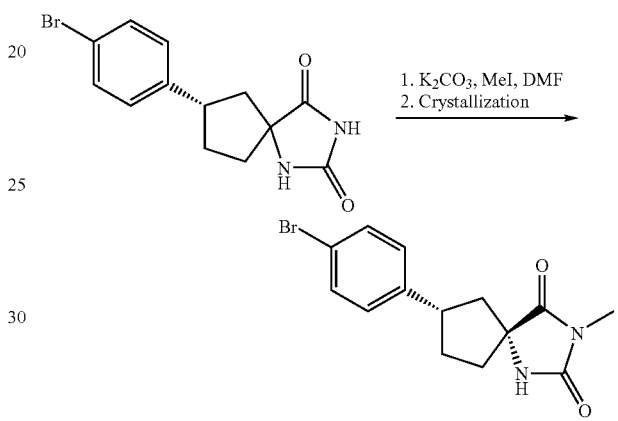

To the flask containing (S)-7-(4-Bromo-phenyl)-1,3-diaza-spiro[4.4]nonane-2,4-dione (1:1 mixture of diastereomers, 180.3 g, 0.583 mol) was added potassium carbonate (120.9 g, 0.875 mol) followed by DMF (1 L). After stirring for 15 minutes at room temperature, methyl iodide (39.9 mL, 0.642 mol) was added in one portion. The reaction was stirred at room temperature for about 48 hours. The reaction mixture was partially concentrated in vacuo at 25° C., removing approximately 400 mL of DMF and excess methyl iodide. The crude mixture was cooled with an ice water bath and water (2 L) was added. After stirring for 1 hour the resulting white precipitate was filtered and rinsed with water (1 L). The filter cake was dried on house vacuum overnight to give 220 g crude (S)-7-(4-Bromo-phenyl)-3-methyl-1,3-diaza-spiro [4.4]nonane-2,4-dione as a mixture of diastereomers.

The two diastereomers can be separated by crystallization as follows: The material was separated into 2 batches of 110 g each. The crude material (110 g) was suspended in ACN (2.5 L), heated to 70° C. until near complete dissolution occurred. The material was filtered rapidly at 70° C. and rinsed with 70° C. ACN (2×500 mL). The combined filtrates were reheated to about 65° C. with stirring. After a clear solution was obtained the mixture was allowed to cool slowly to 50° C. at which point material began to drop out of solution. The solution was allowed to slowly cool to 30° C. with stirring (100 rpm). After aging for 2 hours the solution was filtered and the solid was dried at 65° C. under house vacuum for three hours to give (5R,7S)-7-(4-bromo-phenyl)-3-methyl-1,3-diaza-spiro[4.4]nonane-2,4-dione (22.2 g, 12%). (Note: During an attempt to recrystallize from acetonitrile, a mixture of the N-methyl hydantoins enriched in the (S,S)-diastereomer (2:1 (S,S):(R, S)), a small amount of the (5S, 7S)-7-(4-bromo-phenyl)-3-methyl-1,3-diaza-spiro[4.4]nonane-2,4-dione (40 mg) in pure form was isolated.)

LCMS (Table 1, Method a) R$_t$=2.50 min; m/z: 321 (M−H)$^-$; $^1$H NMR (400 MHz, DMSO-d$_6$) δ 8.56 (s, 1H), 7.50 (d, 2H, J=8.42 Hz), 7.27 (d, 2H, J=8.53 Hz), 3.16-3.31 (m, 1H), 2.84 (s, 3H), 2.46 (dd, 1H, J=13.62, 8.40 Hz), 2.02-2.18 (m, 2H), 1.72-1.95 (m, 3H)

General Procedure D: Hydrolysis of a Hydantoin to the Corresponding Amino Acid

To a suspension of N-alkylated hydantoin (1 equivalent) in water is added dioxane and an inorganic base (such as lithium hydroxide, or sodium hydroxide) (5-15 equivalents, preferably about 8-10 equivalents). The mixture is heated to reflux for a period of 16-48 hours (preferably 24 hours). After cooling to room temperature, the reaction mixture is acidified, and filtered. The filter cake is washed with a suitable solvent and dried under vacuum to give the corresponding amino acid.

Exemplification of General Procedure D:

Preparation of (1R,3S)-1-amino-3-(4-bromo-phenyl)-cyclopentanecarboxylic acid

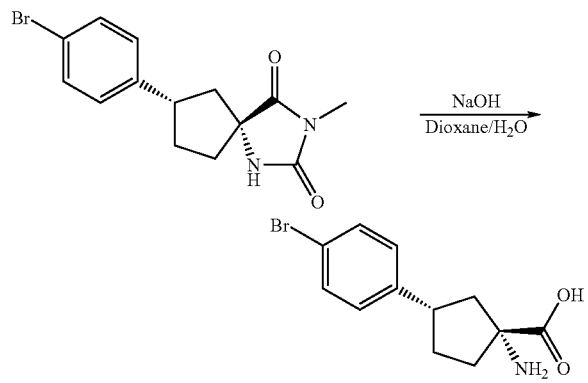

To a slurry of (5R,7S)-7-(4-bromo-phenyl)-3-methyl-1,3-diaza-spiro[4.4]nonane-2,4-dione (79 g, 0.24 mol) in water (1 L) was added 2 M aqueous NaOH (1 L, 2 mol) and dioxane (200 mL). The resulting mixture was heated to reflux for 24 hours. The reaction mixture was cooled to room temperature, diluted with water (2 L) and acidified with concentrated HCl until a precipitate began to form (about pH 7). Acetic acid (about 20 mL) was added, producing a thick precipitate. The white precipitate was collected and washed with water (2×1 L) and EtOAc (1 L). The filter cake was suspended in toluene (1 L) and concentrated in vacuo at 45° C. This process was repeated once more. The white precipitate was dried to a constant weight under vacuum to give (1R,3S)-1-amino-3-(4-bromo-phenyl)-cyclopentanecarboxylic acid (65 g, 95%).

LCMS (Table 1, Method a) R$_t$=1.56 min; m/z: 284/286 (M+H)$^+$; $^1$H NMR (400 MHz, DMSO-d$_6$) δ 7.55 (d, 2H), 7.3 (d, 2H), 3.3 (m, 1H), 2.65 (m, 1H), 2.3 (m, 1H), 2.1-2.2 (m, 2H), 2.0-2.1 (m, 1H), 1.85 (t, 1H)

General Procedure E: Formation of a Ester from an Acid

An acid (1 equivalent) suspended in large excess of methanol is cooled in an ice/water bath and thionyl chloride (5-20 equivalents, preferably 8-12 equivalents) is added dropwise. The resulting mixture is heated to reflux for a period of 2-48 hours (preferably 24-36 hours). The reaction mixture is cooled to room temperature, filtered and concentrated to dryness. The residue is triturated with a suitable solvent (such as EtOAc, or ether) and dried under vacuum to give the desired product.

Exemplification of General Procedure E:

Preparation of (1R,3S)-1-amino-3-(4-bromo-phenyl)-cyclopentanecarboxylic acid methyl ester; hydrochloride

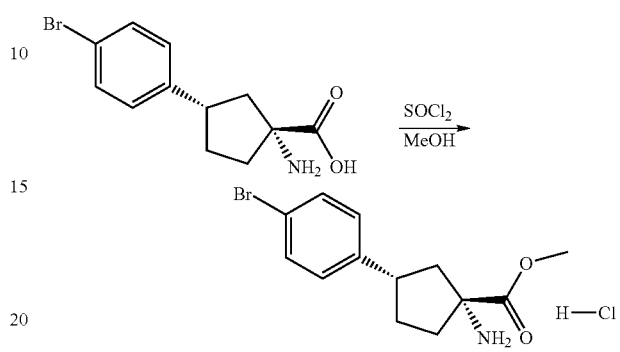

The (1R,3S)-1-amino-3-(4-bromo-phenyl)-cyclopentanecarboxylic acid (79 g, 0.28 mol) suspended in MeOH (1.8 L) was cooled in an ice/water bath and thionyl chloride (178 mL, 2.44 mol) was added dropwise. Following the addition the reaction was heated to reflux, resulting in a nearly homogeneous solution. After refluxing for about 36 hours, the reaction mixture was cooled to room temperature, filtered, and rinsed with MeOH (2×200 mL). The filtrate was concentrated in vacuo to provide a white solid. The white solid was triturated with EtOAc (1 L), collected by filtration, rinsed with EtOAc (2×500 mL), and dried under vacuum to give the (1R,3S)-1-amino-3-(4-bromo-phenyl)-cyclopentanecarboxylic acid methyl ester; hydrochloride as a white solid (79 g, 96%).

$^1$H NMR (400 MHz, DMSO-d$_6$) δ 7.55 (d, 2H), 7.35 (d, 2H), 3.82 (s, 3H), 3.3 (m, 1H), 2.65 (m, 1H), 2.3 (m, 1H), 2.1-2.2 (m, 3H), 1.95-2.05 (t, 1H)

General Procedure F: Cross Coupling to an Aryl Bromide

To a flask charged with an aryl bromide (1 equivalent), an alkyne compound (1.1-10 equivalents, preferably 2-6 equivalents), triphenylphosphine (0-10 mol %, preferably 10 mol %), an organic or inorganic base (such as cesium carbonate, piperidine, diethylamine or triethylamine) (preferably piperidine) (3-8 equivalents, preferably 4-6 equivalents) is added an organic solvent such as acetonitrile, tetrahydrofuran, dioxane or DMF (preferably tetrahydrofuran). The mixture is degassed before adding a palladium catalyst (such as tetrakis (triphenylphosphine)palladium, 2-dicyclohexylphosphino-2',4',6'-triisopropylbiphenyl or bis(triphenylphosphine)palladium(II) chloride) (2-10 mol %, preferably 5 mol %) and copper(I) iodide (1-10 mol %, preferably 2-5 mol %). The reaction mixture is heated at about 45-110° C. (preferably about 60° C.-90° C.) for a period of about 4-48 hours (preferably about 24-36 hours) under inert atmosphere. During the reaction, more alkyne compound (1-8 equivalents, preferably 2-4 equivalents) is added in portions to the reaction mixture to drive the reaction to completion. Upon completion of the reaction, the mixture is concentrated to dryness, dissolved in a suitable organic solvent (such as EtOAc, or DCM), and washed with a saturated aqueous solution of NaHCO$_3$, dried over an appropriate drying reagent (such as MgSO$_4$, or Na$_2$SO$_4$) and concentrated to dryness to give the crude product. The crude product can be purified via flash chromatography or co-crystallization.

Exemplification of General Procedure F:

Preparation of (1R,3S)-methyl 1-amino-3-(4-(7-methoxyhept-1-ynyl)phenyl)cyclopentanecarboxylate

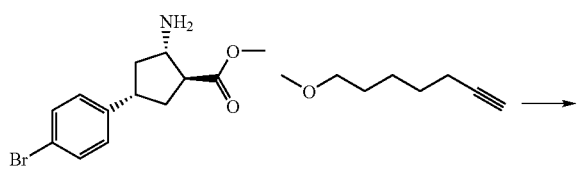

To a 50 mL round bottomed flask equipped with a reflux condenser was charged successively (1R,3S)-methyl 1-amino-3-(4-bromophenyl)cyclopentanecarboxylate hydrochloride salt (0.500 g, 1.494 mmol), trans-bis(benzonitrile)dichloropalladium(II) (0.029 g, 0.075 mmol), 2-dicyclohexylphosphino-2',4',6'-triisopropylbiphenyl (0.107 g, 0.224 mmol), and cesium carbonate (1.947 g, 5.98 mmol). The flask was evacuated and back-filled with nitrogen for three cycles. Then 7-methoxyhept-1-yne (1.16 g, 9.19 mmol) as a solution in acetonitrile (7.0 ml) was added via syringe. The reaction mixture was heated to about 90° C. After about 4 hours the reaction mixture was cooled to ambient temperature and partitioned into water (50 mL) and ethyl acetate (50 mL). The organic phase was separated, washed with saturated sodium bicarbonate solution (50 mL), brine (50 mL), then dried (MgSO$_4$) and concentrated to yield 1.98 g of crude yellow oil. The crude material was purified via Analogix flash chromatography system using RediSep RS 12 g column, with a gradient of 0-5% methanol in ethyl acetate over 25 min. at 15 mL/min. Fractions containing product were combined and concentrated to yield 0.5 g of greenish yellow oil of (1R,3S)-methyl 1-amino-3-(4-(7-methoxyhept-1-ynyl)phenyl)cyclopentanecarboxylate which was used in the next step without further purification.

LCMS (Table 1, Method a) R$_t$=2.09 min; m/z: 344 (M+H)$^+$.

Preparation of (1R,3R)-1-amino-3-[4-(5-phenyl-pent-1-ynyl)-phenyl]-cyclopentanecarboxylic acid methyl ester;

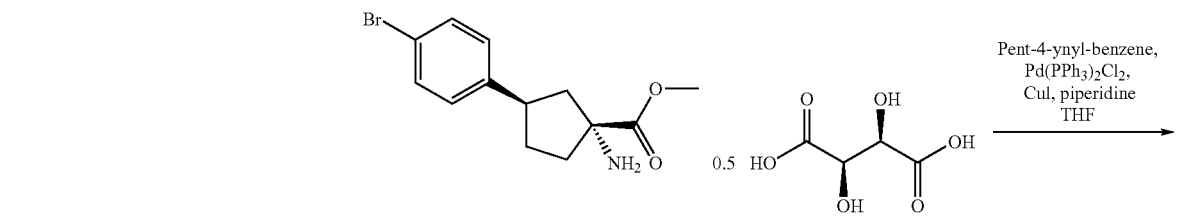

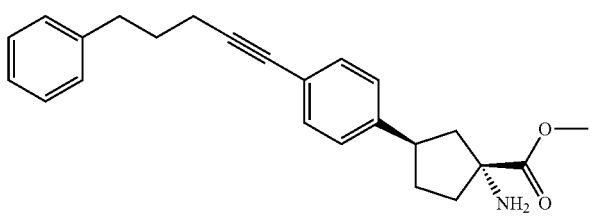

A round bottomed flask was charged with (1R,3R)-methyl 1-amino-3-(4-bromophenyl)cyclopentanecarboxylate, 0.5 L-tartaric acid 2 (1.0 g, 2.68 mmol), copper(I) iodide (5.10 mg, 0.027 mmol), bis(triphenylphosphine)palladium (11) dichloride (0.094 g, 0.134 mmol) and THF (10 mL). The reaction solution was purged with nitrogen. After 15 min piperidine (1.194 mL, 12.06 mmol) and pent-4-ynylbenzene (0.386 g, 2.68 mmol) were added and the reaction mixture was heated to about 65° C. After about 4 hours additional pent-4-ynylbenzene (0.386 g, 2.68 mmol) was added. After about 15 hours the reaction mixture was cooled to about room temperature and partitioned between ethyl acetate and saturated sodium bicarbonate. The organic layer was washed with brine and purified by chromatography on silica gel. The fractions containing the desired product were combined and concentrated in vacuo. The brown oil was diluted with ether (20 mL) and a solution of 1N HCl in ether (4 mL) was added. The solution was concentrated in vacuo to provide (1R,3R)-methyl 1-amino-3-(4-(5-phenylpent-1-ynyl)phenyl)cyclopentanecarboxylate, Hydrochloric Acid (1 g, 2.51 mmol, 94% yield) as a brown foam.

LCMS (Table 1, Method a) $R_t$=2.91 min; m/z: 362 (M+H)$^+$.

Preparation of (1R,3R)-methyl 1-amino-3-(4-(6-methoxyhex-1-ynyl)phenyl)cyclopentanecarboxylate, L-tartaric acid

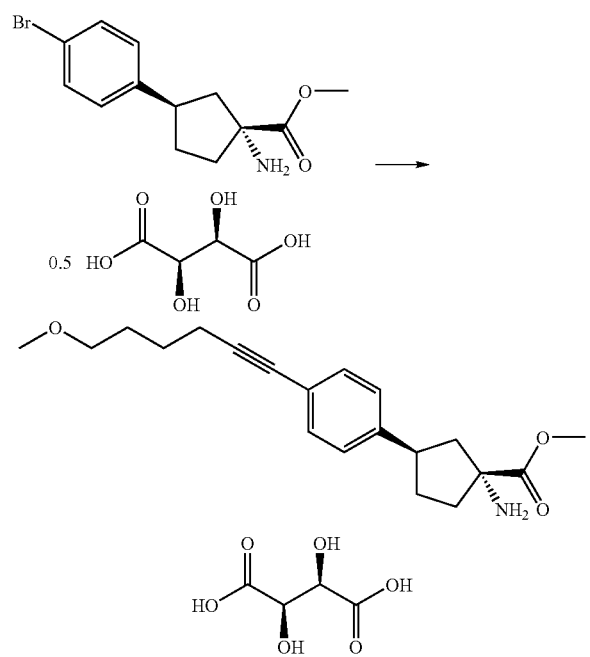

A round bottomed flask was charged with copper (1) iodide (0.102 g, 0.536 mmol), bis(tripheynlphosphine)palladium(II) dichloride (1.128 g, 1.608 mmol), and (1R,3R)-methyl 1-amino-3-(4-bromophenyl)cyclopentanecarboxylate, 0.5 L-tartaric acid 2 (20 g, 53.6 mmol) (that had been free based by partitioning between EtOAc and saturated NaHCO$_3$. The organic layer was separated, dried (NaSO$_4$), filtered and concentrated) THF (150 mL) was added and the reaction mixture was purged with nitrogen. After 5 min piperidine (23.88 mL, 241 mmol) and 7-methoxyhept-1-yne (6.0 g, 54 mmol) was added. The reaction mixture was heated to about 65° C. After about 8 hours additional 7-methoxyhept-1-yne (3.1 g, 27 mmol) was added. After about 20 hours total the reaction mixture was cooled to about room temperature and partitioned between EtOAc/NaHCO$_3$. The organic layer was separated dried (Na$_2$SO$_4$) filtered and concentrated. The crude mixture was purified by chromatography on silica gel (eluting with EtOAc/MeOH). The fractions containing the desired product were concentrated in vacuo. The dark brown oil was dissolved in MeOH (50 mL) and a solution of (2R,3R)-2,3-dihydroxysuccinic acid (9.65 g, 64.3 mmol) in MeOH (15 mL) was added. The solution was concentrated in vacuo and the resulting solid was slurried in isopropyl alcohol (approx 100 mL), filtered and dried in vacuo to provide (1R,3R)-methyl 1-amino-3-(4-(6-methoxyhex-1-ynyl)phenyl)cyclopentanecarboxylate, L-tartaric acid (25 g, 52.1 mmol, 97% yield) as a colorless solid.

LCMS (Table 1, Method a) $R_t$=1.81 min; m/z: 330 (M+H)$^+$.

Preparation of (1R,3R)-methyl 1-amino-3-(4-(3-(benzyloxy)prop-1-ynyl)phenyl)cyclopentanecarboxylate

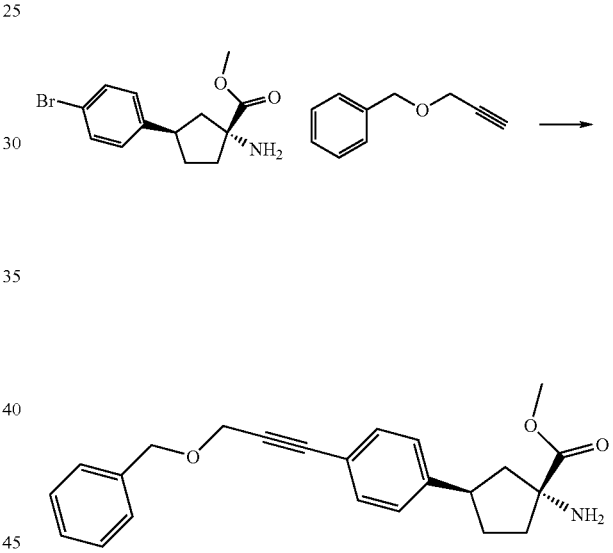

A round bottomed flask was charged with (1R,3R)-methyl 1-amino-3-(4-bromophenyl)cyclopentanecarboxylate, 0.5 L-tartaric acid 2 (30 g, 80 mmol), copper(I) iodide (0.153 g, 0.804 mmol), bis(triphenylphosphine)palladium(II) dichloride (2.82 g, 4.02 mmol) and THF (200 mL). The reaction mixture was purged with nitrogen. After about 15 minutes piperidine (35.8 mL, 362 mmol) and ((prop-2-ynyloxy)methyl)benzene (11.75 g, 80 mmol) were added and the reaction mixture was heated to about 65°. After about 2 hours additional (prop-2-ynyloxy)methyl)benzene (11.75 g, 80 mmol) was added. After about 8 hours the crude reaction mixture was partitioned between EtOAc and saturated NaHCO$_3$. The organic layer was washed with brine, dried (Na$_2$SO$_4$) filtered, concentrated in vacuo and purified by flash chromatography on silica gel (eluting with EtOAC/Heptane followed by EtOAc/MeOH) to provide (1R,3R)-methyl 1-amino-3-(4-(3-(benzyloxy)prop-1-ynyl)phenyl)cyclopentanecarboxylate (25 g, 68.8 mmol, 86% yield) as a brown oil.

LCMS (Table 1, Method a) $R_t$=2.61 min; m/z: 364 (M+H)$^+$.

Preparation of (1R,3S)-1-amino-3-(4-prop-1-ynyl-phenyl)-cyclopentanecarboxylic acid methyl ester; compound with (2R,3R)-2,3-dihydroxy-succinic acid

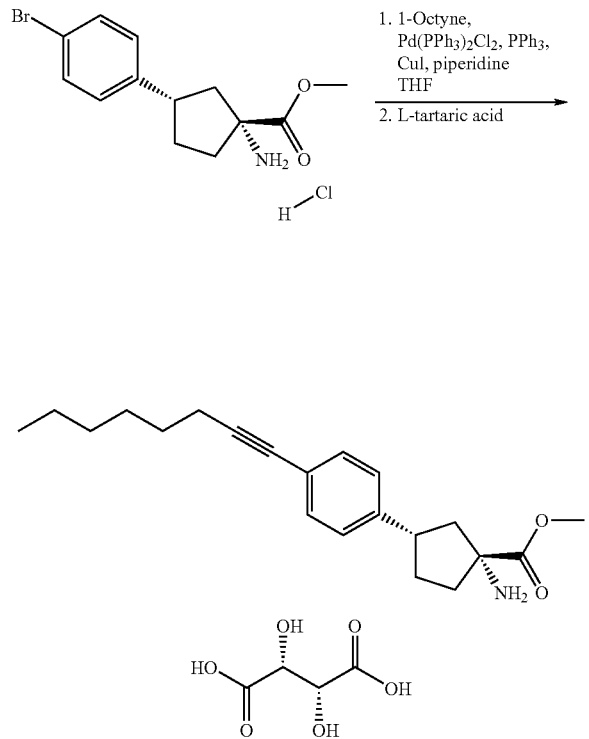

To a two-neck round bottom flask was added (1R,3S)-1-amino-3-(4-bromo-phenyl)-cyclopentanecarboxylic acid methyl ester; hydrochloride (3.94 g, 0.0118 mol), 1-octyne (3.48 mL, 0.0235 mol), triphenylphosphine (0.309 g, 0.00118 mol), piperidine (6.99 mL, 0.0706 mol), and THF (100 mL, 1 mol). The mixture was degassed, and Pd(PPh$_3$)$_2$Cl$_2$ (0.41 g, 0.00059 mol) was added and the mixture was stirred for a few minutes under an atmosphere of nitrogen before addition of the copper(I) iodide (0.11 g, 0.00059 mol). The reaction was stirred under an atmosphere of nitrogen at 60° C. for 2 hours. More 1-octyne (12 mL, 0.081 mmol) was added in 3 portions. The reaction mixture was heated at 60° C. for a total of about 36 hours. The solvent was then removed and crude material was partitioned between EtOAc and saturated NaHCO$_3$. The aqueous layer was back-extracted once with EtOAc. Organic layers were combined, dried over MgSO$_4$ and the solvent was removed under reduced pressure. The residue was purified by silica gel chromatography using 1 L of EtOAc followed by 1 L of 2% MeOH in EtOAc to give 3.38 g crude product as a yellow oil. The crude product was dissolved in minimum amount of MeOH, to which L-tartaric acid (1.69 g) in MeOH was added. Ether was then added dropwise until solution just turned turbid. The mixture was left to crystallize. The solid was collected by filtration, washed with ether to give 3.91 g (72.6%) (1R,3S)-1-amino-3-(4-prop-1-ynyl-phenyl)-cyclopentanecarboxylic acid methyl ester; compound with (2R,3R)-2,3-dihydroxy-succinic acid.

(Tartrate salt) LCMS (Table 1, Method b) R$_t$=2.17 min; m/z: 328 (M+H)$^+$; $^1$H NMR (400 MHz, DMSO-d$_6$) δ 7.30 (m, 2H), 7.24 (m, 2H), 4.4 (s, 2H), 3.89 (m, 3H), 3.42 (m, 1H), 2.7 (m, 1H), 2.46 (m, 1H), 2.39 (m, 2H), 2.22 (m, 1H), 2.15 (m, 1H), 2.05 (m, 1H), 1.95 (m, 1H), 1.55 (m, 2H), 1.45 (m, 2H), 1.33 (m, 4H), 0.9 (m, 3H).

Gram Scale Preparation of (1R,3R)-1-amino-3-(4-prop-1-ynyl-phenyl)-cyclopentanecarboxylic acid methyl ester; Compound with (2R,3R)-2,3-dihydroxy-succinic acid

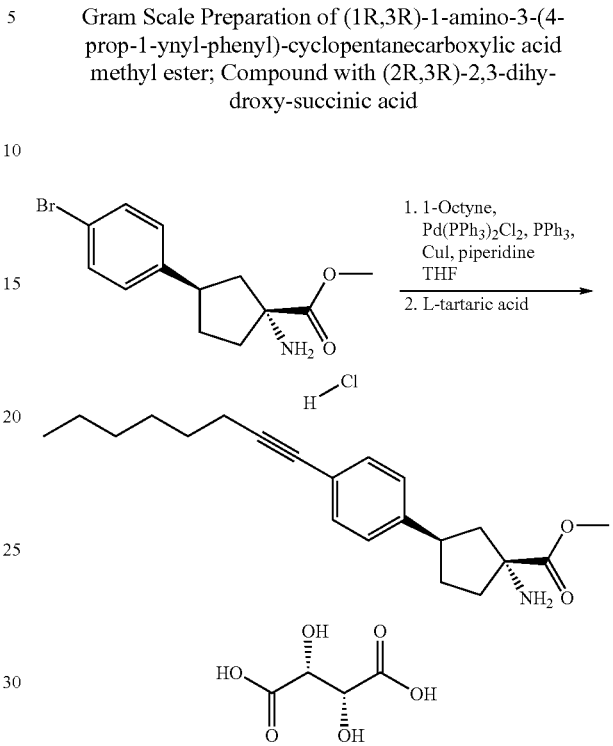

To a three-neck round bottom flask was added (1R,3R)-1-amino-3-(4-bromo-phenyl)-cyclopentanecarboxylic acid methyl ester; hydrochloride (4.00 g, 12.0 mmol), 1-octyne (3.54 mL, 24.0 mmol), triphenylphosphine (314 mg, 1.20 mmol), piperidine (7.13 ml, 72.0 mmol), and THF (100 mL). The mixture was degassed, and Pd(PPh$_3$)$_2$Cl$_2$ (421 mg, 0.60 mmol) was added and the mixture was stirred for a few minutes under an atmosphere of nitrogen before addition of the copper(I) iodide (114 mg, 0.60 mmol). The reaction was stirred under an atmosphere of nitrogen at 60° C. for 4 hours. More 1-octyne (5.31 mL, 36.0 mmol) was added in two portions and the reaction mixture was heated at 60° C. for a total of about 30 hours. The solvent was then removed and crude material was partitioned between EtOAc and saturated NaHCO$_3$. The aqueous layer was back-extracted once with EtOAc. Organic layers were combined, dried over MgSO$_4$ and the solvent was removed under reduced pressure. The residue was purified by silica gel chromatography using 1 L of EA followed by 1 L of 2% MeOH in EtOAc to give 3.52 g (90%) crude product as a yellow oil. A portion of the crude product (60.0 mg, 0.126 mmol) was dissolved in minimum amount of MeOH, to which L-tartaric acid (1.69 g) in MeOH was added. Ether was then added dropwise until solution just turned turbid. The mixture was left to crystallize. The solid was collected by filtration, washed with ether to give 45.0 mg (60%) (1R,3R)-1-amino-3-(4-prop-1-ynyl-phenyl)-cyclopentanecarboxylic acid methyl ester; compound with (2R,3R)-2,3-dihydroxy-succinic acid.

General Procedure G: Reduction of an Alkyne

To a reaction vessel charged with palladium hydroxide on carbon (10-30% by weight, preferably 20% by weight) is added an organic solvent (preferably acetic acid, ethanol or methanol) and an alkyne compound (1 equivalent). The reaction mixture is evacuated, back-filled with nitrogen followed by two cycles of evacuating and back-filling with hydrogen gas. The reaction is continued for a period of about 0.5-24 hours (preferably about 1 hour). The crude mixture is filtered, washed with a suitable solvent such as ethanol, and concentrated. The residue can be purified by crystallization with ethanol/water mixture to give the desired product.

Exemplification of General Procedure G:

Preparation of (1R,3S)-methyl 1-amino-3-(4-(7-methoxyheptyl)phenyl)cyclopentanecarboxylate

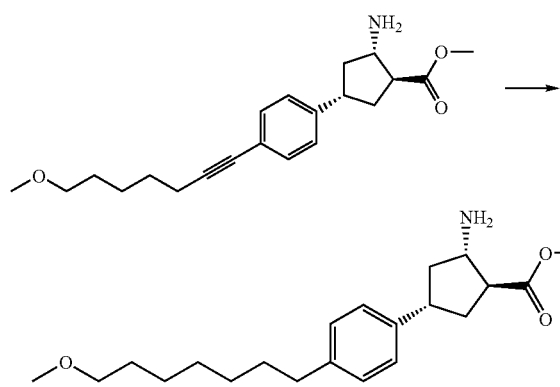

(1R,3S)-methyl 1-amino-3-(4-(7-methoxyhept-1-ynyl)phenyl)cyclopentanecarboxylate was taken up in ethanol (14.94 ml). To this was added Pearlman's Catalyst (0.052 g, 0.075 mmol) and the mixture was stirred at ambient temperature under the atmosphere of hydrogen. After about 15 hours, the reaction mixture was filtered through Celite® and the filtrate was concentrated in vacuo to yield (1R,3S)-methyl 1-amino-3-(4-(7-methoxyheptyl)phenyl)cyclopentanecarboxylate (0.48 g, 1.38 mmol) as dark green oil.

$^1$H NMR (400 MHz, CD$_3$OD) δ ppm 7.24-7.05 (dd, 4H), 3.76 (s, 3H), 3.42-3.34 (m, 2H), 3.31 (s, 3H), 3.27-3.17 (m, 1H), 2.65-2.52 (m, 3H), 2.25 (ddd, J=12.87, 11.07, 7.19 Hz, 1H), 2.12-1.92 (m, 2H), 1.83 (ddd, J=12.85, 7.59, 2.25 Hz, 1H), 1.66 (dd, J=13.26, 11.31 Hz, 1H), 1.62-1.49 (m, 4H), 1.42-1.22 (m, 6H).

Preparation of (1R,3R)-methyl 1-amino-3-(4-(6-methoxyhexyl)phenyl)cyclopentanecarboxylate, L-tartaric acid

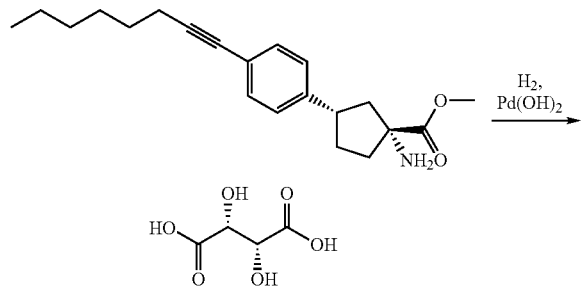

To a slurry of palladium hydroxide on carbon (1.867 g, 2.66 mmol) in MeOH (250 mL) was added a solution of (1R,3R)-methyl 1-amino-3-(4-(6-methoxyhex-1-ynyl)phenyl)cyclopentanecarboxylate, L-tartaric Acid 2 (25.5 g, 53.2 mmol) in MeOH (50 mL). The reaction mixture was purged with hydrogen and an atmosphere of hydrogen was maintained via balloon. After about 15 hours the reaction mixture was filtered through Celite® and concentrated in vacuo to provide (1R,3R)-methyl 1-amino-3-(4-(6-methoxyhexyl)phenyl)cyclopentanecarboxylate, L-tartaric acid 2 (25.6 g, 52.9 mmol, 100% yield) as a colorless solid.

LCMS (Table 1, Method a) R$_t$=1.81 min; m/z: 334 (M+H)$^+$.

Preparation of (5R,7R)-7-(4-(3-hydroxypropyl)phenyl)-3-oxa-1-azaspiro[4.4]nonan-2-one

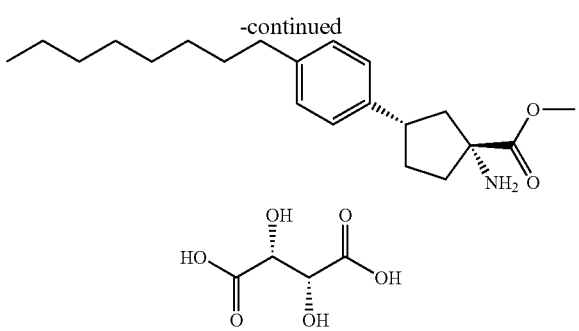

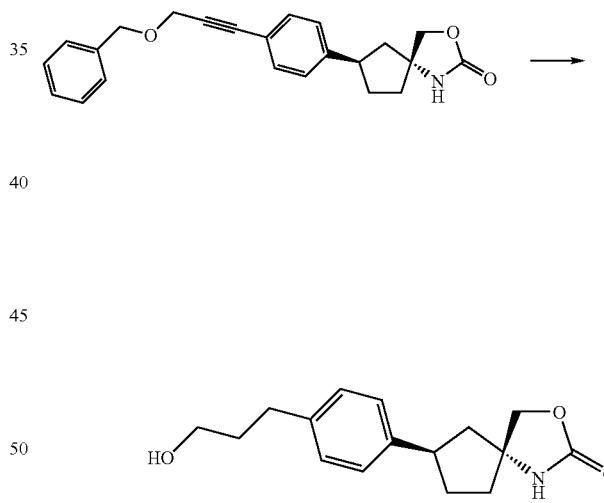

To a suspension of palladium hydroxide on carbon (0.583 g, 0.830 mmol) in MeOH (250 mL) was added a solution of (5R,7R)-7-(4-(3-(benzyloxy)prop-1-ynyl)phenyl)-3-oxa-1-azaspiro[4.4]nonan-2-one (20 g, 41.5 mmol) in MeOH (10 mL). Hydrogen was bubbled through the solution for about 10 minutes and an atmosphere of hydrogen was maintained via balloon. After about 15 hours the reaction mixture was filtered through Celite® and concentrated in vacuo. The crude product was purified by chromatography on silica gel (EtOAc/DCM) to provide (5R,7R)-7-(4-(3-hydroxypropyl)phenyl)-3-oxa-1-azaspiro[4.4]nonan-2-one (5.2 g, 18.89 mmol, 45.5% yield) as a colorless solid.

LCMS (Table 1, Method a) R$_t$=2.39 min; m/z: 393 (M+NH$_4$)$^+$.

Preparation of (1R,3S)-1-amino-3-(4-octyl-phenyl)-cyclopentanecarboxylic acid methyl ester

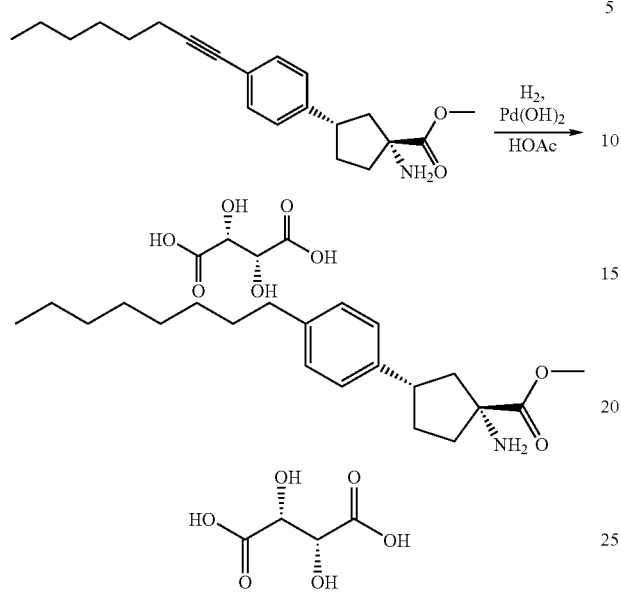

185 mg of palladium hydroxide on carbon (20% by weight) and acetic acid (25 mL, 0.44 mol) were loaded into a Parr shaker. (1R,3S)-1-Amino-3-(4-oct-1-ynyl-phenyl)-cyclopentanecarboxylic acid methyl ester; compound with (2R,3R)-2,3-dihydroxy-succinic acid (2.49 g, 0.00521 mol) was added and the reaction was evacuated, back-filled with nitrogen, followed by two cycles of evacuating and back-filling with hydrogen gas. The reaction was then pressurized to about 50 psi using hydrogen. The reaction was shaken at room temperature for about 50 minutes. The crude mixture was filtered through Celite® and washed with ethanol. The filtrate was concentrated, and the residue was brought up in a small amount of ethanol. Water was added. The mixture was nearly clear. The ethanol was removed under reduced pressure, and the remaining aqueous solution was left to stand. After a few minutes, needle-like crystals began to form. More water was added, and the mixture left to crystallize. The white solid was collected by filtration, and washed with water three times. The white solid was freeze-dried to remove remaining water. 1.9 g (90%) of (1R,3S)-1-amino-3-(4-octyl-phenyl)-cyclopentanecarboxylic acid methyl ester; compound with 0.5 equivalent of (2R,3R)-2,3-dihydroxy-succinic acid was obtained as fluffy white solid.

(½ Tartrate salt) LCMS (Table 1, Method b) $R_t$=2.56 min; m/z: 332 (M+H)$^+$; $^1$H NMR (400 MHz, DMSO-$d_6$) δ 7.2 (m, 2H), 7.1 (m, 2H), 4.35 (s, 1H), 3.86 (s, 3H), 3.33 (m, 1H), 2.67 (m, 1H), 2.57 (m, 2H), 2.4 (m, 1H), 2.19 (m, 1H), 2.13 (m, 2H), 1.95 (m, 1H), 1.59 (m, 2H), 1.3 (m, 10H), 0.9 (m, 3H)

General Procedure H: Reduction of an Ester to the Alcohol

A substituted 1-amino-cyclopentanecarboxylic acid methyl ester dissolved in a suitable solvent (such as tetrahydrofuran or ether) is cooled to below room temperature (about 0-10° C., preferably about 0° C.). To this solution is added slowly a reducing reagent such as LAH (1-5 equivalents, preferably 3 equivalents). Alternatively, the order of addition can be reversed. The reaction mixture is stirred for a period of about 0.5-6 hours (preferably about 0.5-2 hours). The reaction mixture is worked up by successive addition of water (1-15 equivalents, preferably 6.5 equivalents), 2 M NaOH solution (0.05-1 equivalents, preferably 0.25 equivalents), and water (1-30 equivalents, preferably 13 equivalents). After stirring for a period of about 1-24 hours (preferably 2 hours), $Na_2SO_4$ is added and the precipitate is filtered off.

Exemplification of General Procedure H:

Preparation of ((1R,3S)-1-amino-3-(4-(7-methoxy-heptyl)phenyl)cyclopentyl)methanol, Hydrochloric Acid

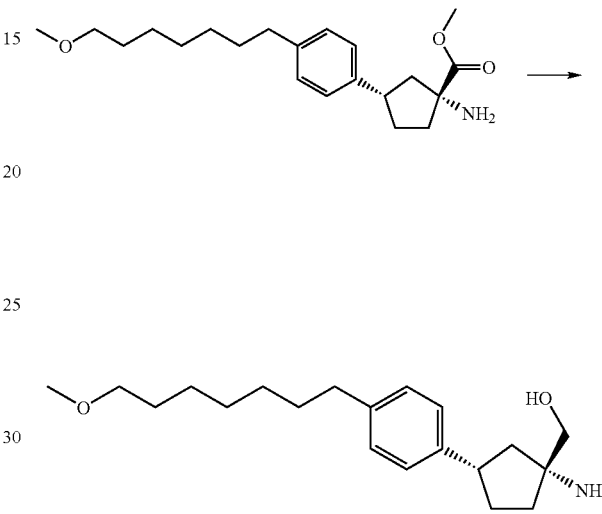

To a solution of (1R,3S)-methyl 1-amino-3-(4-(7-methoxyheptyl)phenyl)cyclopentanecarboxylate (0.480 g, 1.381 mmol) in diethyl ether (57.60 mL) was added lithium aluminium hydride (0.157 g, 4.14 mmol) in portions. The mixture was stirred at ambient temperature for about 2 hours, after which water (157 uL) followed by 2N NaOH (157 uL) followed by water (314 uL) was added to the reaction mixture. The resulting mixture was stirred at ambient temperature for about 15 hours. Sodium sulphate (about 10 g) was added and the reaction mixture was stirred for about 10 minutes then filtered through Celite®. The filter cake was rinsed with dichloromethane (40 mL). The filtrate was concentrated in vacuo to yield 0.5 g of dark green solid. The crude solid was dissolved in dichloromethane (3 mL) and to this was added dropwise 1N HCl solution in diethyl ether (5 mL). Solvent was removed in vacuo and the resulting green film was triturated with diethyl ether (3 mL) until precipitate commenced. The resulting suspension was left to settle at ambient temperature for about 1 hour. Additional diethyl ether (10 mL) was added to the mixture. The precipitate was collected on a fine frit funnel, rinsed with diethyl ether and vacuum dried to provide ((1R,3S)-1-amino-3-(4-(7-methoxyheptyl)phenyl)cyclopentyl)methanol, Hydrochloric Acid (0.186 g, 0.481 mmol, 34.8% yield) as a tan sticky solid.

$^1$H NMR (400 MHz, $CD_3OD$) δ ppm 7.15 (dd, J=27.78, 8.12 Hz, 4H), 3.61 (td, J=11.86, 5.96 Hz, 2H), 3.37 (t, J=6.55 Hz, 2H), 3.31 (s, 3H), 3.19-3.08 (m, 1H), 2.60-2.54 (m, 2H), 2.42 (ddd, J=513.21, 6.96, 1.17 Hz, 1H), 2.13 (m, 1H), 2.02-1.87 (m, 3H), 1.72 (t, J=12.85 Hz, 1H), 1.64-1.48 (m, 4H), 1.32 (t, J=5.71 Hz, 6H); LCMS (Table 1, Method a) $R_t$=3.04 min.; MS m/z: 320.45 (M+H)$^+$.

Preparation of ((1R,3R)-1-amino-3-(4-(5-phenyl-pent-1-ynyl)phenyl)cyclopentyl)methanol

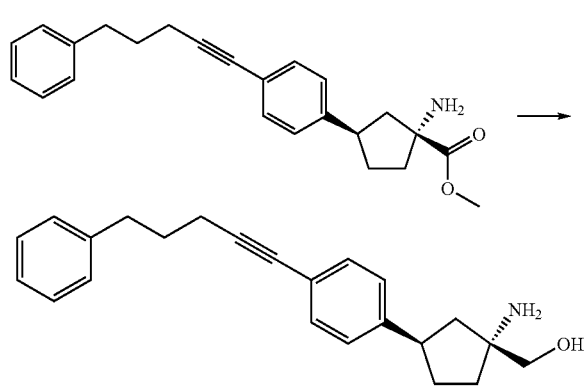

To a suspension of LAH (0.420 g, 11.07 mmol) in Et2O (20 mL) was added a solution of (1R,3R)-methyl 1-amino-3-(4-(5-phenylpent-1-ynyl)phenyl)cyclopentanecarboxylate (1.0 g, 2.77 mmol) in THF (4.0 mL). After about 4 hours water (420 uL) followed by 2N NaOH (420 uL) followed by water (840 uL) was added. After stirring for about 2 days $Na_2SO_4$ and Celite® were added and the reaction mixture was filtered, rinsing with EtOAc. The filtrate was concentrated in vacuo, dissolved in dioxane (20 mL) and treated with 6N HCl (500 uL). The mixture was concentrated in vacuo to provide ((1R,3R)-1-amino-3-(4-(5-phenylpent-1-ynyl)phenyl)cyclopentyl)methanol, Hydrochloric Acid (1.0 g, 2.70 mmol, 98% yield) as a brown foam. The crude product was used without further purification.

LCMS (Table 1, Method a) $R_t$=2.26 min; m/z: 334 $(M+H)^+$.

Preparation of ((1R,3R)-1-amino-3-(4-(3-(benzyloxy)prop-1-ynyl)phenyl)cyclopentyl)methanol

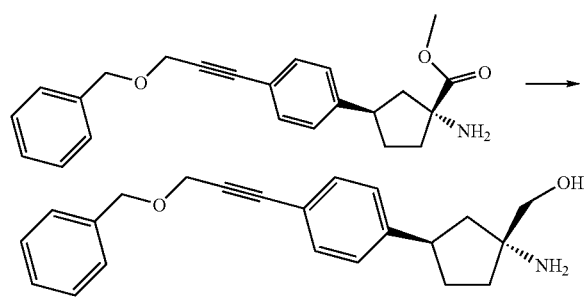

To a slurry of LAH (7.83 g, 206 mmol) in Et2O (500 mL) at about 0° C. was added a solution of (1R,3R)-methyl 1-amino-3-(4-(3-(benzyloxy)prop-1-ynyl)phenyl)cyclopentanecarboxylate (25 g, 68.8 mmol) in THF (100 mL). After about 2 hours water (7.8 mL) followed by 2N NaOH (7.8 mL) followed by water (15 mL) was added. After stirring for about 15 hours $Na_2SO_4$ and Celite® was added to the reaction mixture and the slurry was filtered, rinsing with EtOAc. The filtrate was concentrated in vacuo to provide ((1R,3R)-1-amino-3-(4-(3-(benzyloxy)prop-1-ynyl)phenyl)cyclopentyl)methanol (25 g, 55.9 mmol, 81% yield) as an brown oil.

LCMS (Table 1, Method a) $R_t$=2.53 min; m/z: 336 $(M+H)^+$.

Preparation of [(1R,3S)-1-amino-3-(4-octyl-phenyl)-cyclopentyl]-methanol

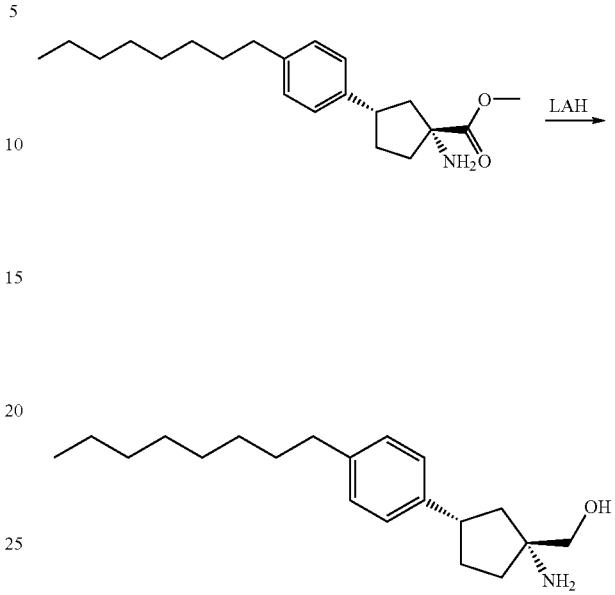

1-Amino-3-(4-octyl-phenyl)-cyclopentanecarboxylic acid methyl ester; hydrochloride (640 mg, 0.0017 mol) was partitioned between Et2O and 2 M NaOH solution. The organic layer was separated, washed with brine, dried over $Na_2SO_4$, filtered and concentrated. The free base was dissolved in Et2O (20 mL) and cooled to 0° C. To this solution was added LAH (130 mg, 0.0035 mol) slowly. After 30 minutes, water (130 uL) was added followed by 2 M NaOH (130 uL) followed by water (260 uL). After stirring for 2 hours, $Na_2SO_4$ was added and the white precipitate was filtered off. 1M HCl in Et2O (3.4 mL) was added to the filtrate and the resulting fine precipitate was collected to provide 470 mg (79%) of the [(1R,3S)-1-amino-3-(4-octyl-phenyl)-cyclopentyl]-methanol; hydrochloride.

LCMS (Table 1, Method a) $R_t$=2.64 min; m/z: 304 $(M+H)^+$; $^1$H NMR (400 MHz, $CDCl_3$) δ 8.26 (bs, 3H), 7.06 (d, 2H), 7.02 (d, 2H), 3.79 (s, 2H), 3.62 (m, 1H), 2.52 (m, 3H), 2.52 (m, 3H), 2.13 (m, 3H), 1.76 (m, 1H), 1.64 (m, 1H), 1.54 (m, 3H), 1.27 (m, 12H), 0.87 (t, 3H)

General Procedure H.1: Reduction of an Ester to the Alcohol

A substituted 1-amino-cyclopentanecarboxylic acid methyl ester dissolved in a suitable organic solvent (preferably EtOH) is added slowly to a solution of a reducing reagent (preferably $NaBH_4$) (1-5 equivalents, preferably 3 equivalents) in a suitable organic solvent (preferably EtOH). The reaction mixture is stirred for a period of about 8-24 hours (preferably about 15 hours). The reaction mixture is worked up by slow addition of an aqueous acid (preferably aqueous hydrochloric acid). The mixture is then partially concentrated to remove the organic solvent then the product is extracted into a suitable organic solvent (preferably EtOAc). The organic layer is concentrated to dryness and the residue is taken up in a suitable organic solvent (ether or dioxane, preferably dioxane) and water (about 1-10% by volume preferably about 1%). After cooling to about room temperature the resulting solid is collected by filtration and dried in vacuo.

Exemplification of General Procedure H.1:

Preparation of ((1R,3R)-1-amino-3-(4-(6-methoxy-hexyl)phenyl)cyclopentyl)methanol, Hydrochloric Acid

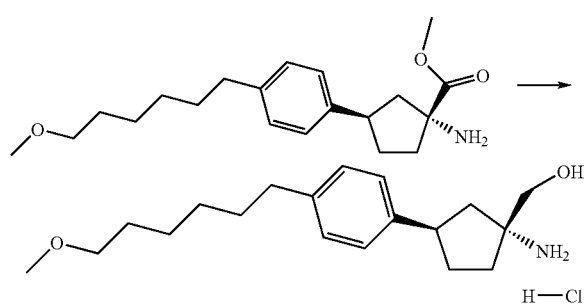

A solution of (1R,3R)-methyl 1-amino-3-(4-(6-methoxy-hexyl)phenyl)cyclopentanecarboxylate (12.84 g, 38.5 mmol) in EtOH (50 mL) was added dropwise to a solution of sodium borohydride (4.37 g, 115 mmol) in EtOH (50 mL). After about 15 hours 2N HCl was added slowly to the reaction mixture. The mixture was partially concentrated in vacuo and partitioned between EtOAc and water. The organic layer was separated and the solvent was removed in vacuo and the residue was dissolved in warm dioxane (100 mL) and water (1 mL) after cooling to about room temperature. The resulting solid was collected by filtration and dried in vacuo to provide ((1R,3R)-1-amino-3-(4-(6-methoxyhexyl)phenyl)cyclopentyl)methanol, hydrochloric acid, monohydrate.

LCMS (Table 1, Method a) $R_t$=1.66 min; m/z: 306 $(M+H)^+$.

General Procedure I: Formation of an Amino-Nitrile from a Ketone

To a substituted cyclopentanone in methanolic ammonia solution is added ammonium chloride (1-4 equivalents, preferably 2 equivalents) and a cyanide salt such as sodium cyanide or potassium cyanide (1-4 equivalents, preferably 2 equivalents). The reaction is capped and stirred at room temperature for a period of 12-72 hours (preferably about 36 hours). The crude reaction mixture is concentrated, partitioned between a suitable solvent (such as EtOAc or DCM) and a saturated aqueous solution of NaHCO₃. The organic layers are combined, washed with water, dried over an appropriated drying reagent (such as Na₂SO₄ or MgSO₄), and concentrated to dryness. The two stereoisomers can be separated by co-crystallization with tartaric acid in methanol.

Exemplification of General Procedure I:

Preparation of (1R,3R)-1-amino-3-(4-methoxy-phenyl)-cyclopentanecarbonitrile; compound with (2R,3R)-2,3-dihydroxy-succinic acid

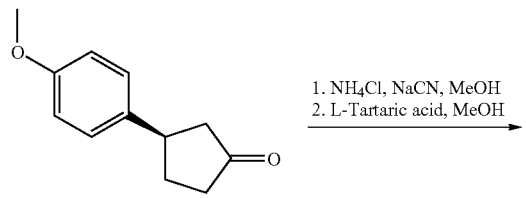

1. NH₄Cl, NaCN, MeOH
2. L-Tartaric acid, MeOH

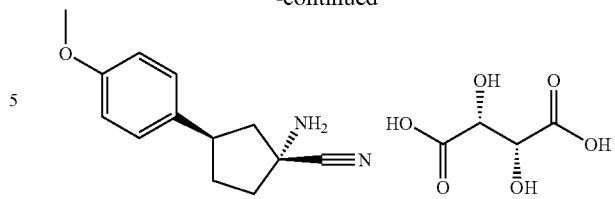

A solution of (R)-3-(4-methoxy-phenyl)-cyclopentanone (11.0 g, 57.9 mmol) in 7 M methanolic ammonia solution was treated with ammonium chloride (6.21 g, 116 mmol) and sodium cyanide (5.68 g, 116 mmol). The reaction was stoppered and stirred at room temperature for about 48 hours. The reaction was concentrated, treated with saturated NaHCO₃ solution (80 mL) and extracted with DCM (2×100 mL). The DCM extracts were washed with water (40 mL), dried over MgSO₄, and concentrated to an oil to give the product as a mixture of diastereomers. The (1R,3R)-isomer was separated as follows:

The residue was dissolved in methanol (100 mL) and the solution is added to a solution of L-tartaric acid (8.69 g, 57.9 mmol) in methanol (100 mL). The resulting solid was collected and triturated repeatedly with portions of methanol (80 mL) until the more soluble isomer was gone as indicated by HPLC (50×4.6 mm ThermoQuest Hypercarb column, 5 μm, part # 35005-025). The remaining white solid was dried to yield 6.0 g (28%) of (1R,3R)-1-amino-3-(4-methoxy-phenyl)-cyclopentanecarbonitrile; compound with (2R,3R)-2,3-dihydroxy-succinic acid.

LCMS (Table 1, Method a) $R_t$=2.26 min; m/z: poor ionization; $^1$H NMR (400 MHz, DMSO-$d_6$) δ 7.18 (d, 2H), 6.85 (d, 2H), 4.22 (s, 2H), 3.72 (s, 3H), 3.30-3.41 (m, 1H), 2.10-2.30 (m, 3H), 1.8-2.0 (m, 2H), 1.6-1.75 (m, 1H).

General Procedure J: Hydrolysis of a Nitrile to the Corresponding Acid

A substituted 1-amino-cyclopentanecarbonitrile in 6 M hydrochloric acid and dioxane is heated at 80-110° C. (preferably about 100° C.) for a period of 12-24 hours (preferably 16 hours). The reaction mixture is cooled on ice. The precipitate is collected by filtration and washed with water to give the desired product.

Exemplification of General Procedure J:

Preparation of (1R,3R)-1-amino-3-(4-methoxy-phenyl)-cyclopentanecarboxylic acid; hydrochloride

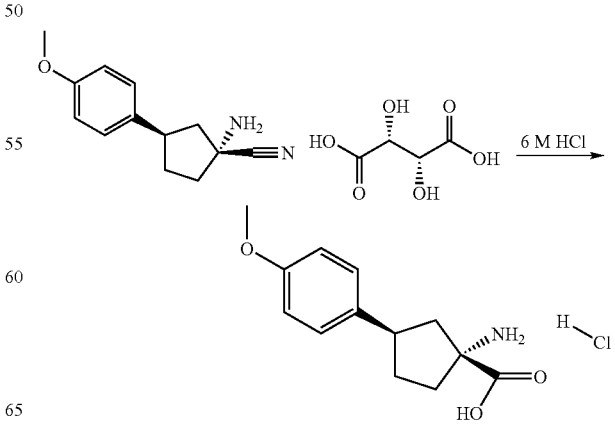

A suspension of (1R,3R)-1-amino-3-(4-methoxy-phenyl)-cyclopentanecarbonitrile; compound with (2R,3R)-2,3-dihydroxy-succinic acid (5.0 g, 13.66 mmol) in 6 M hydrochloric acid (50 mL) and dioxane (5 mL) was heated at 100° C. for about 16 hours under nitrogen. The reaction was cooled on ice and the product was filtered off, washed with water (3×5 mL) and dried to yield 2.72 g (74%) of (1R,3R)-1-amino-3-(4-methoxy-phenyl)-cyclopentanecarboxylic acid, hydrochloride as a white solid.

LCMS (Table 1, Method a) R$_t$=1.43 min; m/z: 236 (M+H)$^+$; $^1$H NMR (400 MHz, DMSO-d$_6$) δ 13.9 (s, 1H), 8.55 (s), 3H), 7.17 (d, 2H), 6.88 (d, 2H), 3.40-3.52 (m, 1H), 2.28-2.40 (m, 2H), 2.13-2.20 (m, 2H), 1.90-1.99 (m, 1H), 1.74-1.85 (m, 1H).

General Procedure K: Formation of an Oxazolidinone from an Amino-Alcohol

To a mixture of amino-alcohol in diethyl carbonate (10-20 equivalents, preferably 15 equivalents) is added potassium carbonate (1-3 equivalents, preferably 1.15 equivalents). The mixture is heated to reflux for a period of 12-48 hours (preferably about 20 hours). The reaction is concentrated and the residue is partitioned between a suitable organic solvent (such as EtOAc or DCM) and water. The organic layer is dried over an appropriate drying reagent (such as MgSO$_4$ or Na$_2$SO$_4$), filtered and concentrated. The crude product is further purified via flash chromatography.

Exemplification of General Procedure K:

Preparation of (5R,7R)-7-(4-methoxy-phenyl)-3-oxa-1-aza-spiro[4.4]nonan-2-one

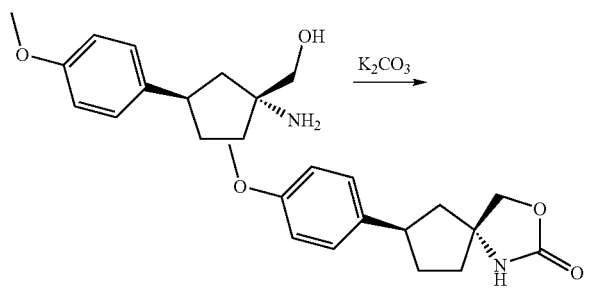

To a suspension of [(1R,3R)-1-amino-3-(4-methoxy-phenyl)-cyclopentyl]-methanol (6.70 g, 30.3 mmol) in diethyl carbonate was added K$_2$CO$_3$ (4.83 g, 35.0 mmol) and the mixture was heated at reflux for about 20 hours. The reaction was concentrated, taken up in EtOAc (150 mL), washed with water (75 mL), dried over Na$_2$SO$_4$, filtered and concentrated. The crude product was further purified via flash chromatography with a gradient of from 40% to 80% EtOAc in heptane. Pure fractions were combined and concentrated to yield 5.99 g (80%) of (5R,7R)-7-(4-methoxy-phenyl)-3-oxa-1-aza-spiro[4.4]nonan-2-one as a white solid.

LCMS (Table 1, Method a) R$_t$=2.18 min; m/z: 248 (M+H)$^+$; $^1$H NMR (400 MHz, DMSO-d$_6$) δ 8.05 (s(broad), 1H), 7.14 (d, 2H), 6.84 (d, 2H), 4.22 (dd, 2H), 3.71 (s, 3H), 3.17 (m, 1H), 1.98-2.15 (m, 3H), 1.7-1.85 (m, 2H), 1.49-1.60 (m, 1H)

General Procedure K.1: Formation of an Oxazolidinone from an Amino-Alcohol

To a solution of an amino alcohol in an organic solvent (preferably toluene) is added an aqueous solution of an inorganic base (preferably potassium hydroxide, 2-20 equivalents, preferably 4 equivalents). To the reaction mixture is added a solution of phosgene in toluene (1-5 equivalents, preferably 1.5 equivalents). After about 4 hours an organic solvent is added to the reaction mixture and the organic layer is separated and concentrated to provide the oxazolidinone.

Exemplification of General Procedure K.1:

Preparation of (5R,7R)-7-(4-(3-(benzyloxy)prop-1-ynyl)phenyl)-3-oxa-1-azaspiro[4.4]nonan-2-one

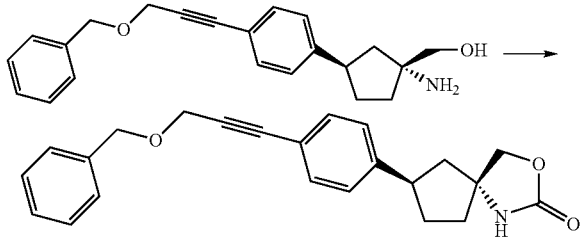

To a solution of ((1R,3R)-1-amino-3-(4-(3-(benzyloxy)prop-1-ynyl)phenyl)cyclopentyl)methanol (25 g, 55.9 mmol) in toluene (200 mL) was added a solution of potassium hydroxide (12.54 g, 224 mmol) in water (40 mL) followed by a solution of 20% phosgene in toluene (41.5 g, 84 mmol). After about 4 hours EtOAc was added and the organic layer was separated and concentrated in vacuo. The crude product was purified by chromatography on silica gel (EtOAc/DCM) to provide (5R,7R)-7-(4-(3-(benzyloxy)prop-1-ynyl)phenyl)-3-oxa-1-azaspiro[4.4]nonan-2-one (20 g, 44.3 mmol, 79% yield) as a brown oil.

LCMS (Table 1, Method a) R$_t$=3.66 min; m/z: 379 (M+NH$_4$)$^+$;

General Procedure L: Deprotection of a Methyl-Ether

A methyl ether compound in a suitable solvent (such as dichloromethane, or dichloroethane) is cooled in an ice bath and BBr$_3$ (1-5 equivalents, preferably 3 equivalents) is added. The reaction mixture is stirred at about 0° C. for a period of 0.5-2 hours (preferably 0.5 hour). The reaction is quenched with a protic solvent such as methanol or water, warmed up to room temperature, and concentrated to dryness. The residue is triturated with water, filtered to give the desired product.

Exemplification of General Procedure L:

Preparation of (5R,7R)-7-(4-hydroxy-phenyl)-3-oxa-1-aza-spiro[4.4]nonan-2-one

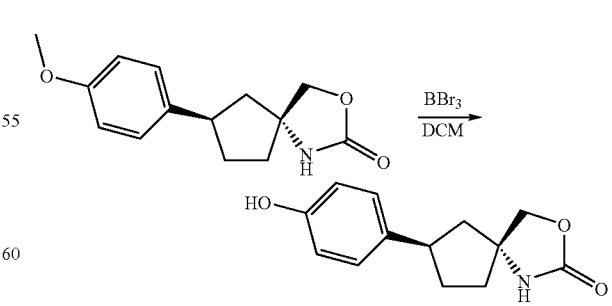

A solution of (5R,7R)-7-(4-methoxy-phenyl)-3-oxa-1-aza-spiro[4.4]nonan-2-one (3.95 g, 16.0 mmol) in DCM (30 mL) was cooled in an ice bath and 1M BBr$_3$ in DCM solution (64.0 mL, 64.0 mmol) was added at a rapid dropwise rate and the reaction was allowed to continue stirring at about 0° C. for about 0.5 hour. The reaction was quenched by dropwise addition of methanol (25.0 mL). The reaction was allowed to warm to room temperature and then concentrated. The residue was triturated with water (50 mL), filtered, rinsed with water (2×5.0 mL), and dried to yield 3.14 g (84%) of (5R,7R)-7-(4-hydroxy-phenyl)-3-oxa-1-aza-spiro[4.4]nonan-2-one as a gray solid.

LCMS (Table 1, Method a) $R_t$=1.70 min; m/z: 234 (M+H)$^+$; $^1$H NMR (DMSO-d$_6$) δ 9.15 (s, 1H), 8.04 (s, 1H), 7.01 (d, 2H), 6.67 (d, 2H), 4.21 (d, d, 2H), 3.11 (m, 1H), 1.97-2.13 (m, 3H), 1.68-1.83 (m, 2H), 1.46-1.58 (m, 1H)

General Procedure M: Alkylation of a Hydroxy-Group

A solution of a phenol, an alcohol (1-3 equivalents, preferably 1.1 equivalents) and resin bound triphenylphospine (1-3 equivalents, preferably 2.2 equivalents) in a suitable solvent (such as tetrahydrofuran, dichloromethane) is cooled to about 0° C. An azodicarboxylate (such as diethyl azodicarboxylate, diisopropyl azodicarboxylate, or di-tert-butyl azodicarboxylate) (1-3 equivalents, preferably 1.1 equivalents) is added to the mixture. The reaction is warmed up to room temperature and shaken for a period of 2-24 hours (preferably 3 hours). The resin is filtered off and rinsed with a suitable solvent (such as tetrahydrofuran, dichloromethane). The filtrate is concentrated to dryness. The crude product is further purified via flash chromatography.

Exemplification of General Procedure M:

Preparation of (5R,7R)-7-(4-(3-(3-methoxyphenoxy) propyl)phenyl)-3-oxa-1-azaspiro[4.4]nonan-2-one

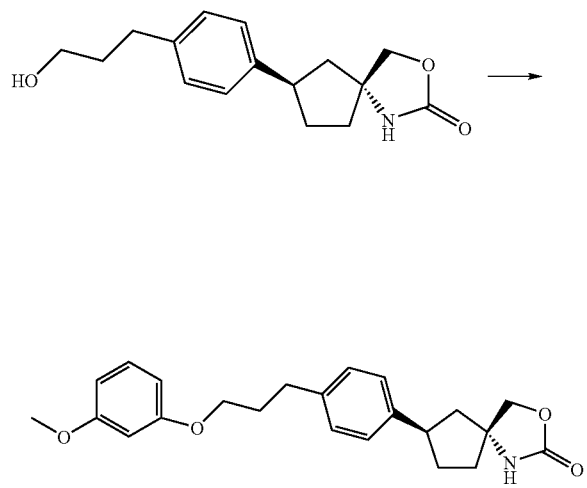

To a solution of (5R,7R)-7-(4-(3-hydroxypropyl)phenyl)-3-oxa-1-azaspiro[4.4]nonan-2-one (5.2 g, 18.89 mmol) in THF (150 mL) was added PS-triphenylphosphine 3 mmol/g (7.43 g, 28.3 mmol) followed by 3-methoxyphenol (2.457 mL, 22.66 mmol). After about 10 minutes a solution of di-tert-butylazodicarboxylate (5.22 g, 22.66 mmol) in THF (10 mL) was added. After about 4 hours the reaction mixture was filtered, rinsing with DCM and EtOAc. The filtrate was concentrated in vacuo and purified by chromatography on silica gel (DCM/EtOAc) to provide (5R,7R)-7-(4-(3-(3-methoxyphenoxy)propyl)phenyl)-3-oxa-1-azaspiro[4.4]nonan-2-one (5.1 g, 13.37 mmol, 70.8% yield) as a colorless solid.

LCMS (Table 1, Method a) $R_t$=3.77 min; m/z: 399 (M+NH$_4$)$^+$.

Preparation of (5R,7R)-7-(4-octyloxy-phenyl)-3-oxa-1-aza-spiro[4.4]nonan-2-one

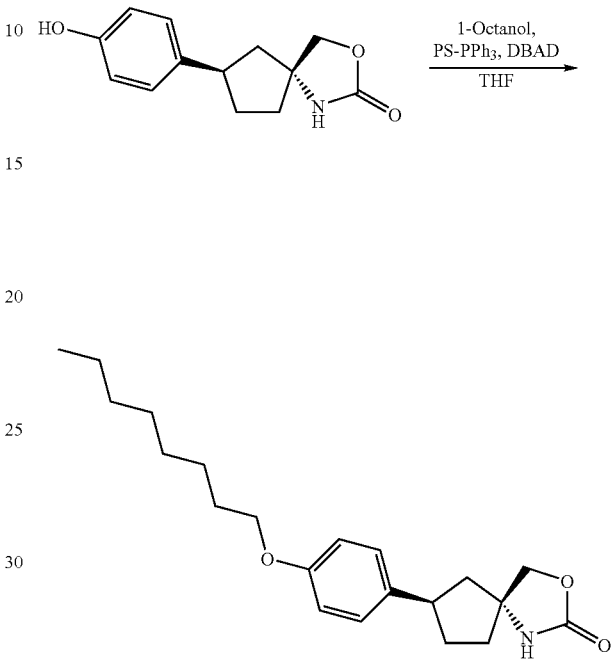

A solution of (5R,7R)-7-(4-hydroxy-phenyl)-3-oxa-1-azaspiro[4.4]nonan-2-one (75 mg, 0.32 mmol), octanol (55.6 µL, 0.35 mmol) and resin bound triphenylphosphine (343 mg, 2 mmol/g, 0.70 mmol) in THF (4.0 mL) was cooled to about 0° C. and di-tert-butyl azodicarboxylate (80.5 mg, 0.35 mmol) was added dropwise. The reaction was allowed to warm up to room temperature for about 3 hours, then the resin was filtered off and washed with DCM (10 mL). The filtrates were combined and concentrated. The crude product was purified on silica gel using a gradient of 30% to 60% EtOAc in heptane. Pure fractions were combined and concentrated to yield 67.0 mg (61%) of (5R,7R)-7-(4-octyloxy-phenyl)-3-oxa-1-aza-spiro[4.4]nonan-2-one as a white solid.

LCMS (Table 1, Method a) $R_t$=3.76 min; m/z: 346 (M+H)$^+$; $^1$H NMR (DMSO-d$_6$) δ 8.04 (s(broad, 1H), 7.10 (d, 2H), 6.81 (d, 2H), 4.20 (dd, 2H), 3.89 (t, 2H), 3.15 (m, 1H), 1.99-2.13 (m, 3H), 1.61-1.82 (m, 4H), 1.46-1.59 (m, 1H), 1.20-1.44 (m, 10H), 0.84 (t, 3H)

General Procedure N: Hydrolysis of an Oxazolidinone

To an oxazolidinone dissolved in a suitable solvent (such as dioxane, or tetrahydrofuran) is added water and an inorganic base (such as lithium hydroxide, sodium hydroxide or potassium hydroxide) (10-20 equivalents, preferably 12-15 equivalents). The mixture is heated to reflux for a period of 2-96 hours (preferably about 10-48 hours). The reaction is concentrated, partitioned between a suitable organic solvent (such as ether, or ethyl acetate) and water. The organic layer is dried over an appropriate drying reagent (such as Na$_2$SO$_4$, MgSO$_4$), filtered and concentrated. The product can be isolated as an ammonium salt by treating the residue with an inorganic acid (such as HCl).

Exemplification of General Procedure N:

Preparation of (((1R,3R)-1-amino-3-(4-(3-(3-methoxyphenoxy)propyl)phenyl)cyclopentyl)methanol, Hydrochloric Acid

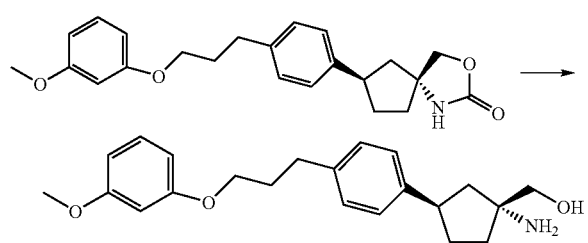

To a solution of (5R,7R)-7-(4-(3-(3-methoxyphenoxy)propyl)phenyl)-3-oxa-1-azaspiro[4.4]nonan-2-one (5.1 g, 13.37 mmol) in 1,4-dioxane (100 mL) and water (20 mL) was added lithium hydroxide hydrate (5.61 g, 134 mmol). The reaction mixture was heated to about 90° C. After about 2 days the reaction mixture was cooled to room temperature and partitioned between EtOAc and water. The organic layer was separated, washed with brine, dried ($Na_2SO_4$), filtered and concentrated in vacuo. The resulting oil was dissolved in dioxane (approx. 50 mL) and 6N HCl (2.5 mL) was added. $Et_2O$ was added to the mixture until a cloudy solution occurred. The solution was aged for 2 h and the resulting solids were collected by filtration to provide ((1R,3R)-1-amino-3-(4-(3-(3-methoxyphenoxy)propyl)phenyl)cyclopentyl)methanol, hydrochloric acid (3.9 g, 9.95 mmol, 74.4% yield) as a colorless solid.

LCMS (Table 1, Method a) $R_t$=2.43 min; mm/z: 356 $(M+H)^+$.

Preparation of [(1R,3R)-1-amino-3-(4-octyloxy-phenyl)-cyclopentyl]-methanol; hydrochloride

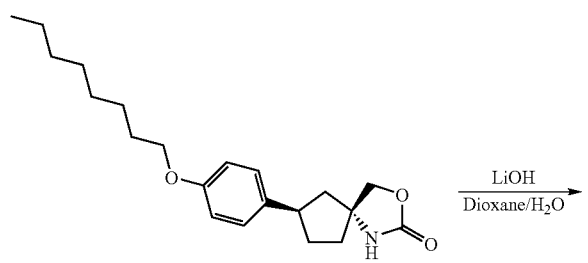

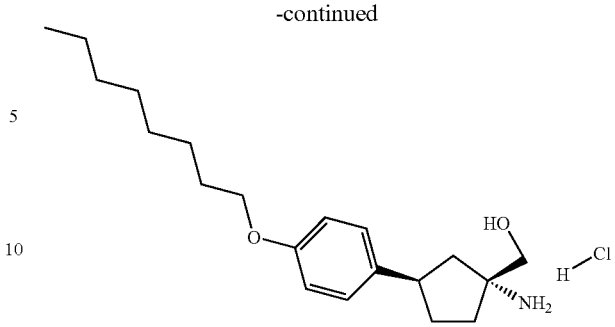

A solution of (5R,7R)-7-(4-octyloxy-phenyl)-3-oxa-1-aza-spiro[4.4]nonan-2-one (61.0 mg, 0.177 mmol) in dioxane (3.0 mL) was treated with lithium hydroxide, hydrate (100 mg, 2.38 mmol) and water (1.0 mL). The mixture was heated to reflux for about 10 hours. The reaction was concentrated, treated with water (10 mL) and extracted twice with ether (10 mL). The ether extracts were dried over $Na_2SO_4$, filtered and concentrated. The residue was treated with 2 M HCl (2.0 mL) to yield a white solid which was collected and dried to yield 33.0 mg (52%) of [(1R,3R)-1-Amino-3-(4-octyloxy-phenyl)-cyclopentyl]-methanol; hydrochloride.

LCMS (Table 1, Method a) $R_t$=2.58 min; m/z: 320 $(M+H)^+$; $^1$H NMR (400 MHz, DMSO-$d_6$) δ 7.89 (s(broad), 3H), 7.12 (d, 2H), 6.83 (d, 2H), 5.56 (s(broad), 1H), 3.90 (t, 2H), 3.46 (m, 1H), 1.96-2.10 (m, 2H), 1.56-1.74 (m, 4H), 1.32-1.42 (m, 2H), 1.18-1.32 (m, 10H), 0.85 (t, 3H)

General Procedure O: Phosphorylation of an Alcohol Followed by Deprotection

An alcohol dissolved in a suitable solvent (such as tetrahydrofuran, dioxane) is treated with a strong base (such as LiHMDS, NaH) (1-2.5 equivalents, preferably 1.1 equivalents) for a period of 10-30 minutes (preferably 20 minutes) under inert atmosphere. Tetrabenzyl diphosphate (1-1.5 equivalents, preferably 1.1 equivalents) is added to the mixture and the reaction mixture is stirred at room temperature for a period of 0.5-4 hours (preferably 1 hour). The reaction is quenched with an acid solution (such as HCl solution in ether, or HCl solution in ethanol) and the resulting solution is concentrated. The residue is dissolved in a suitable solvent (such as acetic acid, or ethanol), to which Pearlman's Catalyst (5-20 mol %, preferably 5-10 mol %) is added. The mixture is attached to a hydrogen balloon and stirred at room temperature for a period of 2-24 hours (preferably 14 hours). The crude reaction is filtered, concentrated and purified by trituration with a suitable solvent (such as a small amount of DMSO and water) to give the desired product.

Exemplification of General Procedure O:

Preparation of phosphoric acid mono-[(1R,3S)-1-amino-3-(4-octyl-phenyl)-cyclopentylmethyl]ester

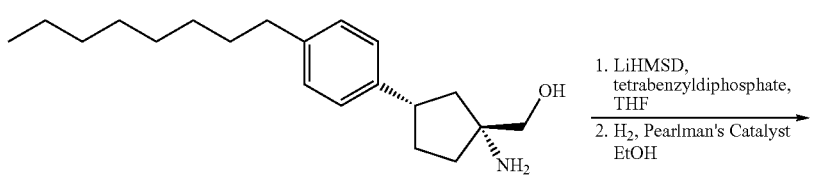

-continued

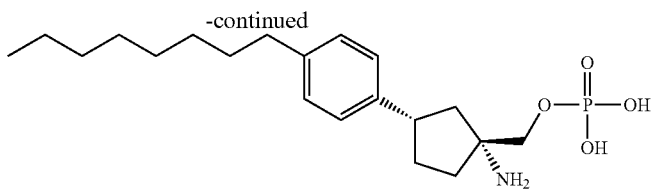

((1R,3S)-1-Amino-3-(4-octylphenyl)cyclopentyl)methanol; tartrate salt (0.250 g) was free-based by partitioning between ether and saturated NaHCO₃ solution, drying over MgSO₄, filtering, and concentrating to give ((1R,3S)-1-amino-3-(4-octylphenyl)cyclopentyl)methanol (138 mg, 0.455 mmol) as a white powder that was used directly in the reaction. A 200 mL round-bottomed flask equipped with rubber septum and nitrogen inlet needle was charged with ((1R, 3S)-1-amino-3-(4-octylphenyl)cyclopentyl)methanol (0.138 g, 0.455 mmol) and THF (10 mL) to give a colorless solution. 1.1 M LiHMDS solution in THF (0.459 mL, 0.500 mmol) was added dropwise via a syringe. The resulting solution was allowed to stir at room temperature for about 20 minutes. Tetrabenzyl diphosphate (0.269 g, 0.500 mmol) was added in one portion. The resulting solution was stirred at room temperature for 1 hour. 1.25 M HCl solution in ethanol (0.728 mL, 0.909 mmol) was added in one portion. The resulting solution was concentrated and the residue was dissolved in EtOH (10 mL) and the reaction flask was charged with Pearlman's Catalyst (0.016 g, 0.023 mmol). The resulting suspension was attached to a hydrogen balloon and stirred at room temperature for 14 hours. The reaction mixture was filtered through a pad of Celite®. The filtrate was concentrated and triturated with water to give a white precipitate that was collected by filtration and washed with DMSO (2×2 mL) followed by water (2×10 mL), and dried under vacuum to give phosphoric acid mono-[(1R,3S)-1-amino-3-(4-octyl-phenyl)-cyclopentylmethyl] ester as a white powder (0.147 g, 84

LCMS (Table 1, Method d) $R_f$=2.36 min; m/z: 382 (M−H)⁻; ¹H NMR (400 MHz, DMSO-d₆) δ 7.89 (s, broad, 3H), 7.12 (d, 2H), 6.83 (d, 2H), 5.56 (s, broad, 1H), 3.90 (t, 2H), 3.46 (m, 1H), 1.96-2.10 (m, 2H), 1.56-1.74 (m, 4H), 1.32-1.42 (m, 2H), 1.18-1.32 (m, 10H), 0.85 (t, 3H)

Exemplification of General Procedure O:
Phosphorylation of an Alcohol Followed by Deprotection An alcohol dissolved in a suitable solvent (such as tetrahydrofuran, dioxane) is treated with a strong base (such as LiHMDS, NaH) (1-2.5 equivalents, preferably 1.0 equivalents) for a period of 10-30 minutes (preferably 20 minutes) under inert atmosphere. Tetrabenzyl diphosphate (1-1.5 equivalents, preferably 1.0 equivalents) is added to the mixture and the reaction mixture is stirred at room temperature for a period of 0.5-4 hours (preferably 2 hour). The reaction is briefly cooled to about 0° C. and the precipitated solid is removed by filtration and the filtrate is concentrated. The residue is taken up in a solution of HBr in acetic acid, stirred at 0-50° C. (preferably room temperature) for 1-30 minutes (preferably 5 minutes) then concentrated. The residue is triturated with a suitable organic solvent such as ether, ethyl acetate or acetonitrile (preferably acetonitrile), then is triturated with dilute aqueous ammonium acetate solution, filtered and dried.

Exemplification of General Procedure O:

Preparation of Phosphoric acid mono-{(1R,3S)-1-amino-3-[3,5-dichloro-4-(2-phenoxy-ethoxy)-phenyl]-cyclopentylmethyl} ester

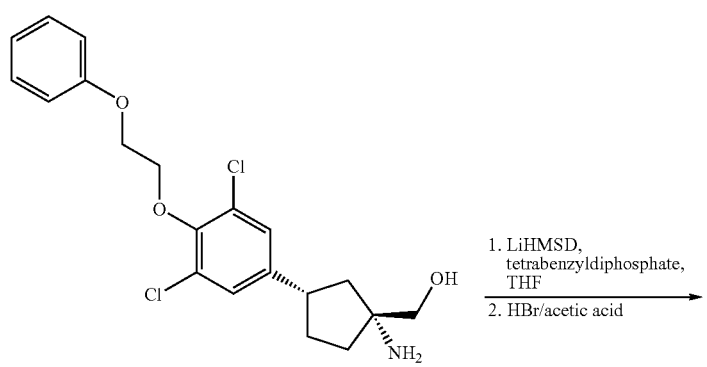

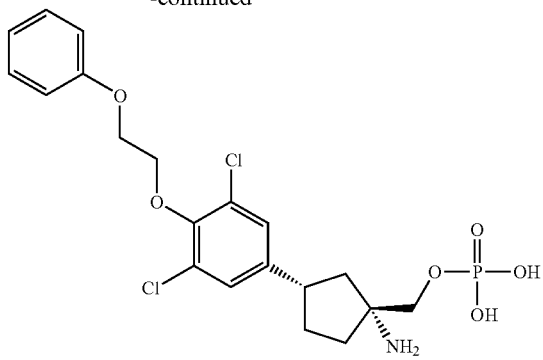

A 25 mL round-bottomed flask equipped with rubber septum and nitrogen inlet needle was charged with {(1R,3S)-1-Amino-3-[3,5-dichloro-4-(2-phenoxy-ethoxy)-phenyl]-cyclopentyl}-methanol (50.0 mg, 0.126 mmol) and THF (4 mL) to give a colorless solution. An LiHMDS solution in THF (1.0 M, 0.126 mL, 0.126 mmol) was added dropwise via a syringe. The resulting solution was allowed to stir at room temperature for about 20 minutes. Tetrabenzyl diphosphate (67.9 mg, 0.126 mmol) was added in one portion. The resulting solution was stirred at room temperature for 2 hour. Cool briefly to 0° C. and filter off solids, washing with THF (1.0 ml). The resulting solution was concentrated and the residue was dissolved in 33% HBr in acetic acid (1.5 ml) and stirred at room temperature for 5 minutes then concentrated. The residue was triturated with ether (2×5.0 ml) and with dilute aqueous ammonium acetate solution (2×5.0 ml) then filtered and dried to yield Phosphoric acid mono-{(1R,3S)-1-amino-3-[3,5-dichloro-4-(2-phenoxy-ethoxy)-phenyl]-cyclopentylmethyl} (34 mg, 57%) as an off-white powder.

LCMS (Table 1, Method d) $R_t$=2.73 min; m/z: 476/478/480 (M–H)$^-$; $^1$H NMR (400 MHz, DMSO-$d_6$+3 uL Tfa) δ 8.15 (s, broad, 3H), 7.40 (s, 2H), 7.29 (m, 2H), 6.94 (m, 3H), 4.32 (s, 4H), 3.96 (m, 2H), 3.33 (m, 1H), 2.11 (m, 3H), 1.85 (m, 1H), 1.71 (m, 2H)

Exemplification of General Procedure O:
Phosphorylation of an Alcohol Followed by Deprotection with HBr An alcohol dissolved in a suitable solvent (such as tetrahydrofuran, dioxane) is treated with a strong base (such as LiHMDS, NaH) (1-2.5 equivalents, preferably 1.1 equivalents) for a period of 10-30 minutes (preferably 20 minutes) under inert atmosphere. Tetrabenzyl diphosphate (1-1.5 equivalents, preferably 1.0 equivalents) is added to the mixture and the reaction mixture is stirred at room temperature for a period of 0.5-20 hours (preferably 16 hour). The reaction is filtered, the solid washed with a suitable solvent (such as THF) and the resulting solution is concentrated. The residue is dissolved in hydrogen bromide in acetic acid and triisopropylsilane (1-3 equivalents, preferably 1.0 equivalent). The reaction is stirred for 10-60 minutes (preferably 30 minutes). The reaction is diluted with a suitable solvent (such as ether), the reaction stirred, and then the solvent is decanted. The resulting residue is stirred in an aqueous solution (such as water or 1 mM ammonium acetate buffer) and the resulting solid collected by vacuum filtration and washed with water to give the desired product.

Exemplification of Procedure O:

Preparation of ((1R,3R)-1-amino-3-(4-(3-(thiophen-2-yl)propoxy)phenyl)cyclopentyl)methyl dihydrogen phosphate

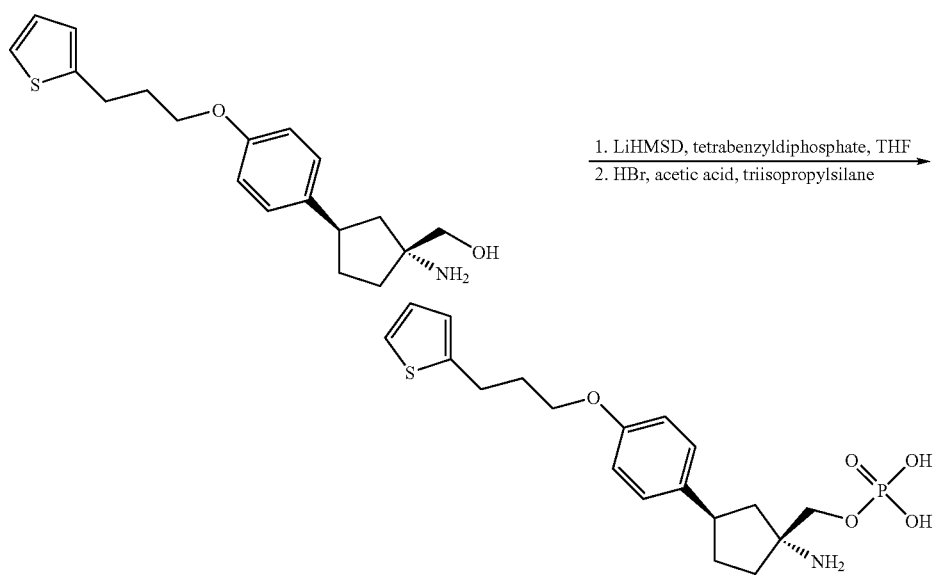

((1R,3R)-1-amino-3-(4-(3-(thiophen-2-yl)propoxy)phenyl) cyclopentyl)methanol (0.05 g, 0.151 mmol) was dissolved in THF (3.02 ml) under nitrogen. Lithium bis(trimethylsilyl) amide (0.151 ml, 0.151 mmol) (Aldrich) was added and the reaction stirred for 30 min. Tetrabenzyl diphosphate (0.081 g, 0.151 mmol) (Fluka) was added and the reaction stirred for 16 h. The resulting solid was removed by vacuum filtration and washed with THF. The filtrate was concentrated and a mixture of hydrogen bromide in acetic acid (0.030 ml, 0.151 mmol) (Aldrich) and triisopropylsilane (0.031 ml, 0.151 mmol) (Aldrich) were added. The reaction was stirred for about 30 min. at which time LC MS showed reaction complete. The reaction was diluted with ether (15 mL), depositing a residue on the sides of the flask, and stirred until the ether was clear. The ether was decanted and the residue washed with ether. 1 mM ammonium acetate buffer (~5 mL) was added and the flask sonicated. A light tan precipitate resulted. The resulting solid was collected by vacuum filtration and washed with water and then acetonitrile to provide ((1R,3R)-1-amino-3-(4-(3-(thiophen-2-yl)propoxy)phenyl)cyclopentyl)methyl dihydrogen phosphate (0.024 g, 0.058 mmol, 38.7% yield) as a tan solid on drying: LC/MS (table 1, method A) $R_t$=2.57 min.; MS m/z: 412.35 (M+H)$^+$.

General Procedure P: Hydrolysis of an Ester to the Acid

To an ester dissolved in a suitable solvent (such as tetrahydrofuran, dioxane) is added a suitable inorganic base (such as lithium hydroxide, sodium hydroxide) (5-10 equivalents, preferably 10 equivalents) and water. The mixture is heated at 45-65° C. (preferably 50° C.) for a period of 2-24 hours (preferably 4-5 hours). The crude reaction is acidified with acid. The precipitate is collected by filtration, washed with ether and water, dried to give the desired product.

Exemplification of General Procedure P:

Preparation of phosphoric acid mono-[(1R,3S)-1-amino-3-(4-octyl-phenyl)-cyclopentylmethyl] ester; hydrochloride

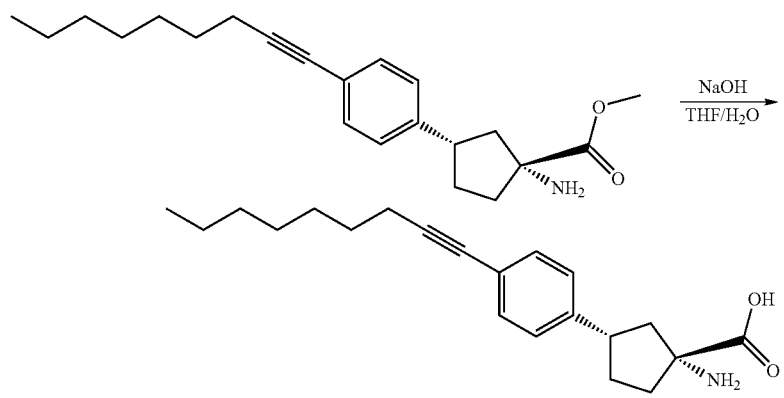

To a solution of (1R,3S)-methyl 1-amino-3-(4-(non-1-ynyl)phenyl)cyclopentane carboxylate (0.600 g, 1.757 mmol) in THF (5 mL), sodium hydroxide (0.703 g, 17.57 mmol) dissolved in water (5 mL) was added. The reaction was heated to 60° C. for 4-5 hours. The reaction mixture was acidified to pH 1-2 with 6 M HCl. The resulting mixture was shaken with 1:1 water and ether mixture (40 mL). The resulting mixture was filtered. The solid was washed a few times with diethyl ether, water, and air-dried to yield 311 mg (48%) phosphoric acid mono-[(1R,3S)-1-amino-3-(4-octyl-phenyl)-cyclopentylmethyl] ester; hydrochloride as a shiny white solid.

LCMS (Table 1, Method b) $R_t$=2.47 min; m/z: 348 (M+H)$^+$; $^1$H NMR (400 MHz, MeOD-d$_4$) δ 7.2 (dd, 4H), 3.48 (m, 1H), 2.73 (m, 1H), 2.51 (m, 1H), 2.39 (m, 1H), 2.26 (m, 1H), 2.13 (m, 1H), 2.03 (m, 1H), 1.85 (m, 1H), 1.59 (m, 2H), 1.47 (m, 2H), 1.33 (m, 6H), 0.99 (t, 3H)

General Procedure Q: Alkylation of Phenol

A solution of substituted phenol in an organic solvent (such as tetrahydrofuran, DMF or dioxane) (preferably DMF) is added dropwise to a stirred suspension of Sodium Hydride in the same solvent at −10-30° C., preferably about 0° C. under an inert atmosphere. The alkylating agent, for example Ethyl bromoacetate, Iodomethane, Iodoethane or tert-Butyl bromoacetate, is added dropwise to the stirred anion and then the reaction is warmed to 20-100° C., preferably room temperature for 1-24 hours. The reaction is then concentrated under reduced pressure and the crude product is taken up in Ethyl acetate, washed with water, dried (Na$_2$SO$_4$), filtered, concentrated and further purified via flash chromatography.

Exemplification of General Procedure Q:

Preparation of (3-Fluoro-phenoxy)-acetic acid ethyl ester

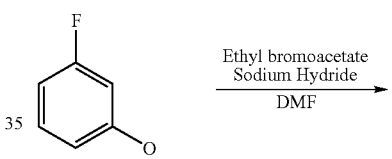

-continued

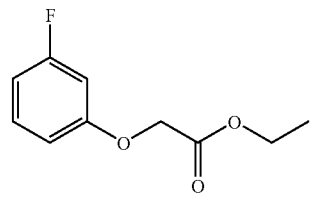

A 50 ml three-necked round-bottomed flask equipped with temperature probe and nitrogen bubbler was charged with Sodium Hydride (785 mg, 19.6 mmol) and DMF (10.0 ml) and cooled to 0° C. A solution of 3-Fluorophenol (2.00 g, 17.8 mmol) in DMF (2.0 ml) was added dropwise maintaining reaction temperature below 10° C. The mixture was stirred for an additional 15 minutes then Ethyl bromoacetate (2.48 ml, 22.3 mmol) was added dropwise maintaining the reaction temperature below 10° C. The reaction was stirred at room temperature for 4 hours. The reaction was then concentrated under reduced pressure and the crude product was taken up in Ethyl acetate, washed with water, dried ($Na_2SO_4$), filtered, concentrated and further purified via flash chromatography using 4:1/heptane:Ethyl acetate as eluant. Fractions containing product were combined and concentrated to afford (3-Fluoro-phenoxy)-acetic acid ethyl ester (2.26 g, 69%) as a clear oil.

LCMS (Table 1, Method a) m/z: poor ionization; $^1$H NMR (400 MHz, DMSO-$d_6$) δ. 7.32 (m, 1H), 6.81 (m, 3H), 4.81 (s, 2H), 4.17 (q, 2H), 1.21 (t, 3H)

Preparation of (3-Ethoxy-phenyl)-acetic acid ethyl ester

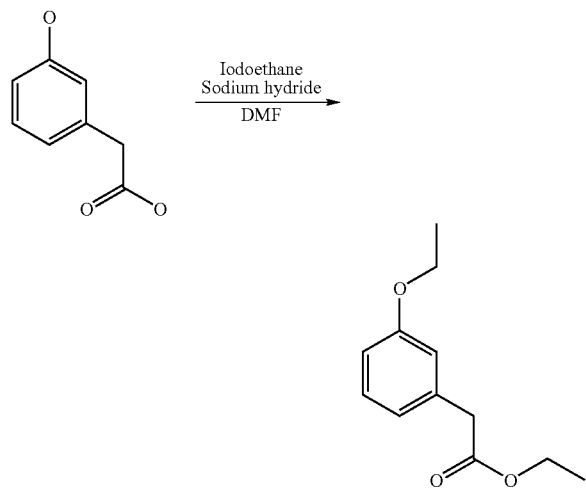

A 100 ml three-necked round-bottomed flask equipped with temperature probe and nitrogen bubbler was charged with Sodium Hydride (2.89 g, 72.3 mmol) and DMF (30.0 ml) and cooled to 0° C. A solution of (3-Hydroxy-phenyl)-acetic acid (5.00 g, 32.9 mmol) in DMF (10.0 ml) was added dropwise maintaining reaction temperature below 10° C. The mixture was stirred for an additional 15 minutes then Ethyl iodide (5.84 ml, 72.3 mmol) was added dropwise maintaining the reaction temperature below 10° C. The reaction was stirred at room temperature overnight. The reaction was then concentrated under reduced pressure and the crude product was taken up in Ethyl acetate, washed with water, dried ($Na_2SO_4$), filtered, concentrated and further purified via flash chromatography using 8:1/heptane:Ethyl acetate as eluant. Fractions containing product were combined and concentrated to afford (3-Ethoxy-phenyl)-acetic acid ethyl ester (3.48 g, 51%) as a clear oil.

LCMS (Table 1, Method a) 3.64 min, m/z: poor ionization; $^1$H NMR (400 MHz, DMSO-$d_6$) δ. 7.22 (m, 1H), 6.83 (m, 3H), 4.15 (q, 2H), 4.03 (q, 2H), 3.57 (s, 2H), 1.40 (t, 3H), 1.25 (t, 3H)

Preparation of (S)-1-Phenoxy-propan-2-ol

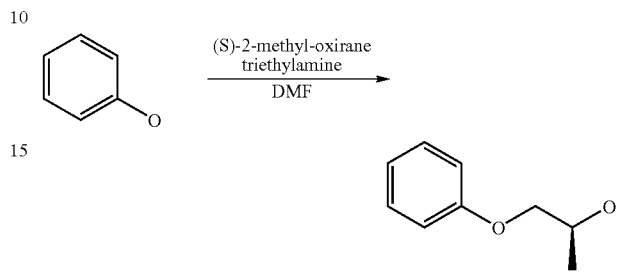

A microwave vessel was charged with (S)-2-methyl-oxirane (0.46 ml, 7.78 mmol), triethylamine (0.33 ml, 2.36 mmol), phenol (222 mg, 2.36 mmol) and DMF (2.0 ml). The mixture was heated by microwave for 20 minutes at 150° C. The reaction was concentrated and dried under reduced pressure. The crude mixture (approximately 9:1) was dissolved in DMF (3.0 ml) and treated with imidazole (160 mg, 2.36 mmol) and Triisopropylchlorosilane (181 mg, 0.94 mmol) overnight at room temperature under nitrogen. The reaction was concentrated under reduced pressure and the crude product was purified via flash chromatography using 3:2/heptane:Ethyl acetate as eluant. Fractions containing product were combined and concentrated to afford (S)-1-Phenoxy-propan-2-ol (390 mg, 62%) as a clear oil.

LCMS (Table 1, Method a) m/z: poor ionization; $^1$H NMR (400 MHz, DMSO-$d_6$) δ. 7.30 (m, 2H), 6.90 (m, 3H), 4.80 (d, 1H), 3.90 (m, 1H), 3.80 (m, 2H), 1.10 (d, 3H)

General Procedure R: Reduction of Carboxylic Acid

A solution of carboxylic acid in an organic solvent (such as tetrahydrofuran or dioxane) (preferably THF) is added dropwise to a stirred solution of Borane in THF at 0-50° C., preferably about 23° C. under an inert atmosphere. The reaction is stirred at warmed to 20-50° C., preferably room temperature for 1-24 hours. The reaction is then quenched by cautious addition of methanol at 0-50° C., preferably about room temperature. The crude product is concentrated under reduced pressure, taken up in Ethyl acetate, washed with water, dried ($Na_2SO_4$), filtered, and concentrated Exemplification of General Procedure R:

Preparation of 2-(3-Methoxy-phenoxy)-ethanol

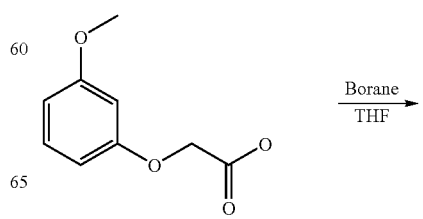

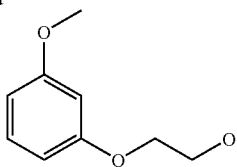

A 250 ml three-necked round-bottomed flask equipped with temperature probe and nitrogen bubbler was charged with 1M Borane/THF solution (60.4 ml, 60.4 m mol) and a solution of (3-Methoxy-phenoxy)-acetic acid (5.00 g, 27.4 mmol) in THF (2.0 ml) was added dropwise, maintaining reaction temperature below 30° C. The reaction was allowed to stir at room temperature overnight. The reaction was quenched by dropwise addition of methanol (20 ml) maintaining the reaction temperature below 35° C. The reaction was stirred at room temperature for 4 hours and concentrated under reduced pressure to yield 2-(3-Methoxy-phenoxy)-ethanol (4.51 g, 98%) as a clear oil which was used without further purification.

LCMS (Table 1, Method a) 2.43 min., m/z: 169 (M+H)$^+$; $^1$H NMR (400 MHz, DMSO-d$_6$) δ. 7.15 (m, 1H), 6.48 (m, 3H), 4.81 (t, 1H), 3.94 (t, 2H), 3.71 (s, 3H), 3.68 (m, 2H)

General Procedure S: Cbz Protection of an Amine

To the appropriately substituted amine in a suitable organic solvent (preferably acetonitrile) and water mixture (about 1:1 to 8:1 ratio, preferably 4:1 ratio) is added N-(Benzyloxycarbonyloxy)succinimide (preferably 1 equivalent) followed by potassium carbonate (preferably 1 equivalent). The reaction mixture is stirred at ambient temperature for a period of 1-4 hours (preferably 1 hour). The solvent is then removed and the remaining aqueous slurry is taken up in water and organic solvent (preferably ethyl acetate). The organic layer is washed with brine, dried over MgSO$_4$ and concentrated in vacuo. The resulting crude can be purified by column chromatography to give the desired product.

Exemplification of General Procedure S:

Preparation of (1R,3R)-methyl 1-(benzyloxycarbonylamino)-3-(4-bromophenyl)cyclopentanecarboxylate

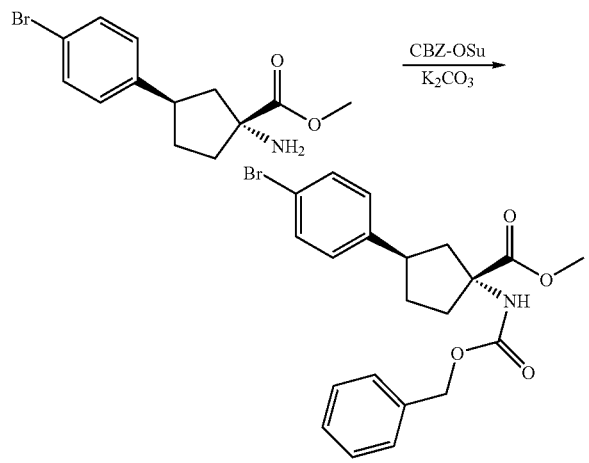

To (1R,3R)-methyl 1-amino-3-(4-bromophenyl)cyclopentanecarboxylate (1.5 g, 5.03 mmol) in acetonitrile (7.2 ml) and water (1.800 ml) was added N-(Benzyloxycarbonyloxy)succinimide (1.254 g, 5.03 mmol) followed by potassium carbonate (0.695 g, 5.03 mmol). The reaction mixture was stirred for 1 hour at room temperature. The solvent was removed and the remaining aqueous slurry was taken up in water and ethyl acetate. The organic layer was removed and washed with brine, dried over MgSO4 and concentrated in vacuo. The crude was purified by flash chromatography to yield (1R,3R)-methyl 1-(benzyloxycarbonylamino)-3-(4-bromophenyl)cyclopentanecarboxylate (1.4 g, 3.24 mmol, 64.4% yield) as an off white gum.

LCMS (Table 1, Method b) R$_f$=3.01 min; nm/z: 433.28 (M+H)$^+$.

General Procedure T: Cross Coupling of an Aryl Bromide to a Boronic Acid

To a flask charged with an aryl bromide (1 equivalent), a boronic acid (1-3 equivalents, preferably 1 equivalents) and an inorganic base (cesium carbonate or sodium carbonate) (preferably cesium carbonate) (3-8 equivalents, preferably 3 equivalents) is added an organic solvent (such as 1,2-dimethoxyethane, dioxane or DMF; preferably 1,2-dimethoxyethane) and water mixture (about 10:1 to 1:1 ratio; preferably 4:1 ratio). The mixture is degassed before adding a palladium catalyst (such as tetrakis(triphenylphosphine)palladium, 1,1'-bis(diphenylphosphino)ferrocene palladium dichloride or bis(triphenylphosphine)palladium(II) chloride; preferably 1,1'-bis(diphenylphosphino) ferrocene palladium dichloride) (2-10 mol %, preferably 5 mol %). The reaction mixture is heated at 100-200° C. (preferably about 120° C.) for a period of 20-60 minutes (preferably 30 minutes) in a microwave reactor. Upon completion of the reaction, the mixture is concentrated to dryness, dissolved in a suitable organic solvent (such as EtOAc, or DCM), and washed with a saturated aqueous solution of NaHCO$_3$, dried over an appropriate drying reagent (such as MgSO$_4$, or Na$_2$SO$_4$) and concentrated to dryness to give the crude product. The crude product is purified via flash chromatography to afford the desired product.

Exemplification of General Procedure T:

Preparation of (1R,3R)-methyl 1-(benzyloxycarbonylamino)-3-(4-vinylphenyl)cyclopentanecarboxylate

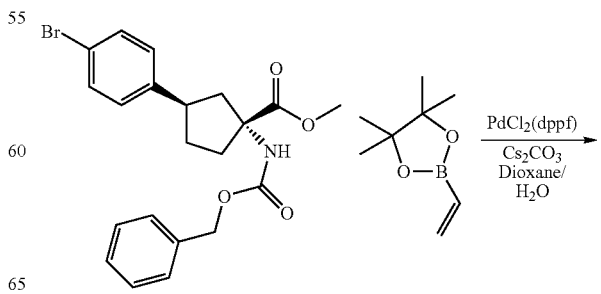

-continued

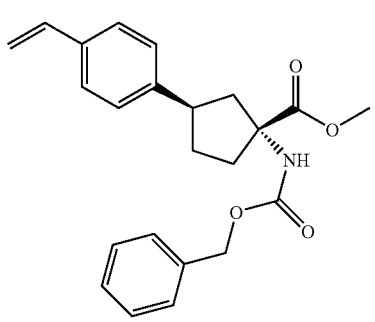

To a 60-mL microwave vial was suspended (1R,3R)-methyl 1-(benzyloxycarbonylamino)-3-(4-bromophenyl)cyclopentanecarboxylate (1.1 g, 2.54 mmol) and 4,4,5,5-tetramethyl-2-vinyl-1,3,2-dioxaborolane (0.431 g, 2.80 mmol) and Cs$_2$CO$_3$ (2.487 g, 7.63 mmol) in DME (30 ml) and Water (7.50 ml). The reaction vessel was purged with nitrogen for 5 minutes. PdCl$_2$(dppf) (0.186 g, 0.254 mmol) was added and the reaction vessel was purged with nitrogen one more time. The reaction mixture was heated to 120° C. in microwave for 30 minutes. The product ((1R,3R)-methyl 1-(benzyloxycarbonylamino)-3-(4-vinylphenyl)cyclopentanecarboxylate (705 mg, 1.858 mmol, 73.0% yield)) was isolated by FCC as a lightly colored oil.

LCMS (Table 1, Method b) R$_t$=2.94 min; m/z: 380.43 (M+H)$^+$.

General Procedure U: Hydroboration Reaction of an Alkene

To a stirred and ice-bath cooled solution of an alkene in an organic solvent (preferably tetrahydrofuran) is added 9-BBN (1-8 equivalents, preferably 4 equivalents) dropwise. The reaction mixture is monitored by TLC to ensure complete conversion to boronate. After the reaction is complete, the ice bath is removed and the reaction is left to stir at ambient temperature for a period of 4-24 hours (preferably 12-20 hours) under inert atmosphere. The reaction mixture is then cooled to about 0° C. and diluted with an organic solvent (such as methanol). An aqueous sodium hydroxide solution (about 4-12 equivalents, preferably 8 equivalents) and 30% w/v hydrogen peroxide solution (about 4-12 equivalents, preferably 8 equivalents) is then poured into the reaction mixture. Stirring is continued for a period of 1-8 hours (preferably 2 hours). The solvent is removed under reduced pressure and the resulting crude can be purified by flash chromatography to afford the desired product.

Exemplification of General Procedure U:

Preparation of (1R,3R)-methyl 1-(benzyloxycarbonylamino)-3-(4-(2-hydroxyethyl)phenyl)cyclopentanecarboxylate

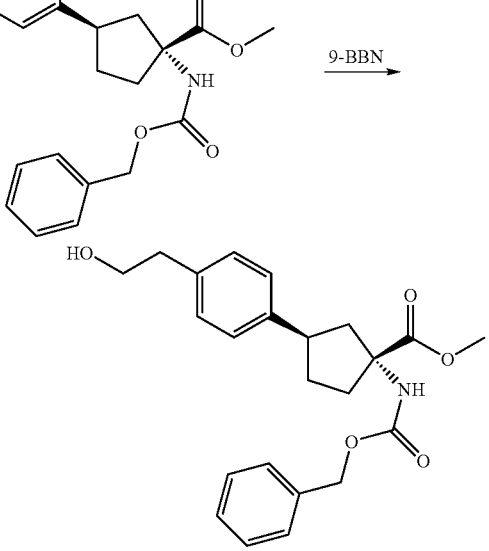

9-BBN (25 ml, 12.50 mmol) was added dropwise to a stirred and cooled solution of (1R,3R)-methyl 1-(benzyloxycarbonylamino)-3-(4-vinylphenyl)cyclopentanecarboxylate (0.682 g, 1.797 mmol) in THF (15 mL). The reaction mixture was checked by TLC to ensure complete conversion to boronate. Once complete the ice bath was removed and stirring was continued overnight. The reaction mixture was cooled to 0° C. and methanol (20 ml) was added. Aqueous NaOH (7.30 ml, 14.59 mmol) and H$_2$O$_2$ (1.522 ml, 14.90 mmol) were poured into the reaction mixture. Stirring was continued for 2 hours. The solvent was removed under reduced pressure and the product purified by FCC to afford (1R,3R)-methyl 1-(benzyloxycarbonylamino)-3-(4-(2-hydroxyethyl)phenyl)cyclopentanecarboxylate (0.507 g, 1.276 mmol, 71.0% yield) as colorless oil.

LCMS (Table 1, Method b) R$_t$=2.53 min; m/z: 398.30 (M+H)$^+$.

General Procedure V: Deprotection of a Cbz Group from an Amine

A Cbz-protected amine dissolved in an organic solvent (such as methanol, ethanol or ethyl acetate; preferably ethanol) is added to a slurry of Pearlman's Catalyst (2-10 mol %, preferably 5 mol %) in an organic solvent (such as methanol, ethanol or ethyl acetate; preferably ethanol). The hydrogen gas is bubbled through the reaction for about 5 minutes. The reaction is stirred under the atmosphere of hydrogen for a period of 1-48 hours (preferably 2-24 hours). The progress of the reaction is monitored via LCMS. The resulting crude reaction mixture is filtered through Celite® and the filtrate is concentrated in vacuo to yield crude product, which can be further purified via column chromatography or used as is for the next step.

Exemplification of General Procedure V:

Preparation of (1R,3R)-methyl 1-amino-3-(4-(2-(3-methoxyphenoxy)ethyl)phenyl)cyclopentanecarboxylate

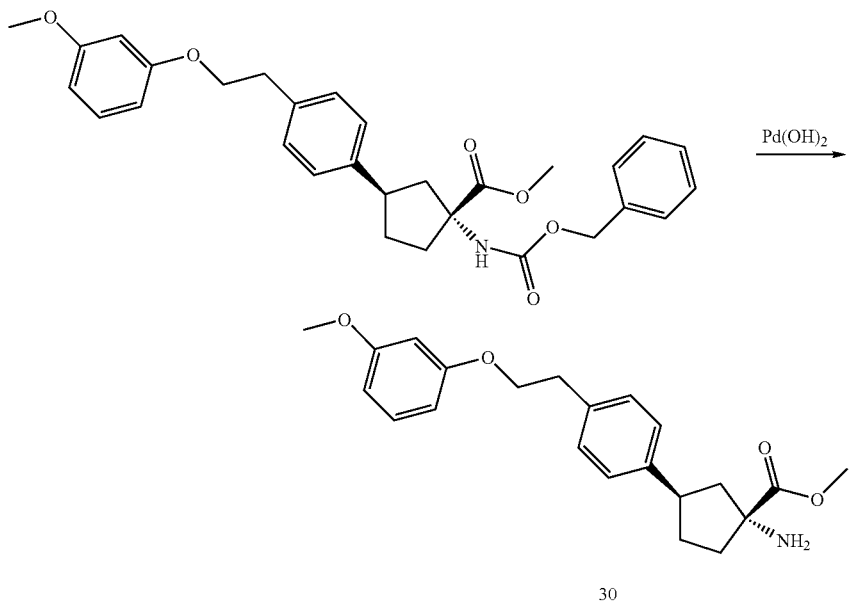

A solution of (1R,3R)-methyl 1-(benzyloxycarbonylamino)-3-(4-(2-(3-methoxyphenoxy)ethyl)phenyl)cyclopentanecarboxylate (0.266 g, 0.528 mmol) in EtOH (2.0 ml) was added to a slurry of Pearlman's Catalyst (0.019 g, 0.026 mmol) in EtOH (5.28 ml). Hydrogen gas was then bubbled through the reaction mixture for 2-3 minutes. The resulting mixture was stirred under the atmosphere of hydrogen overnight. The crude mixture was filtered through Celite® and the filtrate was concentrated in vacuo to yield (1R,3R)-methyl 1-amino-3-(4-(2-(3-methoxyphenoxy)ethyl) phenyl)cyclopentanecarboxylate (157 mg, 0.425 mmol) as colorless oil.

LCMS (Table 1, Method b) $R_t$=1.82 min; m/z: 370.40 (M+H)$^+$.

General Procedure W: Synthesis of an Alpha-Beta Unsaturated Ketone

An organometallic reagent (1-3 equivalents, preferably 1.1 equivalents) is added to a solution of a beta-alkoxy enone in an organic solvent (preferably THF) at about −78° C.-room temperature (preferably 0° C.). Following the addition the reaction mixture is allowed to warm to about room temperature. After 1 h 1N HCl is added until a pH of 1 is obtained. The reaction mixture is taken through an aqueous work-up and the crude product can be purified by chromatography.

Exemplification of General Procedure W:

Preparation of 3-(4-octylphenyl)cyclohex-2-enone

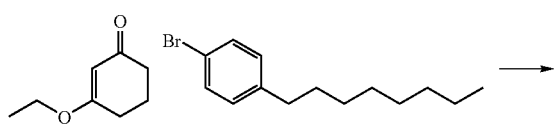

-continued

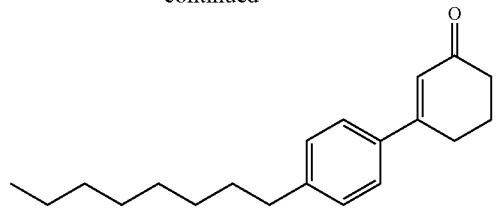

To a suspension of magnesium (1.477 g, 60.8 mmol) in THF (56 mL) was added 1-bromo-4-octylbenzene (15.00 g, 55.7 mmol). After stirring for about 6 h the reaction mixture was added with filtering to a solution of 3-ethoxycyclohex-2-enone (7.10 g, 50.6 mmol) in THF (28.0 mL) at 0° C. Following the addition the reaction mixture was allowed to warm to room temperature. After 1 h 1N HCl was added until a pH of 1 was obtained. The reaction mixture was diluted with Et$_2$O and the organic layer was separated, washed with NaHCO$_3$, and brine, dried with (Na$_2$SO$_4$, filtered and concentrated in vacuo. The crude product was purified by chromatography on silica gel (EtOAc/Hep) to provide 3-(4-octylphenyl)cyclohex-2-enone (9.5 g, 33.4 mmol, 65.9% yield) as a colorless oil.

LCMS (Table 1, Method a) $R_t$=4.53 min; m/z: 285 (M−H)$^-$; $^1$H NMR (400 MHz, DMSO-d6) δ 7.57 (d, 2H), 7.25 (d, 2H), 6.34 (s, 1H), 2.76 (dd, 2H), 2.60 (dd, 2H), 2.40 (dd, 2H), 2.03 (dddd, 2H), 1.58-1.55 (m, 2H), 1.27-1.24 (m, 10H), 0.85 (t, 3H).

General Procedure X: Addition of an Organometallic Reagent to an Ester

To a solution of an ester in an organic solvent (preferably THF) at about −78° C.-room temperature (preferably 0° C.) is added an organometallic reagent (2-10 equivalents, preferably 5 equivalents). After about 2 h the reaction mixture is quenched with water and the crude product is extracted into a suitable organic solvent (preferably ether). The crude product can be purified by chromatography.

Exemplification of General Procedure X:

Preparation of 2-((1R,3R)-1-amino-3-(4-octylphenyl)cyclopentyl)propan-2-ol

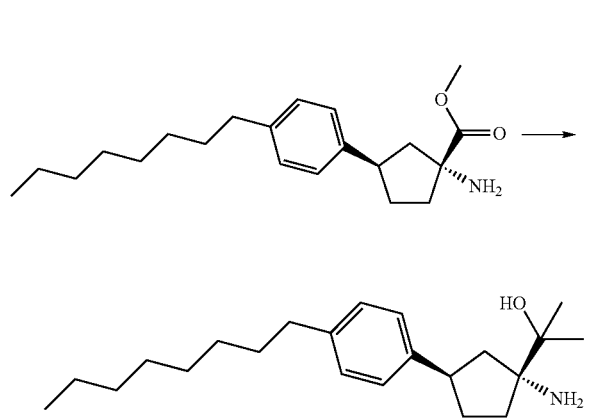

To a solution of (1R,3R)-methyl 1-amino-3-(4-octylphenyl)cyclopentanecarboxylate (640 mg, 1.931 mmol) in THF (20 mL) at 0° C. was added a 3M solution of methylmagnesium iodide (3.22 mL, 9.65 mmol) in THF. After 2 h water was added to the reaction mixture resulting in an emulsion. The reaction mixture was diluted with Et₂O (100 mL) and water (100 mL). To the emulsion was added Rochelle's salt (approx. 5 g). The resulting emulsion was sonicated for 15 min. The organic layer was removed. The aqueous layer was extracted with Et₂O (100 mL) sonicating for 15 min to break up the emulsion. The combined organic layers were dried (Na₂SO₄) filtered and conc. in vacuo. The crude product was purified by chromatography on silica gel (40 g) eluting with DCM:MeOH:HOAc:H₂O (900:90:9:1). The fractions containing the product were combined and concentrated in vacuo. The resulting residue was diluted with water and lyophilized to provide 2-((1R,3R)-1-amino-3-(4-octylphenyl)cyclopentyl)propan-2-ol, Acetic Acid salt (265 mg, 0.677 mmol, 35.1% yield)

LCMS (Table 1, Method a) R$_t$=3.28 min; m/z: 333 (M−H)⁻; ¹H NMR (400 MHz, DMSO-d6) δ 7.15 (d, 2H), 7.08 (d, 2H), 5.30 (bs, 3H), 3.40-3.25 (m, 1H), 2.52-2.50 (m, 2H), 2.20-2.05 (m, 2H), 1.90-1.78 (m, 4H), 1.70-1.60 (m, 1H), 1.51-1.49 (m, 3H), 1.40-1.30 (m, 1H), 1.30-1.25 (m, 10H), 1.17 (s, 6H), 0.85 (t, 3H).

General Procedure Y: Conversion of a Tertiary Alcohol to an Alkane

To a slurry of silica gel and a lewis acid (preferably copper sulfate hydrate) in an organic solvent (preferably toluene) is added a tertiary alcohol. The reaction mixture is heated to about 50-200° C. (preferably 100° C.). After about 2 days a dehydrating reagent (preferably Na2SO4) is added. After about 1 day the reaction mixture is filtered. The resulting alkene is added to a slurry of a metal catalyst (preferably palladium hydroxide on carbon) in an organic solvent (preferably methanol). Hydrogen is bubbled through the solution for about 5 min and an atmosphere of hydrogen is maintained via balloon. After 15 h the reaction mixture is filtered and concentrated in vacuo to provide the alkane.

Exemplification of General Procedure Y:

Preparation of (5R,7R)-7-(4-(7-methyloctyl)phenyl)-3-oxa-1-azaspiro[4.4]nonan-2-one

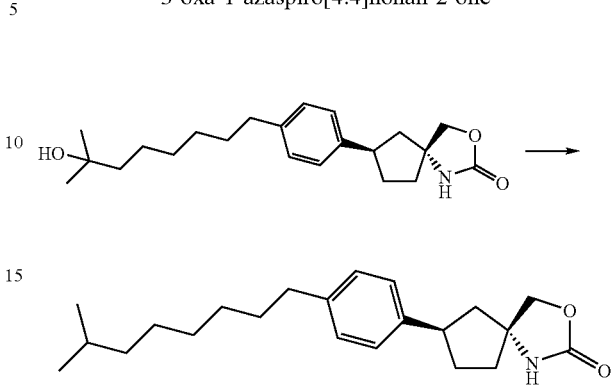

To a slurry of silica gel (1 g) and copper sulfate hydrate (1 g) in toluene (10 mL) was added (5R,7R)-7-(4-(7-hydroxy-7-methyloctyl)phenyl)-3-oxa-1-azaspiro[4.4]nonan-2-one (230 mg, 0.640 mmol). The reaction mixture was heated to 100° C. After 2 days Na₂SO₄ (approx. 500 mg) was added. After an additional 1 day at 100° C. the reaction mixture was cooled to room temperature and filtered, rinsing with EtOAc. The resulting alkene was added to a slurry of palladium hydroxide on carbon (4.49 mg, 0.032 mmol) in MeOH (10.00 mL). Hydrogen was bubbled through the solution for 5 min and an atmosphere of hydrogen was maintained via balloon. After 15 h the reaction mixture was filtered and concentrated in vacuo. The crude alkane was purified by chromatography on silica gel (EtOAc/Hep) to provide (5R,7R)-7-(4-(7-methyloctyl)phenyl)-3-oxa-1-azaspiro[4.4]nonan-2-one (120 mg, 0.349 mmol, 54.6% yield) as a colorless solid.

¹H NMR (400 MHz, DMSO-d₆) δ 8.06 (s, 1H), 7.13 (d, 2H), 7.08 (d, 2H), 4.26 (d, 1H), 4.19 (d, 1H), 3.23-3.16 (m, 1H), 2.55-2.50 (m, 2H), 2.16-2.00 (m, 3H), 1.85-1.75 (m, 2H), 1.60-1.45 (m, 4H), 1.3-1.2 (m, 6H), 1.15-1.10 (m, 2H), 0.84 (d, 6H).

General Procedure Z: Hydration of an Alkyne

An alkyne is dissolved in formic acid and heated to about 50-120° C. (preferably 80° C.). After about 4 h the reaction mixture is cooled to room temperature and concentrated in vacuo, diluted with water and heated to about 50-120° C. (preferably 80° C.). After about 4 h the reaction mixture is purified by RP HPLC.

Exemplification of General Procedure Z:

Preparation of 1-(4-((1R,3R)-3-amino-3-(hydroxymethyl)cyclopentyl)phenyl)-5-phenylpentan-1-one, Acetic Acid salt

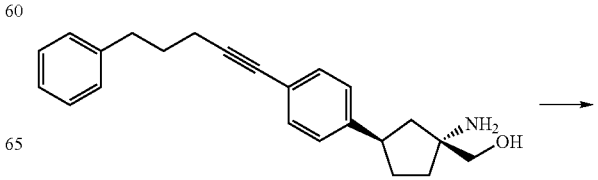

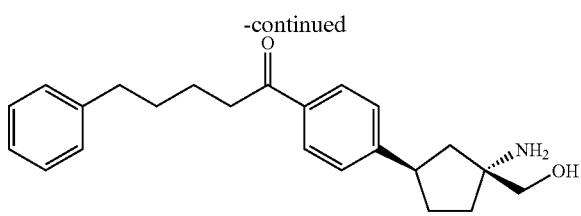

(((1R,3R)-1-amino-3-(4-(5-phenylpent-1-ynyl)phenyl)cyclopentyl)methanol (900 mg, 2.70 mmol) was dissolved in formic acid (20 mL) and heated to about 80° C. After 4 h the reaction mixture was cooled to room temperature, concentrated in vacuo, diluted with water (10 mL) and reheated to about 80° C. After 4 h the reaction mixture was purified by RP HPLC. Concentration of the fractions containing the desired product provided 1-(4-((1R,3R)-3-amino-3-(hydroxymethyl)cyclopentyl)phenyl)-5-phenylpentan-1-one, Acetic Acid (320 mg, 0.778 mmol, 28.8% yield) as an off white foam.

LCMS (Table 1, Method a) $R_t$=2.19 min; m/z: 352 (M−H)$^−$; $^1$H NMR (400 MHz, DMSO-d$_6$) δ 7.87 (d, 2H), 7.36 (d, 2H), 7.29-7.15 (m, 5H), 3.46-3.35 (m, 1H), 3.32 (dd, 2H), 3.00 (dd, 2H), 2.61 (dd, 2H), 2.13-2.08 (m, 1H), 1.93-1.76 (m, 5H), 1.69-1.60 (m, 6H), 1.51-1.41 (m, 1H).

General Procedure AA: Synthesis of an Alkylether

To a strong base (preferably sodium hydride) 0.5-2 equivalents (preferably 1 equivalent) in a suitable solvent (preferably DMF) is added an alkylating agent 1-5 equivalents (preferably 1.2 equivalent) followed by a solution of an alcohol. After the reaction is substantively complete the reaction mixture is taken through an aqueous work up and purified by chromatography or distillation.

Exemplification of General Procedure AA:

Preparation of 7-methoxyhept-1-yne

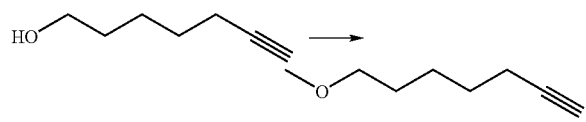

General Procedure AA: Oxidation of an Alcohol to the Ketone

To a slurry of sodium hydride (7.86 g, 197 mmol) in DMF (100 mL) was added methyl iodide (12.29 mL, 197 mmol) followed by a solution of hept-6-yn-1-ol (24.5 g, 197 mmol) in DMF (50 mL). Following the addition the reaction was monitored by TLC. After 2 h additional methyl iodide (6 mL, 50 mmol) was added followed by sodium hydride (1 g, 25 mmol) portions. At 1 h intervals additional sodium hydride (1 g, 25 mmol) portions was added until no alcohol remained as indicated by TLC. Et$_2$O (50 mL) and water (100 mL) was added to the reaction mixture and the layers were separated. The organic layer was washed with brine, dried using Na$_2$SO$_4$, filtered and distilled (145-155° C.) to provide 7-methoxyhept-1-yne (18 g, 121 mmol, 61.7% yield) as a colorless oil.

$^1$H NMR (400 MHz, DMSO-d$_6$) δ. 3.28 (t, 2H), 3.19 (s, 3H), 2.71 (t, 1H), 2.13 (dddd, 2H), 1.51-1.33 (m, 6H).

General Procedure BB: Synthesis of an N-Aryl Prolinol

To a microwave reaction vial is added 1,4-dibromobutan-2-ol (0.5-2 equivalents, preferably 1.1 equivalent), an aniline (0.5-2 equivalents, preferably 1.0 equivalent), potassium carbonate (0.5-2 equivalents, preferably 1.1 equivalent) and a polar protic solvent (preferably water). The reaction vial is heated in a microwave at (50-200 watts, preferably 100 watt), (50-200° C., preferably 120° C., (100-200 psi, preferably 150 psi), (ramp time of 2-10 min, preferably 5 min) and (hold time of 10-30 min, preferably 20 min). After cooling to room temperature an organic solvent (preferably EtOAc) is added to the reaction mixture. The organic layer is removed and concentrated in vacuo. The crude product is purified by flash chromatography on silica gel.

Exemplification of General Procedure BB:

Preparation of 1-(4-octylphenyl)pyrrolidin-3-ol

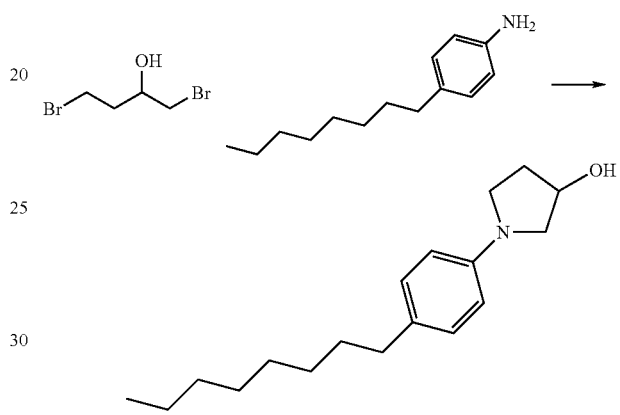

To 10 microwave vials were added 1,4-dibromobutan-2-ol (0.375 mL, 2.75 mmol), 4-octylaniline (0.572 mL, 2.5 mmol), potassium carbonate (0.380 g, 2.75 mmol) and water (3 mL). Each vial was heated in a CEM microwave at 100 watt, 120° C., 150 psi, ramp time 5 min and hold time 20 min. After cooling to room temperature EtOAc (1 mL) was added to each vial. After thorough mixing the organic layers were removed, combined and concentrated in vacuo. The product was purified by flash chromatography on silica gel (eluting with EtOAc/Hep) to provide 1-(4-octylphenyl)pyrrolidin-3-ol (3.7 g, 13.43 mmol, 53.7% yield) as a white solid which was stored under nitrogen in a sealed flask.

LCMS (Table 1, Method a) $R_t$=4.88 min; m/z: 276 (M−H)$^−$; $^1$H NMR (400 MHz, DMSO-d$_6$) δ. 6.95 (d, 2H), 6.41 (d, 2H), 4.88 (d, 1H), 4.37 (m, 1H), 3.36 (dd, 1H), 3.3-3.17 (m, 3H), 3.01 (dd, 1H), 2.43 (t, 2H), 2.06-1.98 (m, 1H), 1.89-1.84 (m, 1H), 1.52-1.47 (m, 2H), 1.29-1.24 (m, 10H), 0.85 (t, 3H).

General Procedure CC: Oxidation of an Alcohol to the Ketone

To a solution of an alcohol in DMSO and an organic solvent (preferably toluene) at −10-10° C. (preferably 0° C.) is added a weak organic base (preferably pyridine, 2-5 equivalents, preferably 3.5 equivalents), followed by a carbodiimide (preferably DCC, 1-3 equivalents, preferably 1.75 equivalents), and an organic acid (preferably TFA, 0.5-2 equivalents, preferably 1 equivalents). Following the addition the reaction mixture is allowed to warm to about room temperature. After about 5 h saturated NaCHCO$_3$ is added to the reaction mixture and the suspension was filtered. The filtrate is partially concentrated in vacuo and the resulting dark oil is extracted with heptane. The heptane extracts are purified by silica gel chromatography.

Exemplification of General Procedure CC:

Preparation of 1-(4-octylphenyl)pyrrolidin-3-one

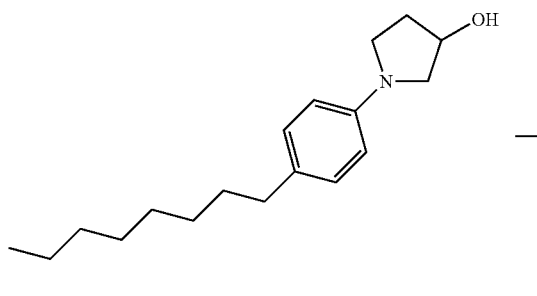

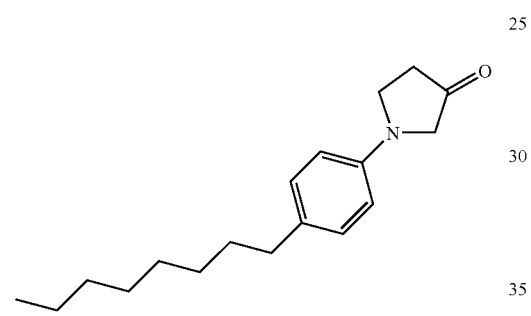

To a solution of 1-(4-octylphenyl)pyrrolidin-3-ol (3.7 g, 13.43 mmol) in DMSO (50 ml) and Toluene (50.0 ml) at 0° C. was added pyridine (3.80 ml, 47.0 mmol), DCC (4.85 g, 23.51 mmol), and TFA (1.035 ml, 13.43 mmol). Following the addition the reaction mixture was allowed to warm to room temperature. After 5 h saturated NaCHCO$_3$ was added to the reaction mixture and the suspension was filtered. The filtrate was partially concentrated in vacuo and the resulting dark oil was extracted with heptane. The heptane extracts were purified by silica gel chromatography eluting with EtOAc/Hep to provide 1-(4-octylphenyl)pyrrolidin-3-one (3.1 g, 11.34 mmol, 84% yield) as a colorless solid.

$^1$H NMR (400 MHz, DMSO-d$_6$) δ. 7.03 (d, 2H), 6.61 (d, 2H), 3.61 (s, 2H), 3.56 (t, 2H), 2.66 (t, 2H), 2.47 (t, 2H), 1.55-1.48 (m, 2H), 1.30-1.20 (m, 10H), 0.85 (t, 3H).

General Procedure DD: Reductive Amination on a Ketone

To a ketone dissolved in a suitable solvent (such as dichloromethane, methanol, tetrahydrofuran, or dimethylformamide, preferably methanol) is added an amine (1-2 equivalents, preferably 1 equivalent), acetic acid (1-5 equivalents, preferably 3 equivalents) and resin-bound sodium cyanoborohydride (1-5 equivalents, preferably 3 equivalents). The reaction mixture is stirred under an inert atmosphere at room temperature for a period of 12-72 hours (preferably 48 hours). Reaction is then filtered to remove the resin-bound borohydride and the resin washed 3× with a suitable solvent (such as dichloromethane, methanol, tetrahydrofuran, or dimethylformamide, preferably methanol). The filtrate is collected, concentrated and chromatographed to give the desired product.

Exemplification of General Procedure DD:

Preparation of Methyl-[3-(4-octyl-phenyl)-cyclopentyl]-amino}-acetic acid

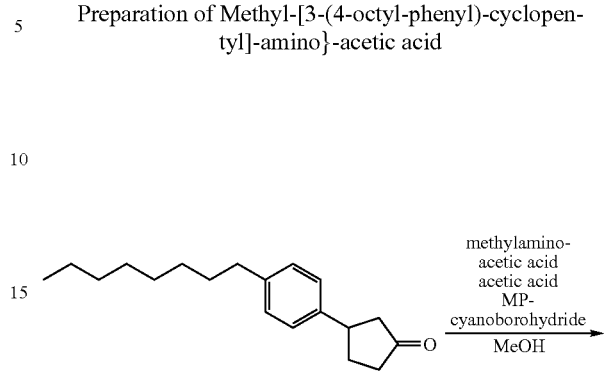

To 3-(4-octyl-phenyl)-cyclopentanone (0.200 g, 0.734 mmol) dissolved in methanol (4.0 mL) was added methylamiono-acetic acid (0.065 g, 0.734 mmol), acetic acid (0.125 mL, 2.20 mmol) and resin-bound sodium cyanoborohydride (0.941 g, 2.20 mmol, 2.34 mmol/g loading). The reaction mixture was stirred under an inert atmosphere at room temperature for 72 hours. The reaction was then filtered to remove the resin-bound borohydride and the resin was washed with MeOH (3×10 mL). The filtrate was collected, concentrated and purified by RP-HPLC (A=50 mM ammonium acetate, B=acetonitrile; 30-80% B over 30.0 min (21.0 mL/min flow rate); 21.2×250 mm Thermo Hyperprep C18 column, 8 μm particles) to give Methyl-[3-(4-octyl-phenyl)-cyclopentyl]-amino}-acetic acid as a white solid (0.112 g, 43%)

LCMS (Table 1, Method f) R$_t$=1.94 min; m/z: 344 (M−H)$^-$, m/z: 346 (M+H)$^+$

Tables Utilizing General Procedures

TABLE A

Examples following general procedures
A, B, C, D, E, F, H (Scheme 1)

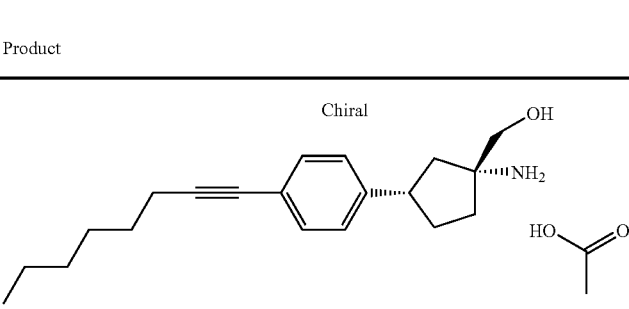

| Ex # | Boronic acid | Alkyne | Product | $R_t$/min (method) | m/z |
|---|---|---|---|---|---|
| A.1 | 4-Bromo-phenyl-boronic acid | Oct-1-yne | (shown above) | 2.44 (a) | 300 (M + H)+ |

Product: [(1R, 3S)-1-Amino-3-(4-oct-1-ynyl-phenyl)-cyclopentyl]-methanol; compound with acetic acid

TABLE B

Examples following general procedures
A, B, C, D, E, F, G, H (Scheme 1)

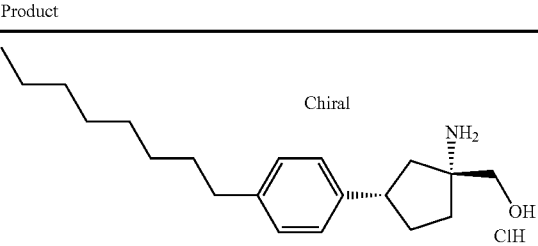

| Ex # | Boronic acid | Alkyne | Product | $R_t$/min (method) | m/z |
|---|---|---|---|---|---|
| B.1 | 4-Bromo-phenyl-boronic acid | Oct-1-yne | (shown above) | 2.75 (a) | 304 (M + H)+ |

Product: [(1R, 3S)-1-Amino-3-(4-octyl-phenyl)-cyclopentyl]-methanol; hydrochloride TABLE B-continued Examples following general procedures
A, B, C, D, E, F, G, H (Scheme 1)

| Ex # | Boronic acid | Alkyne | Product | R$_t$/min (method) | m/z |
|---|---|---|---|---|---|
| B.2 | 4-Bromo-phenyl-boronic acid | Prop-2-ynyloxy-benzene | Product: {(1R, 3S)-1-Amino-3-[4-(3-phenoxy-propyl)-phenyl]-cyclopentyl}-methanol; hydrochloride | 2.17 (a) | 326 (M + H)$^+$ |
| B.3 | 3-Bromo-phenyl-boronic acid | Dec-1-yne | Product: ((3S)-1-Amino-3-(3-decylphenyl)cyclopentyl)methanol; hydrochloride | 3.92 (a) | 332 (M + H)$^+$ |
| B.4 | 3-Bromo-phenyl-boronic acid | Non-1-yne | Product: ((3S)-1-Amino-3-(3-nonylphenyl)cyclopentyl)methanol; hydrochloride | 3.04 (a) | 318 (M + H)$^+$ |
| B.5 | 3-Bromo-phenyl-boronic acid | Oct-1-yne | Product: ((3S)-1-Amino-3-(3-octylphenyl)cyclopentyl)methanol; hydrochloride | 3.32 (a) | 304 (M + H)+ |

TABLE B-continued

Examples following general procedures
A, B, C, D, E, F, G, H (Scheme 1)

Cyclopent-2-enone → (Boronic acid, General Procedure A) → General Procedure B → General Procedure C → General Procedure D → General Procedure E → (Alkyne, General Procedure F) → General Procedure G → General Procedure H → Final product

| Ex # | Boronic acid | Alkyne | Product | R$_t$/min (method) | m/z |
|---|---|---|---|---|---|
| B.6 | 3-Bromo-phenyl-boronic acid | Hept-1-yne | Product: ((3S)-1-Amino-3-(3-heptylphenyl)cyclopentyl)methanol; hydrochloride | 3.00 (a) | 290 (M + H)$^+$ |
| B.7 | 4-Bromo-phenyl-boronic acid | 6-Methoxy-hex-1-yne | Product: ((1R, 3S)-1-Amino-3-(4-(6-methoxyhexyl)phenyl)cyclopentyl)methanol; hydrochloride | 2.51 (a) | 306 (M + H)$^+$ |
| B.8 | 4-Bromo-phenyl-boronic acid | But-3-ynyl-benzene | Product: ((1R, 3S)-1-Amino-3-(4-(4-phenylbutyl)phenyl)cyclopentyl)methanol; hydrochloride | 3.13 (a) | 324 (M + H)$^+$ |
| B.9 | 4-Bromo-phenyl-boronic acid | 6-Ethoxy-hex-1-yne (Q) | Product: ((1R, 3S)-1-Amino-3-(4-(6-ethoxyhexyl)phenyl)cyclopentyl)methanol; hydrochloride (Chiral) | 2.67 (a) | 320.45 (M + H)$^+$ |

TABLE B-continued

Examples following general procedures
A, B, C, D, E, F, G, H (Scheme 1)

cyclopent-2-enone → General Procedure A (Boronic acid) → General Procedure B → General Procedure C → General Procedure D → General Procedure E → General Procedure F (Alkyne) → General Procedure G → General Procedure H → Product

| Ex # | Boronic acid | Alkyne | Product | R$_t$/min (method) | m/z |
|---|---|---|---|---|---|
| B.10 | 4-Bromo-phenyl-boronic acid | 6-isopropoxy-hex-1-yne | | 2.68 (a) | 334 (M + H)$^+$ |

Product: ((1R, 3S)-1-amino-3-(4-(6-isopropoxyhexyl)phenyl)cyclopentyl)methanol; hydrochloride

TABLE C

Examples following general procedures
A, I, J, E, F, H (Scheme 2)

cyclopent-2-enone → General Procedure A (Boronic acid) → General Procedure I → General Procedure J → General Procedure E → General Procedure F (Alkyne) → General Procedure H → Product

| Ex # | Boronic acid | Alkyne | Product | R$_t$/min (method) | m/z |
|---|---|---|---|---|---|
| C.1 | 4-Bromo-phenyl-boronic acid | Oct-1-yne | Chiral | 2.37 (a) | 300 (M + H)$^+$ |
| C.2 | 4-Bromo-phenyl-boronic acid | But-3-ynyl-benzene | Chiral | 2.24 (a) | 320 (M + H)$^+$ |

Product: [(1R, 3R)-1-Amino-3-(4-oct-1-ynyl-phenyl)-cyclopentyl]-methanol; compound with acetic acid Product: {(1R, 3R)-1-Amino-3-[4-(4-phenyl-but-1-ynyl)-phenyl]-cyclopentyl}-methanol; compound with acetic acid TABLE C-continued Examples following general procedures
A, I, J, E, F, H (Scheme 2)

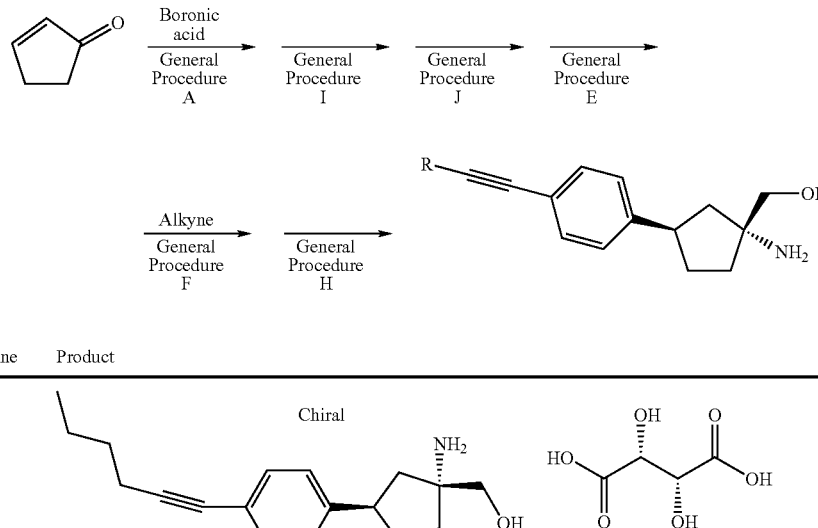

| Ex # | Boronic acid | Alkyne | Product | R₁/min (method) | m/z |
|---|---|---|---|---|---|
| C.3 | 4-Bromo-phenyl-boronic acid | Hex-1-yne | 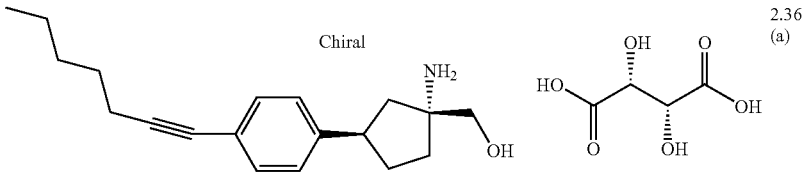<br>Product: [(1R, 3R)-1-Amino-3-(4-hex-1-ynyl-phenyl)-cyclopentyl]-methanol; compound with (2R, 3R)-2,3-dihydroxy-succinic acid | 2.14 (a) | 272 (M + H)⁺ |
| C.4 | 4-Bromo-phenyl-boronic acid | Hept-1-yne | 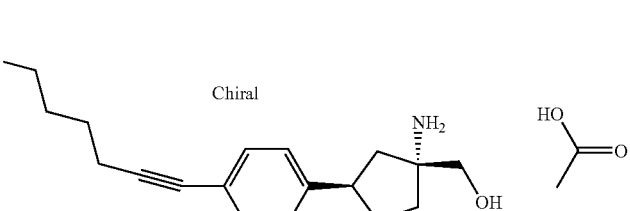<br>Product: [(1R, 3R)-1-Amino-3-(4-hept-1-ynyl-phenyl)-cyclopentyl]-methanol; compound with (2R, 3R)-2,3-dihydroxy-succinic acid | 2.36 (a) | 286 (M + H)⁺ |
| C.5 | 4-Bromo-phenyl-boronic acid | 6-Methoxy-hex-1-yne | 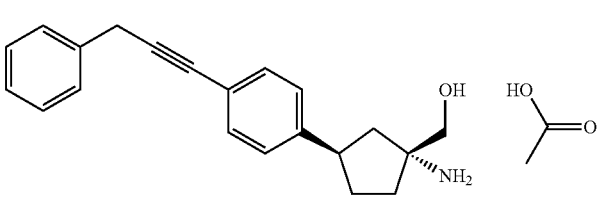<br>Product: {(1R, 3R)-1-Amino-3-[4-(6-methoxy-hex-1-ynyl)-phenyl]-cyclopentyl}-methanol; compound with acetic acid | 1.86 (a) | 302 (M + H)⁺ |
| C.6 | 4-Bromo-phenyl-boronic acid | Prop-2-ynyl-benzene | 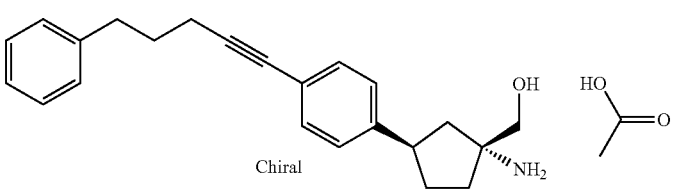<br>Product: {(1R, 3R)-1-Amino-3-[4-(3-phenyl-prop-1-ynyl)-phenyl]-cyclopentyl}-methanol; compound with acetic acid | 2.16 (a) | 306 (M + H)⁺ |
| C.7 | 4-Bromo-phenyl-boronic acid | Pent-4-ynyl-benzene | <br>Product: {(1R, 3R)-1-Amino-3-[4-(5-phenyl-pent-1-ynyl)-phenyl]-cyclopentyl}-methanol; compound with acetic acid | 2.97 (a) | 334 (M + H)⁺ |

TABLE C-continued

Examples following general procedures
A, I, J, E, F, H (Scheme 2)

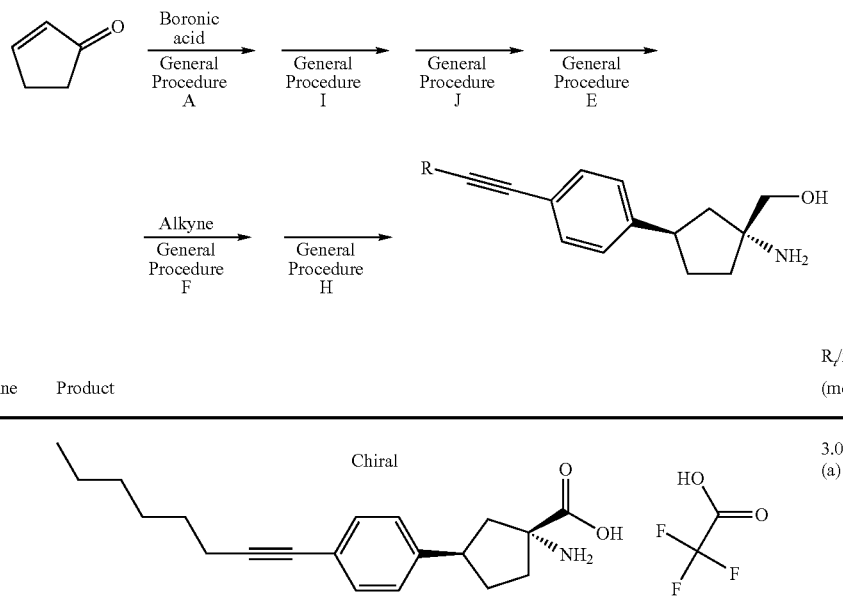

| Ex # | Boronic acid | Alkyne | Product | R$_t$/min (method) | m/z |
|---|---|---|---|---|---|
| C.8 | 4-Bromo-phenyl-boronic acid | Oct-1-yne | (shown above) | 3.02 (a) | 314 (M + H)$^+$ |

Product: (1R, 3R)-1-Amino-3-(4-oct-1-ynyl-phenyl)-cyclopentane-carboxylic acid; compound with trifluoro-acetic acid

TABLE D

Examples following general procedures
A, I, J, E, F, G, H (Scheme 2)

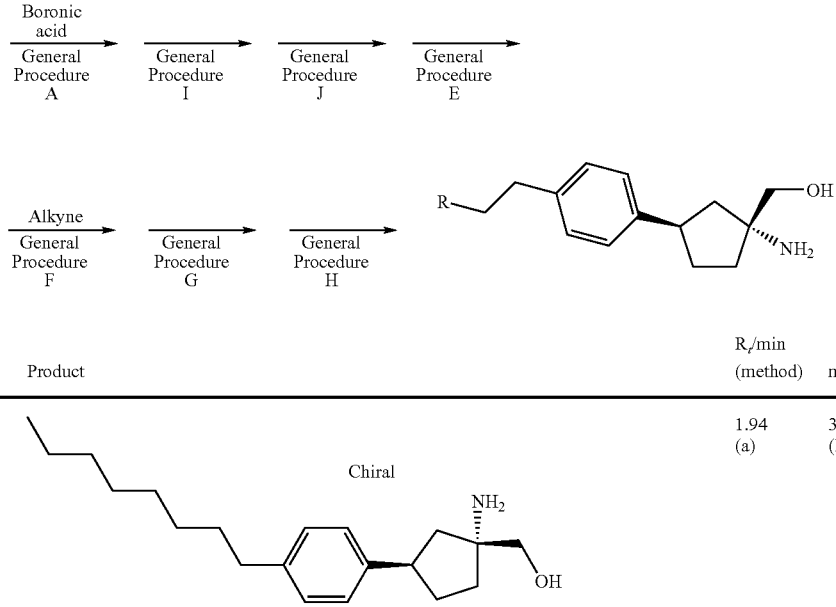

| Ex # | Boronic acid | Alkyne | Product | R$_t$/min (method) | m/z |
|---|---|---|---|---|---|
| D.1 | 4-Bromo-phenyl-boronic acid | Oct-1-yne | (shown above) | 1.94 (a) | 304 (M + H)$^+$ |

Product: [(1R, 3R)-1-Amino-3-(4-octyl-phenyl)-cyclopentyl]-methanol; hydrochloride TABLE D-continued Examples following general procedures
A, I, J, E, F, G, H (Scheme 2)

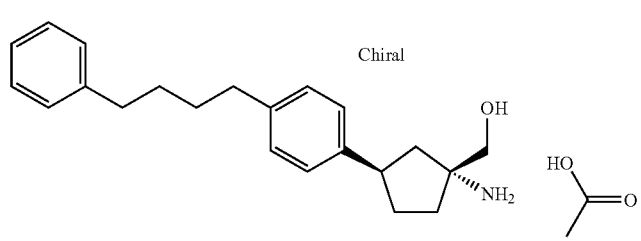

| Ex # | Boronic acid | Alkyne | Product | R$_t$/min (method) | m/z |
|---|---|---|---|---|---|
| D.2 | 4-Bromo-phenyl-boronic acid | But-3-ynyl-benzene | 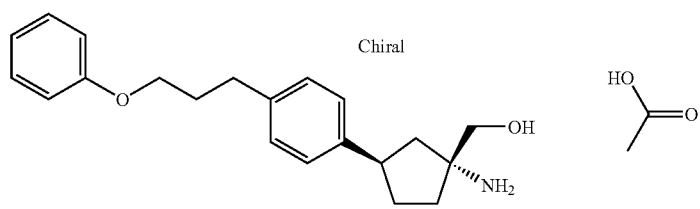 Product: {(1R, 3R)-1-Amino-3-[4-(4-phenyl-butyl)-phenyl]-cyclopentyl}-methanol; compound with acetic acid | 2.85 (a) | 324 (M + H)$^+$ |
| D.3 | 4-Bromo-phenyl-boronic acid | Prop-2-ynyloxy-benzene | Product: {(1R, 3R)-1-Amino-3-[4-(3-phenoxy-propyl)-phenyl]-cyclopentyl}-methanol; compound with acetic acid | 2.18 (a) | 326 (M + H)$^+$ |
| D.4 | 4-Bromo-phenyl-boronic acid | 6-Methoxy-hex-1-yne | 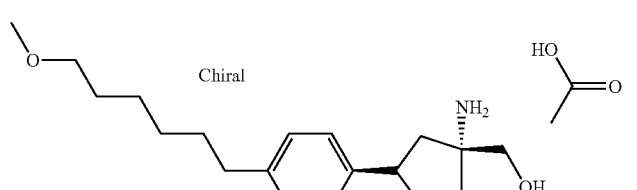 Product: {(1R, 3R)-1-Amino-3-[4-(6-methoxy-hexyl)-phenyl]-cyclopentyl}-methanol; compound with acetic acid | 2.56 (a) | 306 (M + H)$^+$ |
| D.5 | 4-Bromo-phenyl-boronic acid | Prop-2-ynyl-benzene | 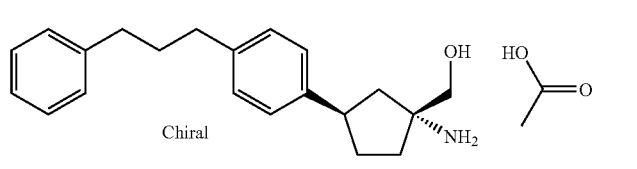 Product: {(1R, 3R)-1-Amino-3-[4-(3-phenyl-propyl)-phenyl]-cyclopentyl}-methanol; compound with acetic acid | 2.27 (a) | 310 (M + H)$^+$ |

TABLE D-continued

*Examples following general procedures*
*A, I, J, E, F, G, H (Scheme 2)*

| Ex # | Boronic acid | Alkyne | Product | $R_t$/min (method) | m/z |
|---|---|---|---|---|---|
| D.6 | 4-Bromo-phenyl-boronic acid | Pent-4-ynyl-benzene | Product: {(1R, 3R)-1-Amino-3-[4-(5-phenyl-pentyl)-phenyl]-cyclopentyl}-methanol; compound with acetic acid | 2.48 (a) | 338 (M + H)+ |
| D.7 | 4-Bromo-phenyl-boronic acid | 4-Propoxy-but-1-yne | Product: {(1R, 3R)-1-Amino-3-[4-(4-propoxy-butyl)-phenyl]-cyclopentyl}-methanol; hydrochloride | 2.58 (a) | 305 (M + H)+ |
| D.8 | 4-Bromo-phenyl-boronic acid | Hept-1-yne | Product: ((1R, 3R)-1-Amino-3-(4-heptylphenyl)cyclopentyl)methanol; hydrochloride | 3.43 (a) | 290 (M + H)+ |
| D.9 | 4-Bromo-phenyl-boronic acid | Hex-1-yne | Product: ((1R, 3R)-1-Amino-3-(4-hexylphenyl)cyclopentyl)methanol; hydrochloride | 3.18 (a) | 276 (M + H)+ |

TABLE D-continued

*Examples following general procedures*
*A, I, J, E, F, G, H (Scheme 2)*

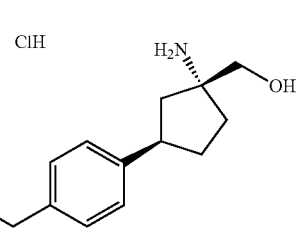

| Ex # | Boronic acid | Alkyne | Product | R_t/min (method) | m/z |
|---|---|---|---|---|---|
| D.10 | 4-Bromo-phenyl-boronic acid | 7-Methoxy-hept-1-yne (Q) | 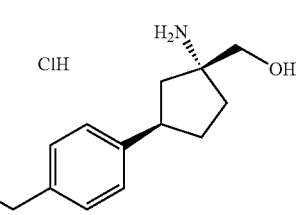<br>Product: ((1R, 3R)-1-Amino-3-(4-(7-methoxyheptyl)phenyl)cyclopentyl)methanol; hydrochloride | 2.83 (a) | 320.42 (M + H)⁺ |
| D.11 | 4-Bromo-phenyl-boronic acid | 6-Ethoxy-hex-1-yne (Q) | 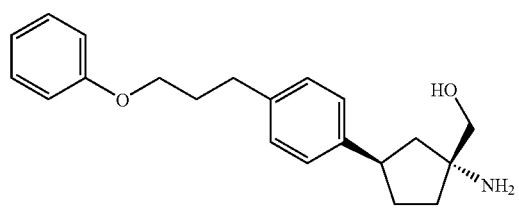<br>Product: ((1R, 3R)-1-Amino-3-(4-(6-ethoxyhexyl)phenyl)cyclopentyl)methanol; hydrochloride | 2.88 (a) | 320.41 (M + H)⁺ |
| D.12 | 4-Bromo-phenyl-boronic acid | (prop-2-ynyloxy) benzene | 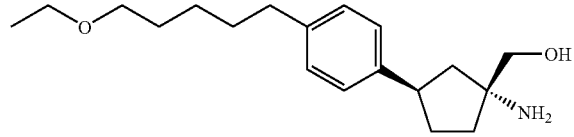<br>Product: ((1R, 3R)-1-amino-3-(4-(3-phenoxypropyl)phenyl)cyclopentyl)methanol; hydrochloride | 2.69 (a) | 326 (M + H)⁺ |
| D.13 | 4-Bromo-phenyl-boronic acid | 5-ethoxy-pent-1-yne | <br>Product: ((1R, 3R)-1-amino-3-(4-(5-ethoxypentyl)phenyl)cyclopentyl)methanol; hydrochloride | 2.37 (a) | 306 (M + H)⁺ |

TABLE D-continued

*Examples following general procedures*
*A, I, J, E, F, G, H (Scheme 2)*

| Ex # | Boronic acid | Alkyne | Product | R$_t$/min (method) | m/z |
|---|---|---|---|---|---|
| D.14 | 4-Bromo-phenyl-boronic acid | 3-(2-methoxy-ethoxy)prop-1-yne | | 1.85 (a) | 308 (M + H)$^+$ |

Product: ((1R, 3R)-1-amino-3-(4-(3-(2-methoxyethoxy)propyl)phenyl)cyclopentyl)methanol; hydrochloride

| D.15 | 4-Bromo-phenyl-boronic acid | 1-(prop-2-ynyloxy)butane | | 3.08 (a) | 306 (M + H)$^+$ |

Product: ((1R, 3R)-1-amino-3-(4-(3-butoxypropyl)phenyl)cyclopentyl)methanol; hydrochloride

| D.16 | 4-Bromo-phenyl-boronic acid | 1-ethynyl-4-methoxy-benzene | | 2.58 (a) | 326 (M + H)$^+$ |

Product: ((1R, 3R)-1-amino-3-(4-(4-methoxyphenethyl)phenyl)cyclopentyl)methanol; hydrochloride

| D.17 | 4-Bromo-phenyl-boronic acid | 1-ethynyl-4-propoxy-benzene | | 3.24 (a) | 354 (M + H)$^+$ |

Product: (1-amino-3-(4-(4-propoxyphenethyl)phenyl)cyclopentyl)methanol; hydrochloride

TABLE E

Examples following general procedures
A, I, J, E, H, K, L, M, N (Scheme 3)

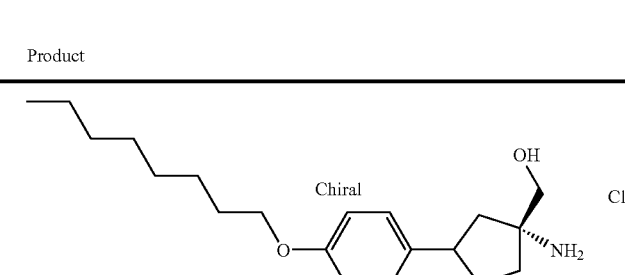

| Ex # | Boronic acid | Alcohol | Product | R$_t$/min (method) | m/z |
|---|---|---|---|---|---|
| E.1 | 4-Methoxy-phenyl boronic acid | Octan-1-ol | 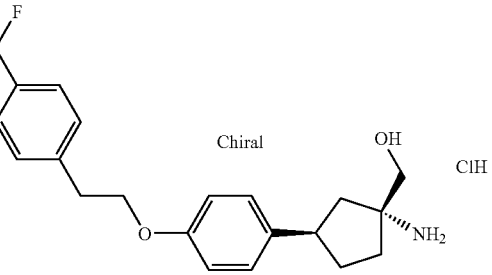 Product: [(1R, 3R)-1-Amino-3-(4-octyloxy-phenyl)-cyclopentyl]-methanol; hydrochloride | 2.58 (a) | 320 (M + H)$^+$ |
| E.2 | 4-Methoxy-phenyl boronic acid | 2-(4-Trifluoro-methyl-phenyl)-ethanol | 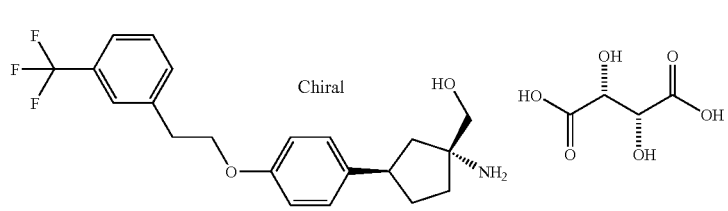 Product: ((1R, 3R)-1-Amino-3-{4-[2-(4-trifluoromethyl-phenyl)-ethoxy]-phenyl}-cyclopentyl)-methanol; hydrochloride | 2.11 (a) | 380 (M + H)$^+$ |
| E.3 | 4-Methoxy-phenyl boronic acid | 2-(3-Trifluoro-methyl-phenyl)-ethanol | 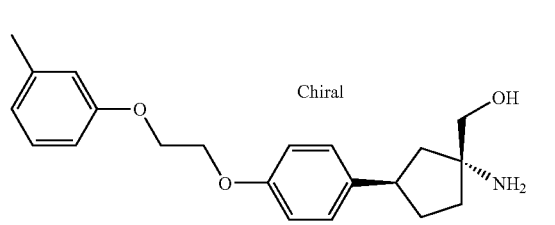 Product: ((1R, 3R)-1-Amino-3-{4-[2-(3-trifluoromethyl-phenyl)-ethoxy]-phenyl}-cyclopentyl)-methanol; compound with (2R, 3R)-2,3-dihydroxy-succinic acid | 2.68 (a) | 380 (M + H)$^+$ |
| E.4 | 4-Methoxy-phenyl boronic acid | 2-m-Tolyl oxy-ethanol |  Product: {(1R, 3R)-1-Amino-3-[4-(2-m-tolyloxy-ethoxy)-phenyl]-cyclopentyl}-methanol; hydrochloride | 2.60 (a) | 342 (M + H)$^+$ |

TABLE E-continued

Examples following general procedures
A, I, J, E, H, K, L, M, N (Scheme 3)

| Ex # | Boronic acid | Alcohol | Product | R$_t$/min (method) | m/z |
|---|---|---|---|---|---|
| E.5 | 4-Methoxyphenyl boronic acid | 4,4,5,5,5-Pentafluoropentan-1-ol | Product: {(1R, 3R)-1-Amino-3-[4-(4,4,5,5,5-pentafluoro-pentyloxy)-phenyl]-cyclopentyl}-methanol; hydrochloride | 2.07 (a) | 368 (M + H)$^+$ |
| E.6 | 4-Methoxyphenyl boronic acid | 2-(4-Methoxyphenyl)-ethanol | Product: ((1R, 3R)-1-Amino-3-{4-[2-(4-methoxy-phenyl)-ethoxy]-phenyl}-cyclopentyl)-methanol; hydrochloride | 1.91 (a) | 342 (M + H)$^+$ |
| E.7 | 4-Methoxyphenyl boronic acid | 2-p-Tolyl-oxy-ethanol | Product: {(1R, 3R)-1-Amino-3-[4-(2-p-tolyloxy-ethoxy)-phenyl]-cyclopentyl}-methanol; hydrochloride | 2.08 (a) | 342 (M + H)$^+$ |
| E.8 | 4-Methoxyphenyl boronic acid | Heptan-1-ol | Product: [(1R, 3R)-1-Amino-3-(4-heptyloxy-phenyl)-cyclopentyl]-methanol; hydrochloride | 2.24 (a) | 306 (M + H)$^+$ |

TABLE E-continued

Examples following general procedures
A, I, J, E, H, K, L, M, N (Scheme 3)

cyclopent-2-enone → Boronic acid / General Procedure A → General Procedure I → General Procedure J → General Procedure E → General Procedure H →

→ General Procedure K → General Procedure L → General Procedure M → Alcohol / General Procedure N → R-O-C6H4-cyclopentyl(CH2OH)(NH2)

| Ex # | Boronic acid | Alcohol | Product | $R_t$/min (method) | m/z |
|---|---|---|---|---|---|
| E.9 | 4-Methoxyphenyl boronic acid | Nonan-1-ol | Product: [(1R, 3R)-1-Amino-3-(4-nonyloxy-phenyl)-cyclopentyl]-methanol; hydrochloride | 2.87 (a) | 334 (M + H)+ |
| E.10 | 4-Methoxyphenyl boronic acid | 2-Pentyloxy-ethanol | Product: {(1R, 3R)-1-Amino-3-[4-(2-pentyloxy-ethoxy)-phenyl]-cyclopentyl}-methanol; hydrochloride | 2.45 (a) | 322 (M + H)+ |
| E.11 | 4-Methoxyphenyl boronic acid | 2-p-Tolyl ethanol | Product: {(1R, 3R)-1-Amino-3-[4-(2-p-tolyl-ethoxy)-phenyl]-cyclopentyl}-methanol; hydrochloride | 2.60 (a) | 326 (M + H)+ |
| E.12 | 4-Methoxyphenyl boronic acid | 3-(4-Methoxyphenyl)-propan-1-ol | Product: ((1R, 3R)-1-Amino-3-{4-[3-(4-methoxy-phenyl)-propoxy]-phenyl}-cyclopentyl)-methanol; hydrochloride | 2.57 (a) | 356 (M + H)+ |

TABLE E-continued

Examples following general procedures
A, I, J, E, H, K, L, M, N (Scheme 3)

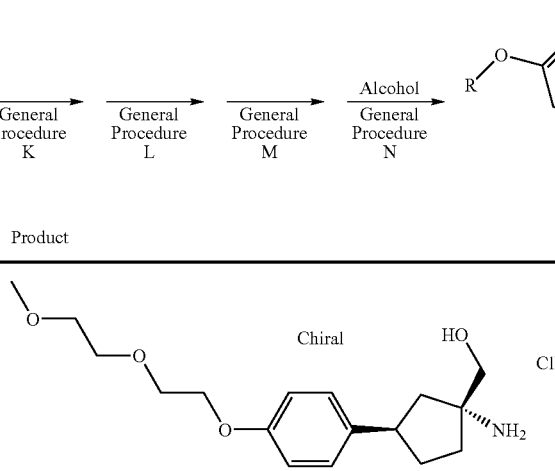

| Ex # | Boronic acid | Alcohol | Product | R,/min (method) | m/z |
|---|---|---|---|---|---|
| E.13 | 4-Methoxy-phenyl boronic acid | 2-(2-Methoxy-ethoxy)-ethanol | 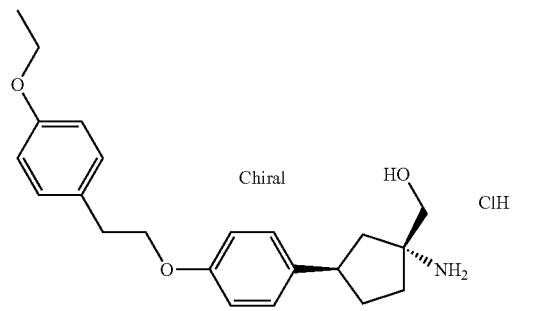 Product: ((1R, 3R)-1-Amino-3-{4-[2-(2-methoxy-ethoxy)-ethoxy]-phenyl}-cyclopentyl)-methanol; hydrochloride | 1.90 (a) | 310 (M + H)+ |
| E.14 | 4-Methoxy-phenyl boronic acid | 2-(4-Ethoxy-phenyl)-ethanol | 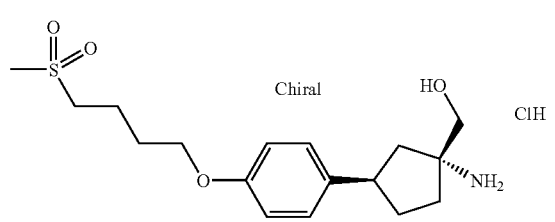 Product: ((1R, 3R)-1-Amino-3-{4-[2-(4-ethoxy-phenyl)-ethoxy]-phenyl}-cyclopentyl)-methanol; hydrochloride | 2.63 (a) | 356 (M + H)+ |
| E.15 | 4-Methoxy-phenyl boronic acid | 4-Methane sulfonyl-butan-1-ol | 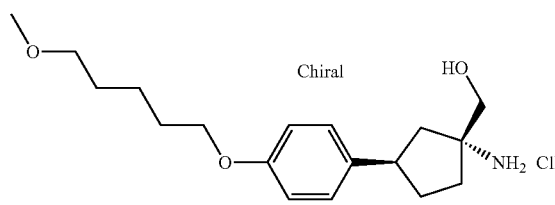 Product: {(1R, 3R)-1-Amino-3-[4-(4-methanesulfonyl-butoxy)-phenyl]-cyclopentyl}-methanol; hydrochloride | 1.78 (a) | 342 (M + H)+ |
| E.16 | 4-Methoxy-phenyl boronic acid | 5-Methoxy pentan-1-ol | Product: {(1R, 3R)-1-Amino-3-[4-(5-methoxy-pentyloxy)-phenyl]-cyclopentyl}-methanol; hydrochloride | 2.13 (a) | 308 (M + H)+ |

TABLE E-continued

*Examples following general procedures*
*A, I, J, E, H, K, L, M, N (Scheme 3)*

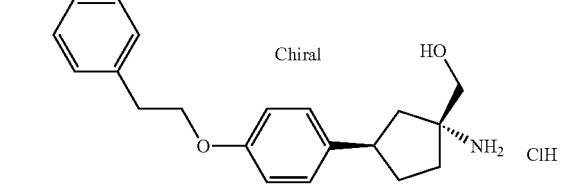

| Ex # | Boronic acid | Alcohol | Product | R$_t$/min (method) | m/z |
|---|---|---|---|---|---|
| E.17 | 4-Methoxy-phenyl boronic acid | 2-(3-Fluoro-4-methoxy-phenyl)-ethanol | 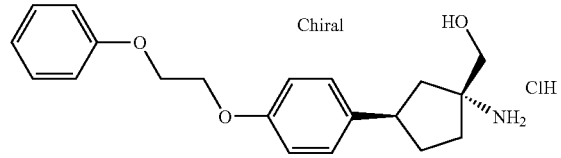 Product: ((1R, 3R)-1-Amino-3-{4-[2-(3-fluoro-4-methoxy-phenyl)-ethoxy]-phenyl}-cyclopentyl)-methanol; hydrochloride | 2.41 (a) | 360 (M + H)$^+$ |
| E.18 | 4-Methoxy-phenyl boronic acid | 2-Phenoxy-ethanol | 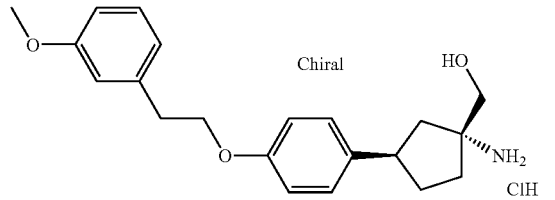 Product: {(1R, 3R)-1-Amino-3-[4-(2-phenoxy-ethoxy)-phenyl]-cyclopentyl}-methanol; hydrochloride | 2.59 (a) | 328 (M + H)$^+$ |
| E.19 | 4-Methoxy-phenyl boronic acid | 2-(3-Methoxy-phenyl)-ethanol | Product: ((1R, 3R)-1-Amino-3-{4-[2-(3-methoxy-phenyl)-ethoxy]-phenyl}-cyclopentyl)-methanol; hydrochloride | 2.63 (a) | 342 (M + H)$^+$ |
| E.20 | 4-Methoxy-phenyl boronic acid | 3-(3-Methoxy-phenyl)-propan-1-ol | 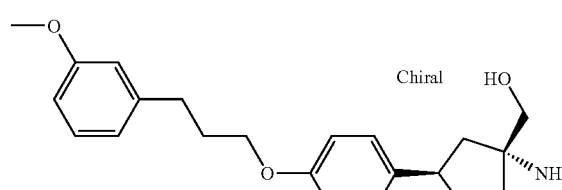 Product: ((1R, 3R)-1-Amino-3-{4-[3-(3-methoxy-phenyl)-propoxy]-phenyl}-cyclopentyl)-methanol; hydrochloride | 2.47 (a) | 356 (M + H)$^+$ |

TABLE E-continued

Examples following general procedures
A, I, J, E, H, K, L, M, N (Scheme 3)

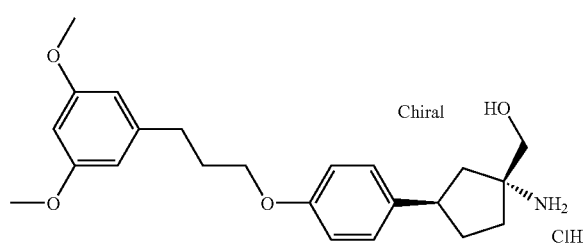

| Ex # | Boronic acid | Alcohol | Product | R₁/min (method) | m/z |
|---|---|---|---|---|---|
| E.21 | 4-Methoxy-phenyl boronic acid | 3-(3,5-Dimethoxy-phenyl)-propan-1-ol | 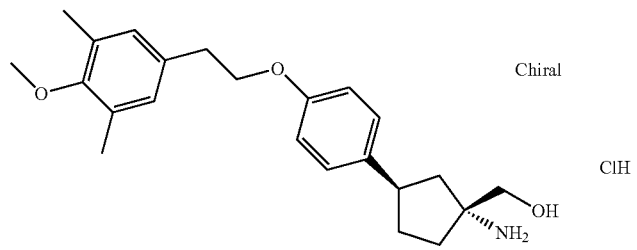 Product: ((1R, 3R)-1-Amino-3-{4-[3-(3,5-dimethoxy-phenyl)-propoxy]-phenyl}-cyclopentyl)-methanol; hydrochloride | 2.33 (a) | 386 (M + H)⁺ |
| E.22 | 4-Methoxy-phenyl boronic acid | 2-(4-Methoxy-3,5-dimethyl-phenyl)-ethanol | 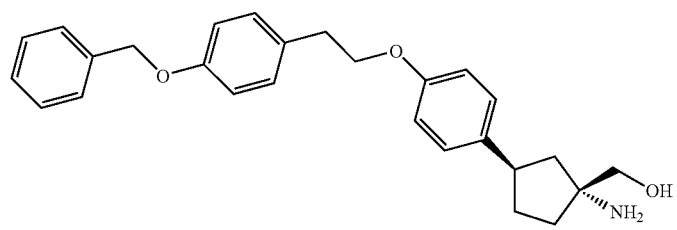 Product: ((1R, 3R)-1-Amino-3-{4-[2-(4-methoxy-3,5-dimethyl-phenyl)-ethoxy]-phenyl}-cyclopentyl)-methanol; hydrochloride | 2.88 (a) | 370 (M + H)⁺ |
| E.23 | 4-Methoxy-phenyl boronic acid | 2-(4-Benzyl oxy-phenyl)-ethanol | 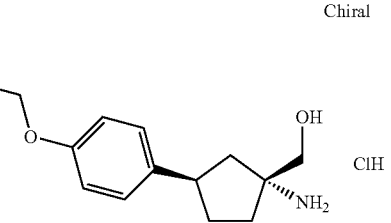 Product: ((1R, 3R)-1-Amino-3-{4-[2-(4-benzyloxy-phenyl)-ethoxy]-phenyl}-cyclopentyl)-methanol | 3.28 (a) | 418 (M + H)⁺ |
| E.24 | 4-Methoxy-phenyl boronic acid | 2-(4-Fluoro-phenoxy)-ethanol | Product: ((1R, 3R)-1-Amino-3-{4-[2-(4-flouro-phenoxy)-ethoxy]-phenyl}-cyclopentyl)-methanol; hydrochloride | 2.41 (a) | 346 (M + H)⁺ |

TABLE E-continued

Examples following general procedures
A, I, J, E, H, K, L, M, N (Scheme 3)

cyclopent-2-enone →(Boronic acid, General Procedure A)→ General Procedure I → General Procedure J → General Procedure E → General Procedure H →

→ General Procedure K → General Procedure L → General Procedure M → (Alcohol, General Procedure N) → R-O-C6H4-cyclopentyl(OH)(NH2)

| Ex # | Boronic acid | Alcohol | Product | R$_t$/min (method) | m/z |
|---|---|---|---|---|---|
| E.25 | 4-Methoxy-phenyl boronic acid | 3-Phenyl-propan-1-ol | Chiral | 2.52 (a) | 326 (M + H)$^+$ |

Product: {(1R, 3R)-1-Amino-3-[4-(3-phenyl-propoxy)-phenyl]-cyclopentyl}-methanol; hydrochloride

| E.26 | 4-Methoxy-phenyl boronic acid | (1-Methyl-1H-benzo-imidazol-2-yl)-methanol | | 1.99 (a) | 352 (M + H)$^+$ |

Product: {(1R, 3R)-1-Amino-3-[4-(1-methyl-1H-benzoimidazol-2-ylmethoxy)-phenyl]-cyclopentyl}-methanol; compound with hydrochloric acid

| E.27 | 4-Methoxy-phenyl boronic acid | 2-(3-Fluoro-phenoxy)-ethanol (Q, H) | | 2.34 (a) | 346 (M + H)$^+$ |

Product: ((1R, 3R)-1-Amino-3-{4-[2-(3-fluoro-phenoxy)-ethoxy]-phenyl}-cyclopentyl)-methanol; compound with hydrochloric acid TABLE E-continued Examples following general procedures
A, I, J, E, H, K, L, M, N (Scheme 3)

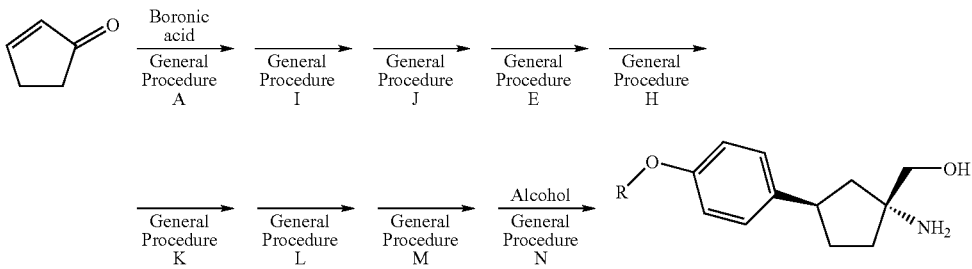

| Ex # | Boronic acid | Alcohol | Product | | $R_t$/min (method) | m/z |
|---|---|---|---|---|---|---|
| E.28 | 4-Methoxy-phenyl boronic acid | (3-Ethoxy-phenyl)-methanol | 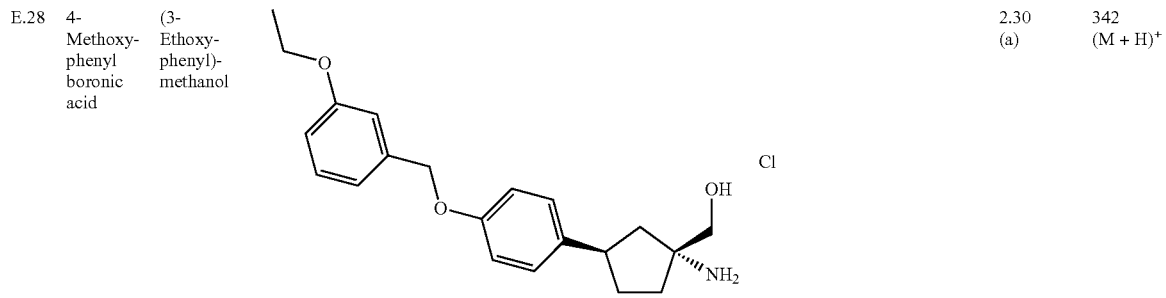 | | 2.30 (a) | 342 (M + H)+ |

Product: {(1R, 3R)-1-Amino-3-[4-(3-ethoxy-benzyloxy)-phenyl]-cyclopentyl}-methanol; compound with hydrochloric acid

| E.29 | 4-Methoxy-phenyl boronic acid | 3-(5-Methyl-oxazol-2-yl-propanol-ol | 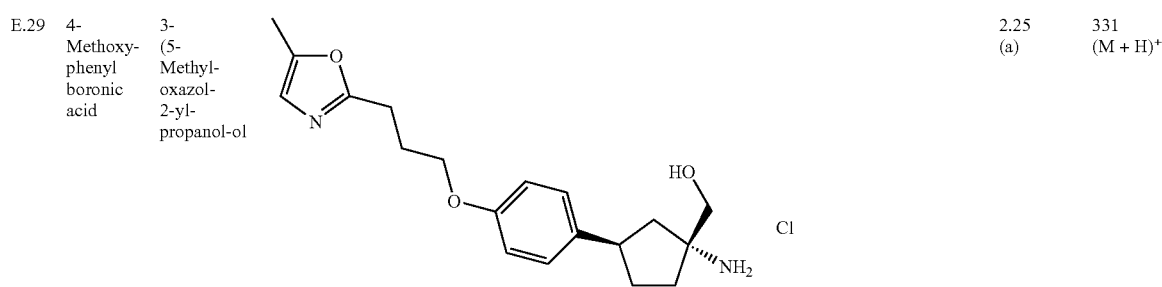 | | 2.25 (a) | 331 (M + H)+ |

Product: ((1R, 3R)-1-Amino-3-{4-[3-(5-methyl-oxazol-2-yl)-propoxy]-phenyl}-cyclopentyl)-methanol; compound with hydrochloric acid

| E.30 | 4-Methoxy-phenyl boronic acid | 2-(2,4-Difluoro-phenoxy)-ethanol (Q, H) | 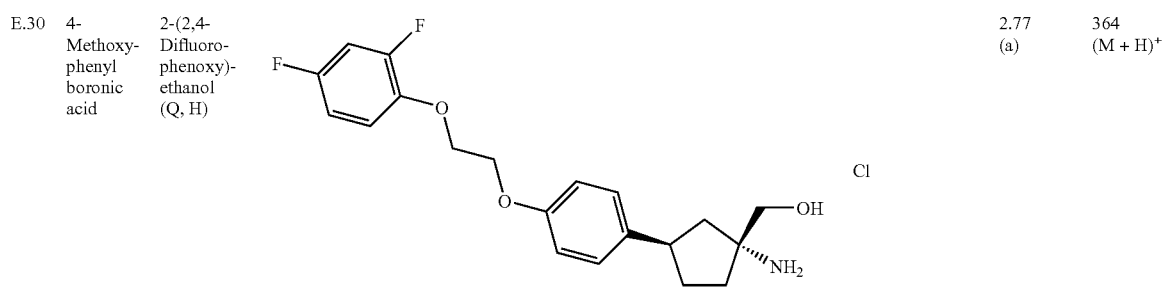 | | 2.77 (a) | 364 (M + H)+ |

Product: ((1R, 3R)-1-Amino-3-{4-[2-(2,4-difluoro-phenoxy)-ethoxy]-phenyl}-cyclopentyl)-methanol; compound with hydrochloric acid TABLE E-continued Examples following general procedures
A, I, J, E, H, K, L, M, N (Scheme 3)

Cyclopentenone →(Boronic acid, General Procedure A)→ General Procedure I → General Procedure J → General Procedure E → General Procedure H → General Procedure K → General Procedure L → General Procedure M →(Alcohol, General Procedure N)→ Product

| Ex # | Boronic acid | Alcohol | Product | R,/min (method) | m/z |
|---|---|---|---|---|---|
| E.31 | 4-Methoxy-phenyl boronic acid | 2-(4-Fluoro-2-methyl-phenoxy)-ethanol (Q, H) | | 2.57 (a) | 360 (M + H)+ |

Product: ((1R, 3R)-1-Amino-3-{4-[2-(4-fluoro-2-methyl-phenoxy)-ethoxy]-phenyl}-cyclopentyl)-methanol; compound with hydrochloric acid

| E.32 | 4-Methoxy-phenyl boronic acid | 2-(3-Methoxy-phenoxy)-ethanol (R) | | 2.60 (a) | 358 (M + H)+ |

Product: ((1R, 3R)-1-Amino-3-{4-[2-(3-methoxy-phenoxy)-ethoxy]-phenyl}-cyclopentyl)-methanol; compound with hydrochloric acid

| E.33 | 4-Methoxy-phenyl boronic acid | 2-(3-Ethoxy-phenyl)-ethanol (Q, H) | | 2.70 (a) | 356 (M + H)+ |

Product: ((1R, 3R)-1-Amino-3-{4-[2-(3-ethoxy-phenyl)-ethoxy]-phenyl}-cyclopentyl)-methanol; compound with hydrochloric acid TABLE E-continued Examples following general procedures
A, I, J, E, H, K, L, M, N (Scheme 3)

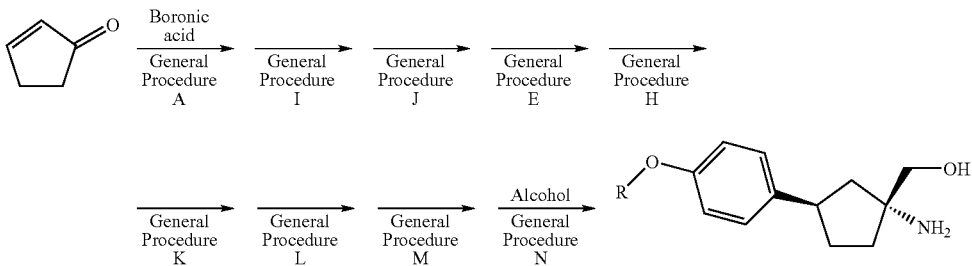

| Ex # | Boronic acid | Alcohol | Product | R$_t$/min (method) | m/z |
|---|---|---|---|---|---|
| E.34 | 4-Methoxy-phenyl boronic acid | 2-(3-Chloro-4-methoxy-phenyl)-ethanol (Q, H) | 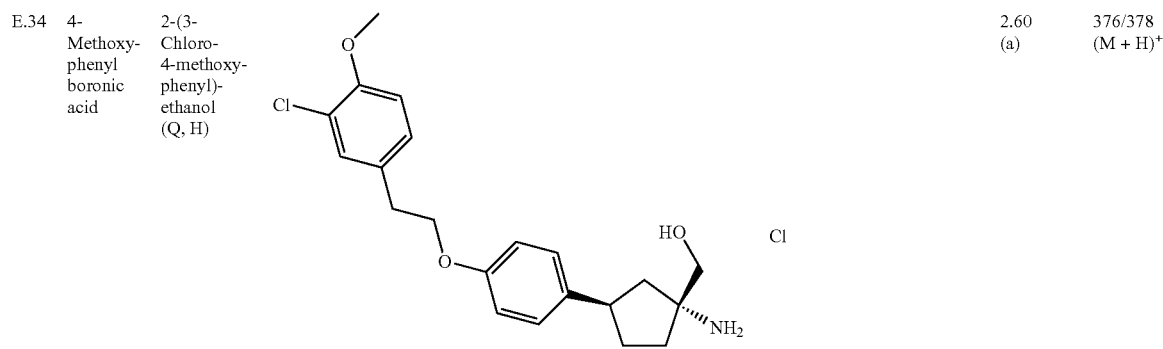 | 2.60 (a) | 376/378 (M + H)$^+$ |

Product: ((1R, 3R)-1-Amino-3-{4-[2-(3-chloro-4-methoxy-phenyl)-ethoxy]-phenyl}-cyclopentyl)-methanol; compound with hydrochloric acid

| E.35 | 4-Methoxy-phenyl boronic acid | (R)-(1-Phenoxy-propan-2-ol (Q) | 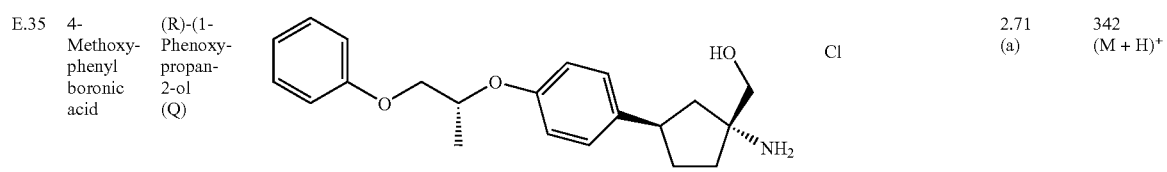 | 2.71 (a) | 342 (M + H)$^+$ |

Product: {(1R, 3R)-1-Amino-3-[4-((R)-1-methyl-2-phenoxy-ethoxy)-phenyl]-cyclopentyl}-methanol; compound with hydrochloric acid

| E.36 | 4-Methoxy-phenyl boronic acid | (S)-1-Phenoxy-propan-2-ol (Q) | 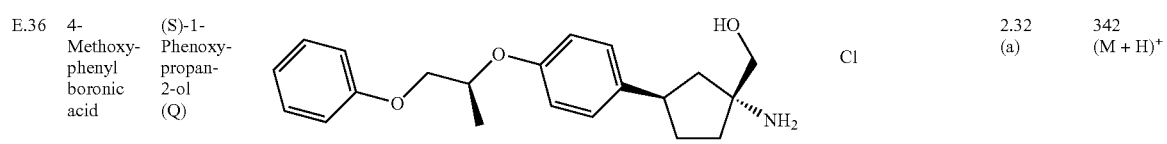 | 2.32 (a) | 342 (M + H)$^+$ |

Product: {(1R, 3R)-1-Amino-3-[4-((S)-1-methyl-2-phenoxy-ethoxy)-phenyl]-cyclopentyl}-methanol; compound with hydrochloric acid TABLE E-continued Examples following general procedures
A, I, J, E, H, K, L, M, N (Scheme 3)

| Ex # | Boronic acid | Alcohol | Product | R,/min (method) | m/z |
|---|---|---|---|---|---|
| E.37 | 4-Methoxy-phenyl boronic acid | 2-(4-Benzyl-oxy-phenyl)-ethanol | Product: ((1R, 3R)-1-Amino-3-{4-[2-(4-benzyloxy-phenyl)-ethoxy]-phenyl}-cyclopentyl)-methanol; compound with hydrochloric acid | 2.49 (a) | 418 (M + H)+ |
| E.38 | 4-Methoxy-phenyl boronic acid | 2-Phenoxy-ethanol | Product: {(1R, 3R)-1-Amino-3-[3-bromo-4-(2-phenoxy-ethoxy)-phenyl]-cyclopentyl}-methanol; hydrochloride | 2.94 (a) | 406/408 (M + H)+ |
| E.39 | 4-Methoxy-phenyl boronic acid | 2-Phenoxy-ethanol | Product: {(1R, 3R)-1-Amino-3-[3-methyl-4-(2-phenoxy-ethoxy)-phenyl]-cyclopentyl}-methanol; hydrochloride | 2.93 (a) | 342 (M + H)+ |

TABLE E-continued

Examples following general procedures
A, I, J, E, H, K, L, M, N (Scheme 3)

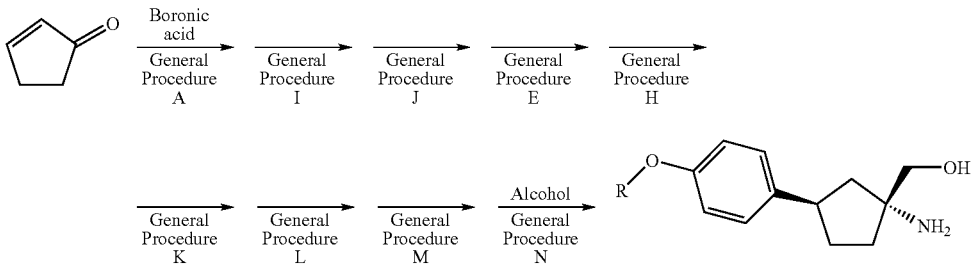

| Ex # | Boronic acid | Alcohol | Product | R$_t$/min (method) | m/z |
|---|---|---|---|---|---|
| E.40 | 4-Methoxy-phenyl boronic acid | 3-(3-Methoxy-phenyl)-propan-1-ol (R) | Product: ((1R, 3R)-1-Amino-3-{3-bromo-4-[3-(3-methoxy-phenyl)-propoxy]-phenyl}-cyclopentyl)-methanol; hydrochloride | 2.60 (a) | 434/436 (M + H)$^+$ |
| E.41 | 4-Methoxy-phenyl boronic acid | 3-(3-Methoxy-phenyl)-propan-1-ol (R) | Product: ((1R, 3R)-1-Amino-3-{4-[3-(3-methoxy-phenyl)-propoxy]-3-phenyl}-cyclopentyl)-methanol; hydrochloride | 3.12 (a) | 370 (M + H)$^+$ |
| E.42 | 4-Methoxy-phenyl boronic acid | 2-Phenoxy-ethanol | Product: {(1R, 3R)-1-Amino-3-[3,5-dichloro-4-(2-phenoxy-ethoxy)-phenyl]-cyclopentyl}-methanol; hydrochloride | 2.93 (a) | 396/398/ 400 (M + H)$^+$ |
| E.43 | 4-Methoxy-phenyl boronic acid | Pentan-1-ol | Product: [(1R, 3R)-1-Amino-3-(3,5-dichloro-4-pentyloxy-phenyl)-cyclopentyl]-methanol; hydrochloride | 3.12 (a) | 346/348/ 350 (M + H)$^+$ |

TABLE E-continued

Examples following general procedures
A, I, J, E, H, K, L, M, N (Scheme 3)

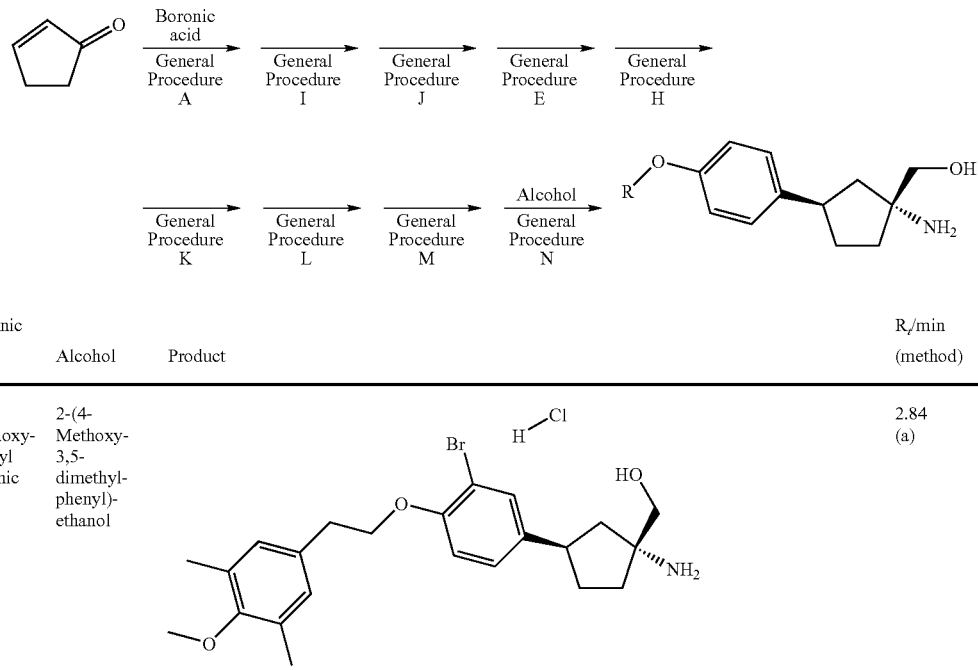

| Ex # | Boronic acid | Alcohol | Product | R$_t$/min (method) | m/z |
|---|---|---|---|---|---|
| E.44 | 4-Methoxy-phenyl boronic acid | 2-(4-Methoxy-3,5-dimethyl-phenyl)-ethanol | 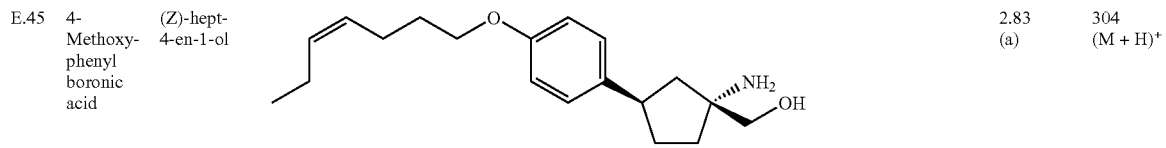 Product: ((1R, 3R)-1-Amino-3-{3-bromo-4-[2-(4-methoxy-3,5-dimethyl-phenyl)-ethoxy]-phenyl}-cyclopentyl)-methanol; hydrochloride | 2.84 (a) | 448/450 (M + H)$^+$ |
| E.45 | 4-Methoxy-phenyl boronic acid | (Z)-hept-4-en-1-ol | 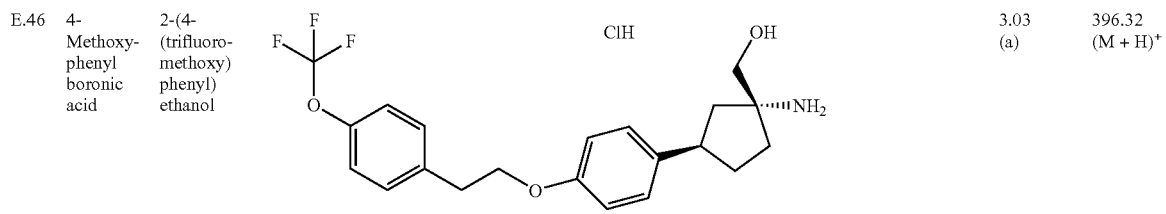 Product: ((1R, 3R)-1-amino-3-(4-((Z)-hept-4-enyloxy)phenyl)cyclopentyl)methanol | 2.83 (a) | 304 (M + H)$^+$ |
| E.46 | 4-Methoxy-phenyl boronic acid | 2-(4-(trifluoro-methoxy)phenyl)ethanol | 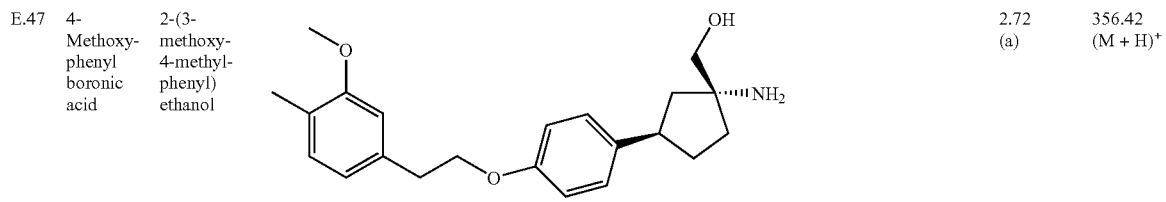 ((1R, 3R)-1-Amino-3-{4-[2-(4-trifluoromethoxy-phenyl)-ethoxy]-phenyl}-cyclopentyl)-methanol; hydrochloride | 3.03 (a) | 396.32 (M + H)$^+$ |
| E.47 | 4-Methoxy-phenyl boronic acid | 2-(3-methoxy-4-methyl-phenyl)ethanol | ((1R, 3R)-1-amino-3-(4-(3-methoxy-4-methylphenethoxy)phenyl)cyclopentyl)methanol | 2.72 (a) | 356.42 (M + H)$^+$ |

TABLE E-continued

Examples following general procedures
A, I, J, E, H, K, L, M, N (Scheme 3)

cyclopent-2-enone → Boronic acid / General Procedure A → General Procedure I → General Procedure J → General Procedure E → General Procedure H → General Procedure K → General Procedure L → General Procedure M → Alcohol / General Procedure N → product: R-O-C6H4-cyclopentyl(NH2)(CH2OH)

| Ex # | Boronic acid | Alcohol | Product | R$_t$/min (method) | m/z |
|---|---|---|---|---|---|
| E.48 | 4-Methoxyphenyl boronic acid | 3-(pyridin-3-yl)propan-1-ol | ((1R, 3R)-1-amino-3-(4-(3-(pyridin-3-yl)propoxy)phenyl)cyclopentyl)methanol | 1.47 (a) | 327.20 (M + H)$^+$ |
| E.49 | 4-Methoxyphenyl boronic acid | 3-(4-fluoro-3-methoxyphenyl)-propan-1-ol | ((1R, 3R)-1-amino-3-(4-(3-(4-fluoro-3-methoxyphenyl)propoxy)phenyl)cyclopentyl)methanol | 2.84 (a) | 374.38 (M + H)$^+$ |
| E.50 | 4-Methoxyphenyl boronic acid | 3-(2-methoxyphenyl)propan-1-ol | ((1R, 3R)-1-amino-3-(4-(3-(2-methoxyphenyl)propoxy)phenyl)cyclopentyl)methanol | 2.92 (a) | 356.42 (M + H)$^+$ |

TABLE E-continued

*Examples following general procedures*
*A, I, J, E, H, K, L, M, N (Scheme 3)*

| Ex # | Boronic acid | Alcohol | Product | R$_t$/min (method) | m/z |
|---|---|---|---|---|---|
| E.51 | 4-Methoxyphenyl boronic acid | 2-(4-methoxy-3-methylphenyl)ethanol | ((1R, 3R)-1-amino-3-(4-(4-methoxy-3-methylphenethoxy)phenyl)cyclopentyl)methanol | 2.95 (a) | 356.42 (M + H)⁺ |
| E.52 | 4-Methoxyphenyl boronic acid | 3-(thiophen-2-yl)propan-1-ol | ((1R, 3R)-1-amino-3-(4-(3-(thiophen-2-yl)propoxy)phenyl)cyclopentyl)methanol | 2.10 (a) | 332.21 (M + H)⁺ |
| E.53 | 4-Methoxyphenyl boronic acid | 3-(pyridin-4-yl)propan-1-ol | ((1R, 3R)-1-amino-3-(4-(3-(pyridin-4-yl)propoxy)phenyl)cyclopentyl)methanol | 1.43 (a) | 327.21 (M + H)⁺ |

TABLE F

Examples following general procedure O (Scheme 4)
The letters in parentheses below the amino-alcohol precursors
indicate the General Procedure by which the amino-alcohol precursor was made.

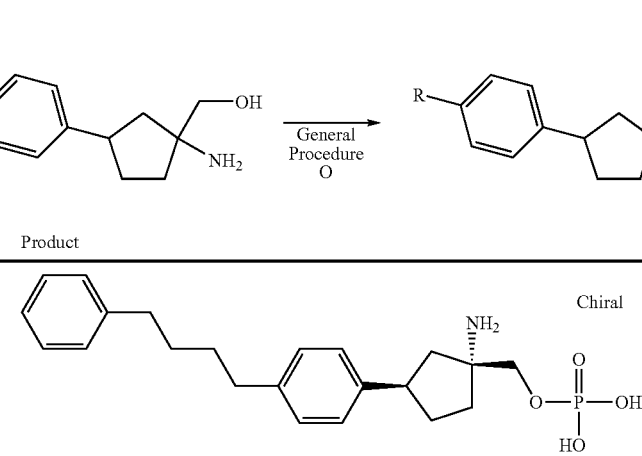

| Ex # | Amino-alcohol | Product | Rt/min (method) | m/z |
|---|---|---|---|---|
| F.1 | {(1R, 3R)-1-Amino-3-[4-(4-phenyl-butyl)-phenyl]-cyclopentyl}-methanol (A, I, J, E, F, G, H) | | 2.13 (a) | 404 (M + H)$^+$ |
| | Product: Phosphoric acid mono-{(1R, 3R)-1-amino-3-[4-(4-phenyl-butyl)-phenyl]-cyclopentylmethyl} ester | | | |
| F.2 | {(1R, 3R)-1-Amino-3-[4-(3-phenoxy-propyl)-phenyl]-cyclopentyl}-methanol (A, I, J, E, F, G, H) | | 2.57 (a) | 406 (M + H)$^+$ |
| | Product: Phosphoric acid mono-{(1R, 3R)-1-amino-3-[4-(3-phenoxy-propyl)-phenyl]-cyclopentylmethyl} ester; hydrochloride | | | |
| F.3 | [(1R, 3S)-1-Amino-3-(4-octyl-phenyl)-cyclopentyl]-methanol (A, B, C, D, E, F, G, H) | | 2.35 (d) | 382 (M − H)$^−$ |
| | Product: Phosphoric acid mono-[(1R, 3S)-1-amino-3-(4-octyl-phenyl)-cyclopentylmethyl] ester | | | |
| F.4 | [(1R, 3R)-1-Amino-3-(4-octyl-phenyl)-cyclopentyl]-methanol (A, I, J, E, F, G, H) | | 2.59 (c) | 384 (M + H)$^+$ |
| | Product: Phosphoric acid mono-[(1R, 3R)-1-amino-3-(4-octyl-phenyl)-cyclopentylmethyl]ester; compound with phosphoric acid | | | |
| F.5 | [(1R, 3S)-1-Amino-3-(3-decyl-phenyl)-cyclopentyl]-methanol (A, I, J, E, F, G, H) | | 1.67 (b) | 412 (M + H)$^+$ |
| | Product: Phosphoric acid mono-[(1R, 3S)-1-amino-3-(3-decyl-phenyl)-cyclopentylmethyl] ester | | | |

TABLE F-continued

Examples following general procedure O (Scheme 4)
The letters in parentheses below the amino-alcohol precursors
indicate the General Procedure by which the amino-alcohol precursor was made.

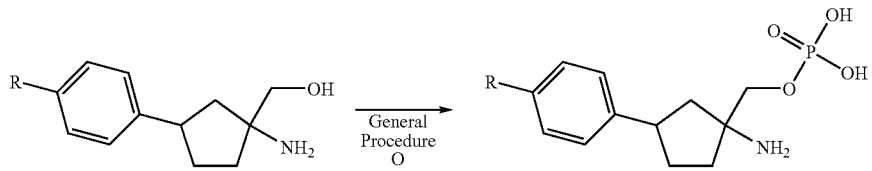

| Ex # | Amino-alcohol | Product | Rt/min (method) | m/z |
|---|---|---|---|---|
| F.6 | [(1R, 3R)-1-Amino-3-(4-nonyloxy-phenyl)-cyclopentyl]-methanol (A, I, J, E, H, K, L, M, N) | Chiral | 2.44 (d) | 330 (M + H)+ |

Product: Phosphoric acid mono-[(1R, 3R)-1-amino-3-(4-nonyloxy-phenyl)-cyclopentylmethyl] ester

| F.7 | {(1R, 3R)-1-Amino-3-[4-(2-p-tolyloxy-ethoxy)-phenyl]-cyclopentyl}-methanol (A, I, J, E, H, K, L, M, N) | Chiral | 1.94 (d) | 422 (M + H)+ |

Product: Phosphoric acid mono-{(1R, 3R)-1-amino-3-[4-(2-p-tolyloxy-ethoxy)-phenyl]-cyclopentylmethyl} ester

| F.8 | ((1R, 3R)-1-Amino-3-{4-[2-(4-methoxy-phenyl)-ethoxy]-phenyl}-cyclopentyl)-methanol (A, I, J, E, H, K, L, M, N) | Chiral | 1.87 (d) | 422 (M + H)+ |

Product: Phosphoric acid mono-((1R, 3R)-1-amino-3-{4-[2-(4-methoxy-phenyl)-ethoxy]-phenyl}-cyclopentylmethyl) ester

| F.9 | {(1R, 3R)-1-Amino-3-[4-(4,4,5,5,5-pentafluoro-pentyloxy)-phenyl]-cyclopentyl}-methanol (A, I, J, E, H, K, L, M, N) | Chiral | 1.99 (d) | 448 (M + H)+ |

Product: Phosphoric acid mono-{(1R, 3R)-1-amino-3-[4-(4,4,5,5,5-pentafluoro-pentyloxy)-phenyl]-cyclopentylmethyl} ester TABLE F-continued

*Examples following general procedure O (Scheme 4)*
*The letters in parentheses below the amino-alcohol precursors*
*indicate the General Procedure by which the amino-alcohol precursor was made.*

| Ex # | Amino-alcohol | Product | | Rt/min (method) | m/z |
|---|---|---|---|---|---|
| F.10 | {(1R, 3R)-1-Amino-3-[4-(3-phenyl-propyl)-phenyl]-cyclopentyl}-methanol (A, I, J, E, F, G, H) | Chiral | | 2.03 (d) | 388 (M − H)⁻ |
| | Product: Phosphoric acid mono-{(1R, 3R)-1-amino-3-[4-(3-phenyl-propyl)-phenyl]-cyclopentylmethyl} ester | | | | |
| F.11 | [(1R, 3R)-1-Amino-3-(4-octyloxy-phenyl)-cyclopentyl]-methanol (A, I, J, E, H, K, L, M, N) | Chiral | | 2.29 (d) | 400 (M + H)⁺ |
| | Product: Phosphoric acid mono-[(1R, 3R)-1-amino-3-(4-octyloxy-phenyl)-cyclopentylmethyl] ester | | | | |
| F.12 | {(1R, 3R)-1-Amino-3-[4-(6-methoxy-hexyl)-phenyl]-cyclopentyl}-methanol (A, I, J, E, F, G, H) | Chiral | | 1.83 (d) | 386 (M + H)⁺ |
| | Product: Phosphoric acid mono-{(1R, 3R)-1-amino-3-[4-(6-methoxy-hexyl)-phenyl]-cyclopentylmethyl} ester | | | | |
| F.13 | [(1R, 3S)-1-Amino-3-(4-octyl-phenyl)-cyclopentyl]-methanol (A, B, C, D, E, F, G, H) | Chiral | | 2.36 (d) | 382 (M − H)⁻ |
| | Product: Phosphoric acid mono-[(1R, 3S)-1-amino-3-(4-octyl-phenyl)-cyclopentylmethyl] ester | | | | |

TABLE F-continued

Examples following general procedure O (Scheme 4)
The letters in parentheses below the amino-alcohol precursors
indicate the General Procedure by which the amino-alcohol precursor was made.

| Ex # | Amino-alcohol | Product | Rt/min (method) | m/z |
|---|---|---|---|---|
| F.14 | [(1R, 3S)-1-Amino-3-(4-heptyl-phenyl)-cyclopentyl]-methanol (A, B, C, D, E, F, G, H) | Product: Phosphoric acid mono-[(1R, 3S)-1-amino-3-(4-heptyl-phenyl)-cyclopentylmethyl] ester | 2.18 (a) | 370 (M + H)+ |
| F.15 | {(1R, 3R)-1-Amino-3-[4-(2-pentyloxy-ethoxy)-phenyl]-cyclopentyl}-methanol (A, I, J, E, H, K, L, M, N) | Product: Phosphoric acid mono-{(1R, 3R)-1-amino-3-[4-(2-pentyloxy-ethoxy)-phenyl]-cyclopentylmethyl} ester | 2.49 (a) | 402 (M + H)+ |
| F.16 | {(1R, 3R)-1-Amino-3-[4-(2-m-tolyloxy-ethoxy)-phenyl]-cyclopentyl}-methanol (A, I, J, E, H, K, L, M, N) | Product: Phosphoric acid mono-{(1R, 3R)-1-amino-3-[4-(2-m-tolyloxy-ethoxy)-phenyl]-cyclopentylmethyl} ester | 2.53 (a) | 422 (M + H)+ |
| F.17 | {(1R, 3R)-1-Amino-3-[4-(2-p-tolyl-ethoxy)-phenyl]-cyclopentyl}-methanol (A, I, J, E, H, K, L, M, N) | Product: Phosphoric acid mono-{(1R, 3R)-1-amino-3-[4-(2-p-tolyl-ethoxy)-phenyl]-cyclopentylmethyl} ester | 2.60 (a) | 406 (M + H)+ |

TABLE F-continued

*Examples following general procedure O (Scheme 4)*
*The letters in parentheses below the amino-alcohol precursors*
*indicate the General Procedure by which the amino-alcohol precursor was made.*

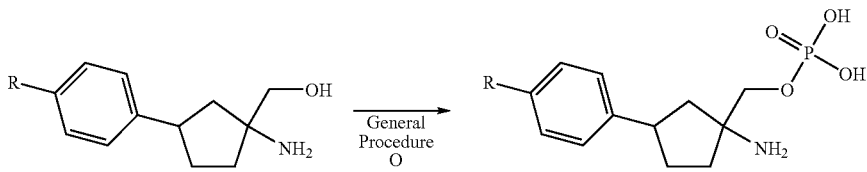

| Ex # | Amino-alcohol | Product | Rt/min (method) | m/z |
|---|---|---|---|---|
| F.18 | [(1R, 3R)-1-Amino-3-(4-heptyloxy-phenyl)-cyclopentyl]-methanol (A, I, J, E, H, K, L, M, N) | 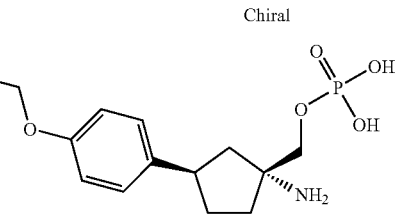 | 2.80 (a) | 386 (M + H)+ |

Product: Phosphoric acid mono-[(1R, 3R)-1-amino-3-(4-heptloxy-phenyl)-cyclopentylmethyl] ester

| F.19 | ((1R, 3R)-1-Amino-3-{4-[3-(4-methoxy-phenyl)-propoxy]-phenyl}-cyclopentyl)-methanol (A, I, J, E, H, K, L, M, N) | 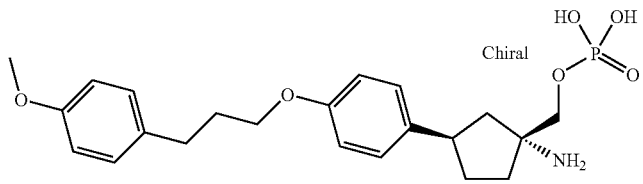 | 2.51 (a) | 436 (M + H)+ |

Product: Phosphoric acid mono-((1R, 3R)-1-amino-3-{4-[3-(4-methoxy-phenyl)-propoxy]-phenyl}-cyclopentylmethyl) ester

| F.20 | ((1R, 3R)-1-Amino-3-{4-[2-(2-methoxy-ethoxy)-ethoxy]-phenyl}-cyclopentyl)-methanol (A, I, J, E, H, K, L, M, N) | 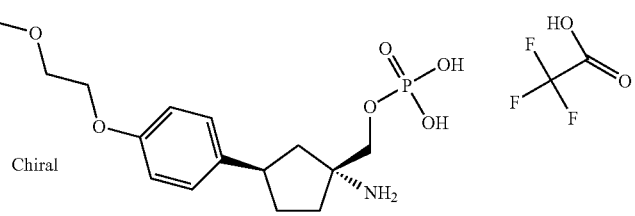 | 1.79 (a) | 390 (M + H)+ |

Product: Phosphoric acid mono-((1R, 3R)-1-amino-3-{4-[2-(2-methoxy-ethoxy)-ethoxy]-phenyl}-cyclopentylmethyl) ester; compound with trifluoro-acetic acid TABLE F-continued

*Examples following general procedure O (Scheme 4)*
*The letters in parentheses below the amino-alcohol precursors*
*indicate the General Procedure by which the amino-alcohol precursor was made.*

| Ex # | Amino-alcohol | Product | Rt/min (method) | m/z |
|---|---|---|---|---|
| F.21 | ((1R, 3R)-1-Amino-3-{4-[2-(4-ethoxy-phenyl)-ethoxy]-phenyl}-cyclopentyl)-methanol (A, I, J, E, H, K, L, M, N) | | 2.63 (a) | 436 (M + H)+ |

Product: Phosphoric acid mono-((1R, 3R)-1-amino-3-{4-[2-(4-ethoxy-phenyl)-ethoxy]-phenyl}-cyclopentylmethyl) ester

| F.22 | {(1R, 3R)-1-Amino-3-[4-(2-phenoxy-ethoxy)-phenyl]-cyclopentyl}-methanol (A, I, J, E, H, K, L, M, N) | | 2.47 (a) | 408 (M + H)+ |

Product: Phosphoric acid mono-{(1R, 3R)-1-amino-3-[4-(2-phenoxy-ethoxy)-phenyl]-cyclopentylmethyl} ester

| F.23 | ((1R, 3R)-1-Amino-3-{4-[2-(3-fluoro-4-methoxy-phenyl)-ethoxy]-phenyl}-cyclopentyl)-methanol (A, I, J, E, H, K, L, M, N) | | 2.53 (a) | 440 (M + H)+ |

Product: Phosphoric acid mono-((1R, 3R)-1-amino-3-{4-[2-(3-fluoro-4-methoxy-phenyl}-ethoxy]-phenyl}-cyclopentylmethyl) ester TABLE F-continued Examples following general procedure O (Scheme 4)
The letters in parentheses below the amino-alcohol precursors
indicate the General Procedure by which the amino-alcohol precursor was made.

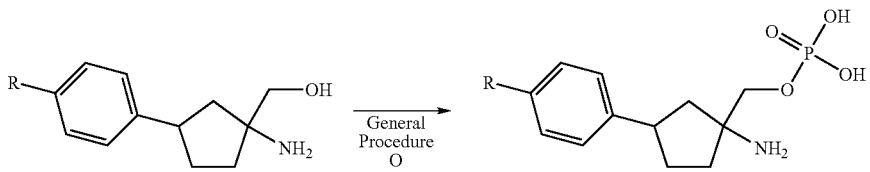

| Ex # | Amino-alcohol | Product | Rt/min (method) | m/z |
|---|---|---|---|---|
| F.24 | ((1R, 3R)-1-Amino-3-{4-[2-(3-methoxy-phenyl)-ethoxy]-phenyl}-cyclopentyl)-methanol (A, I, J, E, H, K, L, M, N) | | 2.57 (a) | 420 (M − H)⁻ |

Product: Phosphoric acid mono-((1R, 3R)-1-amino-3-{4-[2-(3-methoxy-phenyl)-ethoxy]-phenyl}-cyclopentylmethyl) ester

| F.25 | ((1R, 3R)-1-Amino-3-{4-[3-(3-methoxy-phenyl)-propoxy]-phenyl}-cyclopentyl)-methanol (A, I, J, E, H, K, L, M, N) | | 2.63 (a) | 436 (M + H)⁺ |

Product: Phosphoric acid mono-((1R, 3R)-1-amino-3-{4-[3-(3-methoxy-phenyl)-propoxy]-phenyl}-cyclopentylmethyl) ester; hydrochloride

| F.26 | ((1R, 3R)-1-Amino-3-{4-[3-(3,5-dimethoxy-phenyl)-propoxy]-phenyl}-cyclopentyl)-methanol (A, I, J, E, H, K, L, M, N) | | 2.63 (a) | 466 (M + H)⁺ |

Product: Phosphoric acid mono-((1R, 3R)-1-amino-3-{4-[3-(3,5-dimethoxy-phenyl)-propoxy]-phenyl}-cyclopentylmethyl) ester

| F.27 | ((1R, 3R)-1-Amino-3-{4-[2-(4-benzyloxy-phenyl)-ethoxy]-phenyl}-cyclopentyl)-methanol (A, I, J, E, H, K, L, M, N) | | 1.61 (b) | 408 (M + H)⁺ |

Product: Phosphoric acid mono-((1R, 3R)-1-amino-3-{4-[2-(4-hydroxy-phenyl)-ethoxy]-phenyl}-cyclopentylmethyl) ester TABLE F-continued Examples following general procedure O (Scheme 4)
The letters in parentheses below the amino-alcohol precursors
indicate the General Procedure by which the amino-alcohol precursor was made.

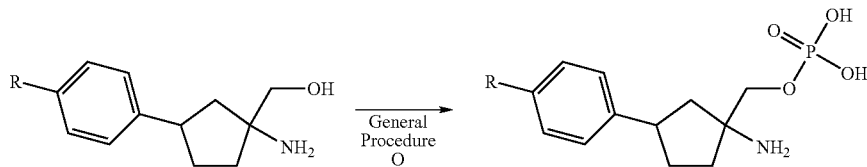

| Ex # | Amino-alcohol | Product | | Rt/min (method) | m/z |
|---|---|---|---|---|---|
| F.28 | {(1R, 3R)-1-Amino-3-[4-(3-phenyl-propoxy)-phenyl]-cyclopentyl}-methanol (A, I, J, E, H, K, L, M, N) | 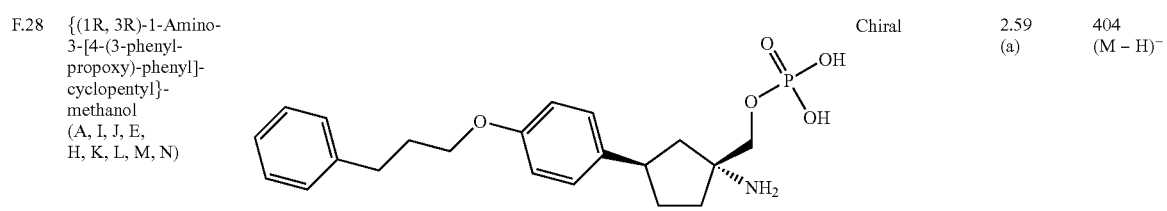 | Chiral | 2.59 (a) | 404 (M − H)⁻ |

Product: Phosphoric acid mono-{(1R, 3R)-1-amino-3-[4-(3-phenyl-propoxy)-phenyl]-cyclopentylmethyl} ester

| F.29 | {(1R, 3S)-1-Amino-3-[4-(3-phenoxy-propyl)-phenyl]-cyclopentyl}-methanol (A, B, C, D, E, F, G, H) | 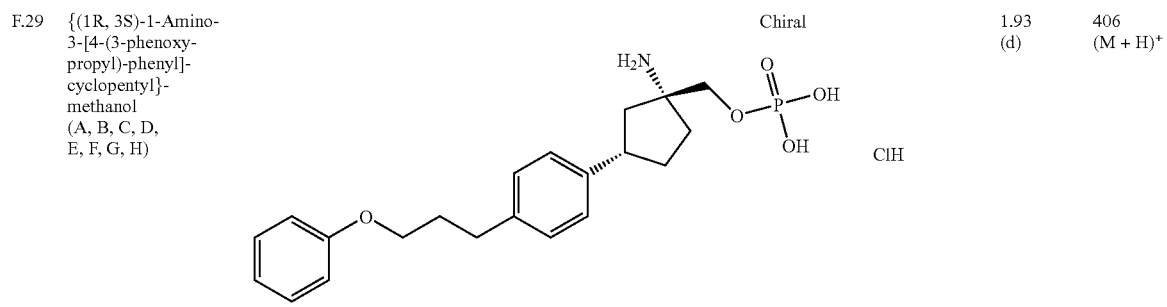 | Chiral | 1.93 (d) | 406 (M + H)⁺ |

Product: Phosphoric acid mono-{(1R, 3S)-1-amino-3-[4-(3-phenoxy-propyl)-phenyl]-cyclopentylmethyl} ester; hydrochloride

| F.30 | ((3S)-1-amino-3-(3-nonylphenyl)cyclopentyl)methanol; hydrochloride (A, B, D, E, F, G, H) | 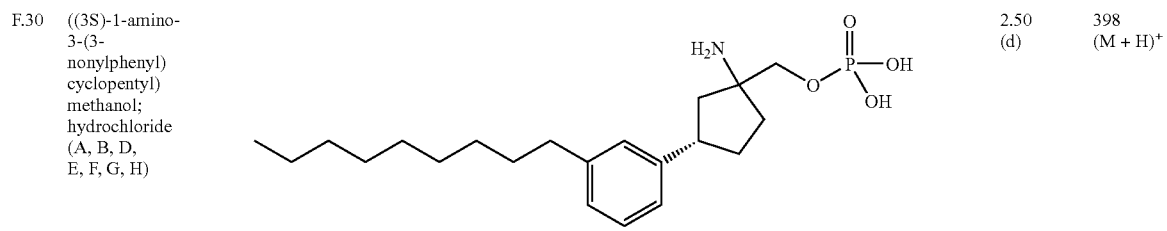 | | 2.50 (d) | 398 (M + H)⁺ |

Product: Phosphoric acid mono-((3S)-1-amino-3-(3-nonylphenyl)cyclopentyl)methyl ester

| F.31 | ((3S)-1-amino-3-(3-octylphenyl)cyclopentyl)methanol; hydrochloride (A, B, D, E, F, G, H) | 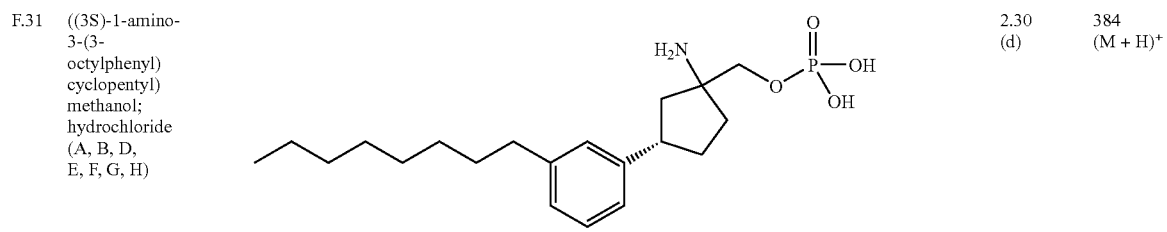 | | 2.30 (d) | 384 (M + H)⁺ |

Product: Phosphoric acid mono-((3S)-1-amino-3-(3-octylphenyl)cyclopentyl)methyl ester TABLE F-continued

*Examples following general procedure O (Scheme 4)*
*The letters in parentheses below the amino-alcohol precursors*
*indicate the General Procedure by which the amino-alcohol precursor was made.*

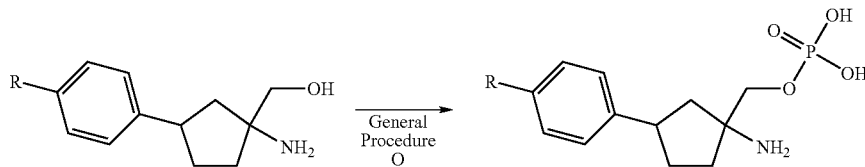

| Ex # | Amino-alcohol | Product | Rt/min (method) | m/z |
|---|---|---|---|---|
| F.32 | ((1R, 3S)-1-Amino-3-(4-(6-methoxyhexyl)phenyl)cyclopentyl)methanol; hydrochloride (A, B, C, D, E, F, G, H) | 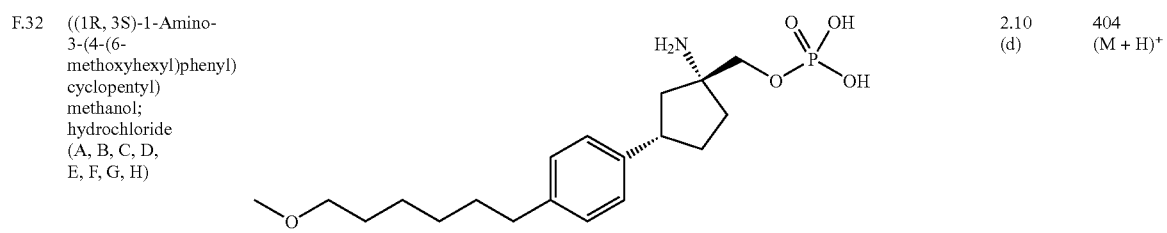 | 2.10 (d) | 404 (M + H)⁺ |

Product: Phosphoric acid mono-((1R, 3S)-1-amino-3-(4-(6-methoxyhexyl)phenyl)cyclopentyl)methyl ester

| F.32 | ((1R, 3S)-1-Amino-3-(4-(4-phenylbutyl)phenyl)cyclopentyl)methanol; hydrochloride (A, B, C, D, E, F, G, H) | 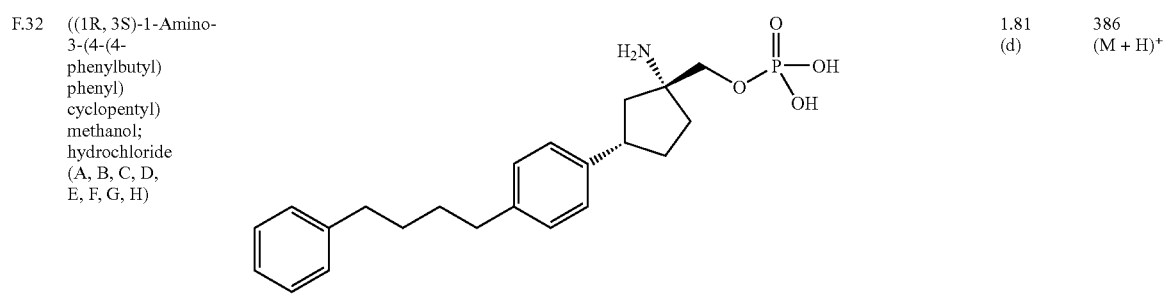 | 1.81 (d) | 386 (M + H)⁺ |

Product: Phosphoric acid mono-((1R, 3S)-1-amino-3-(4-(4-phenylbutyl)phenyl)cyclopentyl)methyl ester

| F.33 | ((1R, 3R)-1-Amino-3-(4-heptyl-phenyl)cyclopentyl)methanol; hydrochloride (A, I, J, E, F, G, H) | 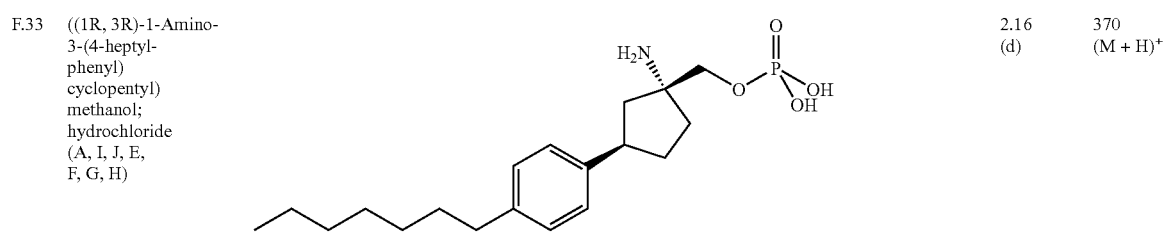 | 2.16 (d) | 370 (M + H)⁺ |

Product: Phosphoric acid mono-((1R, 3R)-1-amino-3-(4-heptylphenyl)cyclopentyl)methyl ester

| F.34 | ((1R, 3R)-1-Amino-3-(4-hexyl-phenyl)cyclopentyl)methanol; hydrochloride (A, I, J, E, F, G, H) | 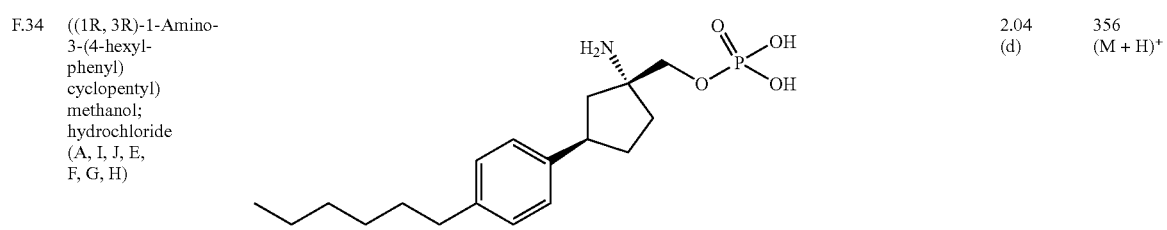 | 2.04 (d) | 356 (M + H)⁺ |

Product: Phosphoric acid mono-((1R, 3R)-1-amino-3-(4-hexylphenyl)cyclopentyl)methyl ester TABLE F-continued Examples following general procedure O (Scheme 4)
The letters in parentheses below the amino-alcohol precursors
indicate the General Procedure by which the amino-alcohol precursor was made.

| Ex # | Amino-alcohol | Product | Rt/min (method) | m/z |
|---|---|---|---|---|
| F.35 | {(1R, 3R)-1-Amino-3-[4-(5-methoxy-pentyloxy)-phenyl]-cyclopentyl}-methanol; hydrochloride (A, I, J, E, H, K, L, M, N) | Product: Phosphoric acid mono-{(1R, 3R)-1-amino-3-[4-(5-methoxy-pentyloxy)-phenyl]-cyclopentylmethyl} ester | 2.13 (a) | 404 (M + H)+ |
| F.36 | ((1R, 3R)-1-Amino-3-{4-[3-(5-methyl-oxazol-2-yl)-propoxy]-phenyl}-cyclopentyl)-methanol; hydrochloride (A, I, J, E, H, K, L, M, N) | Product: Phosphoric acid mono-((1R, 3R)-1-amino-3-{4-[3-(5-methyl-oxazol-2-yl)-propoxy]-phenyl}-cyclopentylmethyl) ester | 2.23 (d) | 386 (M − H)− |
| F.37 | ((1R, 3R)-1-Amino-3-{4-[2-(4-fluoro-phenoxy)-ethoxy]-phenyl}-cyclopentyl)-methanol; hydrochloride (A, I, J, E, H, K, L, M, N) | Product: Phosphoric acid mono-((1R, 3R)-1-amino-3-{4-[2-(4-fluoro-phenoxy)-ethoxy]-phenyl}-cyclopentylmethyl) ester | 2.47 (a) | 426 (M + H)+ |
| F.38 | ((1R, 3R)-1-Amino-3-{4-[2-(3-fluoro-phenoxy)-ethoxy]-phenyl}-cyclopentyl)-methanol; hydrochloride (A, I, J, E, H, K, L, M, N) | Product: Phosphoric acid mono-((1R, 3R)-1-amino-3-{4-[2-(3-fluoro-phenoxy)-ethoxy]-phenyl}-cyclopentylmethyl) ester | 2.52 (a) | 424 (M − H)− |

TABLE F-continued

Examples following general procedure O (Scheme 4)
The letters in parentheses below the amino-alcohol precursors
indicate the General Procedure by which the amino-alcohol precursor was made.

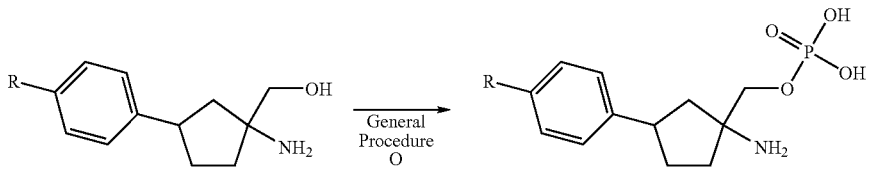

| Ex # | Amino-alcohol | Product | Rt/min (method) | m/z |
|---|---|---|---|---|
| F.39 | ((1R, 3R)-1-Amino-3-{4-[2-(2,4-difluoro-phenoxy)-ethoxy]-phenyl}-cyclopentyl)-methanol; hydrochloride (A, I, J, E, H, K, L, M, N) | 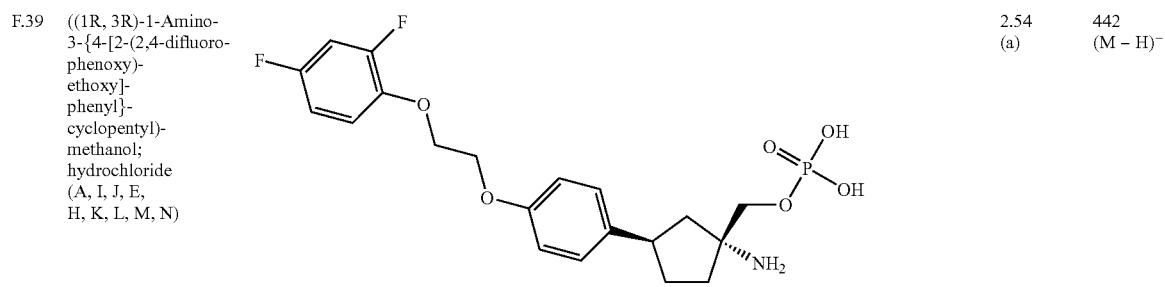 | 2.54 (a) | 442 (M − H)⁻ |

Product: Phosphoric acid mono-((1R, 3R)-1-amino-3-{4-[2-(2,4-difluoro-phenoxy)-ethoxy]-phenyl}-cyclopentylmethyl) ester

| F.40 | ((1R, 3R)-1-Amino-3-{4-[2-(4-fluoro-2-methyl-phenoxy)-ethoxy]-phenyl}-cyclopentyl)-methanol; hydrochloride (A, I, J, E, H, K, L, M, N) | 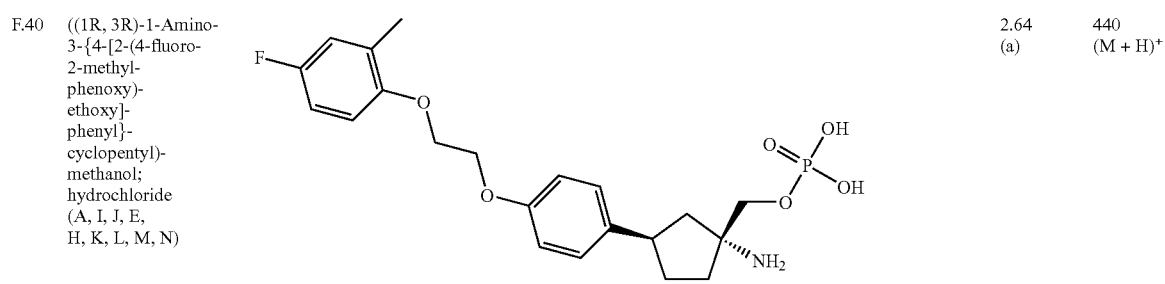 | 2.64 (a) | 440 (M + H)⁺ |

Product: Phosphoric acid mono-((1R, 3R)-1-amino-3-{4-[2-(4-fluoro-2-methyl-phenoxy)-ethoxy]-phenyl}-cyclopentylmethyl) ester

| F.41 | ((1R, 3R)-1-Amino-3-{4-[2-(3-methoxy-phenoxy)-ethoxy]-phenyl}-cyclopentyl)-methanol; hydrochloride (A, I, J, E, H, K, L, M, N) | 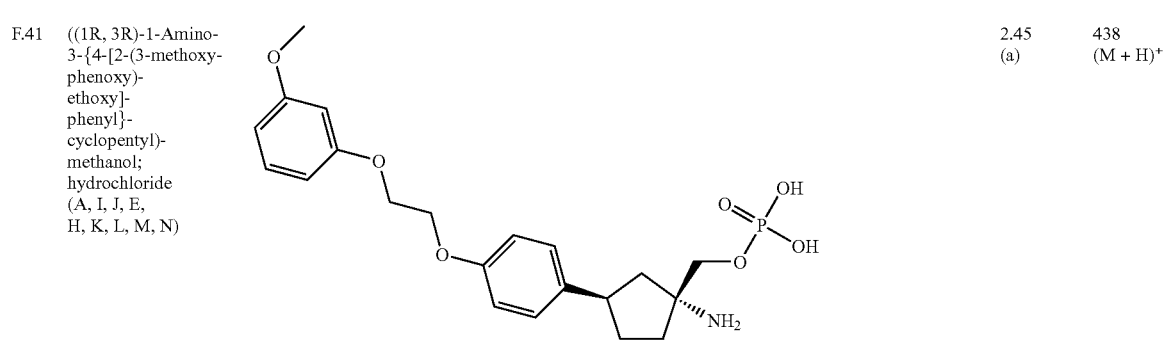 | 2.45 (a) | 438 (M + H)⁺ |

Product: Phosphoric acid mono-((1R, 3R)-1-amino-3-{4-[2-(3-methoxy-phenoxy)-ethoxy]-phenyl}-cyclopentylmethyl) ester TABLE F-continued

*Examples following general procedure O (Scheme 4)*
*The letters in parentheses below the amino-alcohol precursors*
*indicate the General Procedure by which the amino-alcohol precursor was made.*

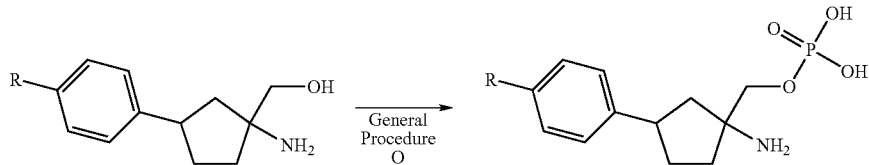

| Ex # | Amino-alcohol | Product | Rt/min (method) | m/z |
|---|---|---|---|---|
| F.42 | ((1R, 3R)-1-Amino-3-{4-[2-(3-ethoxy-phenyl)-ethoxy]-phenyl}-cyclopentyl)-methanol; hydrochloride (A, I, J, E, H, K, L, M, N) | 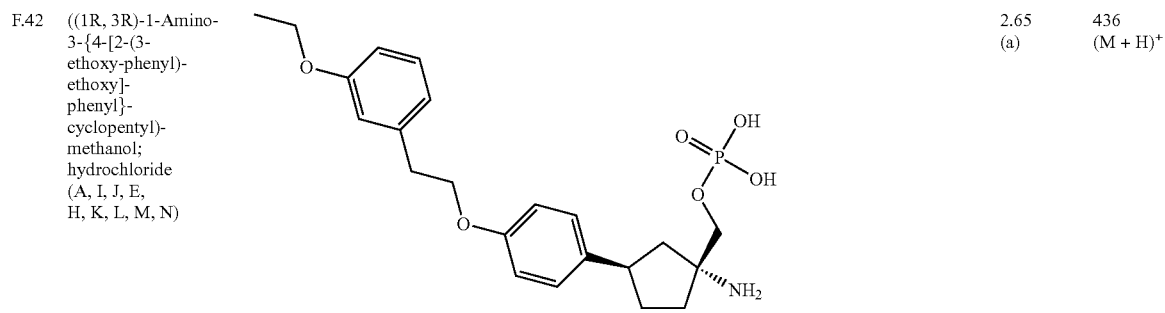 | 2.65 (a) | 436 (M + H)+ |

Product: Phosphoric acid mono-((1R, 3R)-1-amino-3-{4-[2-(3-ethoxy-phenyl)-ethoxy]-phenyl}-cyclopentylmethyl) ester

| F.43 | ((1R, 3R)-1-Amino-3-{4-[2-(3-chloro-4-methoxy-phenyl)-ethoxy]-phenyl}-cyclopentyl)-methanol; hydrochloride (A, I, J, E, H, K, L, M, N) | 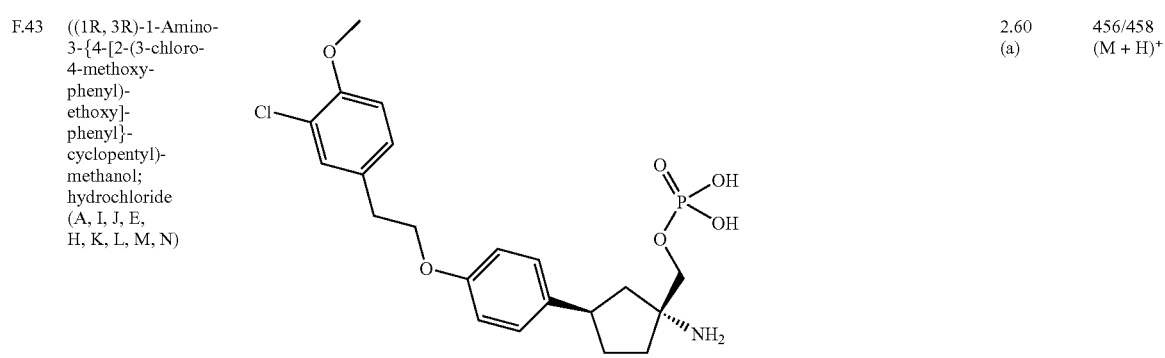 | 2.60 (a) | 456/458 (M + H)+ |

Product: Phosphoric acid mono-((1R, 3R)-1-amino-3-{4-[2-(3-chloro-4-methoxy-phenyl)-ethoxy]-phenyl}-cyclopentylmethyl) ester

| F.44 | {(1R, 3R)-1-Amino-3-[4-((R)-1-methyl-2-phenoxy)-ethoxy)-phenyl]-cyclopentyl)-methanol; hydrochloride (A, I, J, E, H, K, L, M, N) | 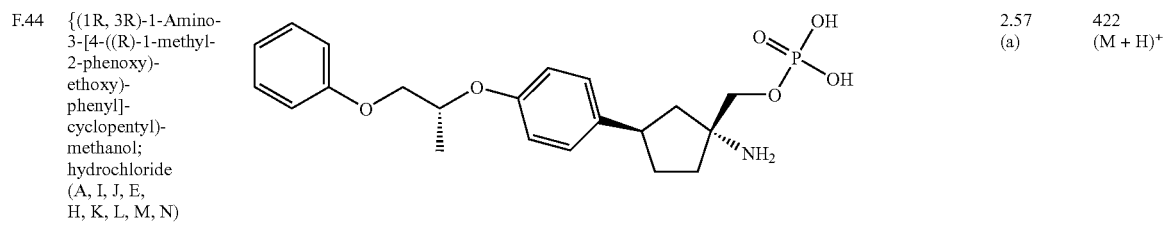 | 2.57 (a) | 422 (M + H)+ |

Product: Phosphoric acid mono-{(1R, 3R)-1-amino-3-[4-((R)-1-methyl-2-phenoxy-ethoxy)-phenyl]-cyclopentylmethyl} ester TABLE F-continued Examples following general procedure O (Scheme 4)
The letters in parentheses below the amino-alcohol precursors
indicate the General Procedure by which the amino-alcohol precursor was made.

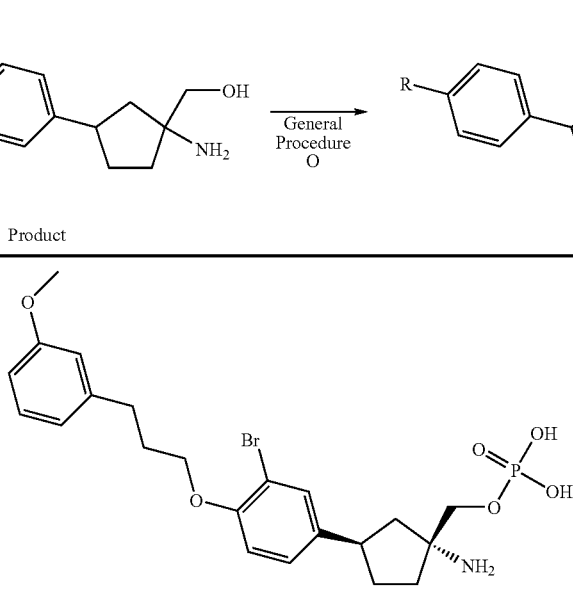

| Ex # | Amino-alcohol | Product | Rt/min (method) | m/z |
|---|---|---|---|---|
| F.45 | ((1R, 3R)-1-Amino-3-{3-bromo-4-[3-(3-methoxy-phenyl)-propoxy]-phenyl}-cyclopentyl)-methanol; hydrochloride (A, I, J, E, H, K, L, M, N) | 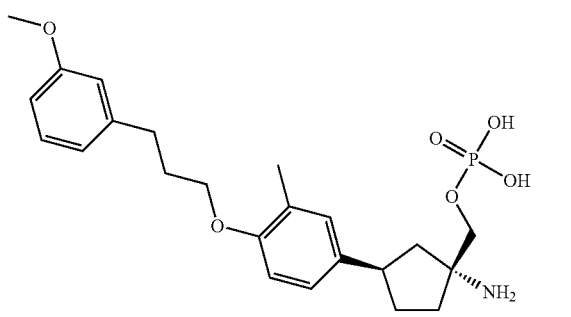 | 2.76 (a) | 514/516 (M + H)+ |

Product: Phosphoric acid mono-((1R, 3R)-1-amino-3-{3-bromo-4-[3-(3-methoxy-phenyl)-propoxy]-phenyl}-cyclopentylmethyl) ester

| F.46 | ((1R, 3R)-1-Amino-3-{4-[3-(3-methoxy-phenyl)-propoxy]-3-methyl-phenyl}-cyclopentyl)-methanol; hydrochloride (A, I, J, E, H, K, L, M, N) | | 2.74 (a) | 450 (M + H)+ |

Product: Phosphoric acid mono-((1R, 3R)-1-amino-3-{4-[3-(3-methoxy-phenyl)-propoxy]-3-methyl-phenyl}-cyclopentylmethyl) ester

| F.47 | {(1R, 3R)-1-Amino-3-[4-((S)-1-methyl-2-phenoxy-ethoxy)-phenyl]-cyclopentyl}-methanol; hydrochloride (A, I, J, E, H, K, L, M, N) | 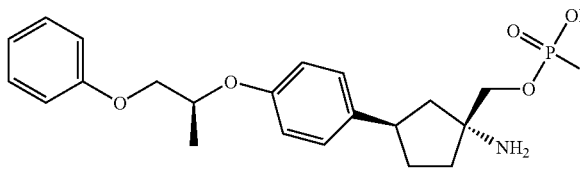 | 2.57 (a) | 422 (M + H)+ |

Product: Phosphoric acid mono-{(1R, 3R)-1-amino-3-[4-((S)-1-methyl-2-phenoxy-ethoxy)-phenyl]-cyclopentylmethyl} ester

| F.48 | {(1R, 3R)-1-Amino-3-[3,5-dichloro-4-(2-phenoxy-ethoxy)-phenyl]-cyclopentyl}-methanol; hydrochloride (A, I, J, E, H, K, L, M, N) | 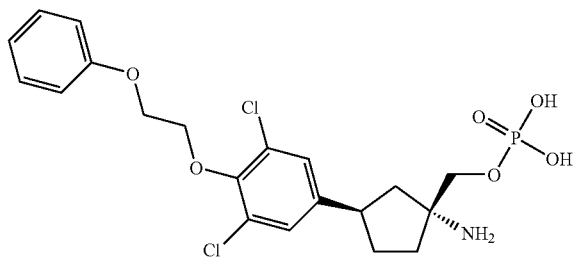 | 2.73 (a) | 476/478 (M + H)+ |

Product: Phosphoric acid mono-{(1R, 3R)-1-amino-3-[3,5-dichloro-4-(2-phenoxy-ethoxy)-phenyl]-cyclopentylmethyl} ester TABLE F-continued Examples following general procedure O (Scheme 4)
The letters in parentheses below the amino-alcohol precursors
indicate the General Procedure by which the amino-alcohol precursor was made.

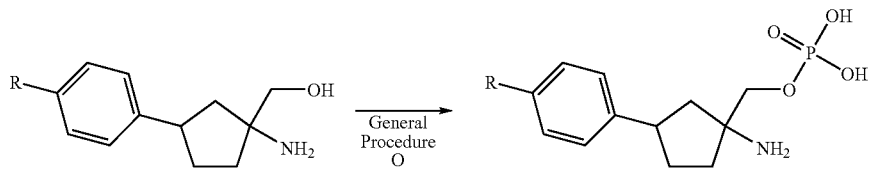

| Ex # | Amino-alcohol | Product | Rt/min (method) | m/z |
|---|---|---|---|---|
| F.49 | [(1R, 3R)-1-Amino-3-(3,5-dichloro-4-pentyloxy-phenyl)-cyclopentyl]-methanol; hydrochloride (A, I, J, E, H, K, L, M, N) | 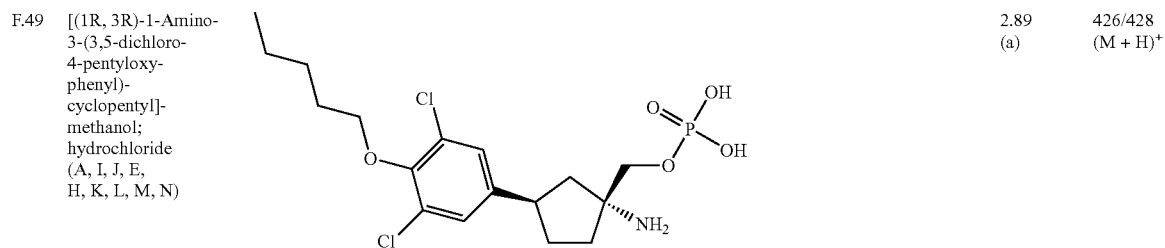 | 2.89 (a) | 426/428 (M + H)+ |

Product: Phosphoric acid mono-[(1R, 3R)-1-amino-3-(3,5-dichloro-4-pentyloxy-phenyl)-cyclopentylmethyl] ester

| F.50 | ((1R, 3R)-1-Amino-3-{3-bromo-4-[2-(4-methoxy-3,5-dimethyl-phenyl)-ethoxy]-phenyl}-cyclopentyl)-methanol; hydrochloride (A, I, J, E, H, K, L, M, N) | 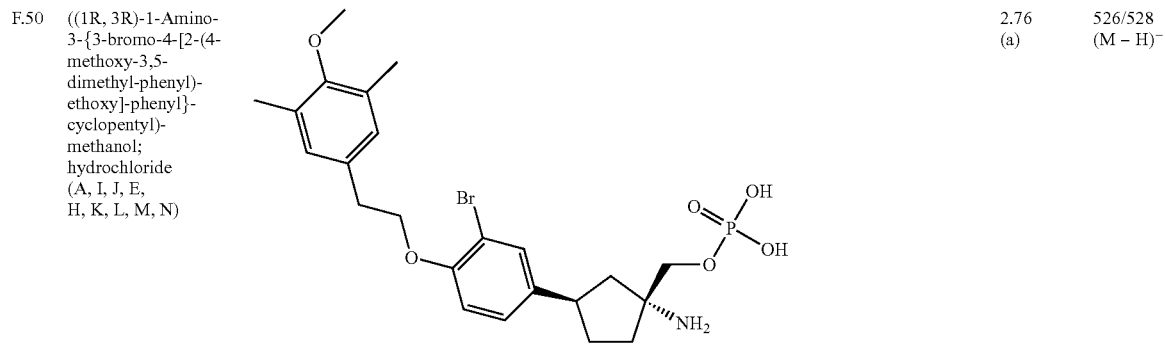 | 2.76 (a) | 526/528 (M − H)− |

Product: Phosphoric acid mono-((1R, 3R)-1-amino-3-{3-bromo-4-[2-(4-methoxy-3,5-dimethyl-phenyl)-ethoxy]-phenyl}-cyclopentylmethyl) ester

| F.51 | ((1R, 3R)-1-Amino-3-{4-[2-(2-methoxy-ethoxy)-ethoxy]-phenyl}-cyclopentyl)-methanol; hydrochloride (A, I, J, E, H, K, L, M, N) | 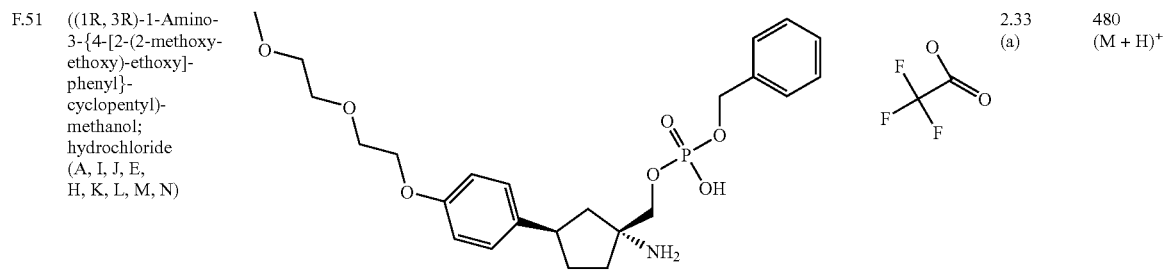 | 2.33 (a) | 480 (M + H)+ |

Product: Phosphoric acid (1R, 3R)-1-amino-3-{4-[2-(2-methoxy-ethoxy)-ethoxy]-phenyl}-cyclopentylmethyl ester benzylester; compound with trifluoro-acetic acid TABLE F-continued Examples following general procedure O (Scheme 4)
The letters in parentheses below the amino-alcohol precursors
indicate the General Procedure by which the amino-alcohol precursor was made.

| Ex # | Amino-alcohol | Product | Rt/min (method) | m/z |
|---|---|---|---|---|
| F.52 | {(1R, 3S)-1-Amino-3-(4-(6-ethoxy-hexyl)phenyl)cyclopentyl}-methanol; (A, B, C, D, E, F (Q), G, H) | Product: Phosphoric acid mono-{(1R, 3S)-1-amino-3-(4-(6-ethoxyhexyl)phenyl)cyclopentyl)methyl} ester | 2.60 (a) | 400.38 (M + H)⁺ |
| F.53 | {(1R, 3R)-1-Amino-3-(4-(7-methoxyheptyl)phenyl)cyclopentyl)}-methanol; (A, I, J, E, F (Q), G, H) | Product: Phosphoric acid mono-{(1R, 3R)-1-amino-3-(4-(7-methoxyheptyl)phenyl)cyclopentyl)methyl} ester | 2.62 (a) | 400.41 (M + H)⁺ |
| F.54 | {(1R, 3R)-1-Amino-3-(4-(6-ethoxyhexyl)phenyl)cyclopentyl)}-methanol; (A, I, J, E, F (Q), G, H) | Product: Phosphoric acid mono-{(1R, 3R)-1-amino-3-(4-(6-ethoxyhexyl)phenyl)cyclopentyl)methyl} ester | 2.62 (a) | 400.38 (M + H)⁺ |
| F.55 | {(1R, 3R)-1-Amino-3-(4-(2-(3-methoxyphenoxy)ethyl)phenyl)cyclopentyl}-methanol; (A, I, J, E, S, T, U, M, V, H) | Product: Phosphoric acid mono-{(1R, 3R)-1-amino-3-(4-(2-(3-methoxyphenoxy)ethyl)phenyl)cyclopentyl)-methyl} ester | 2.52 (a) | 422.39 (M + H)⁺ |

TABLE F-continued

Examples following general procedure O (Scheme 4)
The letters in parentheses below the amino-alcohol precursors
indicate the General Procedure by which the amino-alcohol precursor was made.

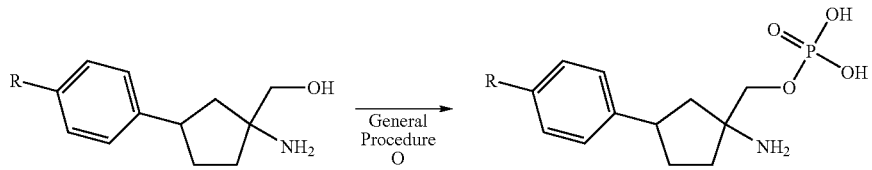

| Ex # | Amino-alcohol | Product | Rt/min (method) | m/z |
|---|---|---|---|---|
| F.56 | ((1R, 3R)-1-amino-3-(4-(4-iso-propoxyphenethyl)phenyl)-cyclopentyl)methanol | Product: ((1R, 3R)-1-amino-3-(4-(4-isopropoxyphenethyl)phenyl)cyclopentyl)methyl dihydrogen phosphate | 2.87 (a) | 434 (M + H)+ |
| F.57 | ((1R, 3S)-1-amino-3-(4-(6-iso-propoxyhexyl)phenyl)cyclopentyl)methanol | Product: (1R, 3S)-1-amino-3-(4-(6-isopropoxyhexyl)phenyl)cyclopentyl)methyl dihydrogen phosphate | 2.83 (a) | 414 (M + H)+ |
| F.58 | ((1R, 3R)-1-amino-3-(4-(7-methyl-octyl)phenyl)cyclopentyl)methanol | Product: (1R, 3R)-1-amino-3-(4-(7-methyloctyl)phenyl)cylopentyl)methyl dihydrogen phosphate | 3.34 (a) | 398 (M + H)+ |
| F.59 | 1-(4-((1R, 3R)-3-amino-3-(hydroxymethyl)cyclopentyl)phenyl)-5-phenylpentan-1-one | Product: ((1R, 3R)-1-amino-3-(4-(5-phenylpentanoyl)phenyl)cyclopentyl)methyl dihydrogen phosphate | 2.64 (a) | 432 (M + H)+ |
| F.60 | (1-amino-3-(4-octylphenyl)cyclohexyl)methanol | Product: (1-amino-3-(4-octylphenyl)cyclohexyl)methyl dihydrogen phosphate | 4.53 (a) | 398 (M + H)+ |

TABLE F-continued

Examples following general procedure O (Scheme 4)
The letters in parentheses below the amino-alcohol precursors
indicate the General Procedure by which the amino-alcohol precursor was made.

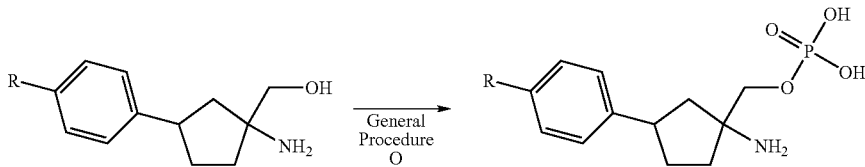

| Ex # | Amino-alcohol | Product | Rt/min (method) | m/z |
|---|---|---|---|---|
| F.61 | ((1R, 3R)-1-amino-3-(4-(4-propoxybutyl)phenyl)cyclopentyl)methanol | Product: ((1R, 3R)-1-amino-3-(4-(4-propoxybutyl)phenyl)cyclopentyl)methyl dihydrogen phosphate | 2.41 (a) | 386 $(M + H)^+$ |
| F.62 | ((1R, 3R)-1-amino-3-(4-(5-ethoxypentyl)phenyl)cyclopentyl)methanol | Product: ((1R, 3R)-1-amino-3-(4-(5-ethoxypentyl)phenyl)cyclopentyl)methyl dihydrogen phosphate | 1.79 (a) | 386 $(M + H)^+$ |
| F.63 | ((1R, 3R)-1-amino-3-(4-(3-butoxypropyl)phenyl)cyclopentyl)methanol | Product: ((1R, 3R)-1-amino-3-(4-(3-butoxypropyl)phenyl)cyclopentyl)methyl dihydrogen phosphate | 2.54 (a) | 386 $(M + H)^+$ |
| F.64 | ((1R, 3R)-1-amino-3-(4-(4-methoxyphenethyl)phenyl)cyclopentyl)methanol | Product: ((1R, 3R)-1-amino-3-(4-(4-methoxyphenethyl)phenyl)cyclopentyl)methyl dihydrogen phosphate | 2.53 (a) | 406 $(M + H)^+$ |
| F.65 | ((1R, 3R)-1-amino-3-(4-(3-(3-methoxyphenoxy)propyl)phenyl)cyclopentyl)methanol | Product: ((1R, 3R)-1-amino-3-(4-(3-(3-methoxyphenoxy)propyl)phenyl)cyclopentyl)methyl dihydrogen phosphate | 2.63 (a) | 436 $(M + H)^+$ |

TABLE F-continued

Examples following general procedure O (Scheme 4)
The letters in parentheses below the amino-alcohol precursors
indicate the General Procedure by which the amino-alcohol precursor was made.

| Ex # | Amino-alcohol | Product | Rt/min (method) | m/z |
|---|---|---|---|---|
| F.66 | ((1R, 3R)-1-amino-3-(4-(2-(3-ethoxyphenoxy)ethyl)phenyl)cyclopentyl)methanol | Product: ((1R, 3R)-1-amino-3-(4-(2-(3-ethoxyphenoxy)ethyl)phenyl)cyclopentyl)methyl dihydrogen phosphate | 2.65 (a) | 436 (M + H)+ |
| F.67 | ((1R, 3R)-1-amino-3-(4-(2-(3-(trifluoromethoxy)phenoxy)ethyl)phenyl)cyclopentyl)methanol | Product: ((1R, 3R)-1-amino-3-(4-(2-(3-(trifluoromethoxy)phenoxy)ethyl)phenyl)cyclopentyl)methyl dihydrogen phosphate | 2.84 (a) | 476 (M + H)+ |
| F.68 | ((1R, 3R)-1-amino-3-(4-((R)-3-phenoxybutyl)phenyl)cyclopentyl)methanol | Product: ((1R, 3R)-1-amino-3-(4-((R)-3-phenoxybutyl)phenyl)cyclopentyl)methyl dihydrogen phosphate | 1.97 (a) | 420 (M + H)+ |
| F.69 | ((1R, 3R)-1-amino-3-(4-(4-propoxyphenethyl)phenyl)cyclopentyl)methanol | Product: ((1R, 3R)-1-amino-3-(4-(4-propoxyphenethyl)phenyl)cyclopentyl)methyl dihydrogen phosphate | 2.87 (a) | 434 (M + H)+ |
| F.70 | ((1R, 3R)-1-amino-3-(4-((R)-3-(3-methoxyphenoxy)butyl)phenyl)cyclopentyl)methanol | Product: ((1R, 3R)-1-amino-3-(4-((R)-3-(3-methoxyphenoxy)butyl)phenyl)cyclopentyl)methyl dihydrogen phosphate | 2.73 (a) | 450 (M + H)+ |
| F.71 | ((1R, 3R)-1-amino-3-(4-((S)-3-(3-methoxyphenoxy)butyl)phenyl)cyclopentyl)methanol | Product: ((1R, 3R)-1-amino-3-(4-((S)-3-(3-methoxyphenoxy)butyl)phenyl)cyclopentyl)methyl dihydrogen phosphate | 2.73 (a) | 450 (M + H)+ |

TABLE F-continued

Examples following general procedure O (Scheme 4)
The letters in parentheses below the amino-alcohol precursors
indicate the General Procedure by which the amino-alcohol precursor was made.

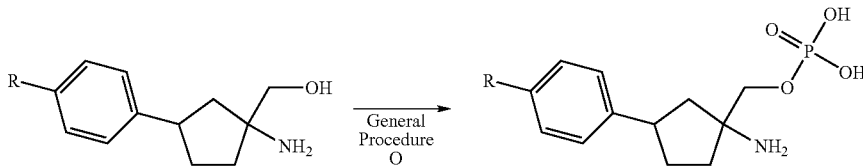

| Ex # | Amino-alcohol | Product | Rt/min (method) | m/z |
|---|---|---|---|---|
| F.72 | ((1R, 3R)-1-amino-3-(4-((S)-3-phenoxybutyl)phenyl)cyclopentyl)methanol | Product: ((1R, 3R)-1-amino-3-(4-((S)-3-phenoxybutyl)phenyl)cyclopentyl)methyl dihydrogen phosphate | 1.97 (a) | 420 (M + H)$^+$ |
| F.73 | (3-amino-1-(4-octylphenyl)pyrrolidin-3-yl)methanol | Product: (3-amino-1-(4-octylphenyl)pyrrolidin-3-yl)methyl dihydrogen phosphate | 2.30 (a) | 385 (M + H)$^+$ |
| F.74 | ((1R, 3R)-1-amino-3-(4-((Z)-hept-4-enyloxy)phenyl)cyclopentyl)methanol | Product: ((1R, 3R)-1-amino-3-(4-((Z)-hept-4-enyloxy)phenyl)cyclopentyl)methyl dihydrogen phosphate | 2.82 (a) | 384 (M + H)$^+$ |
| F.75 | ((1R, 3R)-1-amino-3-(4-(3-(4-fluoro-3-methoxyphenyl)propoxy)phenyl)cyclopentyl)methanol l (A, I, J, E, H, K, L, M, N) | Product: ((1R, 3R)-1-amino-3-(4-(3-(4-fluoro-3-methoxyphenyl)propoxy)phenyl)cyclopentyl)methyl dihydrogen phosphate | 0.85 (a) | 454.38 (M + H)$^+$ |

TABLE F-continued

Examples following general procedure O (Scheme 4)
The letters in parentheses below the amino-alcohol precursors
indicate the General Procedure by which the amino-alcohol precursor was made.

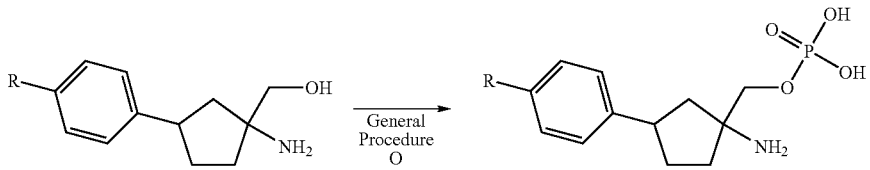

| Ex # | Amino-alcohol | Product | Rt/min (method) | m/z |
|---|---|---|---|---|
| F.76 | ((1R, 3R)-1-amino-3-(4-(3-(2-methoxyphenyl)propoxy)phenyl)cyclopentyl)methanol (A, I, J, E, H, K, L, M, N) | | 2.67 (a) | 436.35 $(M + H)^+$ |

Product: ((1R, 3R)-1-amino-3-(4-(3-(2-methoxyphenyl)propoxy)phenyl)cyclopentyl)methyl dihydrogen phosphate

| F.77 | ((1R, 3R)-1-amino-3-(4-(4-methoxy-3-methylphenethoxy)phenyl)cyclopentyl)methanol (A, I, J, E, H, K, L, M, N) | | 2.67 (a) | 436.42 $(M + H)^+$ |

Product: ((1R, 3R)-1-amino-3-(4-(4-methoxy-3-methylphenethoxy)phenyl)cyclopentyl)methyl dihydrogen phosphate

| F.78 | ((1R, 3R)-1-amino-3-(4-(4-methoxy-3,5-dimethylphenethoxy)phenyl)cyclopentyl)methanol, HCl 1 (A, I, J, E, H, K, L, M, N) | | 1.98 (a) | 450.20 $(M + H)^+$ |

Product: ((1R, 3R)-1-amino-3-(4-(4-methoxy-3,5-dimethylphenethoxy)phenyl)cyclopentyl)methyl dihydrogen phosphate

| F.79 | ((1R, 3R)-1-amino-3-(4-(4-(trifluoromethoxy)phenethoxy)phenyl)cyclopentyl)methanol (A, I, J, E, H, K, L, M, N) | | 2.81 (a) | 474.44 $(M − H)^−$ |

Product: ((1R, 3R)-1-amino-3-(4-(4-(trifluoromethoxy)phenethoxy)phenyl)cyclopentyl)methyl dihydrogen phosphate TABLE F-continued Examples following general procedure O (Scheme 4)
The letters in parentheses below the amino-alcohol precursors
indicate the General Procedure by which the amino-alcohol precursor was made.

| Ex # | Amino-alcohol | Product | Rt/min (method) | m/z |
|---|---|---|---|---|
| F.80 | (3-amino-5-methyl-5-(4-octylphenyl)tetrahydro-furan-3-yl)methanol | Product: ((3S, 5S)-3-amino-5-methyl-5-(4-octylphenyl)tetrahydrofuran-3-yl)methyl dihydrogen phosphate | 2.02 (f) | 400.29 (M + H)+ |
| F.81 | (3-amino-5-(4-octylphenyl)tetrahydro-furan-3-yl)methanol | Product: (3-amino-5-(4-octylphenyl)tetrahydrofuran-3-yl)methyl dihydrogen phosphate | 3.07 (a) | 386.21 (M + H)+ |
| F.82 | ((1R, 3R)-1-amino-3-(4-(3-(thiophen-2-yl)propoxy)phenyl)cyclopentyl)methanol (A, I, J, E, H, K, L, M, N) | Product: ((1R, 3R)-1-amino-3-(4-(3-(thiophen-2-yl)propoxy)phenyl)cyclopentyl)methyl dihydrogen phosphate | 2.57 (a) | 412.35 |
| F.83 | ((1R, 3R)-1-amino-3-(4-(3-methoxy-4-methylphenethoxy)phenyl)cyclopentyl)methanol (A, I, J, E, H, K, L, M, N) | Product: ((1R, 3R)-1-amino-3-(4-(3-methoxy-4-methylphenethoxy)phenyl)cyclopentyl)methyl dihydrogen phosphate | 2.69 (a) | 436.38 |

TABLE F-continued

Examples following general procedure O (Scheme 4)
The letters in parentheses below the amino-alcohol precursors
indicate the General Procedure by which the amino-alcohol precursor was made.

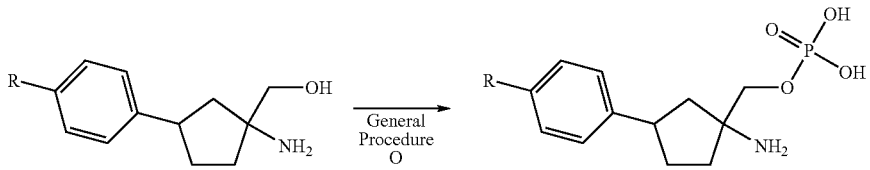

| Ex # | Amino-alcohol | Product | Rt/min (method) | m/z |
|---|---|---|---|---|
| F.84 | ((1R, 3R)-1-amino-3-(4-(3-(pyridin-4-yl)propoxy)phenyl cyclopentyl) methanol (A, I, J, E, H, K, L, M, N) | | 1.58 (a) | 407.23 |

Product: ((1R, 3R)-1-amino-3-(4-(3-(pyridin-4-yl)propoxy)phenyl)cyclopentyl)methyl dihydrogen phosphate

| F.85 | ((1R, 3R)-1-amino-3-(4-(3-(pyridin-3-yl)propoxy)phenyl cyclopentyl) methanol (A, I, J, E, H, K, L, M, N) | | 1.98 (a) | 407.36 |

Product: ((1R, 3R)-1-amino-3-(4-(3-(pyridin-3-yl)propoxy)phenylcyclopentyl)methyl dihydrogen phosphate

TABLE G

Examples following general procedures P (Scheme 5)
The letters in parentheses below the ester precursors indicate the General Procedure by
which the ester was made.

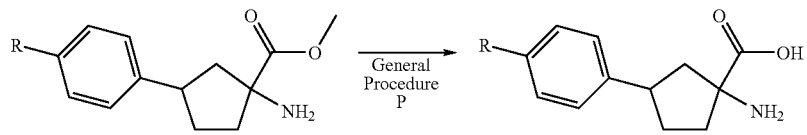

| Ex # | Ester | Product | Rt/min (method) | m/z |
|---|---|---|---|---|
| G.1 | (1R,3S)-1-Amino-3-(4-non-1-ynyl-phenyl)-cyclopentanecarboxylic acid (A, B, C, D, E, F) | Chiral | 2.13 (b) | 328 (M + H)+ |

Product: (1R,3S)-1-Amino-3-(4-non-1-ynyl-phenyl)-cyclopentanecarboxylic acid

TABLE G-continued

Examples following general procedures P (Scheme 5)
The letters in parentheses below the ester precursors indicate the General Procedure by which the ester was made.

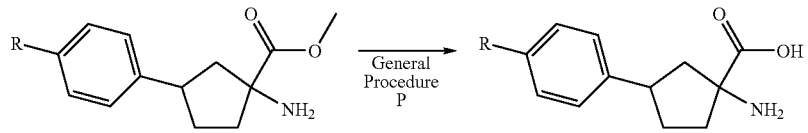

| Ex # | Ester | Product | R$_t$/min (method) | m/z |
|---|---|---|---|---|
| G.2 | (1R,3S)-1-Amino-3-(4-nonyl-phenyl)-cyclopentanecarboxylic acid methyl ester (A, B, C, D, E, F, G) | Product: (1R,3S)-1-Amino-3-(4-nonyl-phenyl)-cyclopentanecarboxylic acid; hydrochloride | 1.73 (b) | 332 (m + H)$^+$ |
| G.3 | (1R,3S)-1-Amino-3-(4-dec-1-ynyl-phenyl)-cyclopentanecarboxylic acid methyl ester (A, B, C, D, E, F) | Product: (1R,3S)-1-Amino-3-(4-dec-1-ynyl-phenyl)-cyclopentanecarboxylic acid; hydrochloride | 1.69 (b) | 342 (M + H)$^+$ |
| G.4 | (1R,3S)-1-Amino 3-(4-decyl-cyclopentanecarboxylic acid methyl ester (A, B, C, D, E, F, G) | Product: (1R,3S)-1-Amino-3-(4-decyl-phenyl)-cyclopentanecarboxylic acid | 2.51 (b) | 346 (M + H)$^+$ |
| G.5 | (1R,3S)-1-Amino-3-[4-(7-methoxy-hept-1-ynyl)-phenyl]-cyclopentanecarboxylic acid methyl ester (A, B, C, D, E, F) | Product: (1R,3S)-1-Amino-3-[4-(7-methoxy-hept-1-ynyl)-phenyl]-cyclopentanecarboxylic acid; hydrochloride | 2.02 (e) | 330 (M + H)$^+$ |

TABLE G-continued

*Examples following general procedures P (Scheme 5)*
*The letters in parentheses below the ester precursors indicate the General Procedure by which the ester was made.*

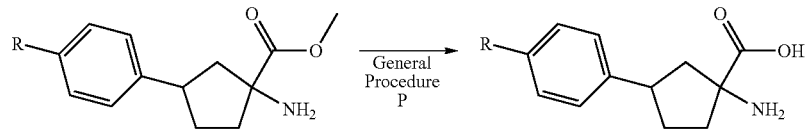

| Ex # | Ester | Product | R$_t$/min (method) | m/z |
|---|---|---|---|---|
| G.6 | (1R,3R)-1-Amino-3-[4-(3-phenoxy-propyl)-phenyl]-cyclopentanecarboxylic acid methyl ester (A, I, J, E, F, G) | Chiral. Product: (1R,3R)-1-Amino-3-[4-(3-phenoxy-propyl)-phenyl]-cyclopentanecarboxylic acid; hydrochloride | 2.66 (a) | 340 (M + H)$^+$ |
| G.7 | (1R,3S)-1-Amino-3-(4-oct-1-ynyl-phenyl)-cyclopentanecarboxylic acid methyl ester (A, B, C, D, E, F) | Chiral. Product: (1R,3S)-1-Amino-3-(4-oct-1-ynyl-phenyl)-cyclopentanecarboxylic acid | 2.30 (a) | 314 (M + H)$^+$ |
| G.8 | (1R,3S)-1-Amino-3-(4-hept-1-ynyl-phenyl)-cyclopentanecarboxylic acid methyl ester (A, B, C, D, E, F) | Chiral. Product: (1R,3S)-1-Amino-3-(4-hept-1-ynyl-phenyl)-cyclopentanecarboxylic acid | 2.14 (a) | 298 (M − H)$^−$ |
| G.9 | (1R,3S)-1-Amino-3-(4-heptyl-phenyl)-cyclopentanecarboxylic acid methyl ester (A, B, C, D, E, F, G) | Chiral. Product: (1R,3S)-1-Amino-3-(4-heptyl-phenyl)-cyclopentanecarboxylic acid | 3.02 (a) | 304 (M + H)$^+$ |

TABLE G-continued

Examples following general procedures P (Scheme 5)
The letters in parentheses below the ester precursors indicate the General Procedure by which the ester was made.

| Ex # | Ester | Product | R$_t$/min (method) | m/z |
|---|---|---|---|---|
| G.10 | (3S)-methyl 1-amino-3-(3-decylphenyl)cyclopentanecarboxylate; hydrochloride (A, B, D, E, F, G) | Product: (3S)-1-Amino-3-(3-decylphenyl)cyclopentanecarboxylic acid | 3.62 (a) | 346 (M + H)$^+$ |
| G.11 | (3S)-methyl 1-amino-3-(3-nonylphenyl)cyclopentanecarboxylate; hydrochloride (A, B, D, E, F, G) | Product: (3S)-1-Amino-3-(3-nonylphenyl)cyclopentanecarboxylic acid | 2.67 (a) | 332 (M + H)$^+$ |
| G.12 | (3S)-methyl 1-amino-3-(3-octylphenyl)cyclopentanecarboxylate; hydrochloride (A, B, D, E, F, G) | Product: (3S)-1-Amino-3-(3-octylphenyl)cyclopentanecarboxylic acid | 2.46 (a) | 318 (M + H)$^+$ |
| G.13 | (3S)-methyl 1-amino-3-(3-(oct-1-ynyl)phenyl)cyclopentanecarboxylate; hydrochloride A, B, D, E, F) | Product: (3S)-1-Amino-3-(3-(oct-1-ynyl)phenyl)cyclopentanecarboxylic acid | 3.06 (a) | 314 (M + H)$^+$ |
| G.14 | (3S)-methyl 1-amino-3-(3-(hept-1-ynyl)phenyl) cyclopentanecarboxylate; hydrochloride (A, B, D, E, F) | Product: (3S)-1-Amino-3-(3-(hept-1-ynyl)phenyl)cyclopentanecarboxylic acid | 2.12 (a) | 300 (M + H)$^+$ |

TABLE G-continued

Examples following general procedures P (Scheme 5)
The letters in parentheses below the ester precursors indicate the General Procedure by which the ester was made.

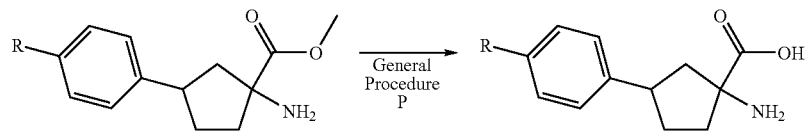

| Ex # | Ester | Product | R$_t$/min (method) | m/z |
|---|---|---|---|---|
| G.15 | (1R,3S)-methyl 1-amino-3-(4-(3-phenylpropyl)phenyl)cyclopentanecarboxylate; hydrochloride (A, B, C, D, E, F, G) | Product: (1R,3S)-1-Amino-3-(4-(3-phenylpropyl)phenyl)cyclopentanecarboxylic acid | 2.91 (a) | 338 (M + H)$^+$ |
| G.16 | (7R)-7-(4-(benzyloxy)-3-chlorophenyl)-1,3-diazaspiro[4.4]nonane-2,4-dione (A, B) | Product: (3R)-1-Amino-3-(4-(benzyloxy)-3-chlorophenyl)cyclopentanecarboxylic acid | 2.12 (c) | 346, 348 (M + H)$^+$ |
| G.17 | (3S)-1-amino-3-(3-chloro-4-methoxyphenyl)cyclopentanecarboxylic acid (A, B, D) | Product: (3S)-1-Amino-3-(3-(dec-1-ynyl)-4-methoxyphenyl)cyclopentanecarboxylic acid | 3.26 (a) | 372 (M + H)$^+$ |

TABLE H

Examples following general procedures A, I, J, E, H, K, L, M, N (Scheme 11)

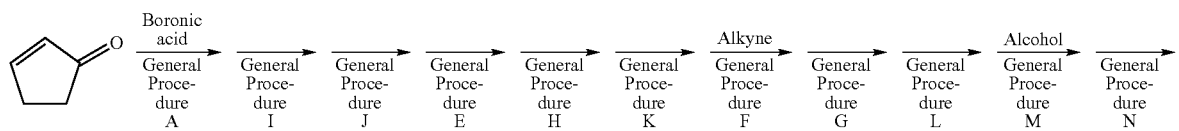

| Ex # | Boronic acid | Alkyne | Alcohol | Product | R$_t$/min (method) | m/z |
|---|---|---|---|---|---|---|
| H.1 | 4-Bromophenyl-boronic acid | 1-ethyl-4-methoxybenzene | propan-2-ol | 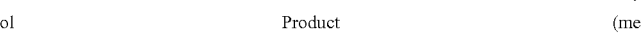 | 2.84 (a) | 355 (M + H)$^+$ |

Product: ((1R,3R)-1-amino-3-(4-(4-isopropoxyphenethyl)phenyl)cyclopentyl)methanol

TABLE I

Examples following general procedures
A, I, J, E, S, T, U, M, V, H
(Scheme 7)

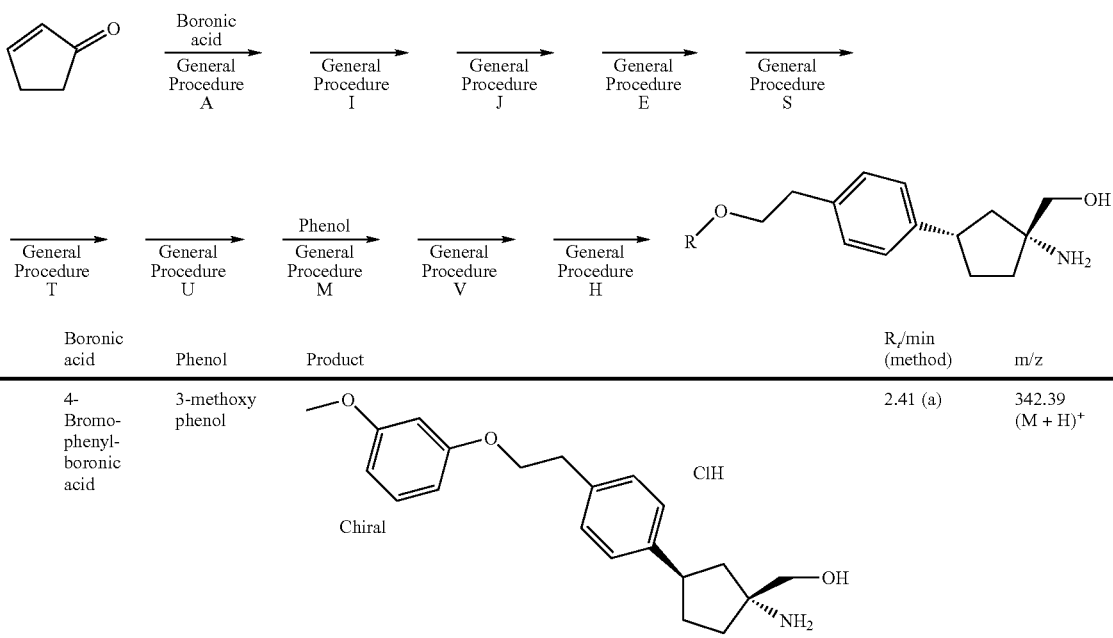

| Ex # | Boronic acid | Phenol | Product | R$_t$/min (method) | m/z |
|---|---|---|---|---|---|
| I.1 | 4-Bromo-phenyl-boronic acid | 3-methoxy phenol | | 2.41 (a) | 342.39 (M + H)$^+$ |

Product: ((1R, 3R)-1-amino-3-(4-(2-(3-methoxyphenoxy)ethyl)phenyl)cyclopentyl)methanol; hydrochloride TABLE I-continued Examples following general procedures
A, I, J, E, S, T, U, M, V, H
(Scheme 7)

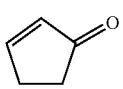

| Ex # | Boronic acid | Phenol | Product | $R_t$/min (method) | m/z |
|---|---|---|---|---|---|
| I.2 | 4-Bromo-phenyl-boronic acid | 4-methoxy phenol | 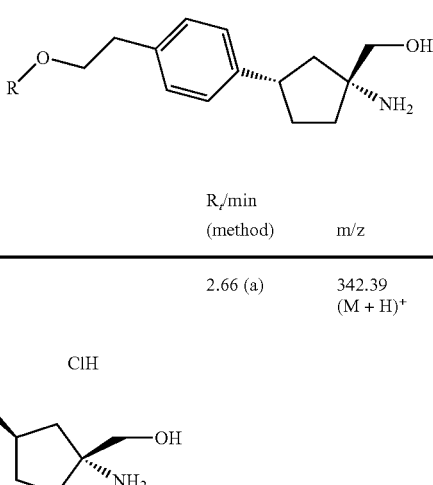 | 2.66 (a) | 342.39 $(M + H)^+$ |

Product: ((1R, 3R)-1-amino-3-(4-(2-(4-methoxyphenoxy)ethyl)phenyl)cyclopentyl)methanol; hydrochloride

TABLE J

Intermediates prepared following general procedure AA (Scheme 8)

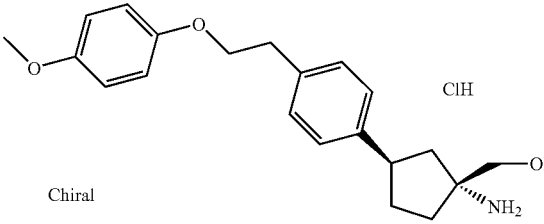

| Ex # | Alcohol | Alkylting agent | Product | $^1$H NMR (400 MHz, DMSO-$d_6$) |
|---|---|---|---|---|
| J.1 | but-3-yn-1-ol | 1-iodopropane | 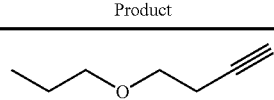<br>Product: 4-propoxybut-1-yne | δ. 3.56 (t, 2H), 3.42 (t, 2H), 2.47 (dt, 2H), 1.98 (t, 1H), 1.62-1.58 (m, 2H), 0.92 (t, 3H). |
| J.2 | prop-2-yn-1-ol | 1-iodobutane | 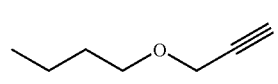<br>Product: 1-(prop-2-ynyloxy)butane | δ. 4.11 (d, 2H), 3.50 (t, 2H), 2.39 (t, 1H), 1.59-1.53 (m, 2H), 1.41-1.34 (m, 2H), 0.91 (t, 3H). |
| J.3 | pent-4-yn-1-ol | iodoethane | 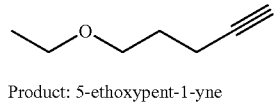<br>Product: 5-ethoxypent-1-yne | δ. 3.53-3.46 (m, 4H), 2.29 (dddd, 2H), 1.94 (t, 1H), 1.79 (dddd, 2H), 1.20 (t, 3H). |
| J.4 | 2-methoxyethnol | 3-bromoprop-1-yne | 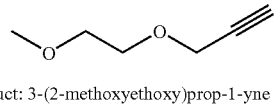<br>Product: 3-(2-methoxyethoxy)prop-1-yne | δ. 4.23 (d, 2H), 3.71 (ddd, 2H), 3.59 (ddd, 2H), 3.41 (s, 3H), 2.45 (t, 1H). |

TABLE J-continued

Intermediates prepared following general procedure AA (Scheme 8)

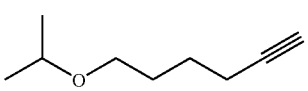

| Ex # | Alcohol | Alkylting agent | Product | $^1$H NMR (400 MHz, DMSO-$d_6$) |
|---|---|---|---|---|
| J.5 | propan-2-ol | hex-5-ynyl 4-methylbenzene-sulfonate | | δ. 3.47 (sep, 1 H), 3.33 (t, 2H), 2.71, (t, 1), 2.14 (ddd, 2H), 1.54-1.43 (m, 4H), 1.04 (d, 6H). |

Product: 4-propoxybut-1-yne

TABLE K

Examples following general procedures BB, CC, B, D, E, H (Scheme 9)

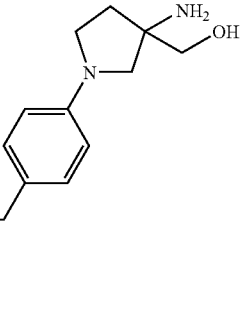

| Ex # | Aniline | Product | R$_t$/min (method) | m/z |
|---|---|---|---|---|
| K.1 | 4-octylaniline | | 3.42 (a) | 305 (M + H)$^+$ |

Product: (3-amino-1-(4-octylphenyl)pyrrolidin-3-yl)methanol

TABLE L

Examples following general procedures A, I, J, E, H, K, L, M, N (Scheme 10)

O=⟨cyclopentenone⟩ → Boronic acid / General Procedure A → General Procedure I → General Procedure J → General Procedure E → General Procedure H → General Procedure K → Alkyne / General Procedure F → Phenol / General Procedure M → General Procedure N → Product (R2, R3, R1, OH, NH2 substituted structure)

| Ex # | Boronic acid | Alkyne | Phenol | Product | R$_t$/min (method) | m/z |
|---|---|---|---|---|---|---|
| L.1 | 4-Bromo-phenyl-boronic acid | ((prop-2-ynyloxy)methyl)benzene | 3-methoxy-phenyl | Product: ((1R,3R)-1-amino-3-(4-(3-(3-methoxyphenoxy)propyl)phenyl)cyclopentyl)methanol; hydrochloride salt | 2.90 (a) | 356 (M + h)$^+$ |
| L.2 | 4-Bromo phenyl-boronic acid | (S)-((pent-4-yn-2-yloxy)methyl)benzene | phenol | Product: ((1R,3R)-1-amino-3-(4-((R)-3-phenoxybutyl)phenyl)cyclopentyl)methanol; hydrochloride salt | 3.21 (a) | 340 (M + H)$^+$ |
| L.3 | 4-Bromo-phenyl-boronic acid | (S)-1-methoxy-3-(pent-4-yn-2-yloxy)benzene | 3-methoxy-phenol | Product: ((1R,3R)-1-amino-3-(4-((R)-3-(3-methoxyphenoxv)butyl)phenyl)cyclopentyl)methanol; hydrochloride salt | 3.11 (a) | 370 (M + H)$^+$ |
| L.4 | 4-Bromo-phenyl-boronic acid | (R)-1-methoxy-3-(pent-4-yn-2-yloxy)benzene | 3-methoxy-phenol | Product: ((1R,3R)-1-amino-3-(4-((S)-3-(3-methoxyphenoxv)butyl)phenyl)cyclopentyl)methanol; hydrochloride salt | 2.98 (a) | 370 (M + H)$^+$ |
| L.5 | 4-Bromo-phenyl-boronic acid | (R)-1-methoxy-3-(pent-4-yn-2-yloxy)benzene | phenol | Product: ((1R,3R)-1-amino-3-(4-((S)-3-phenoxybutyl)phenyl)cyclopentyl)methanol; hydrochloride salt | 2.84 (a) | 340 (M + H)$^+$ |

TABLE M

Examples following general procedures D (Scheme 12)

The letters in parentheses below the ester precursors indicate the General Procedure by which the ester was made.

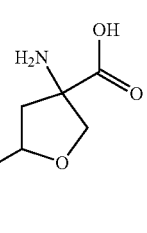

| Ex # | Ester | Product | $R_t$/min (method) | m/z |
|---|---|---|---|---|
| M.1 | 8-(4-octylphenyl)-7-oxa-1,3-diazaspiro[4.4]nonane-2,4-dione) | Product: 3-amino-5-(4-octylphenyl)tetrahydrofuran-3-carboxylic acid | 3.22 (a) | 320.25 |
| M.2 | 8-methyl-8-(4-octylphenyl)-7-oxa-1,3-diazaspiro[4.4]nonane-2,4-dione | Product: 3-amino-5-methyl-5-(4-octylphenyl)tetrahydrofuran-3-carboxylic acid | 2.12 (f) | 334.26 |

TABLE N

Examples following general procedures A, F, G, D (Scheme 13)

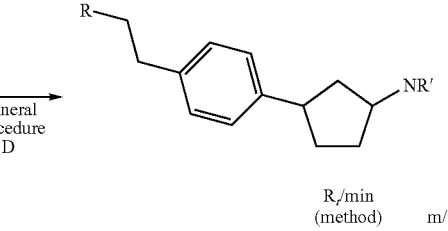

| Ex # | Boronic acid | Alkyne | Product | $R_t$/min (method) | m/z |
|---|---|---|---|---|---|
| N.1 | 4-Bromo-phenyl-boronic acid | Oct-1-yne | Product: 1-[3-(4-Octyl-phenyl)-cyclopentyl]-azetidine-3-carboxylic acid | 1.75 (f) | 358.3 (M + H)+ |

TABLE N-continued

Examples following general procedures A, F, G, D (Scheme 13)

| Ex # | Boronic acid | Alkyne | Product | R$_t$/min (method) | m/z |
|---|---|---|---|---|---|
| N.2 | 4-Bromo-phenyl-boronic acid | Oct-1-yne | Product: [3-(4-Octyl-phenyl)-cyclopentylamino]-acetic acid | 1.74 (f) | 332.3 (M + H)$^+$ |
| N.3 | 4-Bromo-phenyl-boronic acid | Oct-1-yne | Product: 3-[3-(4-Octyl-phenyl)-cyclopentylamino]-propionic acid | 1.91 (a) | 346.3 (M + H)$^+$ |

TABLE O

Examples following general procedures A, I, J, E, F (Scheme 14)

| Ex # | Boronic acid | Alkyne | Product | R$_t$/min (method) | m/z |
|---|---|---|---|---|---|
| O.1 | 4-Bromophenyl-boronic acid | Oct-1-yne | Product: (1R,3S)-1-Amino-3-(4-oct-1-ynyl-phenyl)-cyclopentanecarboxylic acid methyl ester; compound with (2R,3R)-2,3-dihydroxy-succinic acid | 2.14 (b) | 328.2 (M + H)$^+$ |

TABLE P

Examples following general procedures A, I, J, E, F, G (Scheme 15)

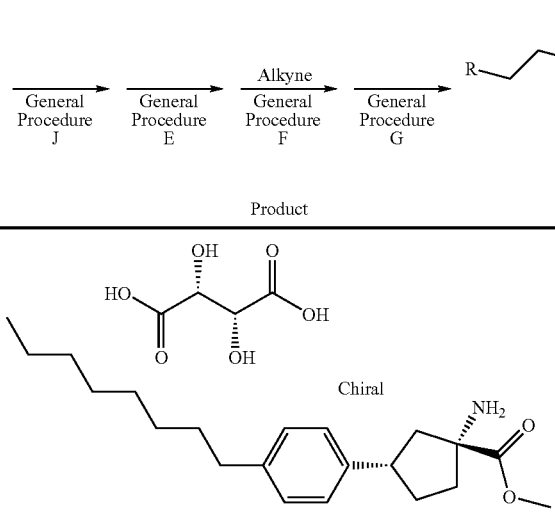

| Ex # | Boronic acid | Alkyne | Product | $R_t$/min (method) | m/z |
|---|---|---|---|---|---|
| P.1 | 4-Bromophenyl-boronic acid | Oct-1-yne | Product: (1R,3S)-1-Amino-3-(4-octyl-phenyl)-cyclopentanecarboxylic acid methyl ester; compound with (2R,3R)-2,3-dihydroxy-succinic acid | 2.67 (b) | 332.3 (M + H)+ |

Preparation of Additional Molecules (not in Tables):

Preparation of 4-Benzyloxy-N-prop-2-ynyl-butyramide

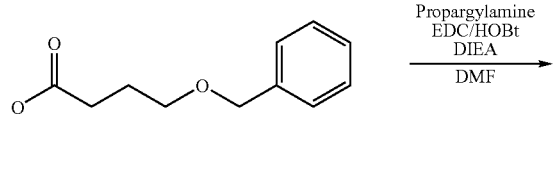

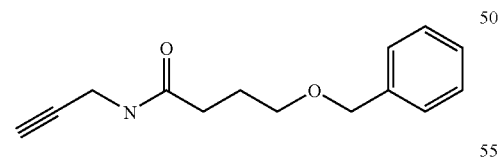

A solution of 4-Benzyloxy-butyric acid (1.00 g, 5.15 mmol) and Propargylamine (284 mg, 5.15 mmol) in DMF (10.3 ml) was treated with Diisopropylethylamine (0.90 ml, 5.15 mmol), Hydroxybenzotriazole (788 mg, 5.15 mmol) and EDC (665 mg, 5.15 mmol) at room temperature. The resulting mixture was stirred overnight at room temperature under nitrogen. The reaction was concentrated under reduced pressure and the crude product is taken up in Ethyl acetate, washed with water, dried using $Na_2SO_4$, filtered, and concentrated to yield 4-Benzyloxy-N-prop-2-ynyl-butyramide (1.02 g, 86%) as a viscous oil.

LCMS (Table 1, Method a) min., m/z:(M+H)+; $^1$H NMR (400 MHz, DMSO-$d_6$) δ. 8.24 (broad t, 1H), 7.30 (m, 5H), 4.43 (s, 2H), 3.82 (m, 2H), 3.40 (t, 2H), 3.31 (s, 1H), 2.16 (t, 2H), 1.76 (m, 2H)

Preparation of 2-(3-Benzyloxy-propyl)-5-methyl-oxazole

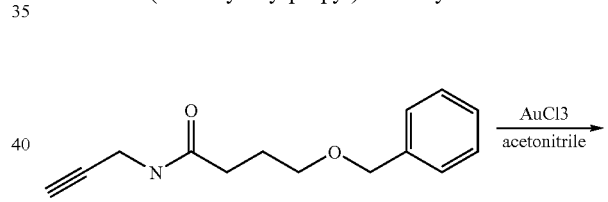

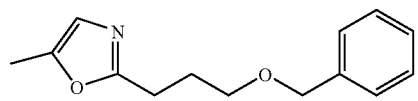

A solution of 4-Benzyloxy-N-prop-2-ynyl-butyramide (500 mg, 2.16 mmol) in acetonitrile (22 ml) was treated with Gold (III) chloride (32.8 mg, 0.108 mmol) at room temperature. The reaction was heated at 50° C. for 8 hours then was allowed to stir at room temperature overnight. The reaction was concentrated under reduced pressure and the residue was purified on silica gel using 1:1/heptane:ethyl acetate as eluant. Fractions that contained product were combined and concentrated under reduced pressure to yield 2-(3-Benzyloxy-propyl)-5-methyl-oxazole (405 mg, 81%) as a clear oil.

LCMS (Table 1, Method a) min., m/z:(M+H)+; 1H NMR (400 MHz, DMSO-d6) δ. 7.32 (m, 5H), 6.67 s, 1H), 4.45 (s, 2H), 3.47 (t, 2H), 2.73 (t, 2H), 2.23 (s, 3H), 1.92 (m, 2H)

Preparation of 3-(5-Methyl-oxazol-2-yl)-propan-1-ol

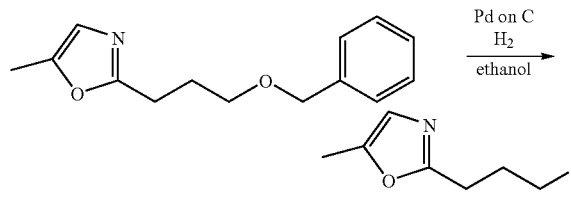

A solution of 2-(3-Benzyloxy-propyl)-5-methyl-oxazole (675 mg, 2.92 mmol) in ethanol (15 ml) containing a suspension of 10% Pd on C (63.9 mg, 0.06 mmol) was hydrogenated overnight at room temperature. The catalyst was removed by filtration through Celite®, then the filtrate was concentrated and the residue was purified on silica gel using 1:1/heptane:ethyl acetate and then ethyl acetate as eluants. Fractions that contained product were combined and concentrated under reduced pressure to yield 3-(5-Methyl-oxazol-2-yl)-propan-1-ol (242 mg, 59%) as an oil.

LCMS (Table 1, Method a) 1.85 min., m/z: 142 (M+H)+; 1H NMR (400 MHz, DMSO-d6) δ. 6.64 (s, 1H), 4.50 (t, 1H), 3.41 (m, 2H), 2.67 (t, 2H), 2.22 (s, 3H), 1.76 (m, 2H)

Preparation of 5-methoxy-pentan-1-ol

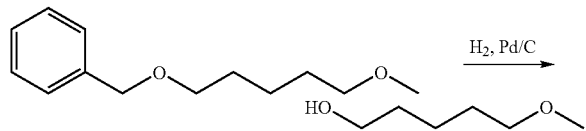

To a flask charged with ((5-methoxypentyloxy)methyl)benzene (4.25 g, 0.0204 mol), palladium on carbon (0.5 g) was added ethanol (40 mL). The mixture was stirred at room temperature under hydrogen (balloon) for 1 hour. The crude mixture was filtered through a pad of Celite®, concentrated, and dried under vacuum to give 5-methoxy-pentan-1-ol (2.40 g, 100%).

1H NMR (400 MHz, DMSO-d6) δ 4.32 (t, 3H), 3.37 (m, 2H), 3.31 (m, 1H), 3.21 (s, 3H), 1.39-1.49 (m, 4H), 1.25-1.32 (m, 2H)

Preparation of 3-(3-methoxy-phenyl)-propan-1-ol

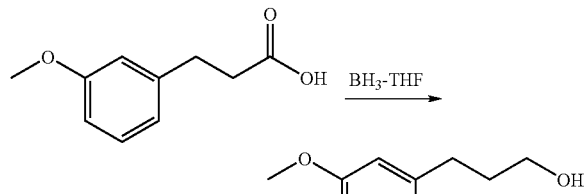

A solution of 3-(3-methoxyphenyl)propanoic acid (2.00 g, 11.10 mmol) in THF (2.0 mL) was added dropwise to a stirred solution of borane-tetrahydrofuran complex (24.42 mL, 24.42 mmol) so as to maintain reaction temperature below 35° C. The mixture was allowed to stir at room temperature overnight. Methanol was added dropwise to the stirred mixture until visible reaction had ceased. An additional 20 mL of methanol was added and the reaction was stirred for 4 hours. The crude mixture was concentrated, filtered and purified by silica gel chromatography (1:1 heptane:EtOAc as eluant). Fractions containing product were combined and concentrated to give 3-(3-methoxy-phenyl)-propan-1-ol as an oil.

1H NMR (400 MHz, DMSO-d6) δ 7.17 (m, 1H), 6.74 (m, 3H), 4.44 (t, 1H), 3.72 (s, 3H), 3.40 (m, 2H), 2.57 (m, 2H), 1.69 (m, 2H)

Preparation of 3-(3,5-dimethoxy-phenyl)-propan-1-ol

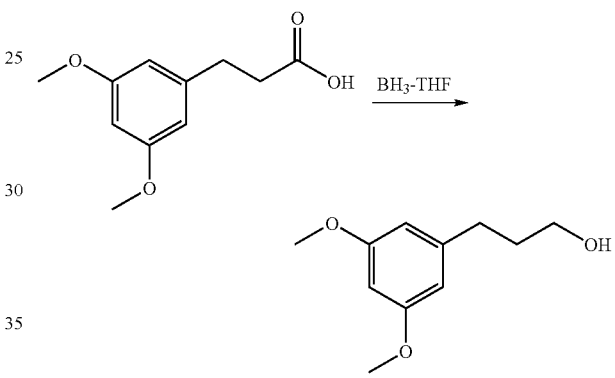

A solution of 3-(3,5-dimethoxyphenyl)propanoic acid (2.00 g, 9.51 mmol) in THF (2.0 mL) was added dropwise to a stirred solution of borane-tetrahydrofuran complex (20.93 mL, 20.93 mmol) so as to maintain reaction temperature below 35° C. The mixture was allowed to stir overnight at room temperature. Methanol was added dropwise to the stirred mixture until visible reaction had ceased. An additional 20 mL of methanol was added and the reaction was stirred for 4 hours. The crude mixture was concentrated, filtered and purified by silica gel chromatography (1:1 heptane:EtOAc as eluant). Fractions containing product were combined and concentrated to give 3-(3,5-dimethoxy-phenyl)-propan-1-ol as an oil.

1H NMR (400 MHz, DMSO-d6) δ 6.34 (d, 2H), 6.29 (t, 1H), 4.43 (t, 1H), 3.71 (s, 6H), 3.40 (m, 2H), 2.57 (m, 2H), 1.69 (m, 2H).

Preparation of 2-(4-fluoro-phenoxy)-ethanol

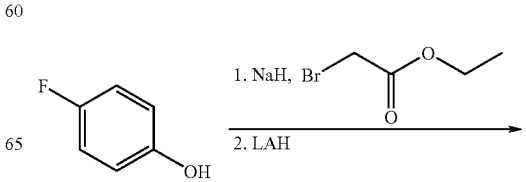

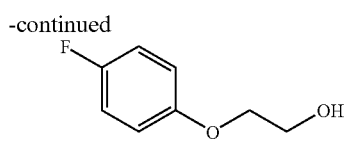

A solution of 4-fluorophenol (2.00 g, 17.84 mmol) in DMF (10 mL) was added dropwise to a stirred suspension of NaH in DMF (2.0 mL) at around 10° C. Ethyl bromoacetate (2.483 mL, 22.30 mmol) was added dropwise and then the reaction mixture was allowed to warm up to room temperature for 4 hours. The solvent was removed under vacuum and the residue was dissolved in methylene chloride and washed 2 times with water, dried over MgSO$_4$, filtered and concentrated to dryness. The crude product was purified on silica gel using (4:1 heptane:EtOAc as eluent) to give ethyl 2-(4-fluorophenoxy)acetate (3.12 g, 95%).

Ethyl 2-(4-fluorophenoxy)acetate (3.12 g, 15.74 mmol) was dissolved in diethyl ether (50 ml) and cooled to about 0° C. Lithium aluminum hydride (1.792 g, 47.2 mmol) was added in portions while maintaining reaction temperature below 35° C. The reaction was allowed to stir at room temperature for one hour. The crude reaction was diluted with ether (50 mL) then cooled in an ice bath and quenched by dropwise addition of water (6.1 mL), then 2 M NaOH (12.2 mL), then water (6.1 mL). The mixture was filtered and concentrated. The crude product was purified on silica gel (4:1 heptane:EtOAc as eluent) to give 2-(4-fluoro-phenoxy)-ethanol (1.36 g, 55%).

$^1$H NMR (400 MHz, DMSO-d$_6$) δ 7.08-7.13 (m, 2H), 6.92-6.96 (m, 2H), 4.84 (t, 1H), 3.95 (t, 2H), 3.69 (m, 2H).

Preparation of 4-{2-[4-((1R,3R)-3-amino-3-hydroxymethyl-cyclopentyl)-phenoxy]-ethyl}-phenol

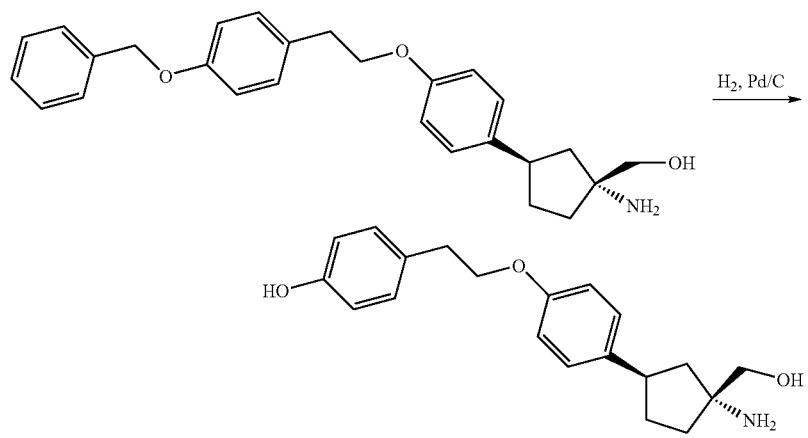

To a solution of ((1R,3R)-1-amino-3-(4-(4-(benzyloxy)phenethoxy)phenyl)cyclopentyl)methanol (250 mg, 0.599 mmol) in ethanol (10 mL) was added Pd/C 10% (20 mg, 0.188 mmol). The mixture was flushed with hydrogen and hydrogenate with a balloon for about 16 hours. The crude mixture was filtered, concentrated and the residue was triturated with ether. The solid was collected and dried under vacuum at 50° C. to give 4-(2-(4-((1R,3R)-3-amino-3-(hydroxymethyl)cyclopentyl)phenoxy)ethyl)phenol (169 mg, 86%) as a white solid.

LCMS (Table 1, Method b) R$_t$=1.75 min; m/z: 328 (M+H)$^+$; $^1$H NMR (400 MHz, DMSO-d$_6$) δ 7.10 (m, 4H), 6.81 (dd, 2H), 6.68 (dd, 2H), 4.63 (b, 1H), 4.05 (t, 2H), 3.31 (s, 3H), 2.88 (t, 2H), 1.98-2.07 (m, 1H), 1.77-1.84 (m, 1H), 1.30-1.65 (m, 5H).

Preparation of 4-((7S)-3-methyl-2,4-dioxo-1,3-diazaspiro[4.4]nonan-7-yl)benzonitrile

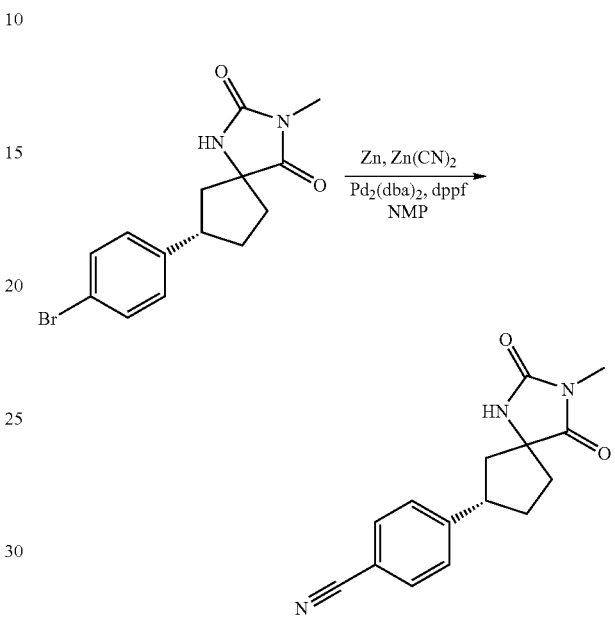

A suspension of (7S)-7-(4-bromophenyl)-3-methyl-1,3-diazaspiro[4.4]nonane-2,4-dione (General procedures A, B, C) (0.500 g, 1.547 mmol) in anhydrous NMP (4.00 ml) was degassed by evacuating the reaction vial then refilling with N$_2$ a couple of times. To this suspension was added zinc (1.012 mg, 0.015 mmol), dppf (0.027 g, 0.048 mmol), zinc cyanide (0.145 g, 1.238 mmol), and Pd$_2$(dba)$_3$ (0.021 g, 0.023 mmol) at ambient temperature. The resulting mixture was heated to 120° C. for about 16 hours. The crude material was filtered through Celite®. The filtrate was taken up in water (70 mL) and ethyl acetate (100 mL). The organic phase was washed with water (50 mL×2) and brine (50 mL), dried (MgSO$_4$) and concentrated to yield 4-((7S)-3-methyl-2,4-dioxo-1,3-diazaspiro[4.4]nonan-7-yl)benzonitrile (0.44 g, 0.20 mmol) as light brown solid.

LCMS (Table 1, Method a) $R_f$=2.04 min; m/z: 270.15 (M+H)$^+$; $^1$H NMR (400 MHz, Methanol-d4) δ ppm 3.52-3.39 (m, 1H), 2.10-1.85 (m, 3H), 2.31-2.15 (m, 3H), 7.69-7.64 (m, 2H), 7.50 (t, J=8.45 Hz, 2H), 2.96 (d, J=2.91 Hz, 3H), 2.59-2.34 (m, 1H).

Preparation of (Z)-N'-hydroxy-4-{(7S)-3-methyl-2,4-dioxo-1,3-diazaspiro[4.4]nonan-7-yl} benzimidamide

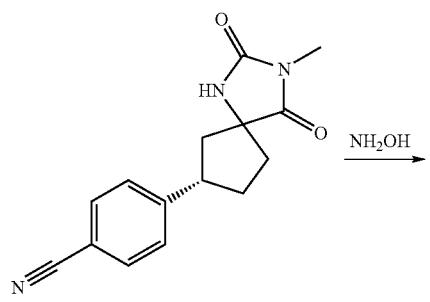

Preparation of (7S)-7-(4-(5-(4-isobutylphenyl)-1,2,4-oxadiazol-3-yl)phenyl)-3-methyl-1,3-diazaspiro[4.4]nonane-2,4-dione

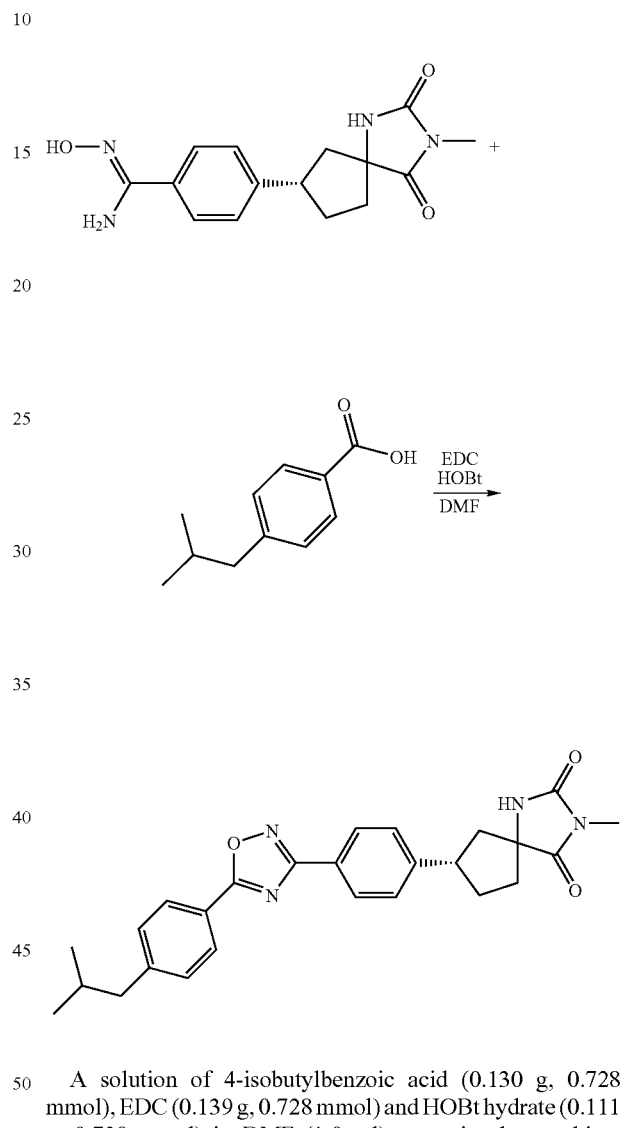

4-((7S)-3-methyl-2,4-dioxo-1,3-diazaspiro[4.4]nonan-7-yl)benzonitrile (0.88 g, 3.27 mmol) was suspended in ethanol (20 ml). To this was added hydroxylamine (0.240 ml, 3.59 mmol) as 50% weight solution in water, and the reaction was heated to 60° C. under an atmosphere of nitrogen for about 20 hours. The reaction mixture was left to cool down to ambient temperature. Solvent was partially removed. The resulting white precipitate was filtered, rinsed with cold ethanol and vacuum-dried to afford (Z)-N'-hydroxy-4-{(7S)-3-methyl-2,4-dioxo-1,3-diazaspiro[4.4]nonan-7-yl}benzimidamide as light brown solid (1.12 g, 3.20 mmol).

LCMS (Table 1, Method a) $R_f$=1.47 min; m/z: 303.33 (M+H)$^+$; $^1$H NMR (400 MHz, Methanol-d4) δ ppm 2.96 (d, J=3.16 Hz, 3H), 2.43-2.33 (m, 1H), 3.39 (ddd, J=18.31, 11.00, 7.39 Hz, 1H), 7.36-7.30 (m, 2H), 7.58 (d, J=8.23 Hz, 2H), 2.29-1.87 (m, 6H).

A solution of 4-isobutylbenzoic acid (0.130 g, 0.728 mmol), EDC (0.139 g, 0.728 mmol) and HOBt hydrate (0.111 g, 0.728 mmol) in DMF (1.0 ml) was stirred at ambient temperature for 1-1.5 hours. To the mixture was added (Z)-N'-hydroxy-4-{(7S)-3-methyl-2,4-dioxo-1,3-diazaspiro[4.4] nonan-7-yl}benzimidamide (0.200 g, 0.662 mmol) as solution in 1.0 ml DMF at ambient temperature. The resulting mixture was heated to about 140° C. for additional 2 hours. Solvent was removed in vacuo. The crude product was purified on a Prep HPLC system using 20-99% 50 mM NH$_4$OAc buffer in acetonitrile at 81 mL/min to afford (7S)-7-(4-(5-(4-isobutylphenyl)-1,2,4-oxadiazol-3-yl)phenyl)-3-methyl-1,3-diazaspiro[4.4]nonane-2,4-dione (0.062 g, 0.139 mmol) as light brown solid.

LCMS (Table 1, Method a) $R_f$=4.48 min; m/z: 445.39 (M+H)$^+$; $^1$H NMR (400 MHz, Methanol-d4) δ ppm 7.53-7.39 (m, 4H), 8.15-8.06 (m, 4H), 3.52-3.41 (m, 1H), 2.98 (d, J=3.39 Hz, 3H), 2.61 (d, J=7.22 Hz, 2H), 2.46-2.37 (m, 1H), 2.35-2.20 (m, 3H), 2.07-1.90 (m, 3H), 0.95 (d, J=6.62 Hz, 6H).

Preparation of (3S)-1-amino-3-(4-(5-(4-isobutylphenyl)-1,2,4-oxadiazol-3-yl)phenyl)-N-methylcyclopentanecarboxamide

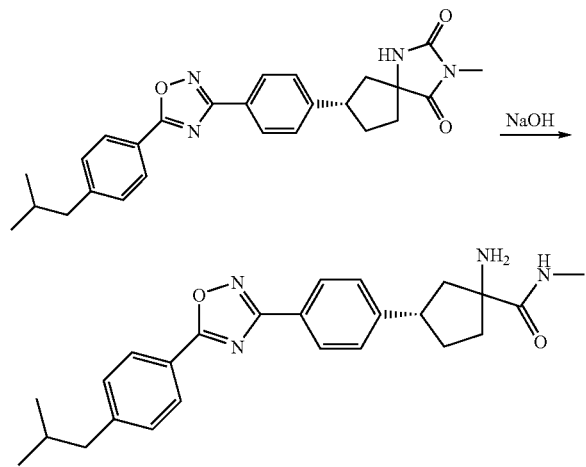

(7S)-7-(4-(5-(4-isobutylphenyl)-1,2,4-oxadiazol-3-yl)phenyl)-3-methyl-1,3-diazaspiro[4.4]nonane-2,4-dione (0.052 g, 0.117 mmol) was taken up in dioxane (1.0 ml). To this was added sodium hydroxide (1.0 ml, 2.000 mmol) as 2M solution. The resulting suspension was heated to 120° C. for about 70 hours, during which more sodium hydroxide solution was added to push the hydrolysis to completion. Heating was stopped and the reaction mixture was concentrated in vacuo. The resulting material was brought up in 1-2 mL DMSO and filtered. The filtrate was purified on a Prep HPLC system using 30-100% acetonitrile in 50 mM NH$_4$OAc buffer at 21 mL/min to yield (3S)-1-amino-3-(4-(5-(4-isobutylphenyl)-1,2,4-oxadiazol-3-yl)phenyl)-N-methylcyclopentanecarboxamide (0.017 g, 0.041 mmol) as off-white solid.

LCMS (Table 1, Method b) R$_t$=1.76 min; nm/z: 419.24 (M+H)$^+$; $^1$H NMR (400 MHz, CDCl$_3$) δ ppm 8.11 (dd, J=9.86, 8.34 Hz, 4H), 7.44 (d, J=8.17 Hz, 2H), 7.32 (d, J=8.16 Hz, 2H), 7.80-7.71 (m, 1H), 3.56-3.36 (m, 1H), 2.86 (d, J=4.81 Hz, 3H), 2.65-2.52 (m, 4H), 2.35-2.23 (m, 1H), 2.05-1.86 (m, 4H), 1.65-1.55 (m, 1H), 0.94 (d, J=6.61 Hz, 6H), 1.34-1.17 (m, 1H).

Preparation of 2-(1-amino-3-(4-octylphenyl)cyclopentyl)acetic acid

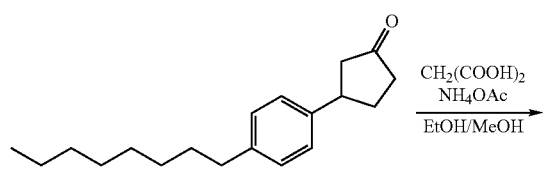

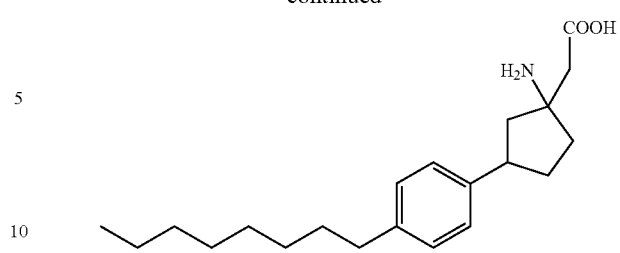

3-(4-Octyl-phenyl)-cyclopentanone, malonic acid (0.076 g, 0.734 mmol), ammonium acetate (0.057 g, 0.734 mmol) were suspended in the mixture of ethanol (1.50 mL, 25.7 mmol) and methanol (0.50 mL, 12.36 mmol) in a 15-mL, 2-necked round-bottomed flask equipped with a condenser. The heterogeneous mixture was heated to reflux at 80° C. for about 24 hours. Heating was removed. The crude mixture was taken up in dichloromethane/water mixture (20 mL/20 mL). The resulting fine suspension was filtered, washed several times with water and dichloromethane, and vacuum-dried to yield 2-(1-amino-3-(4-octylphenyl)cyclopentyl)acetic acid (0.020 g, 0.060 mmol) as off-white solid.

LCMS (Table 1, Method b) R$_t$=1.70 min; m/z: 332.30 (M+H)$^+$; $^1$H NMR (400 MHz, DMSO-d$_6$) δ ppm 8.48 (d, J=18.37 Hz, 3H), 7.17 (d, J=8.01 Hz, 2H), 7.06 (d, J=7.89 Hz, 2H), 3.54-3.00 (m, 1H), 2.85 (d, J=10.82 Hz, 2H), 2.49-2.44 (m, 2H), 2.32-2.17 (m, 1H), 2.11-1.59 (m, 5H), 1.48 (s, 3H), 1.20 (d, J=11.44 Hz, 10H), 0.80 (t, J=6.72, 6.72 Hz, 3H)

Preparation of hept-6-yn-1-ol

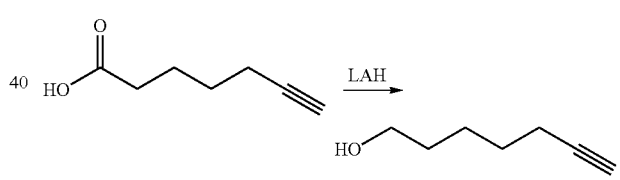

To a round bottom flask equipped with a stirring bar under N$_2$ was added LAH (3.61 g, 95 mmol) and anhydrous diethyl ether (300 ml). The mixture was cooled to 0° C. in an acetonitrile-dry ice bath, a solution of hept-6-ynoic acid (6.00 g, 47.6 mmol) in dry diethyl ether (60.1 ml) was added dropwise with vigorous stirring. The mixture was then allowed to warm to ambient temperature and stirred for an additional hour. Next, 1M HCl solution (159 ml, 159 mmol) was added dropwise and the reaction mixture was stirred at ambient temperature over the weekend. The layers were then separated. The aqueous layer was back-extracted with diethyl ether (150 mL). The combined organic phase was wash with brine (150 mL), dried (MgSO$_4$) and concentrated to yield 5.89 g of colorless liquid. The crude liquid was purified via Analogix FCC system using Biotage RS 330 g column, with a gradient of 0-50% ether/pet. ether over 10 min. at 40 mL/min. then held at 50% for 50 min. Fractions containing product were combined and concentrated to yield hept-6-yn-1-ol (4.94 g, 44.0 mmol) as colorless liquid. The title compound was also prepared according to procedure described by B. W. Gung et al, *Tetrahedron: Asymmetry*, 2005, 16, 3107-3114. $^1$H NMR (400 MHz, DMSO-d$_6$) δ ppm 3.66 (t, J=6.32, 6.32 Hz, 2H), 2.26-2.17 (m, 2H), 1.98-1.92 (m, 1H), 1.66-1.53 (m, 4H), 1.53-1.45 (m, 2H)

Preparation of 2-(3-methoxy-4-methylphenyl)ethanol

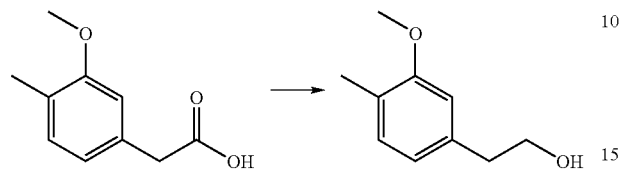

2-(3-methoxy-4-methylphenyl)acetic acid (1 g, 5.55 mmol) was dissolved in Tetrahydrofuran (27.7 ml). A solution of borane tetrahydrofuran complex (12.21 ml, 12.21 mmol) was added slowly under nitrogen. The reaction was stirred for about 18 h. Methanol was slowly to quench the reaction. The mixture was rotovapped. More methanol was added. The mixture was rotovapped. This was repeat two more times. The solution was passed through a short pad of silica gel eluting with 1:1 EtOAc/heptane and then rotovapped to give 2-(3-methoxy-4-methylphenyl)ethanol (0.800 g, 4.81 mmol, 87% yield) as a colorless oil: $^1$H NMR (400 MHz, CDCl$_3$) δ ppm 7.07 (dd, 1H), 6.73 (dd, 1H), 6.69 (s, 1H), 3.86 (t, 2H), 3.30 (s, 3H), 2.84 (t, 2H), 2.14 (s, 3H), 1.41 (s, 1H)

Preparation of 3-(4-fluoro-3-methoxyphenyl)propan-1-ol

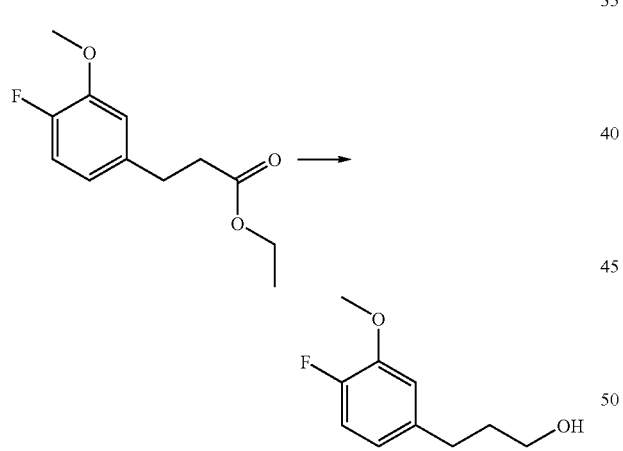

Ethyl 3-(4-fluoro-3-methoxyphenyl)propanoate (1.019 g, 4.50 mmol) was dissolved in THF (22.52 ml) under nitrogen. A solution of lithium aluminum hydride (4.50 ml, 9.01 mmol) was added slowly. TLC shows reaction done after about 10 min. Water (0.35 mL) was slowed added and then the mixture was stirred for 30 min. 1 N NaOH (1.05 mL) was added and the reaction was stirred for 30 min. Additional water was added (0.35 mL) and the solution was stirred and then filtered. The cake was washed with ether and then rotovapped. Ether was added. The solution was dried over magnesium sulfate and then filtered and rotovapped. The solution was passed through silica gel with methylene chloride then ethyl acetate then rotovapped to give 3-(4-fluoro-3-methoxyphenyl)propan-1-ol (0.753 g, 4.09 mmol, 91% yield) as a colorless oil:

$^1$H NMR (400 MHz, CDCl$_3$). δ ppm 6.98 (dd, 1H), 6.80 (dd, 1H), 6.71 (ddd, 1H), 3.89 (s, 3H), 3.68 (t, 2H), 2.68 (t, 2H), 1.94-1.82 (m, 2H), 1.33 (s, 1H)

Preparation of 3-(2-methoxyphenyl)propan-1-ol

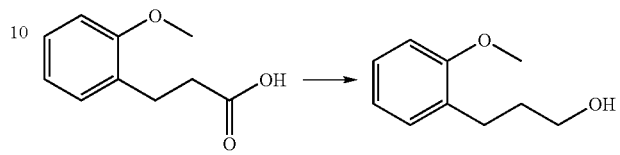

3-(2-methoxyphenyl)propanoic acid (1.0 g, 5.55 mmol) was dissolved in THF (27.7 ml). A solution of borane tetrahydrofuran complex (12.21 ml, 12.21 mmol) was added slowly. The reaction was stirred for about 4 h. Methanol was added and the solvents removed. This process was repeated twice. The solution was passed through a short pad of silica gel with 1:1 ethyl acetate/heptane And then rotovapped to give 3-(2-methoxyphenyl)propan-1-ol (0.946 g, 5.69 mmol, 103% yield) as a colorless oil. $^1$H NMR (400 MHz, CDCl$_3$) δ ppm 7.19 (dt, 1H), 7.15 (dd, 1H), 6.90 (dt, 1H), 6.86 (d, 1H), 3.84 (s, 3H), 3.60 (t, 2H), 2.73 (t, 2H), −1.92-1.79 (m, 2H), 1.76 (s, 1H), Preparation of 2-(4-methoxy-3-methylphenyl)ethanol

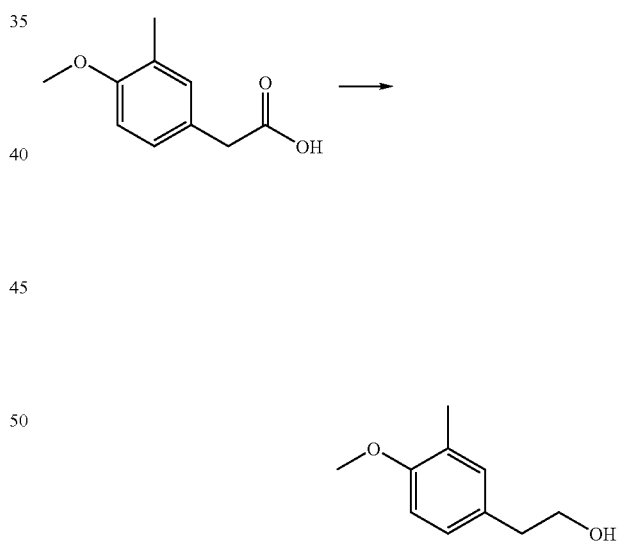

2-(4-methoxy-3-methylphenyl)acetic acid (1 g, 5.55 mmol) was dissolved in Tetrahydrofuran (27.7 ml). A solution of borane tetrahydrofuran complex (12.21 ml, 12.21 mmol) was added slowly under nitrogen. The reaction was stirred for about 18 h. Methanol was slowly added to quench the reaction The solution was rotovapped. More methanol was added. The solution was rotovapped. This was repeated twice. The solution was passed through a short pad of silica gel eluting with 1:1 EtOAc/heptane and then rotovapped to give 2-(4-methoxy-3-methylphenyl)ethanol (0.986 g, 5.93 mmol, 107% yield) as a colorless oil: $^1$H NMR (400 MHz, CDCl$_3$) δ ppm 7.05 (m, 1H), 7.04 (m, 1H), 6.80 (m, 1H), 3.85 (s, 3H), 3.84 (t, 2H), 2.81 (t, 2H), 2.25 (s, 1H), 1.64 (s, 1H)

Preparation of 3-(thiophen-2-yl)propan-1-ol

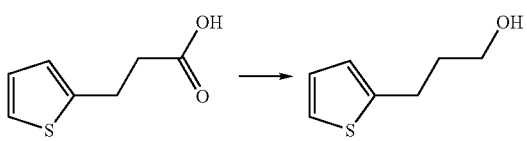

A solution of borane tetrahydrofuran complex (13.03 ml, 13.03 mmol) was added to THF (29.6 ml). 3-(thiophen-2-yl)propanoic acid (0.100 g, 0.640 mmol) was dissolved in THF (5 mL) and added slowly to the reaction. The solution was stirred overnight. Methanol was added and then the solution was rotovapped. More methanol was added and the solution was rotovapped. This was repeated once. The solution was passed through a pad of silica gel eluting with ether and then ethyl acetate and then rotovapped to give 3-(thiophen-2-yl)propan-1-ol (0.820 g, 5.77 mmol, 97% yield) as a light yellow oil: $^1$H NMR (400 MHz, CDCl$_3$). δ ppm 7.12 (m, 1H), 6.92 (dd, 1H), 6.81 (m, 1H), 3.71 (t, 1H), 2.95 (t, 1H), 2.02-1.87 (m, 1H)

Scheme for preparation of furan analogs outlined below:

4-octylbenzaldehyde (10.0 g, 45.8 mmol) (Aldrich) was dissolved in THF (229 ml) under nitrogen. The reaction was cooled to about 0-5° C. in an ice bath. A solution of allylmagnesium bromide (48.1 ml, 48.1 mmol) (Aldrich) was added slowly and the reaction stirred for about 2 h. The reaction was quenched by the addition of saturated ammonium chloride followed by addition of ethyl acetate. The layers were separated and the aqueous extracted with ethyl acetate. The combined extracts were washed with brine, dried over sodium sulfate, filtered, and evaporated to an off-white oil. The residue was dissolved in ether and dried over sodium sulfate and filtered. The solvents were removed under reduced pressure to provide 1-(4-octylphenyl)but-3-en-1-ol (11.54 g, 44.3 mmol, 97% yield) as a light yellow oil: LC/MS (method f) R$_f$=2.90 min.; MS m/z: 243.21 (M-water)$^+$.

Preparation of tert-butyldimethyl(1-(4-octylphenyl)but-3-enyloxy)silane

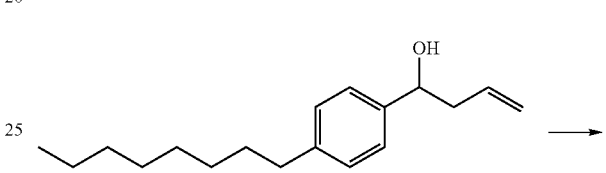

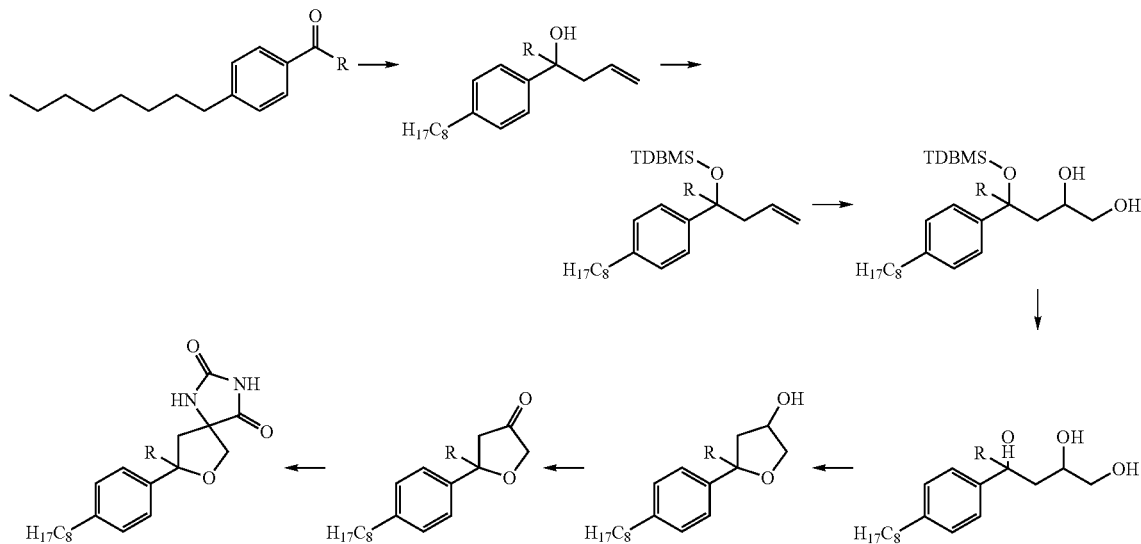

Preparation of 1-(4-octylphenyl)but-3-en-1-ol

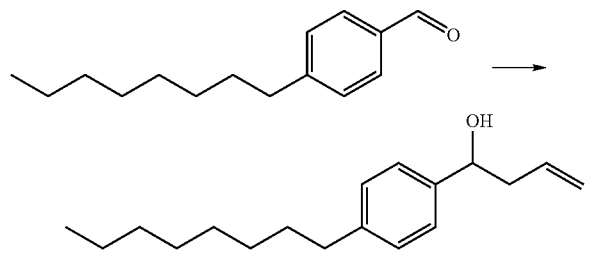

-continued

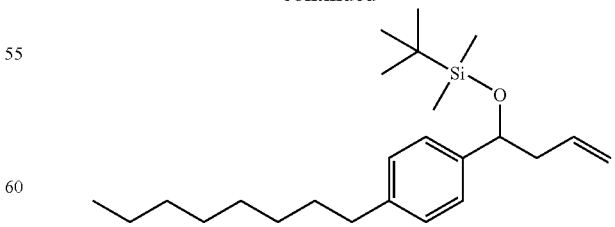

1-(4-octylphenyl)but-3-en-1-ol (11.5 g, 44.2 mmol) and imidazole (3.16 g, 46.4 mmol) were combined in DMF (221 ml). Tert-butyldimethylchlorosilane (6.66 g, 44.2 mmol) was added and the reaction stirred for about 72 h. The reaction was quenched by addition of water and ethyl acetate (500 mL). The layers were separated. The aqueous layer was extracted with ethyl acetate (2×100 mL). The combined ethyl acetate extracts were washed with 5% LiCl solution (3×). The combined extracts were washed with brine, dried over sodium sulfate, filtered, and evaporated to provide tert-butyldimethyl (1-(4-octylphenyl)but-3-enyloxy)silane (19.108 g, 51.0 mmol, 115% yield) as a colorless oil. LC/MS (method f) $R_f$=5.32, 3.89 min.; MS m/z: 243.21 (M-OTBDMS)$^+$.

Preparation of 4-(4-octylphenyl)butane-1,2,4-triol

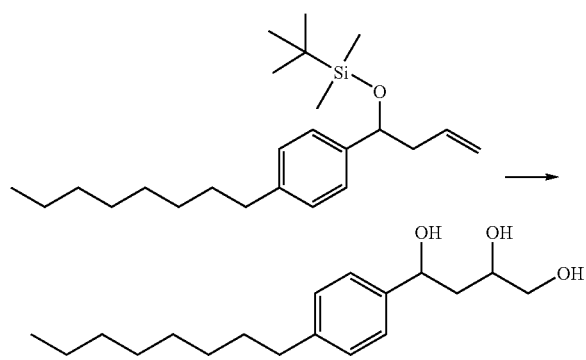

Tert-butyldimethyl(1-(4-octylphenyl)but-3-enyloxy)silane (19.108 g, 51.0 mmol) and NMO (7.17 g, 61.2 mmol) were combined in acetone (227 ml) and water (28.3 ml). Osmium tetroxide (32.0 ml, 2.55 mmol) was added and the reaction stirred for about 2 h. TLC in 1:1 EtOAc/heptane showed reaction complete. Sodium thiosulfate (8.06 g, 51.0 mmol) was added and the reaction stirred for about 3 h resulting in a coarse black precipitate. The solution was poured over 150 mL of silica gel and washed product through thoroughly or washed product through?with ethyl acetate until no more product was eluting as shown by TLC (~700 mL EtOAc). The resulting 4-(Tert-butyldimethylsilyloxy)-4-(4-octylphenyl)butane-1,2-diol (14.68 g, 35.9 mmol) and molecular sieves (5 g) (Aldrich) were combined in THF (359 ml) under nitrogen. TBAF (35.9 ml, 35.9 mmol) (Aldrich) was added and the reaction stirred for about 16 h. The mixture was filtered and the solvents evaporated to provide an orange/brown oil. The oil was passed through a pad of silica gel (150 mL) and washed through with ethyl acetate. Product eluted slowly and took almost 2 L of EtOAc for all product to elute. The solvents were removed under reduced pressure to provide 4-(4-octylphenyl)butane-1,2,4-triol (12.045 g, 40.9 mmol, 114% yield) as an orange oil: LC/MS (Purity QC) $R_f$=3.84, 3.89 min.; MS m/z: 294.40, 294.02 (M+H)$^+$.

Preparation 5-(4-octylphenyl)tetrahydrofuran-3-ol

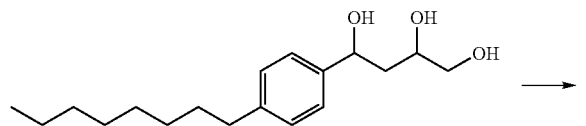

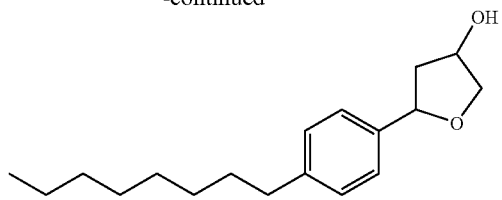

4-(4-octylphenyl)butane-1,2,4-triol (12 g, 40.6 mmol) was dissolved in 1,2-Dichloroethane (815 ml) under nitrogen. p-Toluenesulfonic acid monohydrate (1.55 g, 8.2 mmol) (TCI) was added and the reaction heated at about 50° C. for about 3 h. TLC in 1:1 EtOAc/heptane showed (PMA visualization) reaction complete. The solution was washed with saturated sodium bicarbonate and extract with methylene chloride (2×). The combined extracts were washed with brine, dried over sodium sulfate, filtered, and evaporated to a yellow oil. The resulting oil was chromatographed on 330 g redi-sep column eluting with 20% EtOAc in heptane for 10 min ramping to 50% over 20 min and then holding at 50% until all the product was off (monitor at 223 nm due to weak chromaphore at longer wavelengths). Removed solvent under reduced pressure to provide 5-(4-octylphenyl)tetrahydrofuran-3-ol (7.36 g, 26.6 mmol, 73.3% yield) as a colorless oil: LC/MS (method A) $R_f$=3.76 min.; MS m/z: 277.15 (M+H)$^+$.

Preparation of 5-(4-octylphenyl)dihydrofuran-3(2H)-one

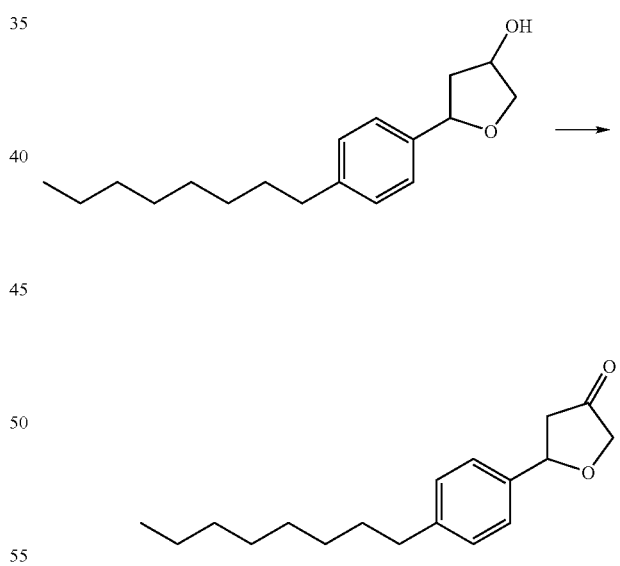

5-(4-octylphenyl)tetrahydrofuran-3-ol (1 g, 3.62 mmol) was dissolved in dichloromethane (36.2 ml) in a sealed vial. PCC (3.12 g, 14.47 mmol) (Aldrich) was added and the reaction stirred for about 16 h. The methylene chloride was evaporated and the residue stirred with ethyl acetate. The ethyl acetate was filtered through a pad of silica gel (approx. 50 mL silica) and product eluted with ethyl acetate. This removed most of the brown color. Concentrate and then chromatograph on a 40 g redi-sep column with 20-50% ethyl acetate in heptane. Remove solvent under reduced pressure to provide 5-(4-octylphenyl)dihydrofuran-3(2H)-one (0.839 g, 3.06 mmol, 85% yield) as a colorless oil: LC/MS (method A) R$_t$=4.14 min.; MS m/z: 275.25 (M+H)$^+$.

8-(4-octylphenyl)-7-oxa-1,3-diazaspiro[4.4]nonane-2,4-dione

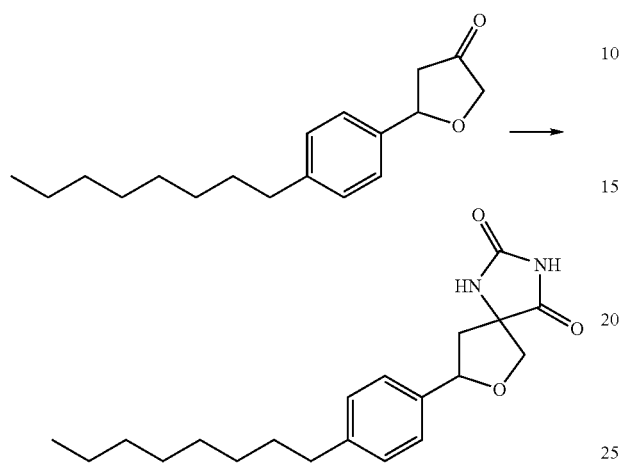

5-(4-octylphenyl)dihydrofuran-3(2H)-one (0.8 g, 2.92 mmol) and ammonium carbonate (1.037 g, 13.12 mmol) (Aldrich) were combined in ethanol (12.05 ml) and water (12.05 ml). Potassium cyanide (0.209 g, 3.21 mmol) (Fluka) was added and the reaction heated at about 80° C. for about 16 h. Cool the reaction and add concentrated HCl until acidic (caution for HCN gas formation). The precipitate was collected by vacuum filtration and washed with water. It was suspended in methylene chloride, filtered, and washed with methylene chloride to provide 8-(4-octylphenyl)-7-oxa-1,3-diazaspiro[4.4]nonane-2,4-dione (0.545 g, 1.582 mmol, 54.3% yield) as a white solid:

LC/MS (method A) R$_t$=4.29 min.; MS m/z: 343.46 (M–H)$^-$.

Preparation of 3-amino-5-(4-octylphenyl)tetrahydrofuran-3-carboxylic acid

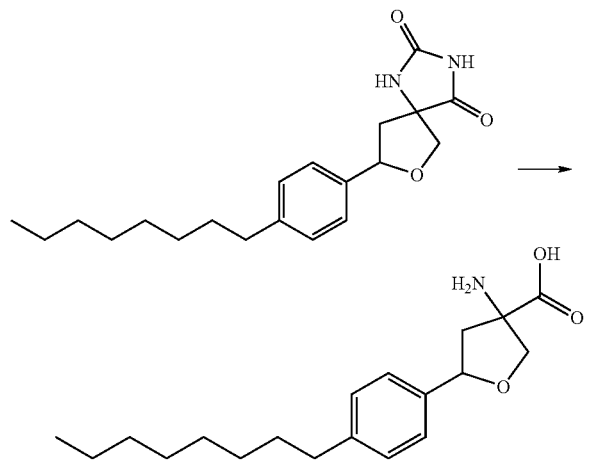

8-(4-Octylphenyl)-7-oxa-1,3-diazaspiro[4.4]nonane-2,4-dione (0.5 g, 1.452 mmol) and sodium hydroxide (10.89 ml, 21.77 mmol) were combined in water (8.54 ml) and equipped with a reflux condensor. The mixture was heated at about 100° C. for about 72 h. The reaction was cooled and acidified with concentrated HCl until pH=4-5. The product was collected by vacuum filtration and dried under vacuum. The residue was purified by flash column chromatography (1"×6" of silica) eluting with 1:1 EtOAc/(6:3:1 CHCl$_3$/MeOH/NH$_4$OH). The product fractions were combined. The solvents were removed under reduced pressure and the residue triturated with ether. The resulting solid was collected by vacuum filtration and washed with ether to provide 3-amino-5-(4-octylphenyl)tetrahydrofuran-3-carboxylic acid (0.280 g, 0.877 mmol, 60.4% yield) as a white solid:

LC/MS (method A) R$_t$=3.22 min.; MS m/z: 320.25 (M+H)$^+$.

Preparation of (3-amino-5-(4-octylphenyl)tetrahydrofuran-3-yl)methanol

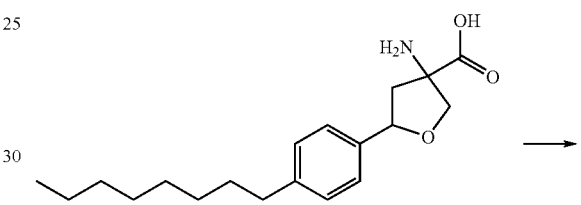

3-Amino-5-(4-octylphenyl)tetrahydrofuran-3-carboxylic acid (0.246 g, 0.770 mmol) was dissolved in THF (15.40 ml). A solution of lithium aluminum hydride (0.770 ml, 1.540 mmol) (Aldrich) was added carefully and the reaction stirred for about 3 h. The reaction was quenched by addition of water (60 uL) and stirred for about 30 min. 10% NaOH (180 uL) was added and the reaction stirred for about 1 h. Finally, water (60 uL) was added and the reaction stirred overnight. The mixture was filtered through Celite® and the solvents removed under reduced pressure. The residue was purified by flash column chromatography (0.5"×7" of silica) eluting with 10% MeOH in methylene chloride and the product fractions combined. The solvents were removed under reduced pressure to provide (3-amino-5-(4-octylphenyl)tetrahydrofuran- 3-yl)methanol (0.1 g, 0.327 mmol, 42.5% yield) as a colorless oil: LC/MS (method A) $R_t$=3.12 min.; MS m/z: 306.42 (M+H)$^+$.

Preparation of (3-amino-5-methyl-5-(4-octylphenyl) tetrahydrofuran-3-yl)methanol

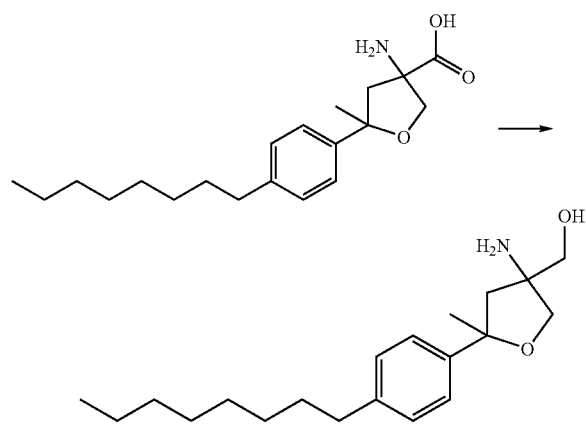

A solution of lithium aluminum hydride (2.70 ml, 5.40 mmol) (Aldrich) was added carefully to THF (17.99 ml) under nitrogen. 3-amino-5-methyl-5-(4-octylphenyl)tetrahydrofuran-3-carboxylic acid (0.6 g, 1.799 mmol) was added in small portions causing vigorous bubbling. The reaction stirred for about 2 h. TLC in 10% MeOH in methylene chloride showed (Hannessian's stain visualization) reaction complete. The reaction was quenched by addition of water (200 uL) and the reaction stirred about 30 min. 10% NaOH (0.6 mL) was added and the reaction stirred about 30 min. Finally, water (200 uL) was added and the reaction stirred about 30 min. The resulting solid was collected by vacuum filtration and washed with ether. The filtrate was concentrated to a colorless oil. The residue was purified by flash column chromatography (40 g Redi-Sep) eluting with 10-20% methanol in methylene chloride and the product fractions combined. Solvents were removed under reduced pressure. The residue was redissolved in methylene chloride and filtered through a syringe filter into a vial and washed through with methylene chloride. Solvent was removed under reduced pressure to provide (3-amino-5-methyl-5-(4-octylphenyl)tetrahydrofuran-3-yl)methanol (0.192 g, 0.601 mmol, 33.4% yield) as a colorless oil that solidified on standing to a white solid:

LCMS (method f) $R_t$=2.21 min.; MS m/z: 320.50 (M+H)$^+$.

Scheme for preparation of phosphonates described below:

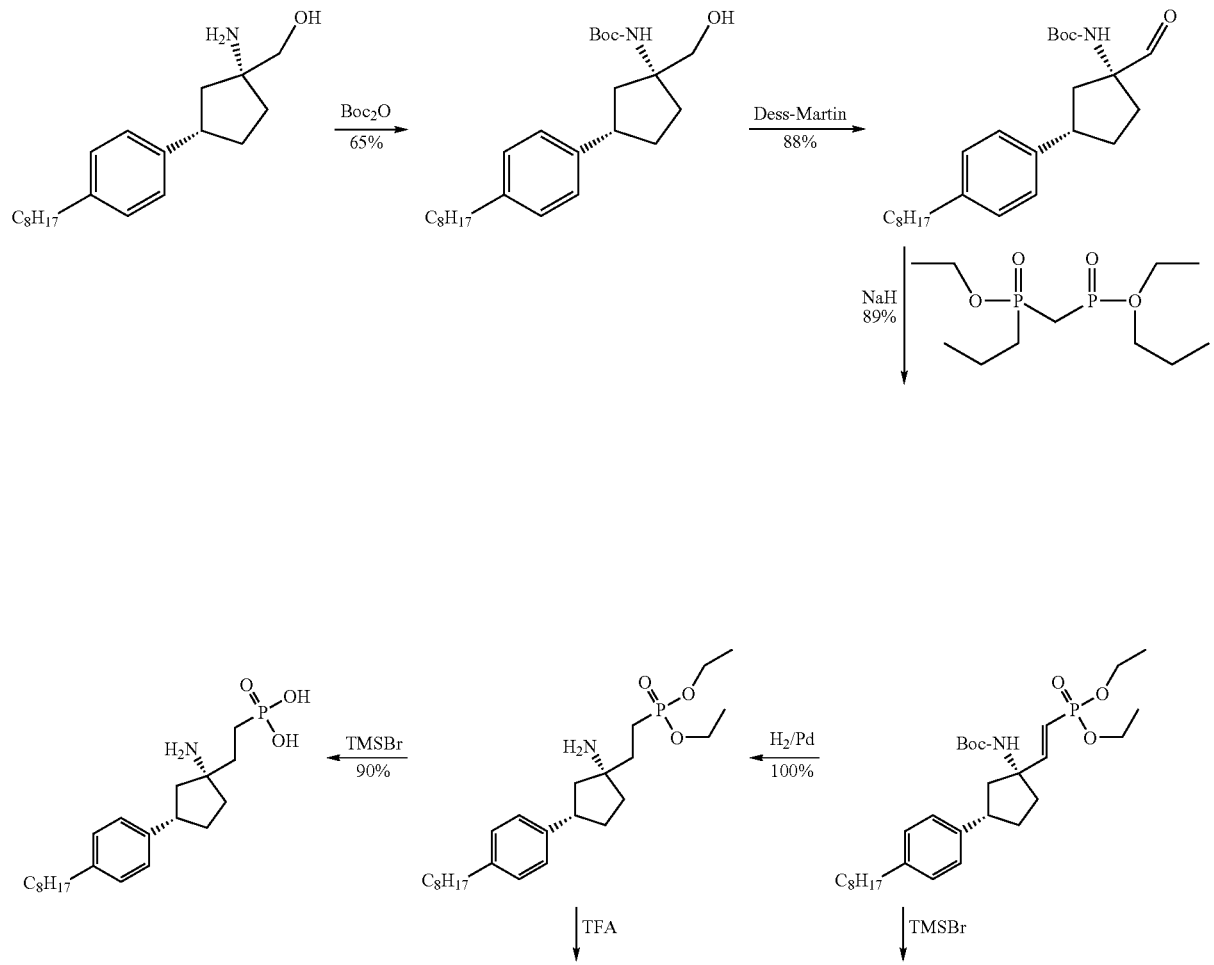

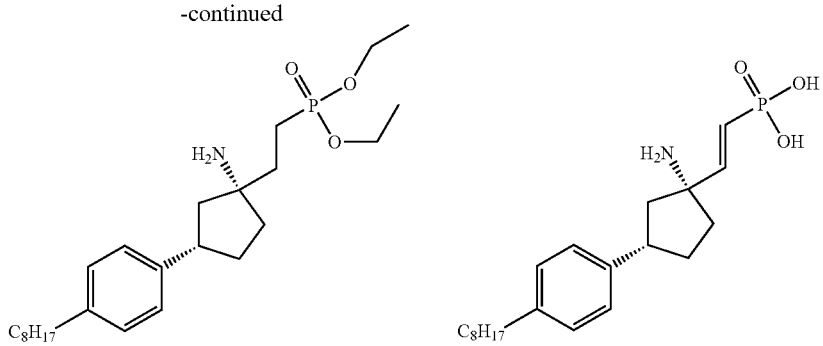

Preparation of tert-butyl (1R,3S)-1-(hydroxymethyl)-3-(4-octylphenyl)cyclopentylcarbamate

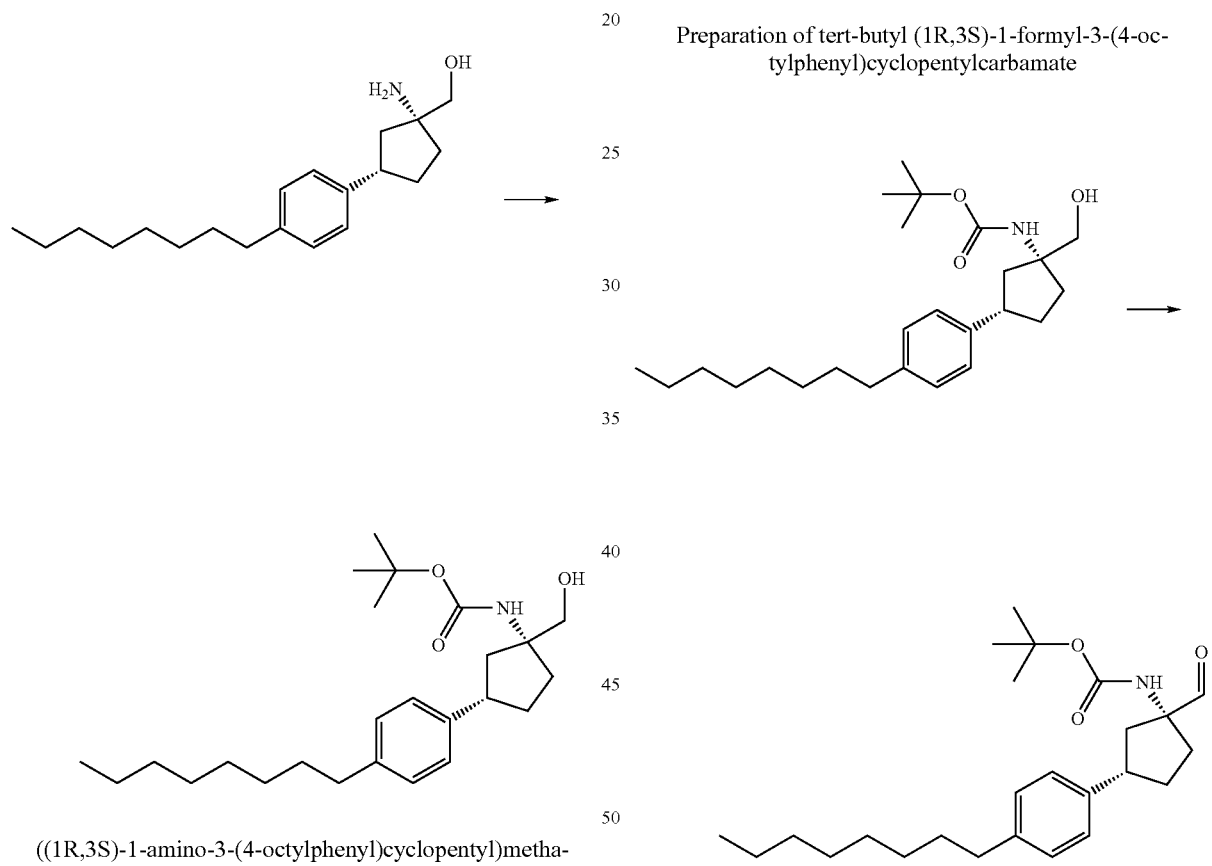

((1R,3S)-1-amino-3-(4-octylphenyl)cyclopentyl)methanol (4.72 g, 15.55 mmol) and pyridine (1.384 ml, 17.11 mmol) (Aldrich) were combined in THF (15.55 ml) under nitrogen to give a colorless solution. Di-tert-butyl dicarbonate (3.93 ml, 17.11 mmol) (Fluka) was added and the reaction stirred for about 4 h and a precipitate formed. TLC in 1:1 EtOAc/heptane showed (KMnO₄ visualization) reaction complete. Ethyl acetate (150 mL) and water (50 mL) were added and the layers separated and extracted with ethyl acetate (2×25 mL). The combined extracts were washed with brine, dried over magnesium sulfate, filtered, and evaporated to an off-white solid. The residue was purified by flash column chromatography (120 g Redi-Sep) eluting with ethyl acetate/heptane and the product fractions combined. The solvent was removed under reduced pressure to provide tert-butyl (1R,3S)-1-(hydroxymethyl)-3-(4-octylphenyl)cyclopentylcarbamate (4.086 g, 10.12 mmol, 65.1% yield) as a white solid: LC/MS (method f) R$_t$=3.44 min.; MS m/z: 404.35 (M+H)⁺.

Preparation of tert-butyl (1R,3S)-1-formyl-3-(4-octylphenyl)cyclopentylcarbamate Tert-butyl (1R,3S)-1-(hydroxymethyl)-3-(4-octylphenyl)cyclopentylcarbamate (3.9 g, 9.66 mmol) was dissolved in dichloromethane (193 ml) under nitrogen to give a colorless solution. Dess-Martin periodinane (4.51 g, 10.63 mmol) (Aldrich) was added and the reaction stirred for about 3 h. LC/MS showed the reaction was complete. Methylene chloride (100 mL) and water (100 mL) were added and the layers separated and extracted with methylene chloride (2×50 mL). The combined extracts were washed with brine, dried over magnesium sulfate, filtered, and evaporated to an off-white solid. The residue was purified by flash column chromatography (120 g Redi-Sep) eluting with ethyl acetate/heptane and the product fractions combined. Solvents were removed under reduced pressure to provide tert-butyl (1R,3S)-1- formyl-3-(4-octylphenyl)cyclopentylcarbamate (3.40 g, 88%) as an off white solid: LC/MS (method f) $R_t$=3.58 min.; MS m/z: 401.36 (M+H)$^+$.

Preparation of tert-butyl (1R,3S)-1-((E)-2-(diethoxyphosphoryl)vinyl)-3-(4-octylphenyl)cyclopentylcarbamate

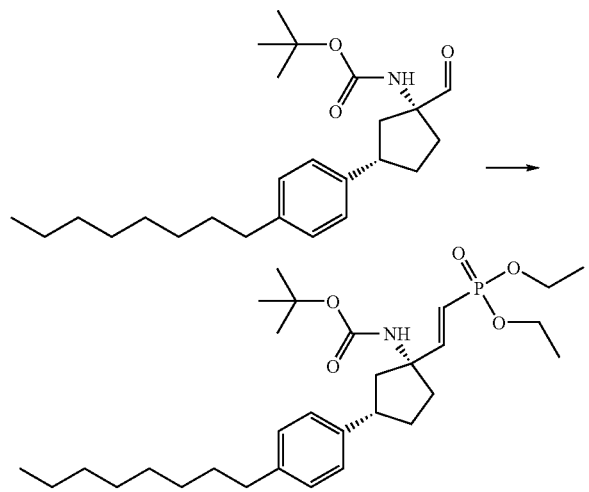

Sodium hydride (0.020 g, 0.498 mmol) (Aldrich) was stirred in THF (3.32 ml) under nitrogen to give a colorless suspension. Tetraethyl methylenediphosphonate (0.124 ml, 0.498 mmol) (ALDRICH) was added and the reaction stirred for about 30 min. Tert-butyl (1R,3S)-1-formyl-3-(4-octylphenyl)cyclopentylcarbamate (0.2 g, 0.498 mmol) was added in small portions and the reaction stirred for about 16 h. Solvents were removed under reduced pressure. Ethyl acetate (50 mL) and water (10 mL) were added and the layers separated and extracted with ethyl acetate (2×10 mL). The combined extracts were washed with brine, dried over sodium sulfate, filtered, and evaporated to a yellow oil. The residue was purified by flash column chromatography (40 g Redi-Sep) eluting with ethyl acetate/heptane and the product fractions combined. The solvent was removed under reduced pressure to provide tert-butyl (1R,3S)-1-((E)-2-(diethoxyphosphoryl)vinyl)-3-(4-octylphenyl)cyclopentylcarbamate (0.237 g, 0.442 mmol, 89% yield) as an orange oil: LC/MS (method f) $R_t$=3.12 min.; MS m/z: 553.42 (M+H$_2$O)$^+$.

Preparation of tert-butyl (1R,3S)-1-(2-(diethoxyphosphoryl)ethyl)-3-(4-octylphenyl)cyclopentylcarbamate

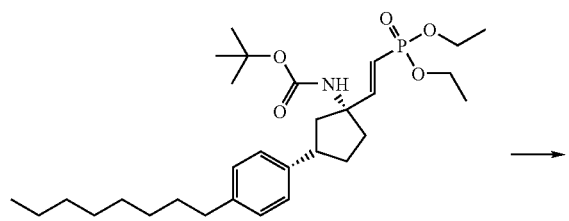

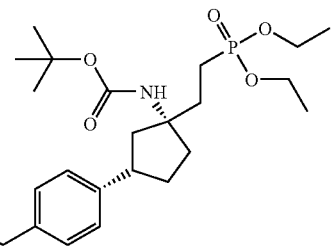

Tert-butyl (1R,3S)-1-((E)-2-(diethoxyphosphoryl)vinyl)-3-(4-octylphenyl)cyclopentylcarbamate (0.237 g, 0.442 mmol) was dissolved in ethanol. Palladium on carbon (0.094 g, 0.088 mmol) was added and the reaction was flushed with hydrogen and hydrogenated at atmospheric pressure for about 72 h. The solution was filtered through a syringe filter and washed through with methanol. Solvent was removed under reduced pressure to provide tert-butyl (1R,3S)-1-(2-(diethoxyphosphoryl)ethyl)-3-(4-octylphenyl)cyclopentylcarbamate (0.236 g, 0.439 mmol, 99% yield) as a colorless oil: LC/MS (method f) $R_t$=3.60 min.; MS m/z: 538.53 (M+H)$^+$.

Preparation of 2-((1R,3S)-1-amino-3-(4-octylphenyl)cyclopentyl)ethylphosphonic acid

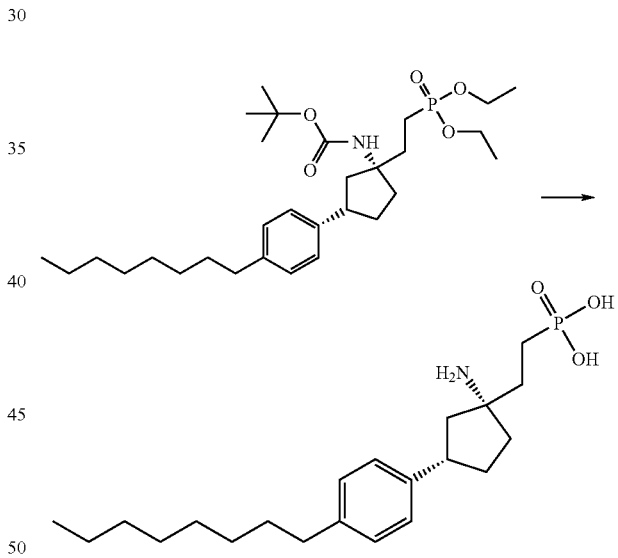

Tert-butyl (1R,3S)-1-(2-(diethoxyphosphoryl)ethyl)-3-(4-octylphenyl)cyclopentylcarbamate (0.236 g, 0.439 mmol) was dissolved in dichloromethane (4.39 ml) under nitrogen to give a colorless solution. Bromotrimethylsilane (0.569 ml, 4.39 mmol) (Aldrich) was added and the reaction stirred for about 4 h. Solvents were removed under reduced pressure. Methanol (4 mL) and water (0.2 mL) were added and the solution was stirred for about 16 h. Solvents were removed under reduced pressure to give a brown oil/solid. Water was added and the solution sonicated while scraping the sides of the vial. The solution was stirred with a stir bar for about 1 h. The resulting solid was collected by vacuum filtration and washed with water and then pentane to provide 2-((1R,3S)-1-amino-3-(4-octylphenyl)cyclopentyl)ethylphosphonic acid (0.150 g, 0.393 mmol, 90% yield) as a off-white solid on drying under vacuum at 60° C.: LC/MS (method a) $R_f$=3.15 min.; MS m/z: 382.27 (M+H)$^+$.

Preparation of (E)-2-((1R,3S)-1-amino-3-(4-octylphenyl)cyclopentyl)vinylphosphonic acid

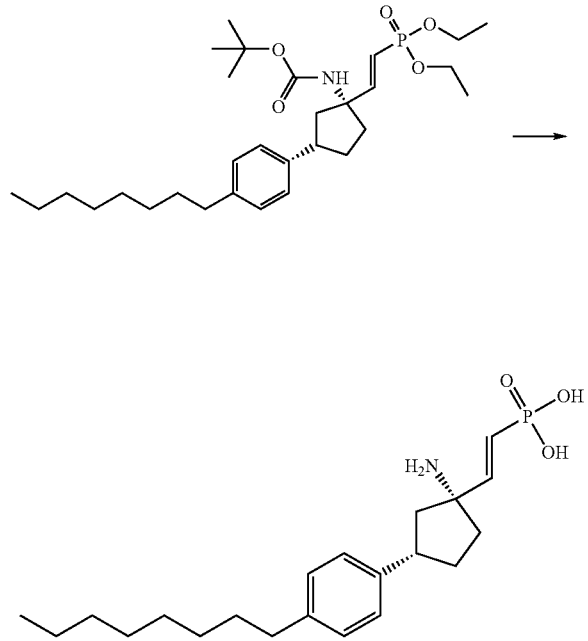

Tert-butyl (1R,3S)-1-((E)-2-(diethoxyphosphoryl)vinyl)-3-(4-octylphenyl)cyclopentylcarbamate (0.2 g, 0.373 mmol) (10035787-0263) was dissolved in dichloromethane (3.73 ml) in a sealed vial to give a colorless solution. Bromotrimethylsilane (0.484 ml, 3.73 mmol) (Fluka) was added and the reaction stirred for about 16 h. Solvents were removed under reduced pressure to a thick oil. Methanol (4 mL) and water (0.2 mL) were added. The solution was sonicated and stirred, resulting in a cloudy reaction where a heavy precipitate forms. The solution was stirred for about 4 h. Add water (5 mL) and more product precipitated. The resulting solid was collected by vacuum filtration, washed with water and then pentane and dried under vacuum to provide (E)-2-((1R,3S)-1-amino-3-(4-octylphenyl)cyclopentyl)vinylphosphonic acid (0.117 g, 0.308 mmol, 83% yield) as a white solid: LCMS (method a) $R_f$=3.01 min.; MS m/z: 380.21 (M+H)$^+$.

Preparation of diethyl 2-((1R,3S)-1-amino-3-(4-octylphenyl)cyclopentyl)ethylphosphonate

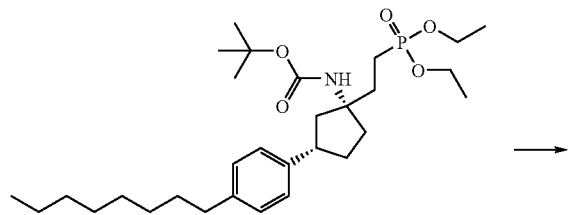

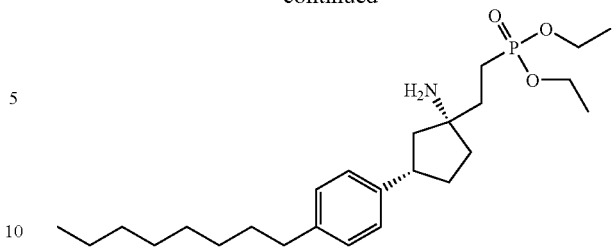

Tert-butyl (1R,3S)-1-(2-(diethoxyphosphoryl)ethyl)-3-(4-octylphenyl)cyclopentylcarbamate (0.2 g, 0.372 mmol) was dissolved in dichloromethane (1.860 ml) in a sealed vial to give a colorless solution. TFA (1.860 ml) was added and the reaction stirred for about 1 h. Solvents were removed under reduced pressure. Methylene chloride (25 mL) and saturated sodium bicarbonate (25 mL) were added and the layers separated and extracted with methylene chloride (2×10 mL). The combined extracts were washed with brine, dried over sodium sulfate, filtered, and evaporated to a yellow oil. The oil was dissolve in ether (15 mL). 1 M HCl in dioxane (3 mL) was added. Solvents were removed under reduced pressure. The solid was redissolved in water and lyophilized. The resulting white/tan solid was suspended in ether and the resulting solid was collected by vacuum filtration and washed with ether then heptane to provide diethyl 2-((1R,3S)-1-amino-3-(4-octylphenyl)cyclopentyl)ethylphosphonate (0.0787 g, 0.180 mmol, 48.4% yield) as a white solid on drying under vacuum: LCMS (method a) $R_f$=3.46 min.; MS m/z: 438.48 (M+H)$^+$.

What is claimed:
1. A compound of Formula I

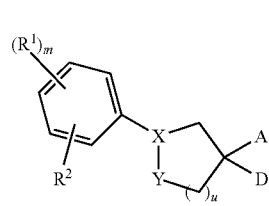

Formula I a pharmaceutically acceptable salt, prodrug, metabolite or an isomer thereof wherein
D is H, N(R$^5$)$_2$ or OR$^6$;
X is CH;
Y is CH$_2$;
A is hydroxy, —CH$_2$OH, —CH(OH)CH$_3$, —C(O)—OCH$_3$, —C(OH)(CH$_3$)$_2$, —O(CH$_2$)$_t$—COOH—, —C(O)—NR$^6$, optionally substituted —(CH$_2$)$_n$—P(=O)(OR$^7$)(OR$^7$), optionally substituted —(CH$_2$)$_n$—O—P(=O)(OR$^7$)(OR$^7$), optionally substituted —(CH$_2$)$_n$—P(=O)(OR$^7$)(R$^7$), —CH=CH—P(=O)(OR$^7$)(OR$^7$), C(O)—NHCH$_3$, COOR$^6$ or —R$^4$—COOH, wherein R$^4$ is straight or branched (C$_1$-C$_{20}$) alkylene, straight or branched (C$_1$-C$_{20}$) alkenylene, straight or branched (C$_1$-C$_{20}$) alkynylene, (C$_3$-C$_{20}$)cycloalkyl, or optionally substituted azetidinyl;
R$^1$ and R$^2$ are independently selected from the group consisting of hydrogen, CF$_3$, halo, (C$_1$-C$_{20}$) alkyl, (C$_1$-C$_{20}$) alkoxy, (C$_3$-C$_{20}$) cycloalkyl substituted alkyl, (C$_3$-C$_{20}$) cycloalkyl substituted alkoxy, (C$_2$-C$_{20}$) alkenyl, aryl substituted (C$_2$-C$_{20}$) alkenyl, (C$_2$-C$_{20}$) alkynyl, aryl substituted (C$_2$-C$_{20}$) alkynyl, aryl, aryl substituted (C$_1$-C$_{20}$)alkyl, heteroaryl substituted (C$_2$-C$_{20}$)alkyl, aryl substituted alkoxy, heteroaryl substituted alkoxy, alkyl substituted aryl, arylalkyl, aryl substituted arylalkyl, arylalkyl substituted arylalkyl, CN and —O-indolizinyl;

wherein such R$^1$ and R$^2$ groups may be optionally substituted with one or more substitutents independently selected from (C$_1$-C$_{20}$) alkyl, CF$_3$, halo, hydroxy, (C$_1$-C$_{20}$) alkoxy, OCF$_3$, and CN;

wherein one or more of the carbon atoms in the R$^1$ or R$^2$ groups can be independently replaced with non-peroxide oxygen, sulfur or NR$^8$;

wherein R$^8$ is hydrogen or (C$_1$-C$_{20}$) alkyl group;

wherein one of R$^1$ and R$^2$ is other than hydrogen; and wherein the alkyl, alkenyl, and alkynyl groups in R$^1$ and R$^2$ are optionally substituted with oxo or halo;

each R$^5$ is independently H, optionally substituted (C$_1$-C$_3$)alkyl, or —C(O)—O—(C$_1$-C$_3$)alkyl-optionally substituted phenyl;

each R$^6$ is optionally substituted (C$_1$-C$_2$)alkyl;

each R$^7$ is independently H, optionally substituted (C$_1$-C$_2$)alkyl or optionally substituted phenyl;

m is 1 or 2;
n is 1, 2 or 3;
t is 1, 2 or 3; and
u is 1;

provided that A and D are not both H at the same time and provided the compound is not

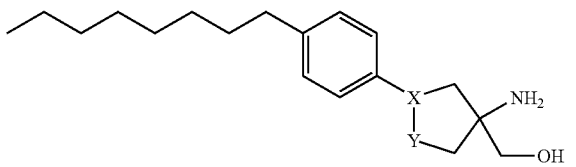

wherein X is CH;
Y is CH$_2$.

2. The compound of claim 1 wherein
A is —C(O)—OCH$_3$, —C(O)—NR$^6$, C(O)—NHCH$_3$, COOR$^6$, —R$^4$—COOH, or optionally substituted azetidinyl, wherein R$^4$ is straight or branched (C$_1$-C$_{20}$) alkylene, straight or branched (C$_1$-C$_{20}$) alkenylene, straight or branched (C$_1$-C$_{20}$) alkynylene;

R$^1$ and R$^2$ are independently selected from the group consisting of hydrogen, halo, (C$_1$-C$_{10}$) alkyl, (C$_1$-C$_{10}$) alkoxy, (C$_3$-C$_{20}$) cycloalkyl substituted alkyl, (C$_3$-C$_{10}$) cycloalkyl substituted alkoxy, (C$_2$-C$_{10}$) alkenyl, aryl substituted (C$_2$-C$_{10}$) alkenyl, (C$_2$-C$_{10}$) alkynyl, aryl substituted (C$_2$-C$_{10}$) alkynyl, aryl, aryl substituted (C$_1$-C$_{10}$) alkyl, heteroaryl substituted (C$_1$-C$_{10}$) alkyl, aryl substituted (C$_1$-C$_{10}$) alkoxy, heteroaryl substituted (C$_1$-C$_{10}$) alkoxy, (C$_1$-C$_{10}$) alkyl substituted aryl, arylalkyl and aryl substituted arylalkyl;

wherein such R$^1$ and R$^2$ groups may be optionally substituted with (C$_1$-C$_{10}$) alkyl, halo, hydroxy, (C$_1$-C$_{10}$) alkoxy, or CN;

wherein one or more of the carbon atoms in the R$^1$ or R$^2$ groups can be independently replaced with non-peroxide oxygen, sulfur or NR$^8$;

wherein R$^8$ is hydrogen or (C$_1$-C$_{10}$) alkyl group;

wherein one of R$^1$ and R$^2$ is other than hydrogen; and wherein the alkyl, alkenyl, and alkynyl groups in R$^1$ and R$^2$ are optionally substituted with oxo or halo.

3. A compound of Formula Ia:

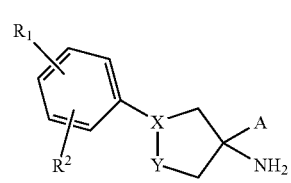

Formula Ia an isomer, stereoisomer, ester, prodrug, and a pharmaceutically acceptable salt thereof, wherein;

X is CH;

Y is CH$_2$

A is —C(O)—OCH$_3$, —COOH, —R$^4$—COOH, —C(O)—NHCH$_3$, or optionally substituted azetidinyl;

wherein R$^4$ is straight or branched (C$_1$-C$_{10}$) alkylene, straight or branched (C$_1$-C$_{10}$) alkenylene, or straight or branched (C$_1$-C$_{10}$) alkynylene;

R$^1$ and R$^2$ are independently selected from the group consisting of hydrogen, halo, (C$_1$-C$_{10}$)alkyl, (C$_1$-C$_{10}$) alkoxy, (C$_3$-C$_{10}$) cycloalkyl substituted alkyl, (C$_3$-C$_{10}$) cycloalkyl substituted alkoxy, (C$_2$-C$_{10}$) alkenyl, aryl substituted (C$_2$-C$_{10}$) alkenyl, (C$_2$-C$_{10}$) alkynyl, aryl substituted (C$_2$-C$_{10}$) alkynyl, aryl, aryl substituted (C$_1$-C$_{10}$)alkyl, heteroaryl substituted (C$_1$-C$_{10}$) alkyl, aryl substituted (C$_1$-C$_{10}$)alkoxy, heteroaryl substituted (C$_1$-C$_{10}$)alkoxy, (C$_1$-C$_{10}$)alkyl substituted aryl, arylalkyl and aryl substituted arylalkyl;

wherein such R$^1$ and R$^2$ groups may be optionally substituted with (C$_1$-C$_{10}$) alkyl, CF$_3$, halo, hydroxy, (C$_1$-C$_{10}$) alkoxy, or CN;

wherein one or more of the carbon atoms in the R$^1$ or R$^2$ groups can be independently replaced with non-peroxide oxygen, sulfur or NR$^8$;

wherein R$^8$ is hydrogen or (C$_1$-C$_{10}$) alkyl group;

wherein one of R$^1$ and R$^2$ is other than hydrogen;

wherein the alkyl, alkenyl, and alkynyl groups in R$^2$ are optionally substituted with oxo or halo;

each R$^5$ is independently H, optionally substituted (C$_1$-C$_3$)alkyl, or —C(O)—O—(C$_1$-C$_3$)alkyl-optionally substituted phenyl;

each R$^6$ is independently optionally substituted (C$_1$-C$_2$) alkyl;

each R$^7$ is independently H, optionally substituted (C$_1$-C$_2$)alkyl or optionally substituted phenyl;

m is 1 or 2; and provided the compound is not

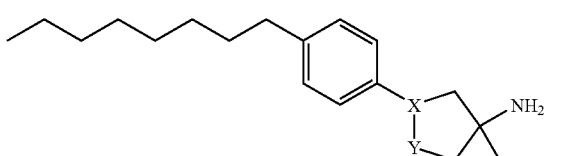

wherein X is CH;
Y is CH$_2$.

4. A compound of Formula Ia:

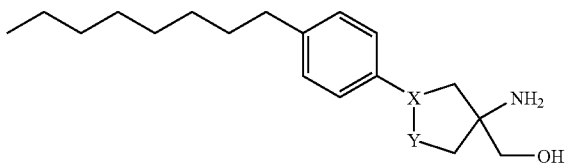

and an isomer, stereoisomer, ester, prodrug, and a pharmaceutically acceptable salt thereof, wherein;
X is CH;
Y is CH$_2$;
A is —CH$_2$—COOH, COOH or

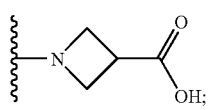

$R^1$ and $R^2$ are independently selected from the group consisting of hydrogen, $(C_1$-$C_{10})$ alkyl, $(C_2$-$C_{10})$ alkenyl, $(C_2$-$C_{10})$ alkynyl, and aryl substituted $(C_1$-$C_{10})$ alkyl;
wherein such $R^1$ and $R^2$ groups may be optionally substituted with $(C_1$-$C_{10})$ alkyl, halo, hydroxy, $(C_1$-$C_{10})$ alkoxy, or cyano;
wherein one or more of the carbon atoms in the $R^1$ or $R^2$ groups can be independently replaced with non-peroxide oxygen; wherein one of $R^1$ and $R^2$ is other than hydrogen;
wherein one of $R^1$ and $R^2$ is other than hydrogen;
wherein the alkyl, alkenyl, and alkynyl groups in $R^2$ are optionally substituted with oxo or halo;
each $R^5$ is independently H, optionally substituted $(C_1$-$C_3)$alkyl, or —C(O)—O—$(C_1$-$C_3)$alkyl-optionally substituted phenyl; and
each $R^6$ is independently optionally substituted $(C_1$-$C_2)$ alkyl;
provided the compound is not

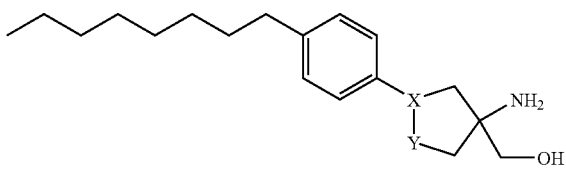

wherein X is CH;
Y is CH$_2$.
5. A compound of Formula Ia:

Formula Ia

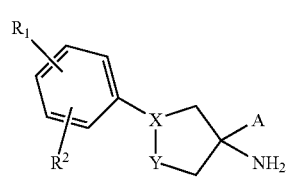

and an isomer, stereoisomer, ester, prodrug, and a pharmaceutically acceptable salt thereof, wherein;

X is CH;
Y is CH$_2$;
A is COOH;
$R^1$ is $(C_1$-$C_{10})$alkyl, $(C_2$-$C_{10})$alkenyl or $(C_2$-$C_{10})$alkynyl;
$R^2$ is H;
provided the compound is not

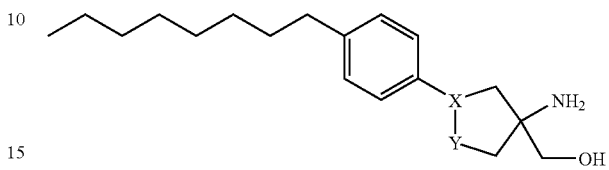

wherein X is CH;
Y is CH$_2$.
6. The compound or

7. The compound according to claim 1 wherein
Y is CH$_2$;
A is —CH$_2$OH, —C(O)OCH$_3$, optionally substituted —(CH$_2$)$_n$—P(=O)(OR$^7$)(OR$^7$), optionally substituted —(CH$_2$)$_n$—O—P(=O)(OR$^7$)(OR$^7$) or —CH=CH—O—P(=O)(OR$^7$)(OR$^7$);
$R^1$ and $R^2$ are independently selected from the group consisting of hydrogen, halo, straight or branched $(C_1$-$C_{10})$ alkyl, $(C_1$-$C_{10})$ alkoxy, $(C_3$-$C_{10})$ cycloalkyl substituted alkyl, $(C_3$-$C_{10})$ cycloalkyl substituted alkoxy, $(C_2$-$C_{10})$ alkenyl, aryl substituted $(C_2$-$C_{10})$ alkenyl, $(C_2$-$C_{10})$ alkynyl, aryl substituted $(C_2$-$C_{10})$ alkynyl, aryl, aryl substituted alkyl, heteroaryl substituted alkyl, aryl substituted alkoxy, heteroaryl substituted alkoxy, $(C_1$-$C_{10})$ alkyl substituted aryl, arylalkyl, aryl substituted arylalkyl, arylalkyl substituted arylalkyl, cyano and —O-indolizinyl;
wherein such $R^1$ and $R^2$ groups may be optionally substituted with one or more substitutents independently selected from straight or branched $(C_1$-$C_{10})$ alkyl, halo, hydroxy, $(C_1$-$C_{20})$ alkoxy, OCF$_3$, and CN;

wherein one or more of the carbon atoms in the $R^1$ or $R^2$ groups can be independently replaced with non-peroxide oxygen, sulfur or $NR^8$;

wherein $R^8$ is hydrogen or $(C_1-C_{10})$ alkyl group; wherein one of $R^1$ and $R^2$ is other than hydrogen; and wherein the alkyl, alkenyl, and alkynyl groups in $R^2$ are optionally substituted with oxo or halo;

$R^6$ is independently optionally substituted $(C_1-C_2)$alkyl;

$R^7$ is independently selected from H or optionally substituted $(C_1-C_2)$alkyl; and u is 1.

8. A compound of Formula Ib:

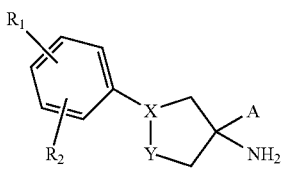

Formula Ib and an isomer, stereoisomer, ester, prodrug, and a pharmaceutically acceptable salt thereof, wherein;

X is CH;

Y is $CH_2$;

A is —$CH_2$—OH, optionally substituted —$CH_2$—P(=O)($OR^7$)($OR^7$) or optionally substituted —$CH_2$—O—P(=O)($OR^7$)($OR^7$);

$R^1$ and $R^2$ are independently selected from the group consisting of hydrogen, halo, $(C_1-C_{20})$ alkyl, $(C_1-C_{20})$ alkoxy, $(C_3-C_{20})$ cycloalkyl substituted alkyl, $(C_3-C_{20})$ cycloalkyl substituted alkoxy, $(C_2-C_{20})$ alkenyl, aryl substituted $(C_2-C_{20})$ alkenyl, $(C_2-C_{20})$ alkynyl, aryl substituted $(C_2-C_{20})$ alkynyl, aryl, aryl substituted alkyl, heteroaryl substituted alkyl, aryl substituted alkoxy, heteroaryl substituted alkoxy, alkyl substituted aryl, arylalkyl and aryl substituted arylalkyl;

wherein one of $R^1$ and $R^2$ is other than hydrogen;

wherein such $R^2$ groups may be optionally substituted with $(C_1-C_{20})$ alkyl, halo, hydroxy, $(C_1-C_{20})$ alkoxy, or cyano;

wherein one or more of the carbon atoms in the $R^1$ or $R^2$ groups can be independently replaced with non-peroxide oxygen, sulfur or $NR^8$; wherein $R^8$ is hydrogen or $(C_1-C_{20})$ alkyl group; and wherein the alkyl, alkenyl, and alkynyl groups in $R^2$ are optionally substituted with oxo or halo;

each $R^7$ is independently H, optionally substituted $(C_1-C_2)$alkyl or optionally substituted phenyl;

provided the compound is not

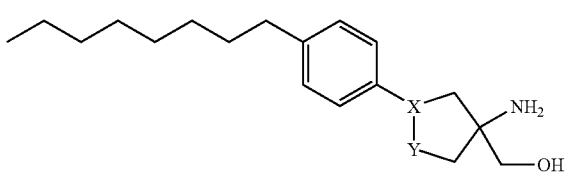

wherein X is CH;
Y is $CH_2$.

9. A compound of Formula Ib:

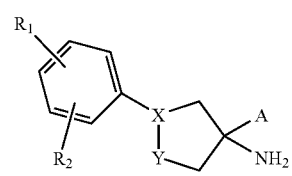

Formula Ib and an isomer, stereoisomer, ester, prodrug, and pharmaceutically acceptable salt thereof, wherein X is CH;

Y is $CH_2$;

A is —$CH_2OH$, optionally substituted —$(CH_2)_n$—O—P(=O)($OR^7$)($OR^7$) or optionally substituted —$(CH_2)_n$—P(=O)($OR^7$)($OR^7$);

$R^1$ and $R^2$ are independently selected from the group consisting of hydrogen, halo, straight or branched $(C_1-C_{10})$ alkyl, aryl substituted $(C_1-C_{10})$ alkyl, heteroaryl substituted alkyl, aryl substituted alkoxy, heteroaryl substituted alkoxy, $(C_1-C_{10})$alkyl substituted aryl, arylalkyl, aryl substituted arylalkyl, arylalkyl substituted arylalkyl, CN and —O-indolizinyl;

wherein such $R^1$ and $R^2$ groups may be optionally substituted with one or more substitutents independently selected from $(C_1-C_{10})$ alkyl, halo and $(C_1-C_{10})$ alkoxy;

wherein one or more of the carbon atoms in the $R^1$ or $R^2$ groups can be independently replaced with non-peroxide oxygen; wherein one of $R^1$ and $R^2$ is other than hydrogen; and wherein the alkyl, alkenyl, and alkynyl groups in $R^2$ are optionally substituted with oxo or halo provided the compound is not

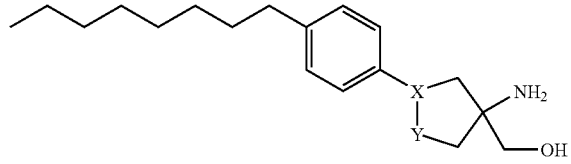

wherein X is CH;
Y is $CH_2$.

10. A compound of Formula Ib:

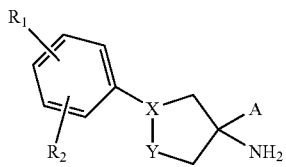

Formula Ib and an isomer, stereoisomer, ester, prodrug, and pharmaceutically acceptable salt thereof, wherein A is —$CH_2OH$ or optionally substituted —$(CH_2)_n$—O—P(=O)($OR^7$)($OR^7$);

$R^1$ and $R^2$ are independently selected from the group consisting of hydrogen, optionally substituted $(C_1-C_{10})$ alkyl;

wherein one or more of the carbon atoms in the $R^1$ or $R^2$ groups can be independently replaced with non-peroxide oxygen; and wherein one of $R^1$ and $R^2$ is other than hydrogen;

provided the compound is not

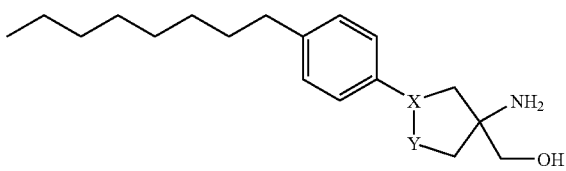

wherein X is CH;
Y is $CH_2$.

11. The compound

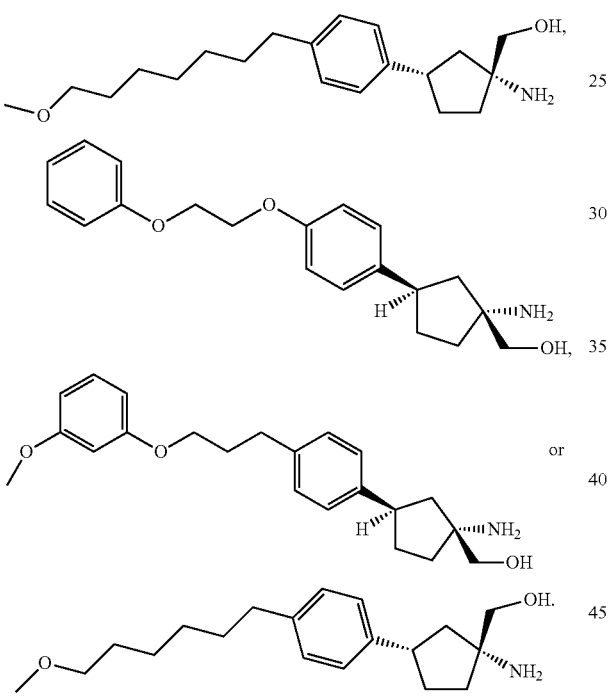

12. A compound of the formula

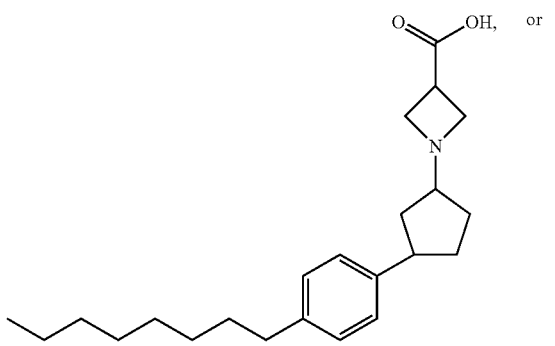

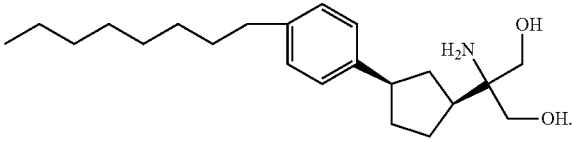

13. A pharmaceutical composition comprising a compound of Formula I

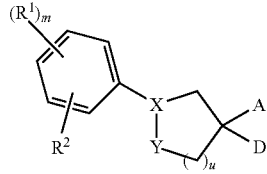

Formula I a pharmaceutically acceptable salt, prodrug, metabolite or an isomer thereof wherein
D is H, $N(R^5)_2$, or $OR^6$;
X is CH;
Y is $CH_2$;
A is H, hydroxy, $-CH_2OH$, $-CH(OH)CH_3$, $-C(O)-OCH_3$, $-C(OH)(CH_3)_2$, $-O(CH_2)_t-COOH$, $-C(O)-NR^6$, optionally substituted $-(CH_2)_n-P(=O)(OR^7)(OR^7)$, optionally substituted $-(CH_2)_n-O-P(=O)(OR^7)(OR^7)$, optionally substituted $-(CH_2)_n-P(=O)(OR^7)(R^7)$, $-CH=CH-P(=O)(OR^7)(OR^7)$, $C(O)-NHCH_3$, CN, $COOR^6$ or $-R^4-COOH$, wherein $R^4$ is straight or branched ($C_1$-$C_{20}$) alkylene, straight or branched ($C_1$-$C_{20}$) alkenylene, straight or branched ($C_1$-$C_{20}$) alkynylene, ($C_3$-$C_{20}$)cycloalkyl, or optionally substituted azetidinyl;
$R^1$ and $R^2$ are independently selected from the group consisting of hydrogen, $CF_3$, halo, ($C_1$-$C_{20}$) alkyl, ($C_1$-$C_{20}$) alkoxy, ($C_3$-$C_{20}$) cycloalkyl substituted alkyl, ($C_3$-$C_{20}$) cycloalkyl substituted alkoxy, ($C_2$-$C_{20}$) alkenyl, aryl substituted ($C_2$-$C_{20}$) alkenyl, ($C_2$-$C_{20}$) alkynyl, aryl substituted ($C_2$-$C_{20}$) alkynyl, aryl, aryl substituted alkyl, heteroaryl substituted alkyl, aryl substituted alkoxy, heteroaryl substituted alkoxy, alkyl substituted aryl, arylalkyl, aryl substituted arylalkyl, arylalkyl substituted arylalkyl, CN and —O-indolizinyl; wherein such $R^1$ and $R^2$ groups may be optionally substituted with one or more substitutents independently selected from ($C_1$-$C_{20}$) alkyl, $CF_3$, halo, hydroxy, ($C_1$-$C_{20}$) alkoxy, $OCF_3$, and CN;
wherein one or more of the carbon atoms in the $R^1$ or $R^2$ groups can be independently replaced with non-peroxide oxygen, sulfur or $NR^8$;
wherein $R^8$ is hydrogen or ($C_1$-$C_{20}$) alkyl group;
wherein one of $R^1$ and $R^2$ is other than hydrogen; and wherein the alkyl, alkenyl, and alkynyl groups in $R^2$ are optionally substituted with oxo or halo;
each $R^5$ is independently H, optionally substituted ($C_1$-$C_3$)alkyl, or $-C(O)-O-(C_1$-$C_3)$alkyl-optionally substituted phenyl;
each $R^6$ is independently H or optionally substituted ($C_1$-$C_2$)alkyl;
each $R^7$ is independently H, optionally substituted ($C_1$-$C_2$)alkyl or optionally substituted phenyl;

m is 1 or 2;
n is 1, 2 or 3;
t is 1, 2 or 3; and
u is 1; or a pharmaceutically acceptable salt, solvate, hydrate, metabolite, prodrug, enantiomer or stereoisomer thereof and a pharmaceutically acceptable diluent or carrier.

14. A compound selected from the group consisting of
((1R,3S)-1-Amino-3-(4-(7-methoxyheptyl)phenyl)cyclopentyl)methanol, hydrochloric acid;
(1R,3S)-1-Amino-3-(4-bromo-phenyl)-cyclopentanecarboxylic acid;
(1R,3S)-1-Amino-3-(4-bromo-phenyl)-cyclopentanecarboxylic acid methyl ester;
(1R,3S)-Methyl 1-amino-3-(4(7-methoxyhept-1-ynyl)phenyl)cyclopentanecarbylate;
(1R,3R)-1-Amino-3-[4-(5-phenyl-pent-1-ynyl)-phenyl]-cyclopentanecarboxylic acid methyl ester;
(1R,3R)-Methyl 1-amino-3-(4-(6-methoxyhex-1-ynyl)phenyl)cyclopentanecarboxylate L-tartaric acid;
(1R,3R)-Methyl 1-amino-3-(4-(3-(benzyloxy)prop-1-ynyl)phenyl)cyclopentanecarboxylate;
(1R,3S)-1-Amino-3-(4-prop-1-ynyl-phenyl)-cyclopentanecarboxylic acid methyl ester;
(1R,3R)-1-Amino-3-(4-prop-1-ynyl-phenyl)-cyclopentanecarboxylic acid methyl ester;
(1R,3S)-Methyl 1-amino-3-(4-(7-methoxyheptyl)phenyl)cyclopentanecarboxylate;
(1R,3R)-Methyl 1-amino-3-(4-(6-methoxyhexyl)phenyl)cyclopentanecarboxylate;
(1R,3S)-1-Amino-3-(4-octyl-phenyl)-cyclopentanecarboxylic acid methyl ester;
((1R,3S)-1-Amino-3-(4-(7-methoxyheptyl)phenyl)cyclopentyl)methanol, hydrochloric acid;
((1R,3R)-1-Amino-3-(4-(5-phenylpent-1-ynyl)phenyl)cyclopentyl)methanol;
((1R,3R)-1-Amino-3-(4-(3-(benzyloxy)prop-1-ynyl)phenyl)cyclopenty)methanol;
[(1R,3S)-1-Amino-3-(4-octyl-phenyl)-cyclopentyl]-methanol;
((1R,3R)-1-Amino-3-(4-(6-ethoxyhexyl)phenyl)cyclopentyl)methanol, hydrochloric acid;
(1R,3R)-1-Amino-3-(4-methoxy-phenyl)-cyclopentanecarbonitrile; compound with (2R,3R)-2,3-dihydroxysuccinic acid;
(1R,3R)-1-Amino-3-(4-methoxy-phenyl)-cyclopentanecarboxylic acid;
((1R,3R)-1-Amino-3-(4-(3-(3-methoxyphenoxy)propyl)phenyl)cyclopentyl)methanol, hydrochloric acid;
[(1R,3R)-1-Amino-3-(4-octyloxy-phenyl)-cyclopentyl]-methanol, hydrochloride;
Phosphoric acid mono-[(1R,3S)-1-amino-3-(4-octyl-phenyl)-cyclopentylmethyl]ester;
Phosphoric acid mono-{(1R,3S)-1-amino-3-[3,5-dichloro-4-(2-phenoxy-ethoxy)-phenyl]-cyclopentylmethyl}ester;
((1R,3R)-1-Amino-3-(4-(3-(thiophen-2-yl)propoxy)phenyl)cyclopentyl)methyl dihydrogen phosphate;
Phosphoric acid mono-[(1R,3S)-1-amino-3-(4-octyl-phenyl)-cyclopentylmethyl]ester; hydrochloride;
(1R,3R)-Methyl 1-amino-3-(4-(2-(3-methoxyphenoxy)ethyl)phenyl)cyclopentanecarboxylate;
2-((1R,3R)-1-Amino-3-(4-octylphenyl)cyclopentyl)propan-2-ol;
1-(4-((1R,3R)-3-Amino-3-(hydroxymethyl)cyclopentyl)phenyl)-5-phenylpentan-1-one, acetic acid salt;
[(1R,3S)-1-Amino-3-(4-oct-1-ynyl-phenyl)-cyclopentyl]-methanol; compound with acetic acid;
[(1R,3S)-1-Amino-3-(4-octyl-phenyl)-cyclopenty]-methanol;
{(1R,3S)-1-Amino-3-[4-(3-phenoxy-propyl)-phenyl]-cyclopentyl}-methanol; hydrochloride;
((3S)-1-Amino-3-(3-decylphenyl)cyclopentyl)methanol;
((3S)-1-Amino-3-(3-nonylphenyl)cyclopentyl)methanol;
((3S)-1-Amino-3-(3-octylphenyl)cyclopentyl)methanol;
((3S)-1-Amino-3-(3-heptylphenyl)cyclopentyl)methanol;
((1R,3S)-1-Amino-3-(4-(6-methoxyhexyl)phenyl)cyclopentyl)methanol;
((1R,3S)-1-Amino-3-(4-(4-phenylbutyl)phenyl)cyclopentyl)methanol;
((1R,3S)-1-Amino-3-(4-(6-ethoxyhexyl)phenyl)cyclopentyl)methanol;
((1R,3S)-1-Amino-3-(4-(6-isopropoxyhexyl)phenyl)cyclopentyl)methanol; hydrochloride;
[(1R,3R)-1-Amino-3-(4-oct-1-ynyl-phenyl)-cyclopentyl]-methanol;
{(1R,3R)-1-Amino-3-[4-(4-phenyl-but-1-ynyl)-phenyl]-cyclopentyl}-methanol;
[(1R,3R)-1-Amino-3-(4-hex-1-ynyl-phenyl)-cyclopentyl]-methanol;
[(1R,3R)-1-Amino-3-(4-1-ynyl-phenyl)-cyclopentyl]-methanol;
{(1R,3R)-1-Amino-3-[4-(6-methoxy-hex-1-ynyl)-phenyl]-cyclopentyl}-methanol;
{(1R,3R)-1-Amino-3-[4-(3-phenyl-prop-1-ynyl)-phenyl]-cyclopentyl}-methanol;
{(1R,3R)-1-Amino-3-[4-(5-phenyl-pent-1-ynyl)-phenyl]-cyclopentyl}-methanol;
(1R,3R)-1-Amino-3-(4-oct-1-ynyl-phenyl)-cyclopentanecarboxylic acid;
[(1R,3R)-1-Amino-3-(4-octyl-phenyl)-cyclopentyl]-methanol;
{(1R,3R)-1-Amino-3-[4-(4-phenyl-butyl)-phenyl]-cyclopenty}-methanol;
[(1R,3R)-1-Amino-3-[4-(3-phenoxy-propyl)-phenyl]-cyclopently]-methanol;
{(1R,3R)-1-Amino-3-[4-(6-methoxy-hexyl)-phenyl]-cyclopentyl}-methanol;
{(1R,3R)-1-Amino-3-[4-(3-phenyl-propyl)-phenyl]-cyclopentyl}-methanol;
{(1R,3R)-1-Amino-3-[4-(5-phenyl-pentyl)-phenyl]-cyclopentyl}-methanol;
{(1R,3R)-1-Amino-3-[4-(4-propoxy-butyl)-phenyl]-cyclopentyl}-methanol;
((1R,3R)-1-Amino-3-(4-heptylphenyl)cyclopentyl)methanol;
((1R,3R)-1-Amino-3-(4-hexylphenyl)cyclopentyl)methanol;
((1R,3R)-1-Amino-3-(4-(7-methoxyheptyl)phenyl)cyclopentyl)methanol;
((1R,3R)-1-Amino-3-(4-(6-ethoxyhexyl)phenyl)cyclopentyl)methanol;
((1R,3R)-1-amino-3-(4-(3-phenoxypropyl)phenyl)cyclopentyl)methanol;
((1R,3R)-1-amino-3-(4-(5-ethoxypentyl)phenyl)cyclopentyl)methanol;
((1R,3R)-1-amino-3-(4-(3-(2-methoxyethoxy)propyl)phenyl)cyclopentyl)methanol;
((1R,3R)-1-Amino-3-(4-(3-butoxypropyl)phenyl)cyclopentyl)methanol;
((1R,3R)-1-Amino-3-(4-(4-methoxyphenethyl)phenyl)cyclopentyl)methanol;

(1-Amino-3-(4-(4-propoxyphenethyl)phenyl)cyclopentyl)methanol;
[(1R,3R)-1-Amino-3-(4-octyloxy-phenyl)-cyclopentyl]-methanol;
((1R,3R)-1-Amino-3-{4-[2-(4-trifluoromethyl-phenyl)-ethoxy]-phenyl}-cyclopentyl)-methanol;
((1R,3R)-1-Amino-3-{4-[2-(3-trifluoromethyl-phenyl)-ethoxy]-phenyl}-cyclopentyl)-methanol;
{(1R,3R)-1-Amino-3-[4-(2-m-tolyloxy-ethoxy)-phenyl]-cyclopentyl}-methanol;
{(1R,3R)-1-Amino-3-[4-(4,4,5,5,5-pentafluoro-pentyloxy)-phenyl]-cyclopentyl}-methanol;
((1R,3R)-1-Amino-3-{4-[2-(4-methoxy-phenyl)-ethoxy]-phenyl}-cyclopentyl)-methanol;
{(1R,3R)-1-Amino-3-[4-(2-p-tolyloxy-ethoxy)-phenyl]-cyclopentyl}-methanol;
[(1R,3R)-1-Amino-3-(4-heptyloxy-phenyl)-cyclopentyl]-methanol;
[(1R,3R)-1-(4-nonyloxy-phenyl)-cyclopentyl]-methanol;
{(1R,3R)-1-Amino-3-[4-(2-pentyloxy-ethoxy)-phenyl]-cyclopentyl}-methanol;
{(1R,3R)-1-Amino-3-[4-(2-p-totyl-ethoxy)-phenyl]-cyclopentyl}-methanol;
((1R,3R)-1-Amino-3-{4-[3-(4-methoxy-phenyl)-propoxy]-phenyl}-cyclopentyl)-methanol;
((1R,3R)-1-Amino-3-{4-[2-(2-methoxy-ethoxy)-ethoxy]-phenyl}-cyclopentyl)-methanol;
((1R,3R)-1-Amino-3-{4-[2-(4-ethoxy-phenyl)-ethoxy]-phenyl}-cyclopentyl)-methanol;
{(1R,3R)-1-Amino-3-[4-(4-methanesulfonyl-butoxy)-phenyl]-cyclopentyl}-methanol;
{(1R,3R)-1-Amino-3-[4-(5-methoxy-pentyloxy)-phenyl]-cyclopentyl}-methanol;
((1R,3R)-1-Amino-3-{4-[2-(3-fluoro-4-methoxy-phenyl)-ethoxy]-phenyl}-cyclopentyl)-methanol;
{(1R,3R)-1-Amino-3-[4-(2-phenoxy-ethoxy)-phenyl]-cyclopentyl}-methanol;
((1R,3R)-1-Amino-3-{4-[2-(3-methoxy-phenyl)-ethoxy]-phenyl}-cyclopentyl)-methanol;
((1R,3R)-1-Amino-3-{4-[3-(3-methoxy-phenyl)-propoxy]-phenyl}-cyclopentyl)-methanol;
((1R,3R)-1-Amino -3-{4-[3-(3,5-dimethoxy-phenyl)-propoxy]-phenyl}-cyclopentyl)-methanol;
((1R,3R)-1-Amino-3-{4-[2-(4-methoxy-3,5-dimethyl-phenyl)-ethoxy]-phenyl}-cyclopentyl)-methanol;
{(1R,3R)-1-Amino-3-[4-(1-methyl-1H--benzoimidazol-2-ylmethoxy)-phenyl]-cyclopentyl}-methanol;
((1R,3R)-1-Amino-3-{4-[2-(3-fluoro-phenoxy)-ethoxy]-phenyl}-cyclopentyl)-methanol;
{(1R,3R)-1-Amino-3-[4-(3-ethoxy-benzyloxy)-phenyl]-cyclopentyl}-methanol;
((1R,3R)-1-Amino-3-{4-[3-(5-methyl-oxazol-2-yl)-propoxy]-phenyl}-cyclopentyl)-methanol;
((1R,3R)-1-Amino-3-{4-[2-(2,4-difluoro-phenoxy)-ethoxy]-phenyl}-cyclopentyl)-methanol;
((1R,3R)-1-Amino-3-{4-[2-(4-fluoro-2-methyl-phenoxy)-ethoxy]-phenyl}-cyclopentyl)-methanol;
((1R,3R)-1-Amino-3-{4-[2-(3-methoxy-phenoxy)-ethoxy]-phenyl}-cyclopentyl)-methanol;
((1R,3R)-1-Amino-3-{4-[2-(3-ethoxy-phenyl)-ethoxy]-phenyl}-cyclopentyl)-methanol;
((1R,3R)-1-Amino-3-{4-[2-(3-chloro-4-methoxy-phenyl)-ethoxy]-phenyl}-cyclopentyl)-methanol;
{(1R,3R)-1-Amino-3-[4-((R)-1-methyl-2-phenoxy-ethoxy)-phenyl]-cyclopentyi}-methanol;
{(1R,3R)-1-Amino-3-[4-((S)-1-methyl-2-phenoxy-ethoxy)-phenyl]-cyclopentyl}-methanol;
((1R,3R)-1-Amino-3-{4-[2-(4-benzyloxy-phenyl)-ethoxy]-phenyl}-cyclopentyl)-methanol;
((1R,3R)-1-Amino-3-{4-[2-(4-fluoro-phenoxy)-ethoxy]-phenyl}-cyclopentyl)-methanol;
{(1R,3R)-1-Amino-3-[4-(3-phenyl-propoxy)-phenyl]-cyclopentyl}-methanol;
{(1R,3R)-1-Amino-3-[4-(1-methyl-1H-benzoimidazol-2-ylmethoxy)-phenyl]-cyclopentyl}-methanol;
((1R,3R)-1-Amino-3-{4-[2-(3-fluoro-phenoxy)-ethoxy]-phenyl}-cyclopentyl)-methanol;
{(1R,3R)-1-Amino-3-[4-(3-ethoxy-benzyloxy)-phenyl]-cyclopentyl}-methanol;
((1R,3R)-1-Amino-3-{4-[3-(5-methyl-oxazol-2-yl)-propoxy]-phenyl}-cyclopentyl)-methanol;
((1R,3R)-1-Amino-3-{4-[2-(2,4-difluoro-phenoxy)-ethoxy]-phenyl}-cyclopentyl)-methanol;
((1R,3R)-1-Amino-3-{4-[2-(4-fluoro-2-methyl-phenoxy)-ethoxy]-phenyl}-cyclopentyl)-methanol;
((1R,3R)-1-Amino-3-{4-[2-(3-methoxy-phenoxy)-ethoxy]-phenyl}-cyclopentyl)-methanol;
((1R,3R)-1-Amino-3-{4-[2-(3-ethoxy-phenyl)-ethoxy]-phenyl}-cyclopentyl)-methanol;
((1R,3R)-1-Amino-3{4-[2-(3-chloro--4-methoxy-phenyl)-ethoxy]-phenyl}-cyclopentyl)-methanol;
{(1R,3R)-1-Amino-3-[4-((R)-1-methyl-2-phenoxy-ethoxy)-phenyl]-cyclopentyl}-methanol;
{(1R,3R)-1-Amino-3-[4-((S)-1-methyl-2-phenoxy-ethoxy)-phenyl]-cyclopentyl}-methanol;
((1R,3R)-1-Amino-3-{4-[2-(4-benzyloxy-phenyl)-ethoxy]-phenyl}-cyclopentyl)-methanol;
{(1R,3R)-1-Amino-3-[3-bromo-4-(2-phenoxy-ethoxy)-phenyl]-cyclopentyl}-methanol;
{(1R,3R)-1-Amino-3-[3-methyl-4-(2-phenoxy-ethoxy)-phenyl]-cyclopentyl}-methanol;
((1R,3R)-1-Amino-3-{3-bromo-4-[3-(3-methoxy-phenyl)-propoxy]-phenyl}-cyclopentyl)-methanol;
((1R,3R)-1-Amino-3-{4-[3-(3-methoxy-phenyl)-propoxy]-3-methyl-phenyl}-cyclopentyl)-methanol;
{(1R,3R)-1-Amino-3-[3,5-dichloro-4-(2-phenoxy-ethoxy)-phenyl]-cyclopentyl}-methanol;
[(1R,3R)-1-Amino-3-(3,5-dichloro-4-pentyloxy-phenyl)-cyclpentyl]-methanol;
((1R,3R)-1-Amino-3-{3-bromo-4-[2-(4-methoxy-3,5-dimethyl-phenyl)-ethoxy]-phenyl}-cyclopentyl)-methanol;
((1R,3R)-1-Amino-3-(4-((Z)-hept-4-enyloxy)phenyl)cyclopentyl)methanol;
((1R,3R)-1-Amino-3-{4-[2-(4-trifluoromethoxy-phenyl)-ethoxy]-phenyl}-cyclopentyl)-methanol;
((1R,3R)-1-Amino-3-(4-(3-methoxy-4-methylphenethoxy)phenyl)cyclopentyl)methanol;
((1R,3R)-1-Amino-3-(4-(3-(pyridin-3-yl)propoxy)phenyl)cyclopentyl)methanol;
((1R,3R)-1-Amino-3-(4-(3-(4-fluoro-3-methoxyphenyl)propoxy)phenyl)cyclopentyl)methanol;
((1R,3R)-1-Amino-3-(4-(3-(2-methoxyphenyl)propoxy)phenyl)cyclopentyl)methanol;
((1R,3R)-1-Amino-3-(4-(4-methoxy-3-methylphenethoxy)phenyl)cyclopentyl)methanol;
((1R,3R)-1-Amino-3-(4-(3-(thiohen-2-yl)propoxy)phenyl)cyclopentyl)methanol;
((1R,3R)-1-Amino-3-(4-(3-(pyridin-4-yl)propoxy)phenyl)cyclopentyl)methanol;
Phosphoric acid mono-{(1R,3R)-1-amino-3-[4-(4-phenyl-butyl)-phenyl]-cyclopentylmethyl}ester;
Phosphoric acid mono-{(1R,3R)-1-amino-3-[4-(3-phenoxy-propyl)-phenyl]-cyclopentylmethyl}ester;

Phosphoric acid mono-[(1R,3S)-1-amino-3-(4-octyl-phenyl)-cyclopentylmethyl]ester;
Phosphoric acid mono-[(1R,3S)-1-amino-3-(3-decyl-phenyl)-cyclopentylmethyl]ester;
Phosphoric acid mono-[(1R,3R)-1-amino-3-(4-nonyloxy-phenyl)-cyclopentylmethyl]ester;
Phosphoric acid mono-{(1R,3R)-1-amino-3-[4-(2-p-tolyloxy-ethoxy)-phenyl]-cyclopentylmethyl}ester;
Phosphoric acid mono-((1R,3R)-1-amino-3-{4-[2-(4-methoxy-phenyl)-ethoxy]-phenyl}-cyclopentylmethyl)ester;
Phosphoric acid mono-{(1R,3R)-1-amino-3-[4-(4,4,5,5,5-pentafluoro-pentyloxy)-phenyl]-cyclopentylmethyl}ester;
Phosphoric acid mono-{(1R,3R)-1-amino-3-[4-(3-phenyl-propyl)-phenyl]-cyclopentylmethyl}ester;
Phosphoric acid mono-[(1R,3R)-1-amino-3-(4-octyloxy-phenyl)-cyclopentylmethyl]ester;
Phosphoric acid mono-{(1R,3R)-1-amino-3-[4-(6-methoxy-hexyl)-phenyl]-cyclopentylmethyl}ester;
Phosphoric acid mono-[(1R,3S)-1-amino-3-(4-octyl-phenyl)-cyclopentylmethyl]ester;
Phosphoric acid mono-[(1R,3S)-1-amino-3-(4-heptyl-phenyl)-cyclopentylmethyl]ester;
Phosphoric acid mono-{(1R,3R)-1-amino-3-[4-(2-pentyloxy-ethoxy)-phenyl]-cyclopentylmethyl}ester;
Phosphoric acid mono-{(1R,3R)-1-amino-3-[4-(2-m-tolyloxy-ethoxy)-phenyl]-cyclopentylmethyl}ester;
Phosphoric acid mono-{(1R,3R)-1-amino-3-[4-(2-p-tolyl-ethoxy)-phenyl]-cyclopentylmethyl}ester;
Phosphoric acid mono-[(1R,3R)-1-amino-3-(4-heptyloxy-phenyl)-cyclopentylmethyl]ester;
Phosphoric acid mono-((1R,3R)-1-amino-3-{4-[3-(4--methoxy-phenyl)-propoxy]-phenyl}-cyclopentylmethyl)ester;
Phosphoric acid mono-((1R,3R)-1-amino-3-{4-[2-(2-methoxy-ethoxy)-ethoxy]-phenyl}-cyclopentylmethyl)ester;
Phosphoric acid mono-((1R,3R)-1-amino-3-{4-[2-(4-ethoxy-phenyl)-ethoxy]-phenyl}-cyclopentylmethyl)ester;
Phosphoric acid mono-{(1R,3R)-1-amino-3-[4-(2-phenoxy-ethoxy)-phenyl]-cyclopentylmethyl}ester;
Phosphoric acid mono-((1R,3R)-1-amino-3-{4-[2-(3-fluoro-4-methoxy-phenyl)-ethoxy]-phenyl}-cyclopentylmethyl)ester;
Phosphoric acid mono-((1R,3R)-1-amino-3-{4-[2-(3-methoxy-phenyl)-ethoxy]-phenyl}-cyclopentylmethyl)ester;
Phosphoric acid mono-((1R,3R)-1-amino-3-{4-[3-(3-methoxy-phenyl)-propoxy]-phenyl}-cyclopentylmethyl)ester;
Phosphoric acid mono-((1R,3R)-1-amino-3-{4-[3-(3,5-dimethoxy-phenyl)-propoxy]-phenyl}-cyclopentylmethyl)ester;
Phosphoric acid mono-((1R,3R)-1-amino-3-{4-[2-(4-hydroxy-phenyl)-ethoxy]-phenyl}-cyclopentylmethyl)ester;
Phosphoric acid mono-{(1R,3R)-1-amino-3-[4-(3-phenyl-propoxy)-phenyl]-cyclopentylmethyl}ester;
Phosphoric acid mono-{(1R,3S)-1-amino-3-[4-(3-phenoxy-propyl)-phenyl]-cyclopentylmethyl}ester;
Phosphoric acid mono-((3S)-1-amino-3-(3-nonylphenyl)cyclopentyl)methyl ester;
Phosphoric acid mono-((3S)-1-amino-3-(3-octylphenyl)cyclopentyl)methyl ester;
Phosphoric acid mono-((1R,3S)-1-amino-3-(4-(6-methoxyhexyl)phenyl)cyclopentyl)methyl ester;
Phosphoric acid mono-((1R,3S)-1-amino-3-(4-(4-phenylbutyl)phenyl)cyclopentyl)methyl ester;
Phosphoric acid mono-((1R,3R)-1-amino-3-(4-heptylphenyl)cyclopentyl)methyl ester;
Phosphoric acid mono-((1R,3R)-1-amino-3-(4-hexylphenyl)cyclopentyl)methyl ester;
Phosphoric acid mono-{(1R,3R)-1-amino-3-[4-(5-methoxy-pentyloxy)-phenyl]-cyclopentylmethyl}ester;
Phosphoric acid mono-((1R,3R)-1-amino-3-{4-[3-(5-methyl-oxazol-2-yl)-propoxy]-phenyl}-cyclopentylmethyl)ester;
Phosphoric acid mono-((1R,3R)-1-amino-3-{4-[2-(4-fluoro-phenoxy)-ethoxy]-phenyl}-cyclopentylmethyl)ester;
Phosphoric acid mono-((1R,3R)-1-amino-3-{4-[2-(3-fluoro-phenoxy)-ethoxy]-phenyl}-cyclopentylmethyl)ester;
Phosphoric acid mono-((1R,3R)-1-amino-3-{4-[2-(2,4-difluoro-phenoxy)-ethoxy]-phenyl}-cyclopentylmethyl)ester;
Phosphoric acid mono-((1R,3)-1-amino-3-{4-[2-(4-fluoro-2-methyl-phenoxy)-ethoxy]-phenyl}-cyclopentylmethyl)ester;
Phosphoric acid mono-((1R,3R)-1-amino-3-{4-[2-(3-methoxy-phenoxy)-ethoxy]-phenyl}-cyclopentylmethyl)ester;
Phosphoric acid mono-((1R,3R)-1-amino-3-{4-[2-(3-ethoxy-phenyl)-ethoxy]-phenyl}-cyclopentylmethyl)ester;
Phosphoric acid mono-((1R,3R)-1-amino-3-{4-[2-(3-chloro-4-methoxy-phenyl)-ethoxy]-phenyl}-cyclopentylmethyl)ester;
Phosphoric acid mono-{(1R,3R)-1-amino-3-[4-((R)-1-methyl-2-phenoxy-ethoxy)-phenyl]-cyclopentylmethyl}ester;
Phosphoric acid mono-((1R,3R)-1-amino-3-{3-bromo-4-[3-(3-methoxy-phenyl)-propoxy]-phenyl}-cyclopentylmethyl)ester;
Phosphoric acid mono-((1R,3R)-1-amino-3-{4-[3-(3--methoxy-phenyl)-propoxy]-3-methyl-phenyl}-cyclopentylmethyl)ester;
Phosphoric acid mono-{(1R,3R)-1-amino-3-[4-((S)-1-methyl-2-phenoxy-ethoxy)-phenyl]-cyclopentylmethyl}ester;
Phosphoric acid mono-{(1R,3R)-1-amino-3-[3,5-dichloro-4-(2-phenoxy-ethoxy)-phenyl]-cyclopentylmethy}ester;
Phosphoric acid mono-[(1R,3R)-1-amino-3-(3,5-dichloro-4-pentyloxy-phenyl)-cyclopentylmethyl]ester;
Phosphoric acid mono-((1R,3R)-1-amino-3-{3-bromo-4-[2-(4-methoxy-3,5-dimethyl-phenyl)-ethoxy]-phenyl}-cyclopentylmethyl)ester;
Phosphoric acid (1R,3R)-1-amino-{4-[2-(2-methoxy-ethoxy)-ethoxy]-phenyl}-cyclopentylmethyl ester benzylester;
Phosphoric acid mono-{(1R,3S)-1-amino-3-(4-(6-ethoxyhexyl)phenyl)cyclopentyl)methyl}ester;
Phosphoric acid mono-{(1R,3R)-1-amino-3-(4-(7-methoxyheptyl)phenyl)cyclopentyl)methyl}ester;
Phosphoric acid mono-{(1R,3R)-1-amino-3-(4-(6-ethoxyhexyl)phenyl)cyclopentyl)methy}ester;
Phosphoric acid mono-{(1R,3R)-1-amino-3-(4-(2-(3-methoxyphenoxy)ethyl)phenyl)cyclopentyl)-methyl}ester;

((1R,3R)-1-Amino-3-(4-(4-isopropoxyphenethyl)phenyl)cyclopentyl)methyl dihydrogen phosphate;
(((1R,3S)-1-Amino-3-(4-(6-isopropoxyhexyl)phenyl)cyclopentyl)methyl dihydrogen phosphate;
((1R,3R)-1-Amino-3-(4-(7-methyloctyl)phenyl)cyclopentyl)methyl dihydrogen phosphate;
((1R,3R)-1-Amino-3-(4-(5-phenylpentanoyl)phenyl)cyclopentyl)methyl dihydrogen phosphate;
((1R,3R)-1-Amino-3-(4-(4-propoxybutyl)phenyl)cyclopentyl)methyl dihydrogen phosphate;
((1R,3R)-1-amino-3-(4-(5-ethoxypentyl)phenyl)cyclopentyl)methyl dihydrogen phosphate;
((1R,3R)-1-Amino-3-(4-(4-methoxyphenethyl)phenyl)cyclopentyl)methyl dihydrogen phosphate;
((1R,3R)-1-Amino-3-(4-(3-(3-methoxyphenoxy)propyl)phenyl)cyclopentyl)methyl dihydrogen phosphate;
((1R,3R)-1-Amino-3-(4-(2-(3-ethoxyphenoxy)ethyl)phenyl)cyclopentyl)methyl dihydrogen phosphate;
((1R,3R)-1-Amino-3-(4-(2-(3-(trifluoromethoxy)phenoxy)ethyl)phenyl)cyclopentyl)methyl dihydrogen phosphate;
((1R,3R)-1-Amino-3-(4-((R)-3-phenoxybutyl)phenyl)cyclopentyl)methyl dihydrogen phosphate;
((1R,3R)-1-Amino-3-(4-(4-propoxyphenethyl)phenyl)cyclopentyl)methyl dihydrogen phosphate;
((1R,3R)-1-Amino-3-(4-((R)-3-(3-methoxyphenoxy)butyl)phenyl)cyclopentyl)methyl dihydrogen phosphate;
((1R,3R)-1-Amino-3-4-((S)-3-(3-methoxyphenoxy)butyl)phenyl)cyclopentyl)methyl dihydrogen phosphate;
((1R,3R)-1-Amino-3-(4-((S)-3-phenoxybutyl)phenyl)cyclopentyl)methyl dihydrogen phosphate;
((1R,3R)-1-Amino-3-(4-((Z)-hept-4-enyloxy)phenyl)cyclopentyl)methyl dihydrogen phosphate;
((1R,3R)-1-Amino-3-(4-(3-(4-fluoro-3-methoxyphenyl)propoxy)phenyl)cyclopentyl)methyl dihydrogen phosphate;
((1R,3R)-1-Amino-3-(4-(3-(2-methoxyphenyl)propoxy)phenyl)cyclopentyl)methyl dihydrogen phosphate;
((1R,3R)-1-Amino-3-(4-(4-methoxy-3-methylphenethoxy)phenyl)cyclopentyl)methyl dihydrogen phosphate;
((1R,3R)-1-Amino-3-(4-(4-methoxy-3,5-dimethylphenethoxy)phenyl)cyclopentyl)methyl dihydrogen phosphate;
((1R,3R)-1-Amino-3-(4-(4-(trifluoromethoxy)phenethoxy)phenyl)cyclopentyl)methyl dihydrogen phosphate;
((1R,3R)-1-Amino-3-(4-(3-(thiophen-2-yl)propoxy)phenyl)cyclopentyl)methyl dihydrogen phosphate;
((1R,3R)-1-Amino-3-(4-(3-(thiophen-2-yl)propoxy)phenyl)cyclopentyl)methyl dihydrogen phosphate;
((1R,3R)-1-Amino-3-(4-(3-(pyridin-4-yl)propoxy)phenyl)cyclopentyl)methyl dihydrogen phosphate;
((1R,3R)-1-Amino-3-(4-(3-(pyridin-3-yl)propoxy)phenyl)cyclopentyl)methyl dihydrogen phosphate;
(1R,3S)-1-Amino-3-(4-non-1-ynyl-phenyl)-cyclopentanecarboxylic acid;
(1R,3S)-1-Amino-3-(4-nonyl-phenyl)-cyclopentanecarboxylic acid;
(1R,3S)-1-Amino-3-(4-dec-1-ynyl-phenyl)-cyclopentanecarboxylic acid;
(1R,3S)-1-Amino-3-(4-decyl-phenyl)-cyclopentanecarboxylic acid;
(1R,3S)-1-Amino-3-[4-(7-methoxy-hept-1-ynyl)-phenyl]-cyclopentanecarboxylic acid;
(1R,3R)-1-Amino-3-[4-(3-phenoxy-propyl)-phenyl]-cyclopentanecarboxylic acid;
(1R,3S)-1-Amino-3-(4-oct-1-ynyl-phenyl)-cyclopentanecarboxylic acid;
(1R,3S)-1-Amino-3-(4-hept-1-ynyl-phenyl)-cyclopentanecarboxylic acid;
(1R,3S)-1-Amino-3-(4-heptyl-phenyl)-cyclopentanecarboxylic acid;
(3S)-1-Amino-3-(3-decylphenyl)cyclopentanecarboxylic acid;
(3S)-1-Amino-3-(3-nonylphenyl)cyclopentanecarboxylic acid;
(3S)-1-Amino-3-(3-octylphenyl)cyclopentanecarboxylic acid;
(3S)-1-Amino-3-(3-(oct-1-ynyl)phenyl)cyclopentanecarboxylic acid;
(3S)-1-Amino-3-(3-(hept-1-ynyl)phenyl)cyclopentanecarboxylic acid;
(1R,3S)-1-Amino-3-(4-(3-phenylpropyl)phenyl)cyclopentanecarboxylic acid;
(3R)-1-Amino-3-(4-(benzyloxy)-3-chlorophenyl)cyclopentanecarboxylic acid;
(3S)-1-Amino-3-(3-(dec-1-ynyl)-4-methoxyphenyl)cyclopentanecarboxylic acid;
((1R,3R)-1-Amino-3-(4-(4-isopropoxyphenethyl)phenyl)cyclopentyl)methanol;
((1R,3R)-1-Amino-3-(4-(2-(3-methoxyphenoxy)ethyl)phenyl)cyclopentyl)methanol;
((1R,3R)-1-Amino-3-(4-(2-(4-methoxyphenoxy)ethyl)phenyl)cyclopentyl)methanol;
((1R,3R)-1-Amino-3-(4-(3-(3-methoxyphenoxy)propyl)phenyl)cyclopentyl)methanol;
((1R,3R)-1-Amino-3-(4-((R)-3-phenoxybutyl)phenyl)cyclopentyl)methanol;
((1R,3R)-1-Amino-3-(4((R)-3-(3-methoxyphenoxy)butyl)phenyl)cyclopentyl)methanol;
((1R,3R)-1-Amino-3-(4-((S)-3-(3-methoxyphenoxy)butyl)phenyl)cyclopentyl)methanol;
((1R,3R)-1-Amino-3-(4-((S)-3-phenoxybutyl)phenyl)cyclopentyl)methanol;
[3-(4-Octyl-phenyl)-cyclopentylamino]-acetic acid;
3-[3-(4-Octyl-phenyl)-cyclopentylamino]-propionic acid;
(1R,3S)-1-Amino-3-(4-oct-1-ynyl-phenyl)-cyclopentanecarboxylic acid methyl ester;
(1R,3S)-1-Amino-3-(4-octyl-phenyl)-cyclopentanecarboxylic acid methyl ester;
4-{2-[4-((1R,3R)-3-Amino-3-hydroxymethyl-cyclopentyl)-phenoxy]-ethyl}-phenol;
(3S)-1-Amino-3-(4-(5-(4-isobutylphenyl)-1,2,4-oxadiazol-3-yl)phenyl)-N-methylcyclopentanecarboxamide;
2-(1-Amino-3-(4-octylphenyl)cyclopentyl)acetic acid;
2-((1R,3S)-1-Amino-3-(4-octylphenyl)cyclopentyl)ethylphosphonic acid;
(E)-2-((1R,3S)-1-Amino-3-(4-octylphenyl)cyclopentyl)vinylphosphonic acid; and
Diethyl 2-((1R,3S)-1-amino-3-(4-octylphenyl)cyclopentyl)ethylphosphonate.

15. The compound according to claim 14 wherein the compound is
((1R,3S)-1-Amino-3-(4-(7-methoxyheptyl)phenyl)cyclopentyl)methanol, hydrochloric acid;
[(1R,3S)-1-Amino-3-(4-octyl-phenyl)-cyclopentyl]-methanol;
[(1R,3R)-1-Amino-3-(4-octyl-phenyl)-cyclopentyl]-methanol;
(1R,3S)-1-Amino-3-(4-decyl-phenyl)-cyclopentanecarboxylic acid;
Phosphoric acid mono-[(1R,3S)-1-amino-3-(4-octyl-phenyl)-cyclopentylmethyl]ester;
((1R,3S)-1-Amino-3-(4-(4-phenylbutyl)phenyl)cyclopentyl)methanol;

{(1R,3R)-1-Amino-3-[4-(2-phenoxy-ethoxy)-phenyl]-cyclopentyl}-methanol;
((1R,3R)-1-Amino-3-{4-[2-(4-methoxy-phenyl)-ethoxyl]-phenyl}-cyclopentyl)-methanol;
{(1R,3R)-1-Amino-3-[4-(5-methoxy-pentyloxy)-phenyl]-cyclopentyl}-methanol;
((1R,3R)-1-Amino-3-{4-[2-(3-methoxy-phenoxy)-ethoxy]-phenyl}-cyclopentyl)-methanol;
((1R,3R)-1-Amino-3-{4-[2-(4-benzyloxy-phenyl)-ethoxy]-phenyl}-cyclopentyl)-methanol;
{(1R,3R)-1-Amino-3-[4-(4-propoxy-butyl)-phenyl]-cyclopentyl}-methanol;
((1R,3R)-1-Amino-3-{4-[3-(4-methoxy-phenyl)-propoxy]-phenyl}-cyclopentyl)-methanol;
((1R,3R)-1-Amino-3-{4-[3-(3-methoxy-phenyl)-propoxy]-phenyl}-cyclopentyl)-methanol;
((1R,3R)-1-Amino-3-{4-[3-(3,5-dimethoxy-phenyl)-propoxy]-phenyl}-cyclopentyl)-methanol;
((1R,3R)-1-Amino-3-{4-[2-(3-fluoro-4-methoxy-phenyl)-ethoxy]-phenyl}-cyclopentyl)-methanol;
((1R,3R)-1-Amino-3-(4-(7-methoxyheptyl)phenyl)cyclopentyl)methanol;
((1R,3R)-1-Amino-3-(4-(6-ethoxyhexyl)phenyl)cyclopentyl)methanol;
(1R,3S)-1-Amino-3-(4-dec-1-ynyl-phenyl)-cyclopentanecarboxylic acid;
((1R,3R)-1-Amino-3-{4-[2-(3-methoxy-phenyl)-ethoxy]-pheny}-cyclopentyl)-methanol;
[(1R,3R)-1-Amino-3-(4-nonyloxy-phenyl)-cyclopentyl]-methanol;
((1R,3R)-1-Amino-3-(4-(4-isopropoxyphenethyl)phenyl)cyclopentyl)methanol;
{(1R,3R)-1-Amino-3-[4-(2-pentyloxy-ethoxy)-phenyl]-cyclopentyl}-methanol;
((1R,3S)-1-Amino-3-(4-(6-isopropoxyhexyl)phenyl)cyclopentyl)methanol;
1-(4-((1R,3R)-3-Amino-3-(hydroxymethyl)cyclopentyl)phenyl)-5-phenylpentan-1-one;
[(1R,3R)-1-amino-3-(4-octyloxy-phenyl)-cyclopentyl]-methanol;
((1R,3R)-1-Amino-3-{4-[2-(4-fluoro-phenoxy)-ethoxy]-phenyl}-cyclopentyl)-methanol;
((1R,3R)-1-Amino-3-{4-[2-(4-benzyloxy-phenyl)-ethoxy]-phenyl}-cyclopentyl)-methanol;
(1-Amino-3-(4-(4-propoxyphenethyl)phenyl)cyclopentyl)methanol;
((1R,3R)-1-Amino-3-{3-bromo-4-[3-(3-methoxy-phenyl)-propoxy]-phenyl}-cyclopentyl)-methanol;
((1R,3S)-1-Amino-3-(4-(6-ethoxyhexyl)phenyl)cyclopentyl)methanol; or
{(1R,3R)-1-Amino-3-[4-(4-phenyl-butyl)-phenyl]-cyclopentyl}-methanol.

16. A packaged pharmaceutical comprising one or more compounds according to Formula I

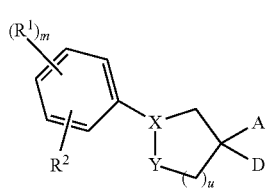

Formula I a pharmaceutically acceptable salt, prodrug, metabolite or an isomer thereof wherein D is H, $N(R^5)_2$, or $OR^6$;
X is CH;
Y is $CH_2$;
A is H, hydroxy, —$CH_2OH$, —$CH(OH)CH_3$, —C(O)—$OCH_3$, —$C(OH)(CH_3)_2$, —$O(CH_2)_t$—COOH, —C(O)—$NR^6$, optionally substituted —$(CH_2)_n$—P(=O)($OR^7$)($OR^7$), optionally substituted —$(CH_2)_n$—O—P(=O)($OR^7$)($OR^7$), optionally substituted —$(CH_2)_n$—P(=O)($OR^7$)($R^7$), —CH=CH—P(=O)($OR^7$)($OR^7$), C(O)—$NHCH_3$, CN, $COOR^6$ or —$R^4$—COOH, wherein $R^4$ is straight or branched ($C_1$-$C_{20}$) alkylene, straight or branched ($C_1$-$C_{20}$) alkenylene, straight or branched ($C_1$-$C_{20}$) alkynylene, ($C_3$-$C_{20}$)cycloalkyl, or optionally substituted azetidinyl;
$R^1$ and $R^2$ are independently selected from the group consisting of hydrogen, $CF_3$, halo, ($C_1$-$C_{20}$) alkyl, ($C_1$-$C_{20}$) alkoxy, ($C_3$-$C_{20}$) cycloalkyl substituted alkyl, ($C_3$—$C_{20}$) cycloalkyl substituted alkoxy, ($C_2$-$C_{20}$) alkenyl, aryl substituted ($C_2$-$C_{20}$) alkenyl, ($C_2$-$C_{20}$) alkynyl, aryl substituted ($C_2$-$C_{20}$) alkynyl, aryl, aryl substituted alkyl, heteroaryl substituted alkyl, aryl substituted alkoxy, heteroaryl substituted alkoxy, alkyl substituted aryl, arylalkyl, aryl substituted arylalkyl, arylalkyl substituted arylalkyl, CN and —O -indolizinyl; wherein such $R^1$ and $R^2$ groups may be optionally substituted with one or more substitutents independently selected from ($C_1$-$C_{20}$) alkyl, $CF_3$, halo, hydroxy, ($C_1$3 -$C_{20}$) alkoxy, $OCF_3$, and CN;
wherein one or more of the carbon atoms in the $R^1$ or $R^2$ groups can be independently replaced with non-peroxide oxygen, sulfur or $NR^8$;
wherein $R^8$ is hydrogen or ($C_1$-$C_{20}$) alkyl group;
wherein one of $R^1$ and $R^2$ is other than hydrogen; and wherein the alkyl, alkenyl, and alkynyl groups in $R^2$ are optionally substituted with oxo or halo;
each $R^5$ is independently H, optionally substituted ($C_1$-$C_3$)alkyl, or —C(O)—O—($C_1$-$C_3$)alkyl-optionally substituted phenyl;
each $R^6$ is independently H or optionally substituted ($C_1$-$C_2$)alkyl;
each $R^7$ is independently H, optionally substituted ($C_1$-$C_2$)alkyl or optionally substituted phenyl;
m is 1 or 2;
n is 1, 2 or 3;
t is 1, 2 or 3; and
u is 1;
or a pharmaceutically acceptable salt, solvate, hydrate, metabolite, prodrug, enantiomer or stereoisomer thereof and instructions for use.

17. The packaged pharmaceutical according to claim 16 wherein the compound or compounds are present in a therapeutically effective amount.

18. A method of making a compound of Formula (Id)

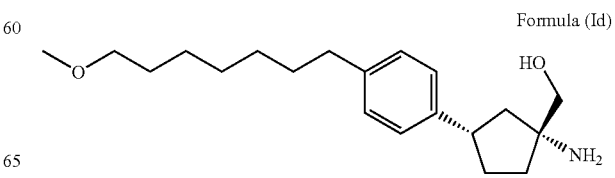

Formula (Id)

comprising the step of reacting a compound of Formula (Ic) with a reducing reagent until the reaction is substantially complete to form a compound of Formula (Id)
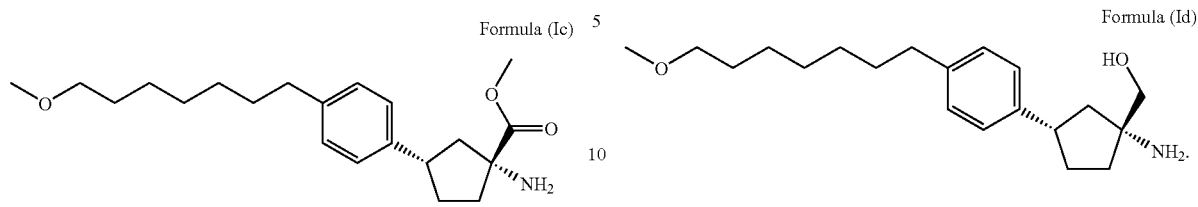
* * * * *

UNITED STATES PATENT AND TRADEMARK OFFICE
CERTIFICATE OF CORRECTION

PATENT NO.      : 8,217,027 B2
APPLICATION NO. : 12/075378
DATED           : July 10, 2012
INVENTOR(S)     : Grier A. Wallace et al.

It is certified that error appears in the above-identified patent and that said Letters Patent is hereby corrected as shown below:

Claim 12, Column 249, line 55
   Insert

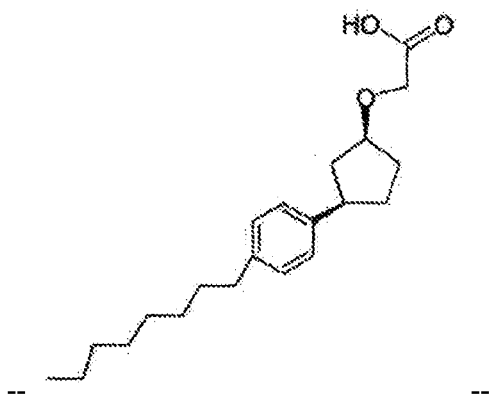

--                                             --

Claim 13, Column 250, line 36-37
   Delete "$(C_1-C_{20})$alkylene, straight or branched $(C_1-C_{20})$alkenylene, straight or branched $(C_1-C_{20})$alkynylene" and insert -- $(C_1-C_{20})$alkylene, straight or branched $(C_2-C_{20})$alkenylene, straight or branched $(C_2-C_{20})$alkynylene --

Claim 14, Column 252, line 25
   Delete "[(*1R,3R*)-1-Amino-3-(4-1-ynyl-phenyl)-cyclopentyl]-methanol" and insert -- [(*1R,3R*)-1-Amino-3-(4-hept-1-ynyl-phenyl)-cyclopentyl]-methanol --

Claim 14, Column 252, line 38
   Delete "{(*1R,3R*)-1-Amino-3-[4-(4-phenyl-butyl)-phenyl]-cyclopenty}-methanol" and insert -- {(*1R,3R*)-1-Amino-3-[4-(4-phenyl-butyl)-phenyl]-cyclopentyl}-methanol --

Signed and Sealed this
Twelfth Day of February, 2013

Teresa Stanek Rea
*Acting Director of the United States Patent and Trademark Office*

Claim 14, Column 253, line 22
Delete "{(*1R,3R*)-1-Amino-3-[4-(2-p-totyl-ethoxy)-phenyl]-cyclopentyl}-methanol" and insert -- {(*1R,3R*)-1-Amino-3-[4-(2-p-tolyl-ethoxy)-phenyl]-cyclopentyl}-methanol --

Claim 14, Column 253, line 46-47
Delete "{(1*R*,3*R*)-1-Amino-3-[4-(1-methyl-1H--1H-benzoimidazol-2-ylmethoxy)-phenyl]-cyclopentyl}-methanol" and insert -- {(1*R*,3*R*)-1-Amino-3-[4-(1-methyl-1H-benzoimidazol-2-ylmethoxy)-phenyl]-cyclopentyl}-methanol --

Claim 14, Column 253, line 64-65
Delete "{(1*R*,3*R*)-1-Amino-3-[4-((*R*)-1-methyl-2-phenoxy-ethoxy)-phenyl]-cyclopentyi}-methanol" and insert -- {(1*R*,3*R*)-1-Amino-3-[4-((*R*)-1-methyl-2-phenoxy-ethoxy)-phenyl]-cyclopentyl}-methanol --

Claim 14, Column 254, lines 23-24
Delete "((1*R*,3*R*)-1-Amino-3-{4-[2-(3-(chloro--4-methoxy-phenyl)-ethoxy]-phenyl}-cyclopentyl)-methanol" and insert -- ((1*R*,3*R*)-1-Amino-3-{4-[2-(3-chloro-4-methoxy-phenyl)-ethoxy]-phenyl}-cyclopentyl)-methanol --

Claim 14, Column 255, lines 34-35
Delete "Phosphoric acid mono-((1*R*,3*R*)-1-amino-3-{4-[3-(4--methoxy-phenyl)-propoxy]-phenyl}-cyclopentylmethyl) ester;" and insert -- Phosphoric acid mono-((1*R*,3*R*)-1-amino-3-{4-[3-(4-methoxy-phenyl)-propoxy]-phenyl}-cyclopentylmethyl) ester; --

Claim 14, Column 256, lines 41-42
Delete "Phosphoric acid mono-((*1R,3R*)-1-amino-3-{4-[3-(3--methoxy-phenyl)-propoxy]-phenyl}-cyclopentylmethyl) ester" and insert -- Phosphoric acid mono-((*1R,3R*)-1-amino-3-{4-[3-(3-methoxy-phenyl)-propoxy]-phenyl}-cyclopentylmethyl) ester --

Claim 14, Column 258, line 15
Insert -- (3*S*)-1-Amino-3-(3-decylphenyl)cyclopentanecarboxylic acid;
(3*S*)-1-Amino-3-(3-nonylphenyl)cyclopentanecarboxylic acid;
(3*S*)-1-Amino-3-(3-octylphenyl)cyclopentanecarboxylic acid;
(3*S*)-1-Amino-3-(3-(oct-1-ynyl)phenyl)cyclopentanecarboxylic acid;
(3*S*)-1-Amino-3-(3-(hept-1-ynyl)phenyl)cyclopentanecarboxylic acid; -- after "(*1R,3S*)-1-Amino-3-(4-heptyl-phenyl)-cyclopentanecarboxylic acid;"

Claim 16, Column 260, line 15
Delete "($C_1$-$C_{20}$)alkylene, straight or branched ($C_1$-$C_{20}$)alkenylene, straight or branched ($C_1$-$C_{20}$)alkynylene," and insert -- ($C_1$-$C_{20}$)alkylene, straight or branched ($C_2$-$C_{20}$)alkenylene, straight or branched ($C_2$-$C_{20}$)alkynylene --

CERTIFICATE OF CORRECTION (continued)
U.S. Pat. No. 8,217,027 B2

Claim 16, Column 260, line 32

Delete "halo, hydroxy, ($C_1$3-$C_{20}$) alkoxy, $OCF_3$, and CN;" and insert -- halo, hydroxy, ($C_1$-$C_{20}$) alkoxy, $OCF_3$, and CN; --